US012735702B2

(12) United States Patent
Nair et al.

(10) Patent No.: US 12,735,702 B2
(45) Date of Patent: *Sep. 15, 2026

(54) ENDOSOMAL CLEAVABLE LINKERS

(71) Applicant: ALNYLAM PHARMACEUTICALS, INC., Cambridge, MA (US)

(72) Inventors: Jayaprakash K. Nair, Cambridge, MA (US); Kallanthottathil G. Rajeev, Cambridge, MA (US); Scott Lentini, Cambridge, MA (US); Christopher S. Theile, Cambridge, MA (US); Martin Maier, Cambridge, MA (US); Ivan Zlatev, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 1255 days.

This patent is subject to a terminal disclaimer.

(21) Appl. No.: 17/668,917

(22) Filed: Feb. 10, 2022

(65) Prior Publication Data

US 2022/0177885 A1 Jun. 9, 2022

Related U.S. Application Data

(63) Continuation of application No. 16/474,776, filed as application No. PCT/US2018/014213 on Jan. 18, 2018, now Pat. No. 11,286,482.

(60) Provisional application No. 62/447,786, filed on Jan. 18, 2017.

(51) Int. Cl.

| | |
|---|---|
| ***C12N 15/11*** | (2006.01) |
| ***C07H 21/02*** | (2006.01) |
| ***C12N 15/113*** | (2010.01) |

(52) U.S. Cl.

CPC ........ *C12N 15/113* (2013.01); *C12N 2310/14* (2013.01); *C12N 2310/141* (2013.01); *C12N 2310/314* (2013.01); *C12N 2310/315* (2013.01); *C12N 2310/3183* (2013.01); *C12N 2310/3519* (2013.01); *C12N 2310/51* (2013.01)

(58) Field of Classification Search

CPC .............. C12N 15/114; C12N 2310/14; C12N 2310/141; C12N 2310/314; C12N 2310/315; C12N 2310/3183; C12N 2310/3519; C12N 2310/51; C12N 2310/318; C12N 15/111; A61P 25/00; A61P 25/04; A61P 29/02; A61P 31/04; A61P 31/10; A61P 31/12; A61P 33/00; A61P 35/00; A61P 37/02; A61P 43/00; C07H 21/02

See application file for complete search history.

(56) References Cited

U.S. PATENT DOCUMENTS

| | | | |
|---|---|---|---|
| 7,528,118 B2 | 5/2009 | Soutschek | |
| 2006/0148740 A1 | 7/2006 | Platenburg | |
| 2010/0249214 A1 | 9/2010 | Brown | |
| 2010/0330155 A1 | 12/2010 | Berry | |
| 2011/0123520 A1* | 5/2011 | Manoharan ........ | A61K 48/0008 435/325 |

FOREIGN PATENT DOCUMENTS

| | | | | |
|---|---|---|---|---|
| WO | 9518792 A1 | 7/1995 | | |
| WO | WO-2005051429 A2 * | 6/2005 | .............. | A61P 43/00 |
| WO | 2010054266 A2 | 5/2010 | | |
| WO | 2013074974 A2 | 5/2013 | | |
| WO | 2014062697 A2 | 4/2014 | | |
| WO | WO-2015002511 A1 * | 1/2015 | .............. | A61P 35/00 |
| WO | 2017015109 A1 | 1/2017 | | |

OTHER PUBLICATIONS

Zartler, Edward R., and Gary E. Martin. "The use of 1H-31P GHMBC and covariance NMR to unambiguously determine phosphate ester linkages in complex polysaccharide mixtures." Journal of biomolecular NMR 51.3 (2011): 357-367. (Year: 2011).*

Lopez-Otin et al., "Proteases: Multifunctional Enzymes in Life and Disease", The Journal of Biological Chemistry, 283, (45.), 30433-30437, (2008).

* cited by examiner

*Primary Examiner* — Abigail Vanhorn

(74) *Attorney, Agent, or Firm* — Nixon Peabody LLP; David S. Resnick; Ravinderjit S. Braich

(57) ABSTRACT

The present disclosure relates generally to cleavable linkers and uses thereof.

28 Claims, 39 Drawing Sheets

Specification includes a Sequence Listing.

Q48

Q306

Q303

Q305

Q198

Q304

Q312

Q313

Q314

Q315

Q316

Q317

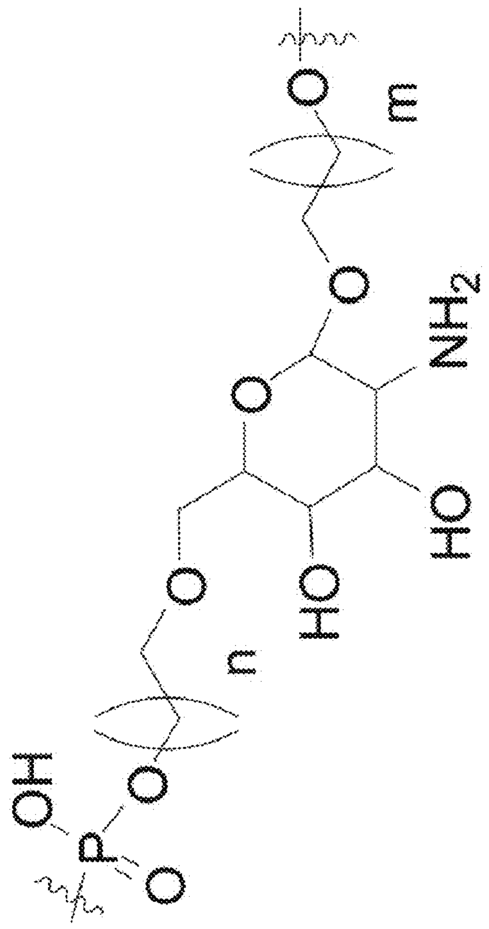
FIG. 2C
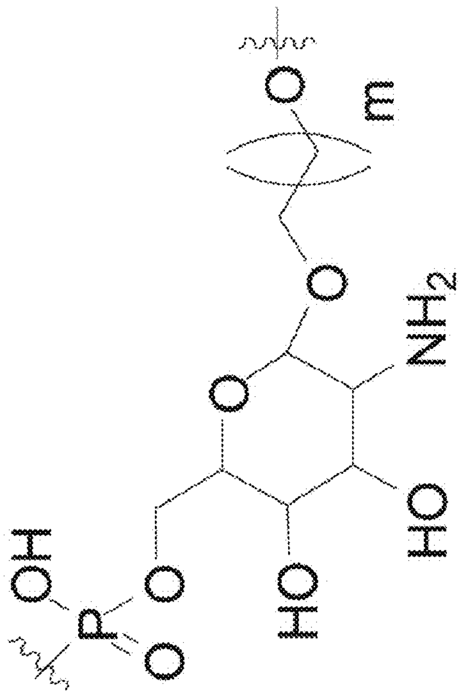

SEQUENCE LISTING

```
<160> NUMBER OF SEQ ID NOS: 70

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
            20                  25


<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

Ala Ala Leu Ala Glu Ala Leu Ala Glu Ala Leu Ala Glu Ala Leu Ala
1 5 10 15

Glu Ala Leu Ala Glu Ala Leu Ala Ala Ala Ala Gly Gly Cys
20 25 30

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Ala Leu Glu Ala Leu Ala Glu Ala Leu Glu Ala Leu Ala Glu Ala
1 5 10 15

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gly Leu Phe Glu Ala Ile Glu Gly Phe Ile Glu Asn Gly Trp Glu Gly
1 5 10 15

Met Ile Trp Asp Tyr Gly
20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Gly Leu Phe Gly Ala Ile Ala Gly Phe Ile Glu Asn Gly Trp Glu Gly
1 5 10 15

Met Ile Asp Gly Trp Tyr Gly
20

<210> SEQ ID NO 6
<211> LENGTH: 48
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Gly Leu Phe Glu Ala Ile Glu Gly Phe Ile Glu Asn Gly Trp Glu Gly
1 5 10 15

Met Ile Asp Gly Trp Tyr Gly Cys Gly Leu Phe Glu Ala Ile Glu Gly
20 25 30

Phe Ile Glu Asn Gly Trp Glu Gly Met Ile Asp Gly Trp Tyr Gly Cys
35 40 45

<210> SEQ ID NO 7
<211> LENGTH: 44
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 7

```
Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
            20                  25                  30

Glu Asn Gly Trp Glu Gly Met Ile Asp Gly Gly Cys
        35                  40
```

<210> SEQ ID NO 8
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35
```

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys
```

<210> SEQ ID NO 10
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (17)..(17)
<223> OTHER INFORMATION: Norleucine
<220> FEATURE:
<221> NAME/KEY: MOD_RES
<222> LOCATION: (38)..(38)
<223> OTHER INFORMATION: Norleucine

<400> SEQUENCE: 10

```
Gly Leu Phe Glu Ala Ile Glu Gly Phe Ile Glu Asn Gly Trp Glu Gly
1               5                   10                  15

Xaa Ile Asp Gly Lys Gly Leu Phe Glu Ala Ile Glu Gly Phe Ile Glu
            20                  25                  30
```

```
Asn Gly Trp Glu Gly Xaa Ile Asp Gly
        35                  40


<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Phe Glu Ala Leu Leu Glu Leu Leu Glu Ser Leu Trp Glu Leu Leu
1               5                   10                  15

Leu Glu Ala


<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Phe Lys Ala Leu Leu Lys Leu Leu Lys Ser Leu Trp Lys Leu
1               5                   10                  15

Leu Leu Lys Ala
            20


<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Phe Arg Ala Leu Leu Arg Leu Leu Arg Ser Leu Trp Arg Leu
1               5                   10                  15

Leu Leu Arg Ala
            20


<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30


<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 15

Gly Leu Phe Phe Glu Ala Ile Ala Glu Phe Ile Glu Gly Gly Trp Glu
1 5 10 15

Gly Leu Ile Glu Gly Cys
20

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Gly Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

His His His His His Trp Tyr Gly
1 5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Cys His Lys Lys Lys Lys Lys Lys His Cys
1 5 10

<210> SEQ ID NO 19
<211> LENGTH: 16
<212> TYPE: PRT
<213> ORGANISM: Drosophila sp.

<400> SEQUENCE: 19

Arg Gln Ile Lys Ile Trp Phe Gln Asn Arg Arg Met Lys Trp Lys Lys
1 5 10 15

<210> SEQ ID NO 20
<211> LENGTH: 14
<212> TYPE: PRT
<213> ORGANISM: Human immunodeficiency virus

<400> SEQUENCE: 20

Gly Arg Lys Lys Arg Arg Gln Arg Arg Arg Pro Pro Gln Cys
1 5 10

<210> SEQ ID NO 21
<211> LENGTH: 27

```
<212> TYPE: PRT
<213> ORGANISM: Unknown
<220> FEATURE:
<223> OTHER INFORMATION: Description of Unknown:
      Signal sequence based peptide

<400> SEQUENCE: 21

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25


<210> SEQ ID NO 22
<211> LENGTH: 18
<212> TYPE: PRT
<213> ORGANISM: Mus sp.

<400> SEQUENCE: 22

Leu Leu Ile Ile Leu Arg Arg Arg Ile Arg Lys Gln Ala His Ala His
1               5                   10                  15

Ser Lys


<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25


<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Leu Ala Leu Lys Leu Ala Leu Lys Ala Leu Lys Ala Ala Leu Lys
1               5                   10                  15

Leu Ala


<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Arg Arg Arg Arg Arg Arg Arg
1               5


<210> SEQ ID NO 26
<211> LENGTH: 10
<212> TYPE: PRT
<213> ORGANISM: Unknown
```

```
<220> FEATURE:
<223> OTHER INFORMATION: Description of Unknown:
      Bacterial cell wall permeating peptide

<400> SEQUENCE: 26

Lys Phe Phe Lys Phe Phe Lys Phe Phe Lys
1               5                   10


<210> SEQ ID NO 27
<211> LENGTH: 37
<212> TYPE: PRT
<213> ORGANISM: Unknown
<220> FEATURE:
<223> OTHER INFORMATION: Description of Unknown:
      LL-37 peptide

<400> SEQUENCE: 27

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35


<210> SEQ ID NO 28
<211> LENGTH: 31
<212> TYPE: PRT
<213> ORGANISM: Unknown
<220> FEATURE:
<223> OTHER INFORMATION: Description of Unknown:
      cecropin P1 peptide

<400> SEQUENCE: 28

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30


<210> SEQ ID NO 29
<211> LENGTH: 30
<212> TYPE: PRT
<213> ORGANISM: Unknown
<220> FEATURE:
<223> OTHER INFORMATION: Description of Unknown:
      Alpha-defensin peptide

<400> SEQUENCE: 29

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30


<210> SEQ ID NO 30
<211> LENGTH: 36
<212> TYPE: PRT
<213> ORGANISM: Unknown
<220> FEATURE:
<223> OTHER INFORMATION: Description of Unknown:
      Beta-defensin peptide

<400> SEQUENCE: 30

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30
```

Lys Cys Cys Lys
35

<210> SEQ ID NO 31
<211> LENGTH: 42
<212> TYPE: PRT
<213> ORGANISM: Unknown
<220> FEATURE:
<223> OTHER INFORMATION: Description of Unknown:
PR-39 peptide

<400> SEQUENCE: 31

Arg Arg Arg Pro Arg Pro Pro Tyr Leu Pro Arg Pro Arg Pro Pro Pro
1 5 10 15

Phe Phe Pro Pro Arg Leu Pro Pro Arg Ile Pro Pro Gly Phe Pro Pro
20 25 30

Arg Phe Pro Pro Arg Phe Pro Gly Lys Arg
35 40

<210> SEQ ID NO 32
<211> LENGTH: 13
<212> TYPE: PRT
<213> ORGANISM: Unknown
<220> FEATURE:
<223> OTHER INFORMATION: Description of Unknown:
indolicidin peptide

<400> SEQUENCE: 32

Ile Leu Pro Trp Lys Trp Pro Trp Trp Pro Trp Arg Arg
1 5 10

<210> SEQ ID NO 33
<211> LENGTH: 16
<212> TYPE: PRT
<213> ORGANISM: Unknown
<220> FEATURE:
<223> OTHER INFORMATION: Description of Unknown:
RFGF peptide

<400> SEQUENCE: 33

Ala Ala Val Ala Leu Leu Pro Ala Val Leu Leu Ala Leu Leu Ala Pro
1 5 10 15

<210> SEQ ID NO 34
<211> LENGTH: 11
<212> TYPE: PRT
<213> ORGANISM: Unknown
<220> FEATURE:
<223> OTHER INFORMATION: Description of Unknown:
RFGF analogue peptide

<400> SEQUENCE: 34

Ala Ala Leu Leu Pro Val Leu Leu Ala Ala Pro
1 5 10

<210> SEQ ID NO 35
<211> LENGTH: 12
<212> TYPE: PRT
<213> ORGANISM: Unknown
<220> FEATURE:
<223> OTHER INFORMATION: Description of Unknown:
bactenecin peptide

<400> SEQUENCE: 35

Arg Lys Cys Arg Ile Val Val Ile Arg Val Cys Arg
1 5 10

<210> SEQ ID NO 36
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 36
gccagguaag uau 13

<210> SEQ ID NO 37
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 37
ccagguaagu au 12

<210> SEQ ID NO 38
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
cagguaagua u 11

<210> SEQ ID NO 39
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
cagguaagua 10

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
aacaguguuc uugcucuaua a 21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 41
caggaucauc ucaagucuua a 21

<210> SEQ ID NO 42
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 42
uuauagagca agaacacugu uuu 23

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 43
uuaagacuug agaugauccu ggc 23

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 44
auagagcaag aacacuguuu u 21

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 45
acaggaucau cucaagucuu aa 22

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46
caggaucauc ucaagucuua a 21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47
aacaguguuc uugcucuaua a 21

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 48
gatcaggauc aucucaaguc uuaa 24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 49
gatcaggauc aucucaaguc uuaa 24

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 50
aacaguguuc uugcucuaua agatcaggau caucucaagu cuuaa 45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 51
aacaguguuc uugcucuaua agatcaggau caucucaagu cuuaa 45

<210> SEQ ID NO 52
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 52
gaucaggauc aucucaaguc uuaa 24

<210> SEQ ID NO 53
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 53
gaucaggauc aucucaaguc uuaa 24

<210> SEQ ID NO 54
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 54
aacaguguuc uugcucuaua agaucaggau caucucaagu cuuaa 45

<210> SEQ ID NO 55
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
aacaguguuc uugcucuaua agaucaggau caucucaagu cuuaa 45

<210> SEQ ID NO 56
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
aacaguguuc uugcucuaua agaucaggau caucucaagu cuuaa 45

<210> SEQ ID NO 57
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
aacaguguuc uugcucuaua agaucaggau caucucaagu cuuaa 45

<210> SEQ ID NO 58
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
aacaguguuc uugcucuaua agaucaggau caucucaagu cuuaa 45

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 59
aacaguguuc uugcucuaua auatcaggau caucucaagu cuuaa 45

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 60
aacaguguuc uugcucuaua agatcaggau caucucaagu cuuaa 45

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 61
aacaguguuc uugcucuaua agagcaggau caucucaagu cuuaa 45

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 62
aacaguguuc uugcucuaua agatcaggau caucucaagu cuuaa 45

<210> SEQ ID NO 63
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
aacaguguuc uugcucuaua auagcaggau caucucaagu cuuaa 45

<210> SEQ ID NO 64
<211> LENGTH: 45

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 64
aacaguguuc uugcucuaua agaucaggau caucucaagu cuuaa 45

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 65
aacaguguuc uugcucuaua atttcaggau caucucaagu cuuaa 45

<210> SEQ ID NO 66
<211> LENGTH: 45
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 66
aacaguguuc uugcucuaua auuucaggau caucucaagu cuuaa 45

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 67
aacaguguuc uugcucuaua agatcaggau caucucaagu cuuaa 45

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 68
aacaguguuc uugcucuaua agaucaggau caucucaagu cuuaa 45

<210> SEQ ID NO 69
<211> LENGTH: 45
<212> TYPE: RNA
<213> ORGANISM: Artificial Sequence
<220> FEATURE:
<223> OTHER INFORMATION: Description of Artificial Sequence: Synthetic
oligonucleotide -continued

```
<400> SEQUENCE: 69

aacaguguuc uugcucuaua agaucaggau caucucaagu cuuaa                45


<210> SEQ ID NO 70
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70

aacaguguuc uugcucuaua auuucaggau caucucaagu cuuaa                45
```

ENDOSOMAL CLEAVABLE LINKERS

CROSS REFERENCE TO RELATED APPLICATIONS

This application is a continuation under 35 U.S.C. § 120 of copending U.S. application Ser. No. 16/474,776 filed on Jun. 28, 2019, which is a 35 U.S.C. § 371 National Phase Entry Application of International Application No. PCT/US18/14213 filed Jan. 18, 2018, which designates the U.S. and claims benefit under 35 U.S.C. § 119(e) of the U.S. Provisional Application No. 62/447,786, filed Jan. 18, 2017, the contents of all which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 30, 2018, is named 051058-088781-PCT_SL.txt and is 21.711 bytes in size.

TECHNICAL FIELD

The present disclosure relates generally to cleavable linkers and uses thereof.

BACKGROUND

There is need in the art for linkers that undergo cleavage, for example endosomal cleavage and/or are protease cleavable. This disclosure provides some answers to that need.

SUMMARY OF THE INVENTION

In one aspect provided herein are cleavable linkers, e.g., endosomal cleavable and/or protease cleavable. In some embodiments, a cleavable linker described herein can be comprised in a larger linker. In some embodiments, the cleavable linker is a carbohydrate linker that is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linker is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions). In some embodiments, the linker is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum). Exemplary compounds for producing cleavable linkers of the invention are described in Schemes 7-11 in Examples 7-11. In some embodiments, the cleavable linker is a linker shown in shown in FIGS. 1A-6.

Without limitations, the cleavable linkers described herein can be used for any molecule needing cleavage in endo-lysosomal compartments. The cleavable linkers described herein can be particularly effective in pro-drug approaches especially for hydrophobic conjugates, attaching endosomal cleavable agents, or any other agents that may need to be activated or liberated in endo-lysosomal compartments. Accordingly, the linkers described herein can be used for multiple applications, such as, but not limited to, multi-targeted molecules and prodrugs.

In one aspect, provided herein are prodrug conjugates comprising a cleavable linker described herein.

In another aspect, provided herein are conjugate comprising an endosomal agent linked to a ligand via a cleavable linker described herein.

In yet another aspect, provided herein are conjugates comprising a nucleic acid based effector molecule conjugated with a ligand via a cleavable linker described herein. Without limitations, any nucleic acid based effector molecule capable of modulating gene expression of a target can be comprised in the conjugate.

In still another aspect, provided herein are multi-targeted molecules. Generally, the multi-targeted molecules comprise at least two nucleic acid based effector molecules, wherein said at least two nucleic acid based effector molecules linked to each other by a cleavable linker described herein. Without limitations, any nucleic acid based effector molecule capable of modulating gene expression of a target can be comprised in the multi-targeted molecules disclosed herein.

By a "nucleic acid based effector molecule" is meant a modified or unmodified single-stranded or double-stranded nucleic acid molecule capable of modulating gene expression of a target gene. Exemplary nucleic acid based effector molecules capable of modulating gene expression of a target gene include, but are not limited to, double-stranded and single-stranded RNA interference agents (such as siRNA and shRNA, and also referred to as dsRNA agents herein), antisense oligonucleotides, microRNAs, anti-microRNAs or antimirs, supermirs, antagomirs, ribozymes, triplex-forming oligonucleotides, decoy oligonucleotides, RNA activators, U1 adaptors, guide RNA (gRNA) of CRISPR Cas and the like.

It is noted that said at least two effector molecules are two separate effector molecules. In other words, the at least two effector molecules do not overlap with each other. As such, the multi-targeted molecules disclosed herein differ from molecules where one effector molecule is directed to two different targets, for example, double-stranded effector molecules where each strand is directed to a different target or an effector molecule comprising a sequence, wherein at least a portion of the sequence is complementary to or can hybridize with two different target sequences.

In some embodiments, the multi-targeted molecule or an effector molecule in the multi-targeted molecule or does not modulate unspecific gene expression by two different mechanisms. For example, the multi-targeted molecule or an effector molecule in the multi-targeted molecule does not modulate gene expression via RNA interference and targeting a seed region of a microRNA.

In some embodiments, each nucleic acid based effector molecule in the multi-targeted molecule can modulate gene expression of a target nucleic acid. Without limitations, each effector molecule in the multi-targeted molecule can be directed to the same target gene, different target genes, different positions with the same target gene, or different transcripts of the same target gene. Further, it is noted that said effector molecules comprised in the multi-targeted molecules disclosed herein can comprise any of the nucleic acid modifications, motifs or structures described herein.

Moreover, the effector molecules comprised in the multi-targeted molecules described herein have comparable gene expression modulating activity compared to the gene expression modulating activity when said effector molecules are not part of a multi-targeted molecule. In other words, an effector molecule has similar gene expression modulating activity when it is part of a multi-targeted molecule disclosed herein relative to when it is not part of a multi-targeted molecule. In some embodiments, the effector molecules comprised in the multi-targeted molecule described herein can independently modulate gene expression of their respective target nucleic acids by at least 50% (e.g., 50%, 60%, 70%, 75%, 80%, 85%, 90%, 95% or more) relative to their modulation of gene expression when not part of a multi-targeted molecule. In some embodiments, one of the effector molecules in the multi-targeted molecule modulates gene expression at a higher level relative to the other effector molecule in said multi-targeted molecule. In some embodiments, said at least two effector molecules in multi-targeted molecule modulate gene expression at similar levels (e.g., within 10%, 7.5%, 5%, 2.5% or less of each other).

The inventors have found that multi-targeted molecules conjugated with a ligand are particularly effective in modulating gene expression. Accordingly, in some embodiments, at least one ligand is conjugated with the multi-targeted molecule. As such, multi-targeted molecules conjugated with at least one ligand are also referred to as "conjugated multi-targeted molecule" herein. Without limitation, the ligand can be present in any of the effector molecules in the multi-targeted molecule. Further, the ligand can be present at any position of the effector molecule and/or the multi-targeted molecule. For example, the ligand can be conjugated at the 5'-end, 3'-end an internal position of an effector molecule, or combinations thereof in the multi-targeted molecule. In some embodiments, at least two ligands are conjugated with the multi-targeted molecule. The said at least two ligands can be the same, different or any combinations of same and different. The two ligands can be conjugated at independently at any position in the multi-targeted molecule. In some embodiments, at least two effector molecules in the multi-targeted molecule have at least one ligand attached thereto. Without wishing to be bound by a theory, a ligand can improve delivery or pharmacokinetic profile of the conjugated multi-targeted molecule.

In some embodiments, the cleavable linkers described herein can be used in the multi-targeted single entity conjugates described in PCT application no. PCT/US2016/042498, filed Jul. 15, 2016, the content of which is incorporated herein by reference in its entirety.

BRIEF DESCRIPTION OF THE DRAWINGS

FIGS. 1A-6 show structures of exemplary cleavable linkers. FIGS. 1A-1B show various carbohydrate and non-carbohydrate linkers used in bis(siRNA) designs described in Example 28, Table 1. FIGS. 2A-5M show exemplary monosaccharides (FIGS. 2A-2I and 3A-3F) or di or tri saccharides (FIGS. 4A-4B and 5A-5M) of various modified carbohydrates, such as Galactose. Galactosamine, Glucose, Glucosamine, Mannose, and Mannosamine derivatives. FIG. 6 shows exemplary protease cleavable linkers. In FIGS. 2A-5M, n is 1-12 and m is 1-12.

DETAILED DESCRIPTION OF THE INVENTION

Figure 1A:
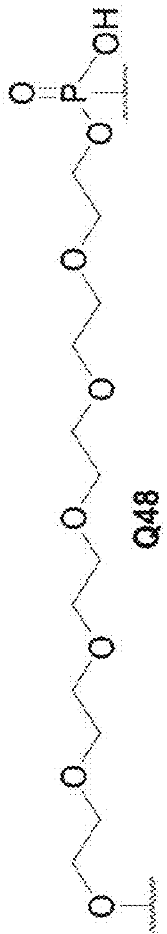
Figure 1A:
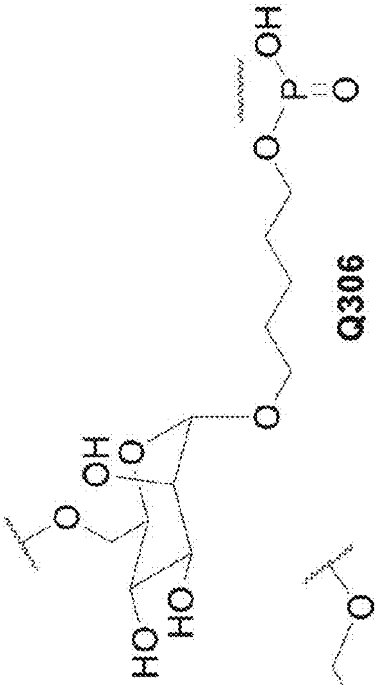
Figure 1A:
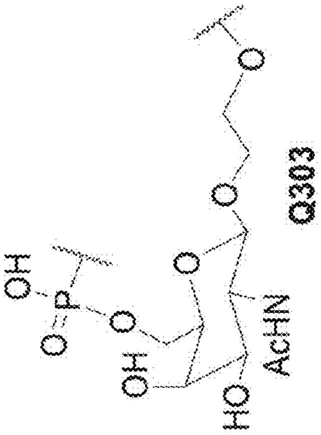
Figure 1A:
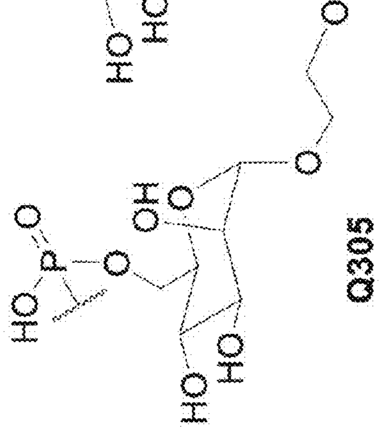
Figure 1A:
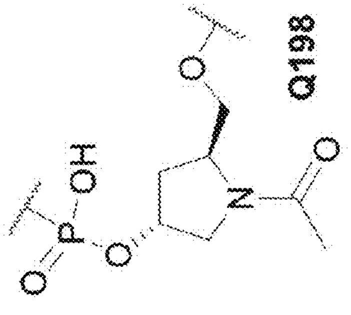
Figure 1A:
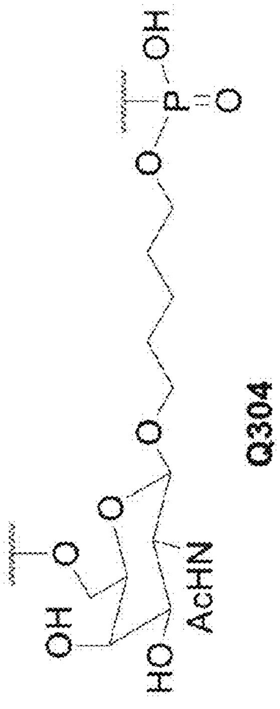

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Effector Molecules

The skilled person is well aware that double-stranded oligonucleotides comprising a duplex structure of between 20 and 23, but specifically 21, base pairs have been hailed as particularly effective in inducing RNA interference (Elbashir et al., EMBO 2001, 20:6877-6888). However, others have found that shorter or longer double-stranded oligonucleotides can be effective as well.

As used herein, the term "siRNA" refers to an agent that mediates the targeted cleavage of an RNA transcript. These agents associate with a cytoplasmic multi-protein complex known as RNAi-induced silencing complex (RISC). Agents that are effective in inducing RNA interference are also referred to as siRNA, RNAi agent, or iRNA agent, herein. As used herein, the term siRNA includes microRNAs and pre-microRNAs. As used herein, the terms "siRNA activity" and "RNAi activity" refer to gene silencing by an siRNA.

The double-stranded oligonucleotides comprise two oligonucleotide strands that are sufficiently complementary to hybridize to form a duplex structure. Generally, the duplex structure is between 15 and 35, more generally between 18 and 25, yet more generally between 19 and 24, and most generally between 19 and 21 base pairs in length. In some embodiments, longer double-stranded oligonucleotides of between 25 and 30 base pairs in length are preferred. In some embodiments, shorter double-stranded oligonucleotides of between 10 and 15 base pairs in length are preferred. In another embodiment, the double-stranded oligonucleotide is at least 21 nucleotides long.

In some embodiments, the double-stranded oligonucleotide comprises a sense strand and an antisense strand, wherein the antisense RNA strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 21 nucleotides in length.

The phrase "antisense strand" as used herein, refers to an oligomeric compound that is substantially or 100% complementary to a target sequence of interest. The phrase "antisense strand" includes the antisense region of both oligomeric compounds that are formed from two separate strands, as well as unimolecular oligomeric compounds that are capable of forming hairpin or dumbbell type structures. The terms "antisense strand" and "guide strand" are used interchangeably herein.

The phrase "sense strand" refers to an oligomeric compound that has the same nucleoside sequence, in whole or in part, as a target sequence such as a messenger RNA or a sequence of DNA. The terms "sense strand" and "passenger strand" are used interchangeably herein.

In some embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40 or more nucleotide pairs in length.

In some embodiments, the antisense strand of a double-stranded oligonucleotide is equal to or at least 14, 15, 16, 17, 18, 19, 20, 21, 22, 23, 23, 24, 25, 26, 27, 28, 29, 30, 31, 32, 33, 34, 35, 36, 37, 38, 39, or 40 or more nucleotides in length.

In some embodiments, the sense strand of a double-stranded oligonucleotide is equal to or at least 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40 or more nucleotides in length.

In some embodiments, one strand has at least one stretch of 1-10 single-stranded nucleotides in the double-stranded region. By "stretch of single-stranded nucleotides in the double-stranded region" is meant that there is present at least one nucleotide in the double-stranded region that is not basepaired with another nucleotide. When the stretch of single-stranded nucleotides is present internally in the double-stranded region, at least one nucleotide base pair can be present at both ends of the single-stranded stretch. When present at the end of a double-stranded region, the stretch of single-stranded nucleotides can be a singe-stranded overhang. The stretch of single-stranded nucleotides in the double-stranded region can be in the form of a bulge or one- or more mismatched nucleotides. In some embodiments, both strands have at least one stretch of 1-5 (e.g., 1, 2, 3, 4, or 5) single-stranded nucleotides in the double stranded region. When both strands have a stretch of 1-5 (e.g., 1, 2, 3, 4, or 5) single-stranded nucleotides in the double stranded region, such single-stranded nucleotides can be opposite to each other (e.g., a stretch of mismatches) or they can be located such that the second strand has no non-basepaired nucleotides opposite to the single-stranded oligonucleotides of the first strand and vice versa (e.g., a single-stranded loop). In some embodiments, the single-stranded nucleotides are present within 8 nucleotides from either end, for example 8, 7, 6, 5, 4, 3, or 2 nucleotide from either the 5' or 3' end of the region of complementarity between the two strands.

Hairpin and dumbbell type oligonucleotides will have a duplex region equal to or at least 14, 15, 15, 16, 17, 18, 19, 29, 21, 22, 23, 24, or 25 nucleotide pairs. The duplex region can be equal to or less than 200, 100, or 50, in length. In some embodiments, ranges for the duplex region are 15-30, 17 to 23, 19 to 23, and 19 to 21 nucleotides pairs in length.

In some embodiments, the nucleic acid based effector molecule is a hairpin oligonucleotides that can have a single strand overhang or terminal unpaired region, in some embodiments at the 3', and in some embodiments on the antisense side of the hairpin. In some embodiments, the overhangs are 1-4, more generally 2-3 nucleotides in length. The hairpin oligonucleotides that can induce RNA interference are also referred to as "shRNA" herein.

In certain embodiments, two oligonucleotide strands specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA and an RNA:RNA duplex.

In some embodiments, the effector molecule is a double-stranded RNA (dsRNA) agent, i.e., siRNA, for inhibiting the expression of a target gene. It is understood that dsRNA, siRNA, oligonucleotides can be used interchangeably unless otherwise stated. The dsRNA agent comprises a sense strand and an antisense strand, each strand having 14 to 40 nucleotides. The dsRNA agent is represented by formula (I):

(I)

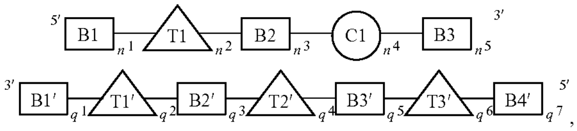

In formula (I), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In some embodiments, B1, B2, B3, B1', B2', B3', and B4' each contain 2'-OMe modifications.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In some embodiments, C1 has thermally destabilizing modification selected from the group consisting of: i) mismatch with the opposing nucleotide in the antisense strand; ii) abasic modification selected from the group consisting of:

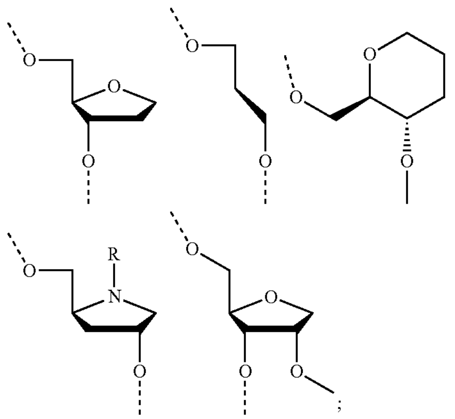

and iii) sugar modification selected from the group consisting of:

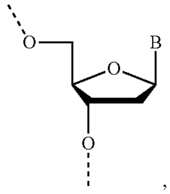

2'-deoxy ,

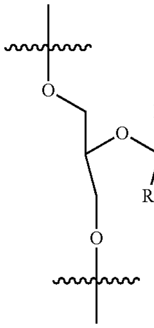

,

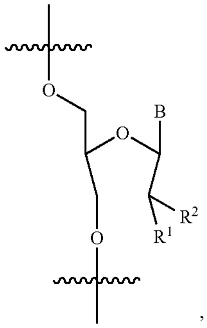

,

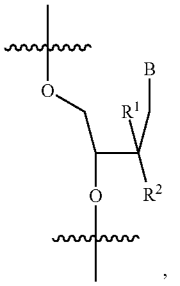

,

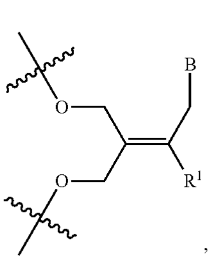

, and

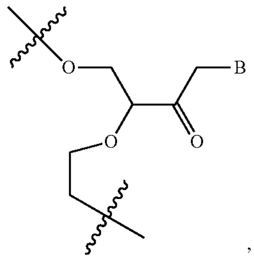

, wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In some embodiments, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

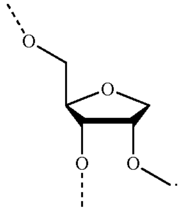

T1, T1', T2', and T3' each independently represent a nucleotide comprising a modification providing the nucleotide a steric bulk that is less or equal to the steric bulk of a 2'-OMe modification. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In some embodiments, T1 is DNA. In some embodiments, T1' is DNA, RNA or LNA. In some embodiments, T2' is DNA or RNA. In some embodiments, T3' is DNA or RNA.

$n^1$, $n^3$, and $q^1$ are independently 4 to 15 nucleotides in length.

$n^5$, $q^3$, and $q^7$ are independently 1-6 nucleotide(s) in length.

$n^4$, $q^2$, and $q^6$ are independently 1-3 nucleotide(s) in length.

$q^5$ is independently 0-10 nucleotide(s) in length.

$n^2$ and $q^4$ are independently 0-3 nucleotide(s) in length.

Alternatively, $n^4$ is 0-3 nucleotide(s) in length.

In some embodiments, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, $n^4$, $q^2$, and $q^6$ are each 1.

In some embodiments, $n^2$, $n^4$, $q^2$, $q^4$, and $q^6$ are each 1.

In some embodiments, C1 is at position 14-17 of the 5'-end of the sense strand, when the sense strand is 19-22 nucleotides in length, and $n^4$ is 1.

In some embodiments, T3' starts at position 2 from the 5' end of the antisense strand. In one example, T3' is at position 2 from the 5' end of the antisense strand and $q^6$ is equal to 1.

In some embodiments, T1' starts at position 14 from the 5' end of the antisense strand. In one example, T1' is at position 14 from the 5' end of the antisense strand and $q^2$ is equal to 1.

In some embodiments, T1' and T3' are separated by 11 nucleotides in length (i.e. not counting the T1' and T3' nucleotides.

In some embodiments, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In some embodiments, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In some embodiments, T1 is at cleavage site of the sense strand. In one example, T1 is at position 11 from the 5' end of the sense strand, when the sense strand is 19-22 nucleotides in length, and $n^2$ is 1.

In some embodiments, T2' starts at position 6 from the 5' end of the antisense strand. In one example, T2' is at positions 6-10 from the 5' end of the antisense strand, and $q^4$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2-F, $q^2$ is 1, B2' is 2'-OMe or 2'-F, $q^3$ is 4, $q^4$ is 0, BY is 2'-OMe or 2'-F, $q^5$ is 7, T3' is 2'-F, $q^6$ is 1, B4' is 2'-OMe, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'—OMe or 2'-F, $q^3$ is 4, $q^4$ is 0, B3' is 2'-OMe or 2'-F, $q^5$ is 7, T3' is 2'-F, $q^6$ is 1, B4' is 2'- OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1.

In some embodiments, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In some embodiments, 100%, 95%, 90%, 85%, 80%, 75%, 70%, 65%, 60%, 55%, 50%, 45%, 40%, 35% or 30% of the dsRNA agent of the invention is modified.

in some embodiments, each of the sense and antisense strands of the dsRNA agent is independently modified with acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), or 2'-ara-F.

In some embodiments, each of the sense and antisense strands of the dsRNA agent contains at least two different modifications.

In some embodiments, the dsRNA agent of Formula (I) further comprises 3' and/or 5' overhang(s) of 1-10 nucleotides in length. In one example, dsRNA agent of formula (I) comprises a 3' overhang at the 3'-end of the antisense strand and a blunt end at the 5'-end of the antisense strand. In another example, the dsRNA agent has a 5' overhang at the 5'-end of the sense strand.

In some embodiments, the dsRNA agent of the invention does not contain any 2'-F modification.

In some embodiments, the dsRNA agent of the invention contains one, two, three, four, five, six, seven, eight, nine, ten, eleven or twelve 2'-F modification(s). In one example, the effector molecule of the invention contains nine or ten 2'-F modifications.

In some embodiments, the sense strand and/or antisense strand of the dsRNA agent comprises one or more blocks of phosphorothioate or methylphosphonate internucleotide linkages. In one example, the sense strand comprises one block of two phosphorothioate or methylphosphonate internucleotide linkages. In one example, the antisense strand comprises two blocks of two phosphorothioate or methylphosphonate internucleotide linkages. For example, the two blocks of phosphorothioate or methylphosphonate internucleotide linkages are separated by 16-18 phosphate internucleotide linkages.

In some embodiments, each of the sense and antisense strands of the dsRNA agent has 15-30 nucleotides. In one example, the sense strand has 19-22 nucleotides, and the antisense strand has 19-25 nucleotides. In another example, the sense strand has 21 nucleotides, and the antisense strand has 23 nucleotides.

In some embodiments, the nucleotide at position 1 of the 5'-end of the antisense strand in the duplex is selected from the group consisting of A, dA, dU, U, and dT. In some embodiments, at least one of the first, second, and third base pair from the 5'-end of the antisense strand is an AU base pair.

In some embodiments, the antisense strand of the dsRNA agent of the invention is 100% complementary to a target RNA to hybridize thereto and inhibits its expression through RNA interference. In another embodiment, the antisense strand of the dsRNA agent of the invention is at least 95%, at least 90%, at least 85%, at least 80%, at least 75%, at least 70%, at least 65%, at least 60%, at least 55%, or at least 50% complementary to a target RNA.

In one aspect, the invention relates to a dsRNA agent capable of inhibiting the expression of a target gene. The dsRNA agent comprises a sense strand and an antisense strand, each strand having 14 to 40 nucleotides. The sense strand contains at least one thermally destabilizing nucleotide, wherein at at least one said thermally destabilizing nucleotide occurs at or near the site that is opposite to the seed region of the antisense strand (i.e. at position 2-8 of the 5-end of the antisense strand), For example, the thermally destabilizing nucleotide occurs between positions 14-17 of the 5'-end of the sense strand when the sense strand is 21 nucleotides in length. The antisense strand contains at least two modified nucleic acids that are smaller than a sterically demanding 2'-OMe modification. Preferably, the two modified nucleic acids that is smaller than a sterically demanding 2'-OMe are separated by 11 nucleotides in length. For example, the two modified nucleic acids are at positions 2 and 14 of the 5'end of the antisense strand.

In a particular embodiment, the dsRNA agents of the present invention comprise:

(a) a sense strand having:
 (i) a length of 21 nucleotides;
 (ii) an ASGPR ligand attached to the 3'-end, wherein said ASGPR ligand comprises three GalNAc derivatives attached through a trivalent branched linker; and
 (iii) 2'-F modifications at positions 1, 3, 5, 7, 9 to 11, 13, 17, 19, and 21, and 2'-OMe modifications at positions 2, 4, 6, 8, 12, 14 to 16, 18, and 20 (counting from the 5' end);
 and
(b) an antisense strand having:
 (i) a length of 23 nucleotides;
 (ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
 (iii) phosphorothioate internucleotide linkages between nucleotide positions 21 and 22, and between nucleotide positions 22 and 23 (counting from the 5' end);
 wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
 (i) a length of 21 nucleotides;
 (ii) an ASGPR ligand attached to the 3'-end, wherein said ASGPR ligand comprises three GalNAc derivatives attached through a trivalent branched linker;
 (iii) 2'-F modifications at positions 1, 3, 5, 7, 9 to 11, 13, 15, 17, 19, and 21, and 2'-OMe modifications at positions 2, 4, 6, 8, 12, 14, 16, 18, and 20 (counting from the 5' end); and
 (iv) phosphorothioate internucleotide linkages between nucleotide positions 1 and 2, and between nucleotide positions 2 and 3 (counting from the 5' end);
 and
(b) an antisense strand having:
 (i) a length of 23 nucleotides;
 (ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and
 (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
 (i) a length of 21 nucleotides;
 (ii) an ASGPR ligand attached to the 3'-end, wherein said ASGPR ligand comprises three GalNAc derivatives attached through a trivalent branched linker;
 (iii) 2'-OMe modifications at positions 1 to 6, 8, 10, and 12 to 21, 2'-F modifications at positions 7, and 9, and a desoxy-nucleotide (e.g. dT) at position 11 (counting from the 5' end); and
 (iv) phosphorothioate internucleotide linkages between nucleotide positions 1 and 2, and between nucleotide positions 2 and 3 (counting from the 5' end);
 and
(b) an antisense strand having:
 (i) a length of 23 nucleotides;
 (ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end); and
 (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
 (i) a length of 21 nucleotides;
 (ii) an ASGPR ligand attached to the 3'-end, wherein said ASGPR ligand comprises three GalNAc derivatives attached through a trivalent branched linker;
 (iii) 2'-OMe modifications at positions 1 to 6, 8, 10, 12, 14, and 16 to 21, and 2'-F modifications at positions 7, 9, 11, 13, and 15; and
 (iv) phosphorothioate internucleotide linkages between nucleotide positions 1 and 2, and between nucleotide positions 2 and 3 (counting from the 5' end);
 and
(b) an antisense strand having:
 (i) a length of 23 nucleotides;
 (ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-OMe modifications at positions 1 to 9, and 12 to 21, and 2'-F modifications at positions 10, and 11; and
   (iv) phosphorothioate internucleotide linkages between nucleotide positions 1 and 2, and between nucleotide positions 2 and 3 (counting from the 5' end);
   and
(b) an antisense strand having:
   (i) a length of 23 nucleotides;
   (ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
   (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-F modifications at positions 1, 3, 5, 7, 9 to 11, and 13, and 2'-OMe modifications at positions 2, 4, 6, 8, 12, and 14 to 21; and
   (iv) phosphorothioate internucleotide linkages between nucleotide positions 1 and 2, and between nucleotide positions 2 and 3 (counting from the 5' end);
   and
(b) an antisense strand having:
   (i) a length of 23 nucleotides;
   (ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and
   (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and
   (iv) phosphorothioate internucleotide linkages between nucleotide positions 1 and 2, and between nucleotide positions 2 and 3 (counting from the 5' end);
   and
(b) an antisense strand having:
   (i) a length of 25 nucleotides;
   (ii) 2'-OMe modifications at positions 1, 4, 6, 7, 9, 11 to 13, 15, 17, and 19 to 23, 2'-F modifications at positions 2, 3, 5, 8, 10, 14, 16, and 18, and desoxy-nucleotides (e.g. dT) at positions 24 and 25 (counting from the 5' end); and
   (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a four nucleotide overhang at the 3'-end of the antisense strand, and a blunt end at the 5'-end of the antisense strand.

In another particular embodiment, the dsRNA agents of the present invention comprise:

(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-OMe modifications at positions 1 to 6, 8, and 12 to 21, and 2'-F modifications at positions 7, and 9 to 11; and
   (iv) phosphorothioate internucleotide linkages between nucleotide positions 1 and 2, and between nucleotide positions 2 and 3 (counting from the 5' end);
   and
(b) an antisense strand having:
   (i) a length of 23 nucleotides;
   (ii) 2'-OMe modifications at positions 1, 3 to 5, 7, 8, 10 to 13, 15, and 17 to 23, and 2'-F modifications at positions 2, 6, 9, 14, and 16 (counting from the 5' end); and
   (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-OMe modifications at positions 1 to 6, 8, and 12 to 21, and 2'-F modifications at positions 7, and 9 to 11; and (iv) phosphorothioate internucleotide linkages between nucleotide positions 1 and 2, and between nucleotide positions 2 and 3 (counting from the 5' end);

and (b) an antisense strand having:

(i) a length of 23 nucleotides;

(ii) 2'-OMe modifications at positions 1, 3 to 5, 7, 10 to 13, 15, and 17 to 23, and 2'-F modifications at positions 2, 6, 8, 9, 14, and 16 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:

(i) a length of 19 nucleotides;

(ii) an ASGPR ligand attached to the 3'-end, wherein said ASGPR ligand comprises three GalNAc derivatives attached through a trivalent branched linker;

(iii) 2'-OMe modifications at positions 1 to 4, 6, and 10 to 19, and 2'-F modifications at positions 5, and 7 to 9; and (iv) phosphorothioate internucleotide linkages between nucleotide positions 1 and 2, and between nucleotide positions 2 and 3 (counting from the 5' end);

and (b) an antisense strand having:

(i) a length of 21 nucleotides;

(ii) 2'-OMe modifications at positions 1, 3 to 5, 7, 10 to 13, 15, and 17 to 21, and 2'-F modifications at positions 2, 6, 8, 9, 14, and 16 (counting from the 5' end); and (iii) phosphorothioate internucleotide linkages between nucleotide positions 1 and 2, between nucleotide positions 2 and 3, between nucleotide positions 19 and 20, and between nucleotide positions 20 and 21 (counting from the 5' end);

wherein the dsRNA agents have a two nucleotide overhang at the 3'-end of the antisense strand, and a blunt end at the 5'-end of the antisense strand.

In one embodiment, the dsRNA agents described herein further comprise a thermally destabilizing modification at position 7 counting from the 5'-end of the antisense from, at position 15 counting from the 5'-end of sense strand, position 21 counting from the 5'-end of the sense strand, or combinations thereof.

In one aspect, the invention relates to a dsRNA agent capable of inhibiting the expression of a target gene. The dsRNA agent comprises a sense strand and an antisense strand, each strand having 14 to 40 nucleotides. The sense strand contains at least one thermally destabilizing nucleotide, wherein at least one said thermally destabilizing nucleotide occurs at or near the site that is opposite to the seed region of the antisense strand (i.e. at position 2-8 of the 5'-end of the antisense strand). For example, the thermally destabilizing nucleotide occurs between positions 14-17 of the 5'-end of the sense strand when the sense strand is 21 nucleotides in length. The antisense strand comprises two modified nucleic acids that are smaller than a sterically demanding 2'-OMe modification separated by 11 nucleotides in length. For example, the two modified nucleic acids are at positions 2 and 14 of the 5'end of the antisense strand.

In one embodiment, the sense strand of the dsRNA agent further comprises an endonuclease susceptible modified nucleotide at the cleavage site of the sense strand. In one example, the endonuclease susceptible modified nucleotide is at position 11 from the 5' end of the sense strand.

In some embodiments, the effector molecule is a microRNA. MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

In some embodiments, the effector molecule is a ribozyme. Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

In some embodiments, the effector is an aptamer. Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9(1999), and Hermann and Patel, Science 287:820-5 (2000). Aptamers can be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target.

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Accordingly, in some embodiments, the effector molecule is a decoy oligonucleotide.

Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to up-regulate genes that are suppressed by the binding of a transcription factor. Examples of the utilization of decoy oligonucleotides can be found in Mann et al., J. Clin. Invest., 2000, 106: 1071-1075, which is expressly incorporated by reference herein, in its entirety.

In some embodiments, the effector molecule is a miRNA mimic. MicroRNA mimics (miRNA mimics) represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs). In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded oligonucleotides.

In some embodiments, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

In some embodiments, the effector molecule is a supermir. A supermir refers to an oligonucleotide, e.g., single stranded, double stranded or partially double stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. A supermir featured in the invention can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

In some embodiments, the effector molecule is an antimir. The terms "antimir" "microRNA inhibitor" or "miR inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands. Furthermore, microRNA inhibitors can be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

In some embodiments, the effector molecule is an antagomir. Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate intersugar linkage and, for example, a cholesterol-moiety at 3'-end. In a preferred embodiment, antagomir comprises a 2'-O-methyl modification at all nucleotides, a cholesterol moiety at 3'-end, two phsophorothioate intersugar linkages at the first two positions at the 5'-end and four phosphorothioate linkages at the 3'-end of the molecule. Antagomirs can be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety.

In some embodiments, the effector molecule is a U1 adaptor. U1 adaptors inhibit polyA sites and are bifunctional oligonucleotides with a target domain complementary to a site in the target gene's terminal exon and a 'U1 domain' that binds to the U1 smaller nuclear RNA component of the U1 snRNP. See for example, Int. Pat. App. Pub. No. WO2008/121963 and Goraczniak, et al., 2008, Nature Biotechnology, 27(3), 257-263, each of which is expressly incorporated by reference herein, in its entirety. U1 snRNP is a ribonucleoprotein complex that functions primarily to direct early steps in spliceosome formation by binding to the pre-mRNA exon-intron boundary, Brown and Simpson, 1998, Annu Rev Plant Physiol Plant Mol Biol 49:77-95.

In some embodiments, the U1 adaptor comprises at least one annealing domain (targeting domain) linked to at least one effector domain (U1 domain), wherein the annealing domain hybridizes to a target gene sequence and the effector domain hybridizes to the U1 snRNA of U1 snRNP. In some embodiments, the U1 adaptor comprises one annealing domain. In some embodiments, the U1 adaptor comprises one effector domain.

Without wishing to be bound by theory, the annealing domain will typically be from about 10 to about 50 nucleotides in length, more typically from about 10 to about 30 nucleotides or about 10 to about 20 nucleotides. In some preferred embodiments, the annealing domain is 10, 11, 12, 13, 14, 15, 16, 17, 18, 19, 20, or 21 nucleotides in length. The annealing domain may be at least 75%, at least 80%, at least 85%, at least 90%, at least 95%, at least 97%, or, more preferably, 100% complementary to the target gene. In some embodiments, the annealing domain hybridizes with a target site within the 3' terminal exon of a pre-mRNA, which includes the terminal coding region and the 3'UTR and polyadenylation signal sequences (e.g., through the polyadenylation site). In another embodiment, the target sequence is within about 500 basepair, about 250 basepair, about 100 basepair, or about 50 basepair of the poly (A) signal sequence of the pre-mRNA. In some embodiments, the annealing domain comprises 1, 2, 3, or 4, mismatches with the target gene sequence.

The effector domain may be from about 8 nucleotides to about 30 nucleotides, from about 10 nucleotides to about 20 nucleotides, or from about 10 to about 15 nucleotides in length. The U1 domain can hybridize with U1 snRNA, particularly the 5'-end and more specifically nucleotides 2-11. In another embodiment, the U1 domain is perfectly complementary to nucleotides 2-11 of endogenous U1 snRNA. In some embodiments, the U1 domain comprises a nucleotide sequence selected from the group consisting of 5'-GCCAGGUAAGUAU-3' (SEQ ID NO: 36), 5'-CCAGGUAAGUAU-3' (SEQ ID NO: 37), 5'-CAGGUAAGUAU-3' (SEQ ID NO: 38), 5'-CAGGUAAGU-3',5'-CAGGUAAG-3' and 5'-CAGGUAA-3'. In some embodiments, the U1 domain comprises a nucleotide sequence 5'-CAGGUAAGUA-3' (SEQ ID NO: 39). Without wishing to be bound by theory, increasing the length of the U1 domain to include basepairing into stem 1 and/or basepairing to position 1 of U1 snRNA improves the U1 adaptor's affinity to U1 snRNP.

The annealing and effector domains of the U1 adaptor can be linked such that the effector domain is at the 5' end and/or 3' end of the annealing domain. The two domains can be linked by such that the 3' end of one domain is linked to 5' end of the other domain, or 3' end of one domain is linked to 3' end of the other domain, or 5' end of one domain is linked to 5' end of the other domain. The annealing and effector domains can be linked directly to each other or by a nucleotide based or non-nucleotide based linker. When the linker is nucleotide based, the linker can comprise 1, 2, 3, 4, 5, 6, 7, 8, 9, 10, up to 15, up to 20, or up to 25 nucleotides.

In some embodiments, the linker between the annealing domain and the effector domain is a cleavable linker described herein. In some embodiments, the linker between the annealing domain and the effector domain is multivalent, e.g., trivalent, tetravalent or pentavalent. Without wishing to be bound by theory, a multivalent linker can be used to link together a single annealing domain with a plurality of adaptor domains.

It is to be understood that the U1 adaptor can comprise any oligonucleotide modification described herein. Exemplary modifications for U1 adaptors include those that increase annealing affinity, specificity, bioavailability in the cell and organism, cellular and/or nuclear transport, stability, and/or resistance to degradation.

Recent studies have found that dsRNA can also activate gene expression, a mechanism that has been termed "small RNA-induced gene activation" or RNAa (activating RNA). See for example Li, L. C. et al. *Proc Natl Acad Sci USA*. (2006), 103(46):17337-42 and Li L. C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa has also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites. In some embodiments, the RNA activator can increase the expression of a gene. In some embodiments, increased gene expression inhibits viability, growth development, and/or reproduction.

Accordingly, in some embodiments, the effector molecule is activating RNA.

In some embodiments, the effector molecule is a triplex forming oligonucleotide (TFO). Recent studies have shown that triplex forming oligonucleotides can be designed which can recognize and bind to polypurine/polypyrimidine regions in double-stranded helical DNA in a sequence-specific manner. These recognition rules are outline by Maher III, L. J., et al., *Science* (1989) vol. 245, pp 725-730; Moser, H. E., et al., *Science* (1987) vol. 238, pp 645-630; Beal, P. A., et al., *Science* (1992) vol. 251, pp 1360-1363; Conney, M., et al., *Science* (1988) vol. 241, pp 456-459 and Hogan, M. E., et al., EP Publication 375408. Modification of the oligonucleotides, such as the introduction of intercalators and intersugar linkage substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 1 12:487-94). In general, the triplex-forming oligonucleotide has the sequence correspondence:

```
oligo
3'-A G G T

duplex
5'-A G C T

duplex
3'-T C G A
```

However, it has been shown that the A-AT and G-GC triplets have the greatest triple helical stability (Reither and Jeltsch, BMC Biochem, 2002 Sep. 12, Epub). The same authors have demonstrated that TFOs designed according to the A-AT and G-GC rule do not form non-specific triplexes, indicating that the triplex formation is indeed sequence specific.

Thus for any given sequence a triplex forming sequence can be devised. Triplex-forming oligonucleotides preferably are at least 15, more preferably 25, still more preferably 30 or more nucleotides in length, up to 50 or 100 nucleotides.

Formation of the triple helical structure with the target DNA induces steric and functional changes, blocking transcription initiation and elongation, allowing the introduction of desired sequence changes in the endogenous DNA and resulting in the specific down-regulation of gene expression. Examples of such suppression of gene expression in cells treated with TFOs include knockout of episomal supFGl and endogenous HPRT genes in mammalian cells (Vasquez et al., Nucl Acids Res. 1999; 27: 1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-I gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both down-regulation and up-regulation of expression of endogenous genes (Seidman and Glazer, J Clin Invest 2003; 112:487-94). Detailed description of the design, synthesis and administration of effective TFOs can be found in U.S. Pat. App. Nos. 2003 017068 and 2003 0096980 to Froehler et al, and 2002 0128218 and 2002 0123476 to Emanuele et al, and U.S. Pat. No. 5,721,138 to Lawn, contents of which are herein incorporated in their entireties.

Multi-Targeted Molecules

In one aspect, provided herein are multi-targeted molecules. Generally, the multi-targeted molecules comprise at least two nucleic acid based effector molecules, wherein said at least two nucleic acid based effector molecules are covalently or non-covalently linked to each other. Without limitations, any nucleic acid based effector molecule capable of modulating gene expression of a target can be comprised in the multi-targeted molecules disclosed herein.

In some embodiments, at least one effector molecule in the multi-targeted molecule is an siRNA. In some embodiments, the multi-targeted molecule comprises at least two siRNAs. Without limitations, the two siRNAs can be same or different. For example, the two siRNA can be directed to the same target or different targets. Additionally, the two siRNA can be directed to the different region on the same target.

In some embodiments, the multi-targeted molecule is assembled from two separate siRNA molecules, wherein at least one of the siRNAs has at least one ligand attached thereto. In some other embodiments, the multi-targeted molecule is assembled from two separate siRNA molecules, wherein each siRNA has at least one ligand attached thereto.

In various embodiments of the multi-targeted molecule, where at least two siRNAs, each having at least one ligand, are linked to each other, said at least two ligands can be the same or they can be different. Further, the said at least ligands can be conjugated independently at any position of the respective siRNAs. For example, one ligand can be attached to the sense strand of the first siRNA and the other can be attached to the sense strand of the second siRNA, or one ligand can be attached to the sense strand of the first siRNA and the other can be attached to the antisense strand of the second siRNA, or one ligand can be attached to the antisense strand of the first siRNA and the other can be attached to the antisense strand of the second siRNA. Without limitations, the first ligand can be attached independently at the 5'-end, 3'-end or at an internal position of one strand (sense or antisense) of the first siRNA. Similarly, the second ligand can be attached independently at the 5'-end, 3'-end or at an internal position of one strand (sense or antisense) of the second siRNA.

In some embodiments, one ligand is conjugated to 3'-end of a sense strand of the first siRNA and the other ligand is conjugated to the 3'-end of an antisense strand of the second siRNA. In some embodiments, one ligand is conjugated to 5'-end of a sense strand of the first siRNA and the other ligand is conjugated to the 3'-end of an antisense strand of the second siRNA. In some embodiments, one ligand is conjugated to 3'-end of a sense strand of the first siRNA and the other ligand is conjugated to the 5'-end of an antisense strand of the second siRNA. In some embodiments, one ligand is conjugated to 5'-end of a sense strand of the first siRNA and the other ligand is conjugated to the 5'-end of an antisense strand of the second siRNA. In some embodiments, one ligand is conjugated to 3'-end of a sense strand first siRNA and the other ligand is conjugated at an internal position of an antisense strand of the second siRNA. In some embodiments, one ligand is conjugated to 5'-end of a sense strand of the first siRNA and the other ligand is conjugated at an internal position of an antisense strand of the second siRNA. In some embodiments, one ligand is conjugated to 3'-end of an antisense strand of the first siRNA and the other ligand is conjugated at an internal position of a sense strand of the second siRNA. In some embodiments, one ligand is conjugated to 5'-end of an antisense strand of the first siRNA and the other ligand is conjugated at an internal position of a sense strand of the second siRNA. In some embodiments, one ligand is conjugated at an internal position of an antisense strand of the first siRNA and the other ligand is conjugated at an internal position of a sense strand of the second siRNA.

In some embodiments, one ligand is conjugated to 3'-end of a first sense strand and the other ligand is conjugated to the 3'-end of a second sense strand. In some embodiments, one ligand is conjugated to 3'-end of a first sense strand and the other ligand is conjugated to the 5'-end of a second sense strand. In some embodiments, one ligand is conjugated to 5'-end of a first sense strand and the other ligand is conjugated to the 3'-end of a second sense strand. In some embodiments, one ligand is conjugated to 5'-end of a first sense strand and the other ligand is conjugated to the 5'-end of a second sense strand. In some embodiments, one ligand is conjugated to 3'-end of a first sense strand and the other ligand is conjugated at an internal position of a second sense strand. In some embodiments, one ligand is conjugated to 5'-end of a first sense strand and the other ligand is conjugated to an internal position of a second sense strand. In some embodiments, one ligand is conjugated at an internal position of a first sense strand and the other ligand is conjugated at an internal position of a second sense strand. In some embodiments, one ligand is conjugated to 3'-end of a first antisense strand and the other ligand is conjugated to the 3'-end of a second antisense strand. In some embodiments, one ligand is conjugated to 3'-end of a first antisense strand and the other ligand is conjugated to the 5'-end of a second antisense strand. In some embodiments, one ligand is conjugated to 5-end of a first antisense strand and the other ligand is conjugated to the 3'-end of a second antisense strand. In some embodiments, one ligand is conjugated to 5'-end of a first antisense strand and the other ligand is conjugated to the 5'-end of a second antisense strand. In some embodiments, one ligand is conjugated to 3'-end of a first antisense strand and the other ligand is conjugated at an internal position of a second antisense strand. In some embodiments, one ligand is conjugated to 5'-end of a first antisense strand and the other ligand is conjugated to an internal position of a second antisense strand. In some embodiments, one ligand is conjugated at an internal position of a first antisense strand and the other ligand is conjugated at an internal position of a second antisense strand.

In some embodiments, the multi-targeted molecule is assembled from two siRNAs wherein sense strand of the first siRNA is covalently linked to the sense strand of the second siRNA. Without limitations, the two sense strands can be linked to each other in any orientation. For example, 3'-end of the first sense strand can be linked to 5'-end of the second sense strand; 3'-end of the first sense strand can be linked to 3'-end of the second sense strand; or 5'-end of the first sense strand can be linked to 5'-end of the second sense strand.

In some embodiments, the multi-targeted molecule is assembled from two siRNAs wherein antisense strand of the first siRNA is covalently linked to the antisense strand of the second siRNA. Without limitations, the two antisense strands can be linked to each other in any orientation. For example, 3'-end of the first antisense strand can be linked to 5'-end of the second antisense strand; 3'-end of the first antisense strand can be linked to 3'-end of the second antisense strand; or 5'-end of the first antisense strand can be linked to 5'-end of the second antisense strand.

In some embodiments, the multi-targeted molecule is assembled from two siRNAs wherein sense strand of the first siRNA is covalently linked to the antisense strand of the second siRNA. Without limitations, the sense strand of the first siRNA can be linked to the antisense strand of the second siRNA in any orientation. For example, 3-end of the sense strand can be linked to 5'-end of the antisense strand; 3'-end of the sense strand can be linked to 3'-end of the antisense strand; or 5'-end of the sense strand can be linked to 5'-end of the antisense strand.

In some embodiments, the multi-targeted molecule is assembled from two siRNAs wherein sense strand of the first siRNA is covalently linked to the sense strand of the second siRNA and antisense strand of the first siRNA is covalently linked to the antisense strand of the second siRNA. In some embodiments, the multi-targeted molecule is assembled from two siRNAs wherein antisense strand of the first siRNA is covalently linked to the sense strand of the second siRNA and sense strand of the first siRNA is covalently linked to the antisense strand of the second siRNA.

In some embodiments, at least one of the effector molecules in the multi-targeted molecules disclosed herein is an antisense oligonucleotide (ASO). In some embodiments, the multi-targeted molecule is assembled from two antisense oligonucleotides. Without limitations, the antisense oligonucleotides can be same or different.

The two antisense oligonucleotides can be linked to each other at either end. For example, 3'-end of a first antisense oligonucleotide can be linked to either the 3'- or 5'-end of a second antisense oligonucleotide. Alternatively, 5'-end of a first antisense oligonucleotide can be linked to either the 3'- or 5'-end of a second antisense oligonucleotide.

In some embodiments, least one of the effector molecules in the multi-targeted molecules disclosed herein is a siRNA and least one of the effector molecules is an antisense oligonucleotide.

In some embodiments, at least one of the effector molecules in the multi-targeted molecules disclosed herein is a microRNA. In some embodiments, the multi-targeted molecule comprises at least two microRNAs. Without limitations, the microRNAs can be same or different.

In some embodiments, least one of the effector molecules in the multi-targeted molecules disclosed herein is a siRNA and least one of the effector molecules is a microRNA.

In some embodiments, at least one of the effector molecules in the multi-targeted molecules disclosed herein is a ribozyme. In some embodiments, the multi-targeted molecule comprises at least two ribozymes. Without limitations, the ribozymes can be same or different.

In some embodiments, least one of the effector molecules in the multi-targeted molecules disclosed herein is a siRNA and least one of the effector molecules is a ribozyme.

In some embodiments, at least one of the effector molecules in the multi-targeted molecules disclosed herein is an aptamer. In some embodiments, the multi-targeted molecule comprises at least two aptamers. Without limitations, the aptamers can be same or different.

In some embodiments, least one of the effector molecules in the multi-targeted molecules disclosed herein is a siRNA and least one of the effector molecules is an aptamer.

In some embodiments, at least one of the effector molecules in the multi-targeted molecules disclosed herein is a decoy oligonucleotide. In some embodiments, the multi-targeted molecule comprises at least two decoy oligonucleotides. Without limitations, the decoy oligonucleotides can be same or different.

In some embodiments, least one of the effector molecules in the multi-targeted molecules disclosed herein is a siRNA and least one of the effector molecules is a decoy oligonucleotide.

In some embodiments, at least one of the effector molecules in the multi-targeted molecules disclosed herein is a miRNA mimic. In some embodiments, the multi-targeted molecule comprises at least two miRNA mimics. Without limitations, the miRNA mimics can be same or different.

In some embodiments, least one of the effector molecules in the multi-targeted molecules disclosed herein is a siRNA and least one of the effector molecules is a miRNA mimic.

In some embodiments, at least one of the effector molecules in the multi-targeted molecules disclosed herein is a supermir. In some embodiments, the multi-targeted molecule comprises at least two supermirs. Without limitations, the supermirs can be same or different.

In some embodiments, least one of the effector molecules in the multi-targeted molecules disclosed herein is a siRNA and least one of the effector molecules is a supermir.

In some embodiments, at least one of the effector molecules in the multi-targeted molecules disclosed herein is an antimir. In some embodiments, the multi-targeted molecule comprises at least two antimirs. Without limitations, the antimirs can be same or different.

In some embodiments, least one of the effector molecules in the multi-targeted molecules disclosed herein is a siRNA and least one of the effector molecules is an antimir.

In some embodiments, at least one of the effector molecules in the multi-targeted molecules disclosed herein is an antagomir. In some embodiments, the multi-targeted molecule comprises at least two antagomirs. Without limitations, the antagomirs can be same or different.

In some embodiments, least one of the effector molecules in the multi-targeted molecules disclosed herein is a siRNA and least one of the effector molecules is an antagomir.

In some embodiments, at least one of the effector molecules in the multi-targeted molecules disclosed herein is a U1 adaptor. In some embodiments, the multi-targeted molecule comprises at least two U1 adaptors. Without limitations, the U1 adaptors can be same or different.

In some embodiments, least one of the effector molecules in the multi-targeted molecules disclosed herein is a siRNA and least one of the effector molecules is a U1 adaptor.

In some embodiments, at least one of the effector molecules in the multi-targeted molecules disclosed herein is an activating RNA. In some embodiments, the multi-targeted molecule comprises at least two activating RNAs. Without limitations, the activating RNAs can be same or different.

In some embodiments, least one of the effector molecules in the multi-targeted molecules disclosed herein is a siRNA and least one of the effector molecules is an activating RNA.

In some embodiments, at least one of the effector molecules in the multi-targeted molecules disclosed herein is a triplex forming oligonucleotide. In some embodiments, the multi-targeted molecule comprises at least two triplex forming oligonucleotides. Without limitations, the Triplex forming oligonucleotides can be same or different.

In some embodiments, least one of the effector molecules in the multi-targeted molecules disclosed herein is a siRNA and least one of the effector molecules is a triplex forming oligonucleotide.

Conjugates Comprising One Effector Molecule Conjugated with a Ligand

In another aspect, provided herein are conjugates comprising one effector molecule conjugated with a ligand via a cleavable linker described herein. Without limitations, the effector molecule can selected from the group consisting of double-stranded and single-stranded RNA interference agents (such as siRNA and shRNA, and also referred to as dsRNA agents herein), antisense oligonucleotides, microRNAs, anti-microRNAs or antimirs, supermirs, antagomirs, ribozymes, triplex-forming oligonucleotides, decoy oligonucleotides, RNA activators, U1 adaptors, and guide RNA (gRNA) of CRISPR Cas. In some embodiments, the effector molecule is an siRNA.

Without limitations, the ligand can be linked at any position of the effector molecule. For example, when the effector molecule is an siRNA, the ligand can be linked at the 5'-end, 3'-end or at an internal position of either the sense or antisense strand of the siRNA.

Ligands

In general, ligands modify one or more properties of the attached molecule (e.g., multi-targeted molecule, effector molecule or endosomal agent) including but not limited to pharmacodynamic, pharmacokinetic, binding, absorption, cellular distribution, cellular uptake, charge and clearance. Ligands are routinely used in the chemical arts and are linked directly or via an optional linking moiety or linking group to a parent compound. A preferred list of ligands includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Preferred ligands amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765): a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., di-hexadecyl-rac-glycerol or triethylammonium-1,2-di-O-hexadecyl-rac-glycero-3—H-phosphonate (Manoharan et al., Tetrahedron Lett., 1995, 36, 3651: Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996, 277, 923).

Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, $[MPEG]_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), Golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and branched polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptides include, but are not limited to,

```
(GALA)
                                        (SEQ ID NO: 1)
AALEALAEALEALAEALEALAEAAAAGGC;

(EALA)
                                        (SEQ ID NO: 2)
AALAEALAEALAEALAEALAEALAAAAGGC;

                                        (SEQ ID NO: 3)
ALEALAEALEALAEA;

(INF-7)
                                        (SEQ ID NO: 4)
GLFEAIEGFIENGWEGMIWDYG;

(Inf HA-2)
                                        (SEQ ID NO: 5)
GLFGAIAGFIENGWEGMIDGWYG;

(diINF-7)
                                        (SEQ ID NO: 6)
GLFEAIEGFIENGWEGMIDGWYGCGLFEAIEGFIENGWEGMID GWYGC;
```

-continued

```
(diINF-3)
                                        (SEQ ID NO: 7)
GLFEAIEGFIENGWEGMIDGGCGLFEAIEGFIENGWEGMIDGGC;

(GLF)
                                        (SEQ ID NO: 8)
GLFGALAEALAEALAEHLAEALAEALEALAAGGSC;

(GALA-INF3)
                                        (SEQ ID NO: 9)
GLFEAIEGFIENGWEGLAEALAEALEALAAGGSC;

(INF-5, n is norleucine)
                                        (SEQ ID NO: 10)
GLF EAI EGFI ENGW EGnI DG K GLF EAI EGFI ENGW
EGnI DG;

(JTS-1)
                                        (SEQ ID NO: 11)
LFEALLELLESLWELLLEA;

(ppTG1)
                                        (SEQ ID NO: 12)
GLFKALLKLLKSLWKLLLKA;

(ppTG20)
                                        (SEQ ID NO: 13)
GLFRALLRLLRSLWRLLLRA;

(KALA)
                                        (SEQ ID NO: 14)
WEAKLAKALAKALAKHLAKALAKALKACEA;

(HA)
                                        (SEQ ID NO: 15)
GLFFEAIAEFIEGGWEGLIEGC;

(Melittin)
                                        (SEQ ID NO: 16)
GIGAVLKVLTTGLPALISWIKRKRQQ;

                                        (SEQ ID NO: 17)
H5WYG;
and

                                        (SEQ ID NO: 18)
CHK6HC.
```

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (also referred to as XTC herein).

Synthetic polymers with endosomolytic activity amenable to the present invention are described in U.S. Pat. App. Pub. Nos. 2009/0048410; 2009/0023890; 2008/0287630; 2008/0287628; 2008/0281044; 2008/0281041; 2008/0269450; 2007/0105804; 20070036865; and 2004/0198687, contents of which are hereby incorporated by reference in their entirety.

Exemplary cell permeation peptides include, but are not limited to, RQIKIWFQNRRMKWKK (penetratin) (SEQ ID NO: 19); GRKKRRQRRRPPQC (Tat fragment 48-60) (SEQ ID NO: 20); GALFLGWLGAAGSTMGAWSQPKKKRKV (signal sequence based peptide) (SEQ ID NO: 21); LLIILRRRIRKQAHAHSK (PVEC) (SEQ ID NO: 22); GWTLNSAGYLLKINLKA- LAALAKKIL (transportan) (SEQ ID NO: 23); KLALKLALKALKAALKLA (amphiphilic model peptide) (SEQ ID NO: 24); RRRRRRRRR (Arg9) (SEQ ID NO: 25); KFFKFFKFFK (Bacterial cell wall permeating peptide) (SEQ ID NO: 26): LLGDFFRKSKEKIGKEFKRIVQRIKDFLRNLVPRTES (LL-37) (SEQ ID NO: 27); SWLSKTAKKLENSAKKRISEGIAIAIQGGPR (cecropin P1) (SEQ ID NO: 28); ACYCRIPACIAGERRYGTCIYQGRLWAFCC (α-defensin) (SEQ ID NO: 29); DHYNCVSSGGQCLYSACPIFTKIQGTCYRGKAKCCK (β-defensin) (SEQ ID NO: 30); RRRPRPPYLPRPRPPPFFPPRLPPRIPPGFPPRFPPRFPGKR-NH2 (PR-39) (SEQ ID NO: 31); ILPWKWPWWPWRR-NH2 (indolicidin) (SEQ ID NO: 32); AAVALLPAVLLALLAP (RFGF) (SEQ ID NO: 33); AALLPVLLAAP (RFGF analogue) (SEQ ID NO: 34); and RKCRIVVIRVCR (bactenecin) (SEQ ID NO: 35).

Exemplary cationic groups include, but are not limited to, protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid), and $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactosamine (GalNAc), multivalent GalNAc, e.g. GalNAc2 and GalNAc3; D-mannose, multivalent mannose, multivalent lactose. N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,552,545; 6,335,434 and 7,128,893, contents of which are herein incorporated in their entireties by reference.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2, 4, 6-triiodophenol and flufenamic acid). Oligomeric compounds that comprise a number of phosphorothioate intersugar linkages are also known to bind to serum protein, thus short oligomeric compounds, e.g. oligonucleotides of comprising from about 5 to 30 nucleotides (e.g., 5 to 25 nucleotides, preferably 5 to 20 nucleotides, e.g., 5, 6, 7, 8, 9, 10, 11, 12, 13, 14, 15, 16, 17, 18, 19, or 20 nucleotides), and that comprise a plurality of phosphorothioate linkages in the backbone are also amenable to the present invention as ligands (e.g. as PK modulating ligands). The PK modulating oligonucleotide can comprise at least 3, 4, 5, 6, 7, 8, 9, 10, 11, 12, 13, 14, 15 or more phosphorothioate and/or phosphorodithioate linkages. In some embodiments, all internucleotide linkages in PK modulating oligonucleotide are phosphorothioate and/or phosphorodithioates linkages. In addition, aptamers that bind serum components (e.g. serum proteins) are also amenable to the present invention as PK modulating ligands. Binding to serum components (e.g. serum proteins) can be predicted from albumin binding assays, such as those described in Oravcova, et al., Journal of Chromatography B (1996), 677: 1-27.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

The ligand or tethered ligand can be present on a monomer when said monomer is incorporated into the effector molecule or a component of the multi-targeted molecule. In some embodiments, the ligand can be incorporated via coupling to a "precursor" monomer after said "precursor" monomer has been incorporated into the effector molecule or a component of the multi-targeted molecule. For example, a monomer having, e.g., an amino-terminated tether (i.e., having no associated ligand), e.g., monomer-linker-$NH_2$ can be incorporated into the effector molecule or a component of the multi-targeted molecule. In a subsequent operation, i.e., after incorporation of the precursor monomer into the effector molecule or a component of the multi-targeted molecule, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in click chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

In some embodiments, ligand can be conjugated to nucleobases, sugar moieties, or internucleosidic linkages of the effector molecule or the multi-targeted molecule. Conjugation to purine nucleobases or derivatives thereof can occur at any position including, endocyclic and exocyclic atoms. In some embodiments, the 2-, 6-, 7-, or 8-positions of a purine nucleobase are attached to a ligand. Conjugation to pyrimidine nucleobases or derivatives thereof can also occur at any position. In some embodiments, the 2-, 5-, and 6-positions of a pyrimidine nucleobase can be substituted with a ligand. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligonucleotides. Generally, an oligonucleotide is attached to a conjugate moiety by contacting a reactive group (e.g., OH, SH, amine, carboxyl, aldehyde, and the like) on the oligonucleotide with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

The ligand can be attached to the effector molecules, the multi-targeted molecules or the endosomal agents via a carrier monomer, e.g., a ligand carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier monomer into the backbone, e.g., the phosphate, or modified phosphate, e.g., sulfur containing, backbone, of an oligonucleotide. A "tethering attachment point" (TAP) in refers to an atom of the carrier monomer, e.g., a carbon atom or a heteroatom (distinct from an atom which provides a backbone attachment point), that connects a selected moiety. The selected moiety can be, e.g., a carbohydrate, e.g. monosaccharide, disaccharide, trisaccharide, tetrasaccharide, oligosaccharide and polysaccharide. Optionally, the selected moiety is connected by an intervening tether to the carrier monomer. Thus, the carrier will often include a functional group, e.g., an amino group, or generally, provide a bond, that is suitable for incorporation or tethering of another chemical entity, e.g., a ligand to the constituent atom.

Representative U.S. patents that teach the preparation of conjugates of nucleic acids include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928;

5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; contents of which are herein incorporated in their entireties by reference.

In certain embodiments, the effector molecule or the multi-targeted molecule comprises a ligand having a structure shown below:

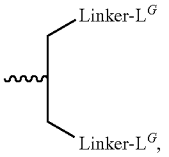
,
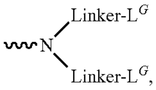
,
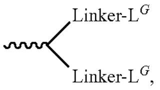
, or
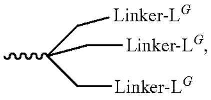
, wherein:

$L^G$ is independently for each occurrence a ligand, e.g., carbohydrate, e.g. monosaccharide, disaccharide, trisaccharide, tetrasaccharide, polysaccharide; and Z', Z", Z'" and Z"" are each independently for each occurrence O or S.

In certain embodiments, the effector molecule or the multi-targeted molecule comprises a ligand of Formula (II), (III), (IV) or (V):

Formula (II)

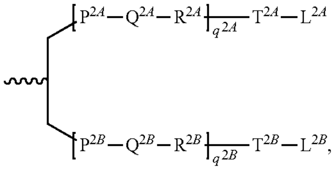
,

Formula (III)

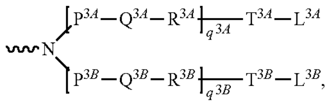
,

Formula (IV)

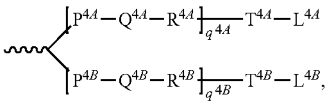
, or

Formula (V)

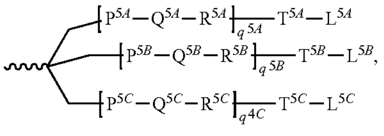
, wherein:

$q^{2A}$, $q^{2B}$, $q^{3A}$, $q^{3B}$, $q4^{4}$, $q^{4B}$, $q^{5A}$, $q^{5B}$ and $q^{5C}$ represent independently for each occurrence 0-20 and wherein the repeating unit can be the same or different;

Q and Q' are independently for each occurrence is absent, $—(P^7\text{-}Q^7\text{-}R^7)_p\text{-}T^7\text{-}$ or $\text{-}T^7\text{-}Q^7\text{-}T^{7\prime}\text{-}B\text{-}T^{8\prime}\text{-}Q^8\text{-}T^8$;

$P^{2A}$, $P^{2B}$, $P^{3A}$, $P^{3B}$, $P^{4A}$, $P^{4B}$, $P^{5A}$, $P^{5B}$, $P^{5C}$, $P^7$, $T^{2A}$, $T^{2B}$, $T^{3A}$, $T^{3B}$, $T^{4A}$, $T^{4B}$, $T^{4A}$, $T^{5B}$, $T^{5C}$, $T^7$, $T^{7'}$, $T^8$ and $T^{8'}$ are each independently for each occurrence absent, CO, NH, O, S, OC(O), NHC(O), $CH_2$, $CH_2NH$ or $CH_2O$;

B is —$CH_2$—$N(B^L)$—$CH_2$—;

$B^L$ is -$T^B$-$Q^B$-$T^{B'}$-$R^x$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$, $Q^7$, $Q^8$ and $Q^B$ are independently for each occurrence absent, alkylene, substituted alkylene and wherein one or more methylenes can be interrupted or terminated by one or more of O, S, S(O), $SO_2$, $N(R^N)$, C(R')═C(R'), C≡C or C(O);

$T^B$ and $T^{B'}$ are each independently for each occurrence absent, CO, NH, O, S, OC(O), OC(O)O, NHC(O), NHC(O)NH, NHC(O)O, $CH_2$, $CH_2NH$ or $CH_2O$;

$R^x$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid;

$R^1$, $R^2$, $R^{2A}$, $R^{2B}$, $R^{3A}$, $R^{3B}$, $R^{4A}$, $R^{4B}$, $R^{5A}$, $R^{5B}$, $R^{5C}$, $R^7$ are each independently for each occurrence absent, NH, O, S. $CH_2$, C(O)O, C(O)NH, $NHCH(R^a)C(O)$, —C(O)—$CH(R^a)$—NH—, CO, CH═N—O,

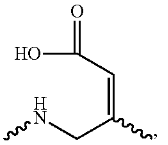 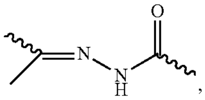,

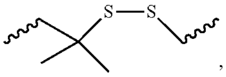, 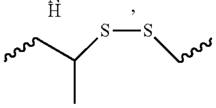,

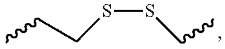, or heterocyclyl;

$L^1$, $L^{2A}$, $L^{2B}$, $L^{3A}$, $L^{3B}$, $L^{4A}$, $L^{4B}$, $L^{5A}$, $L^{5B}$ and $L^{5C}$ are each independently for each occurrence a carbohydrate, e.g., monosaccharide, disaccharide, trisaccharide, tetrasaccharide, oligosaccharide and polysaccharide;

R' and R" are each independently H, $C^1$-$C_6$ alkyl, OH, SH, or $N(R^N)_2$;

$R^N$ is independently for each occurrence H, methyl, ethyl, propyl, isopropyl, butyl or benzyl;

$R^a$ is H or amino acid side chain;

Z', Z", Z''' and Z'''' are each independently for each occurrence O or S;

p represent independently for each occurrence 0-20.

In certain embodiments, the effector molecule or the multi-targeted molecule comprises a ligand of structure:

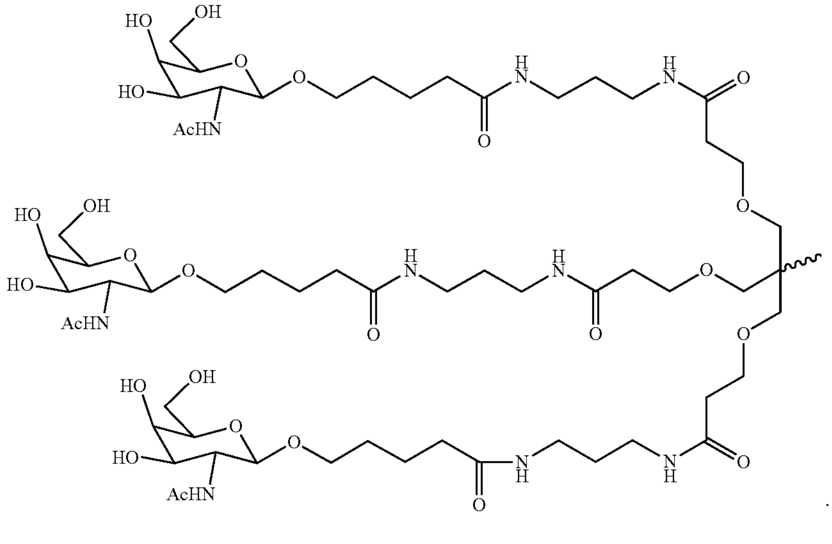 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O].

In certain embodiments, the effector molecule or the multi-targeted molecule comprises a ligand of structure:

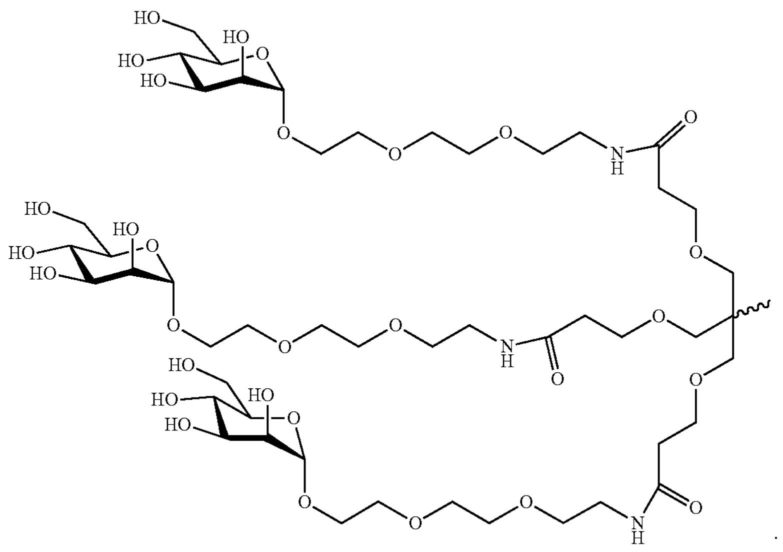

In certain embodiments, the effector molecule or the multi-targeted molecule comprises a ligand of structure:

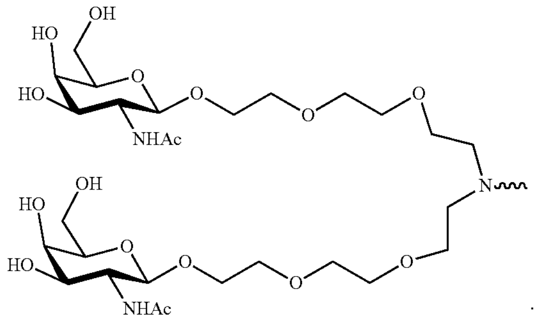

In certain embodiments, the effector molecule or the multi-targeted molecule comprises a ligand of structure:

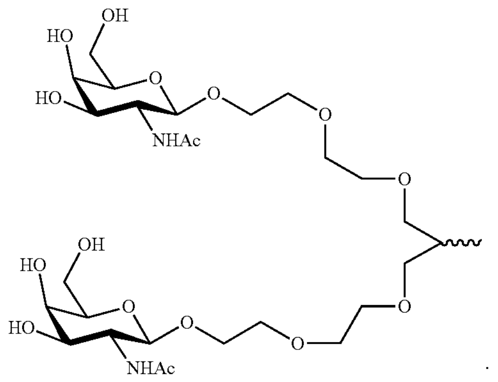

In certain embodiments, the effector molecule or the multi-targeted molecule comprises a ligand of structure:

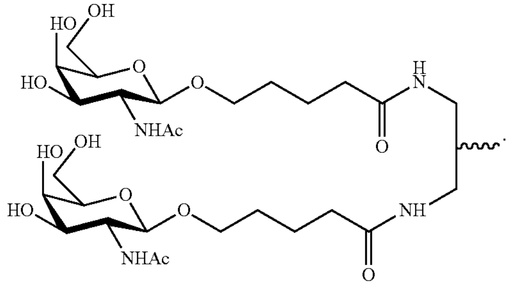

In certain embodiments, the effector molecule or the multi-targeted molecule comprises a ligand of structure:

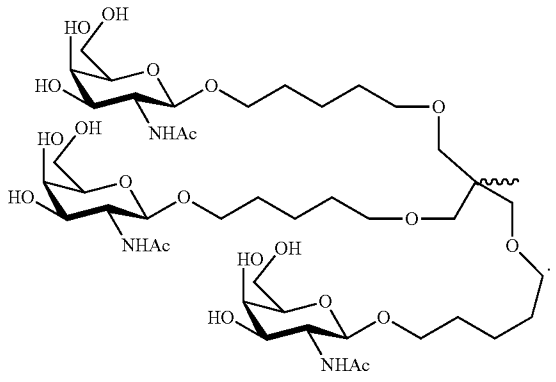

In certain embodiments, the effector molecule or the multi-targeted molecule comprises a ligand of structure:
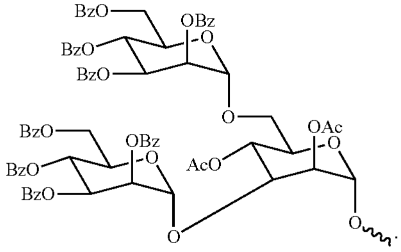
In certain embodiments, the effector molecule or the multi-targeted molecule comprises a ligand of structure:
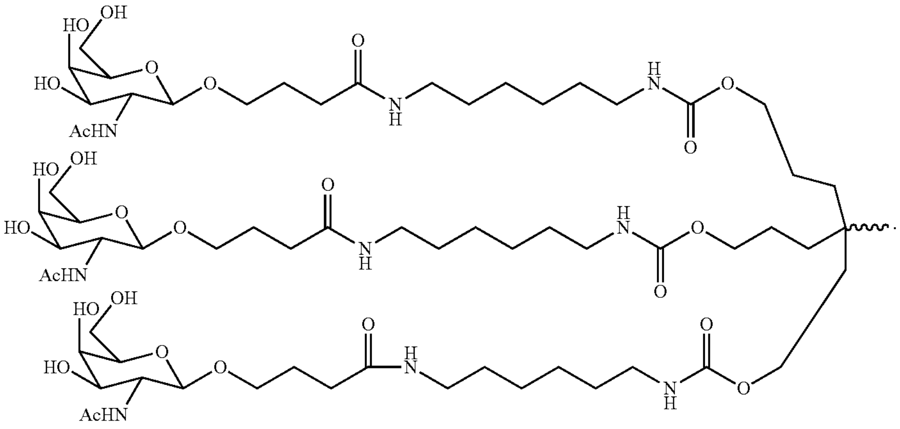 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCOC(=O)NCCCCCCNC(=O)CCCOC2OC(CO)C(O)C(O)C2NC(C)=O)OC(CO)C(O)C1O]
In certain embodiments, the effector molecule or the multi-targeted molecule comprises a ligand of structure:
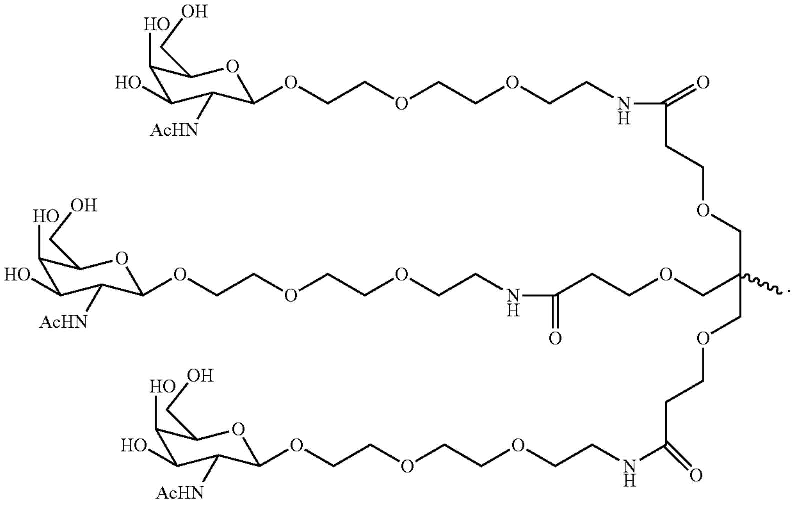 [SMILES: CC(=O)NC1C(OCCOCCOCCNC(=O)CCOCC(C)(COCCC(=O)NCCOCCOCCOC2OC(CO)C(O)C(O)C2NC(C)=O)COCCC(=O)NCCOCCOCCOC2OC(CO)C(O)C(O)C2NC(C)=O)OC(CO)C(O)C1O]

In certain embodiments, the effector molecule or the multi-targeted molecule comprises a ligand of structure:
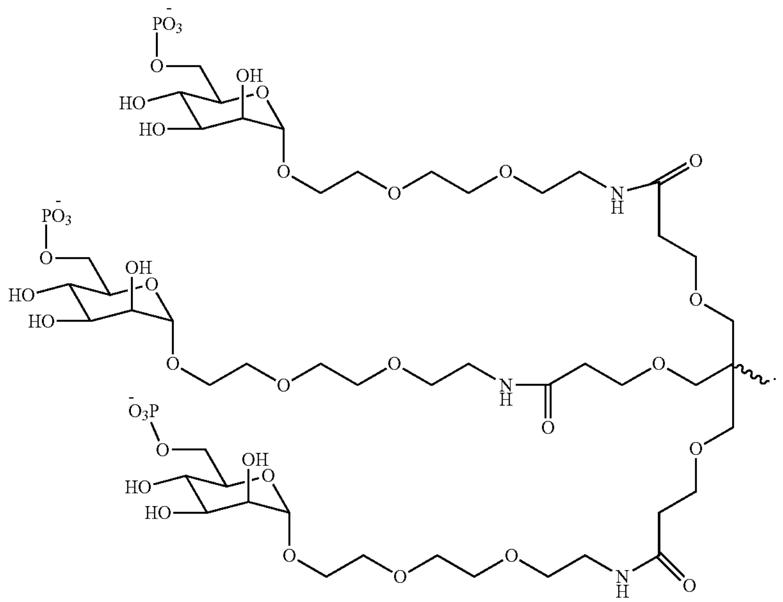
In certain embodiments, the effector molecule or the multi-targeted molecule comprises a ligand of structure:
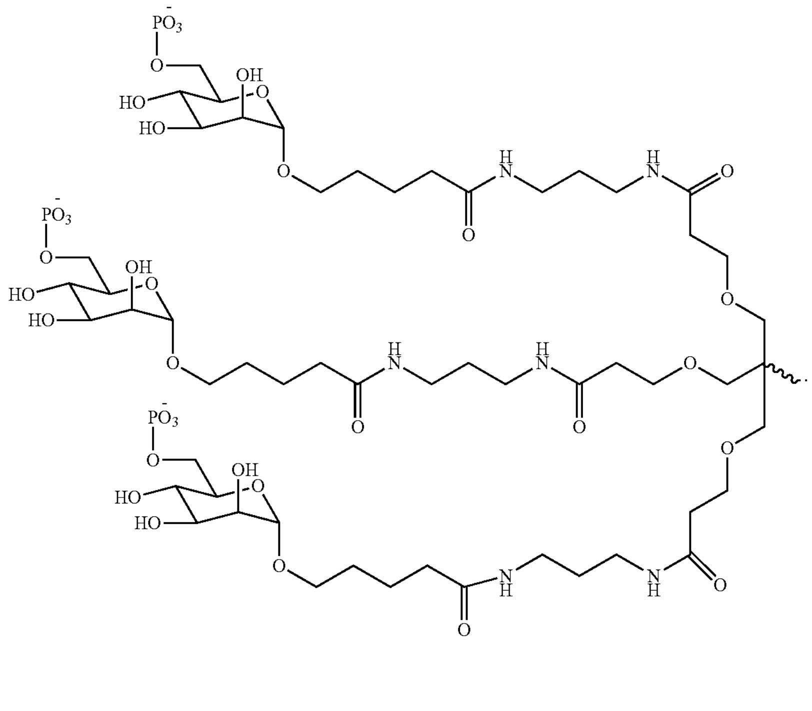

In certain embodiments, the effector molecule or the multi-targeted molecule comprises a monomer of structure:

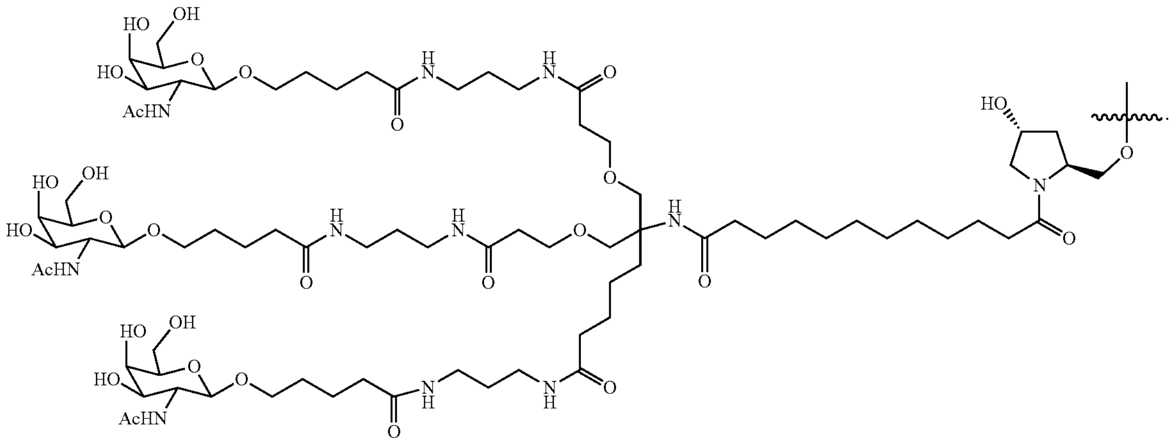 [SMILES: *OC[C@@H]1C[C@@H](O)CN1C(=O)CCCCCCCCCCC(=O)NC(CCCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

In certain embodiments, the effector molecule or the multi-targeted molecule comprises a ligand of structure:

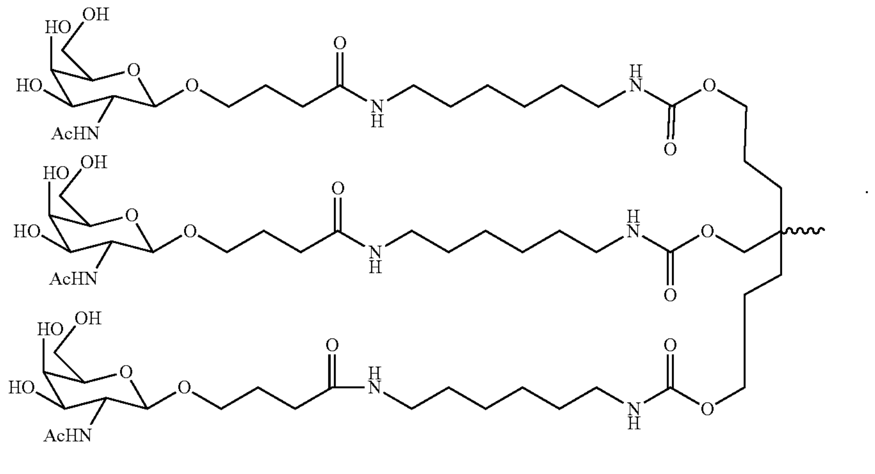 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)COC(=O)NCCCCCCNC(=O)CCCOC2OC(CO)C(O)C(O)C2NC(C)=O)OC(CO)C(O)C1O]

In some embodiments, the ligand in the effector molecule linked to a ligand via a cleavable linker describe herein is a ligand described above.

In some embodiments, the ligand in the endosomal agent linked to a ligand via a cleavable linker describe herein is a ligand described above.

In certain embodiments, the effector molecule or the multi-targeted molecule comprises a monomer of structure:

MONOMER 1
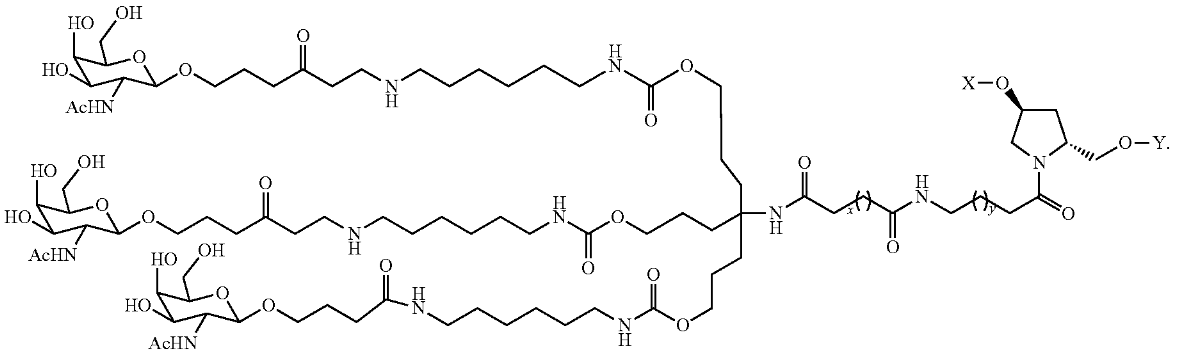
x = 1-30
y = 1-15
In certain embodiments, the effector molecule or the multi-targeted molecule comprises a monomer of structure:
MONOMER 2
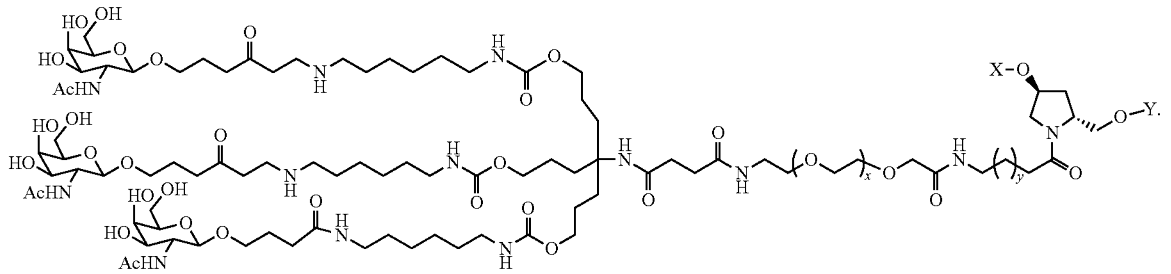
x = 1-30
y = 1-15
In certain embodiments, the effector molecule or the multi-targeted molecule comprises a monomer of structure:
MONOMER 3
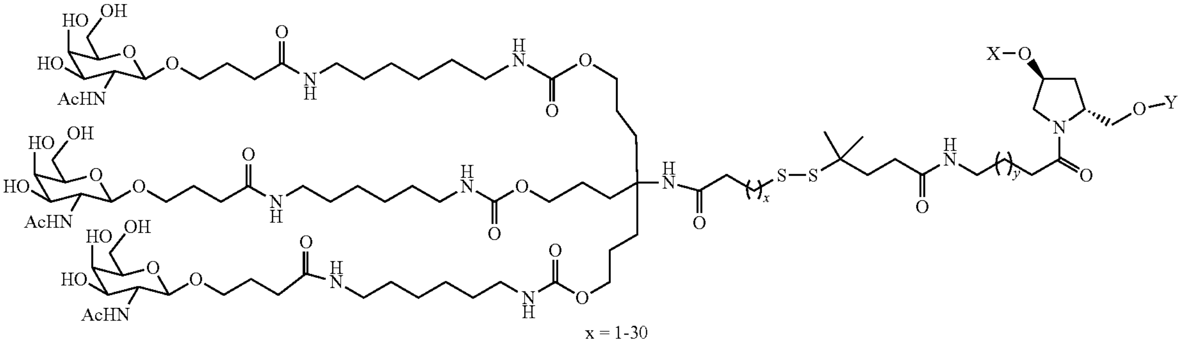
x = 1-30
y = 1-15

In certain embodiments, the effector molecule or the multi-targeted molecule comprises a monomer of structure:

MONOMER 4

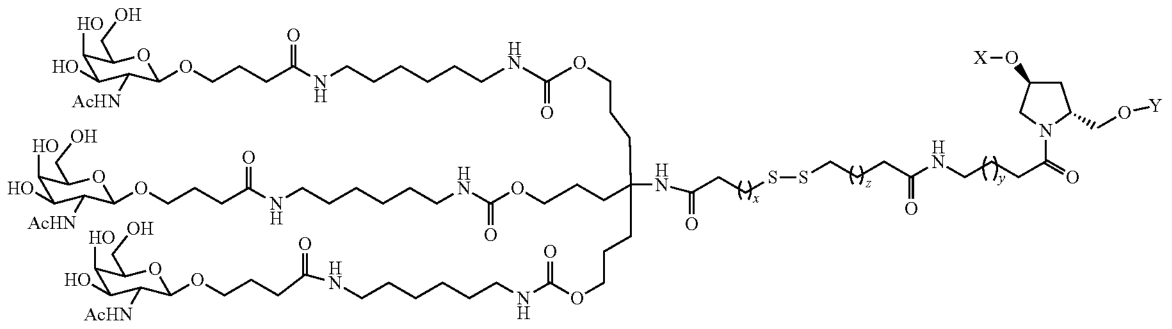

x = 1-30
y = 1-15
z = 1-20

In certain embodiments, the effector molecule or the multi-targeted molecule comprises a monomer of structure:

MONOMER 5

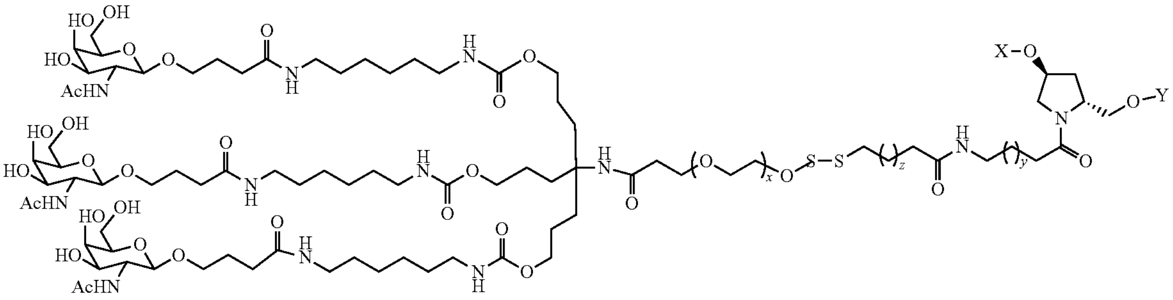

x = 1-30
y = 1-15
z = 1-20

In certain embodiments, the effector molecule or the multi-targeted molecule comprises a monomer of structure:

MONOMER 6

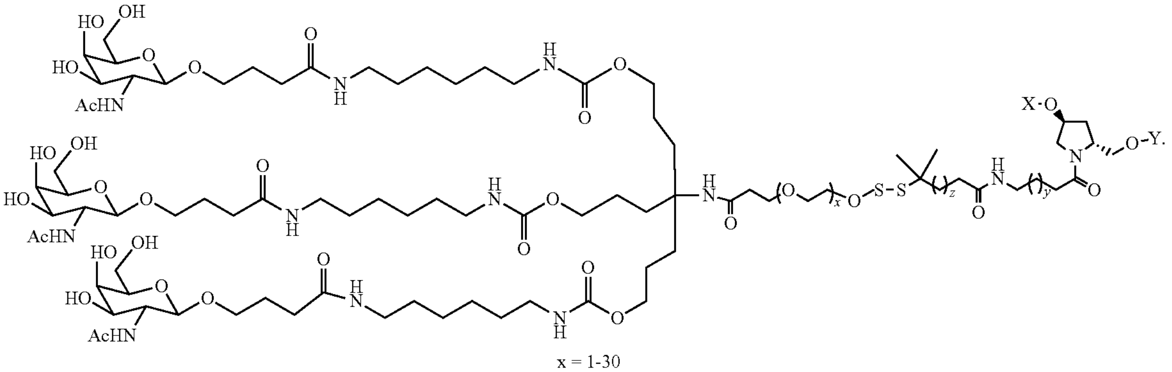

x = 1-30
y = 1-15
z = 1-20

In certain embodiments, the effector molecule or the multi-targeted molecule comprises a ligand of structure:

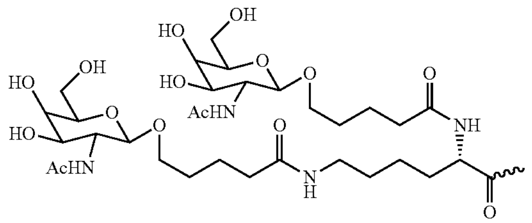

In certain embodiments, the effector molecule or the multi-targeted molecule comprises a ligand of structure:

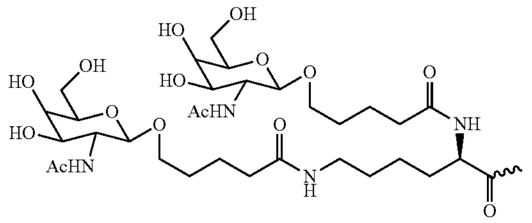

In certain embodiments, the effector molecule or the multi-targeted molecule comprises a ligand of structure:

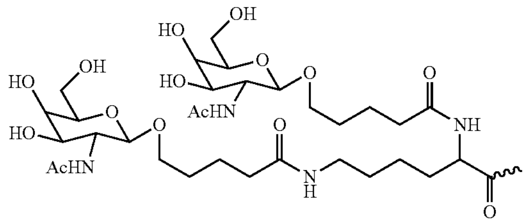

In certain embodiments, the effector molecule or the multi-targeted molecule comprises a ligand of structure:

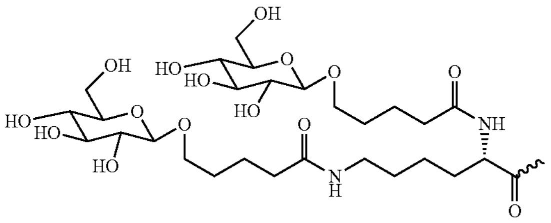

In certain embodiments, the effector molecule or the multi-targeted molecule comprises a ligand of structure:

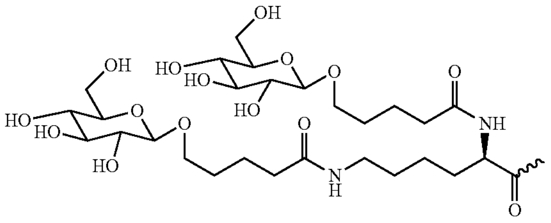

In certain embodiments, the effector molecule or the multi-targeted molecule comprises a ligand of structure:

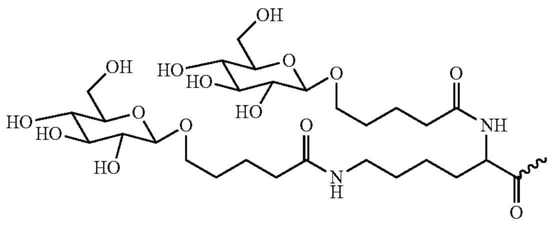

In certain embodiments, the effector molecule or the multi-targeted molecule comprises a ligand of structure:

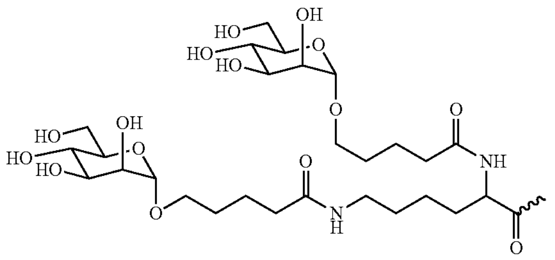

In certain embodiments, the effector molecule or the multi-targeted molecule comprises a ligand of structure:

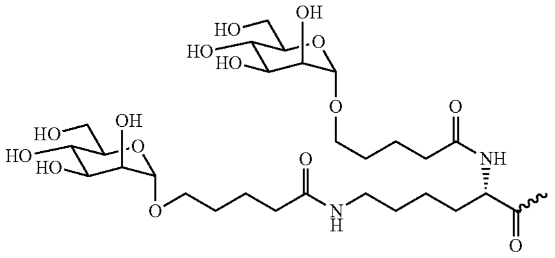

In certain embodiments, the effector molecule or the multi-targeted molecule comprises a ligand of structure:

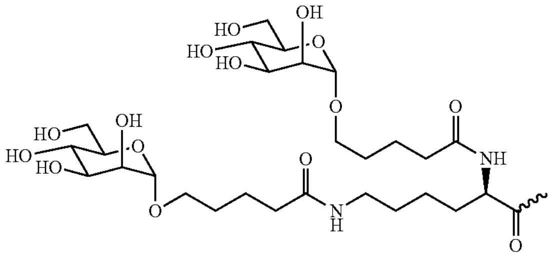

In certain embodiments, the effector molecule or the multi-targeted molecule comprises a monomer of structure:

MONOMER 7

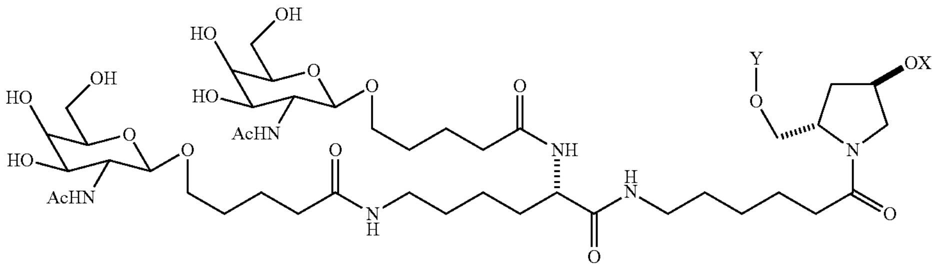

In certain embodiments, the effector molecule or the multi-targeted molecule comprises a monomer of structure:

MONOMER 8

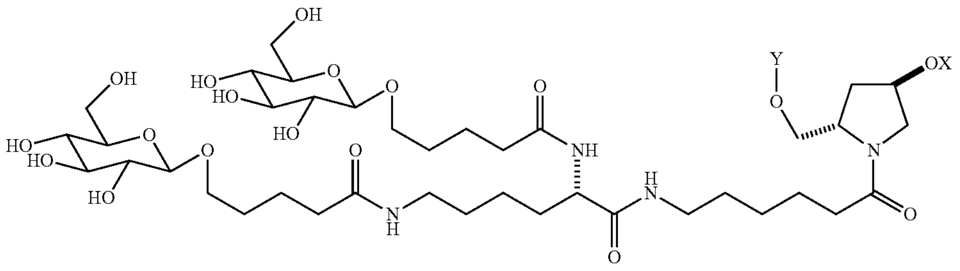

In certain embodiments, the effector molecule or the multi-targeted molecule comprises a monomer of structure:

MONOMER 9

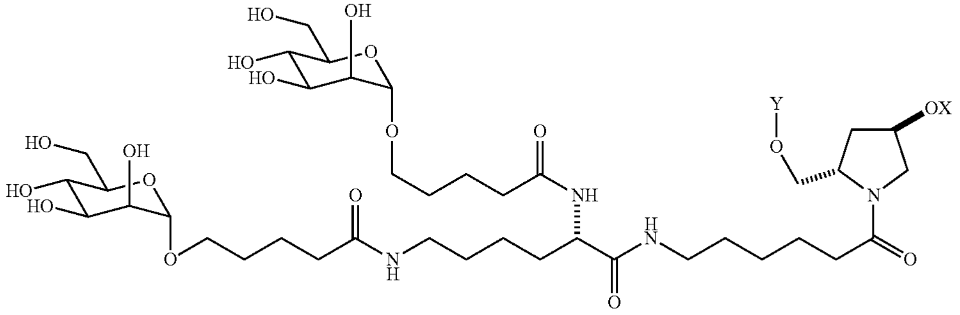

In certain embodiments, the effector molecule or the multi-targeted molecule comprises a monomer of structure:

MONOMER 10

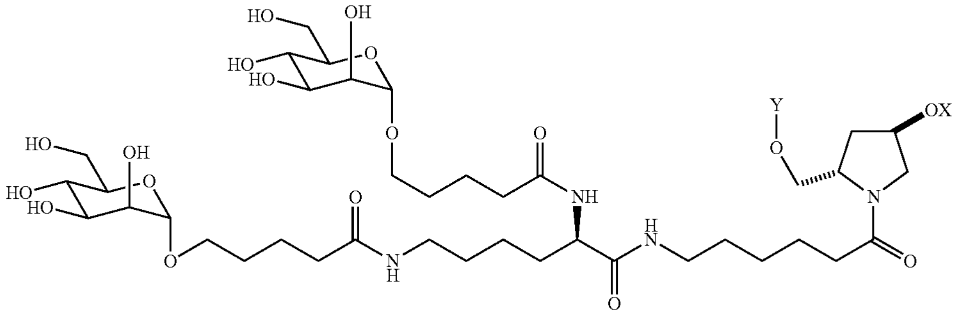

In certain embodiments, the effector molecule or the multi-targeted molecule comprises a monomer of structure:

MONOMER 11

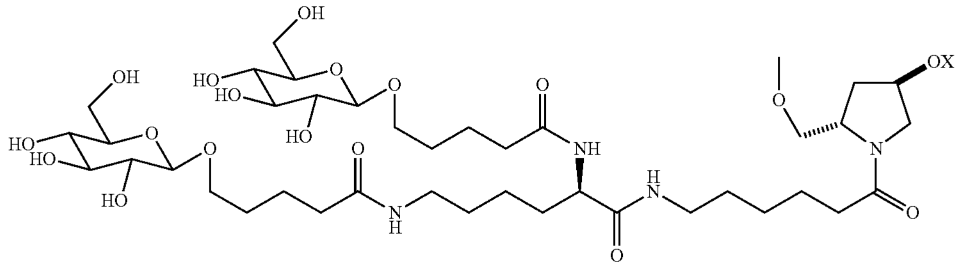

In certain embodiments, the effector molecule or the multi-targeted molecule comprises a monomer of structure:

MONOMER 12

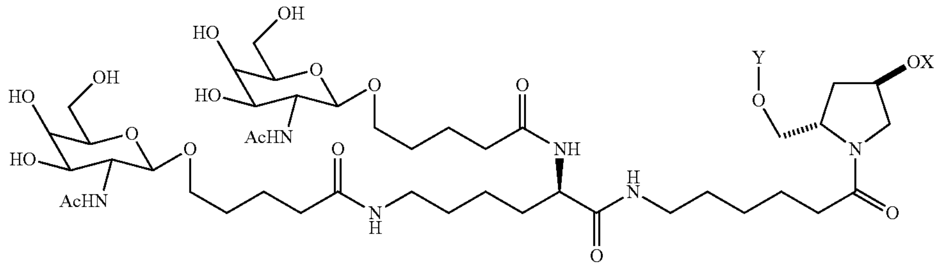

In some embodiments both $L^{2A}$ and $L^{2B}$ are different.

In some preferred embodiments both $L^{3A}$ and $L^{3B}$ are the same.

In some embodiments both $L^{3A}$ and $L^{3B}$ are different.

In some preferred embodiments both $L^{4A}$ and $L^{4B}$ are the same.

In some embodiments both $L^{4A}$ and $L^{4B}$ are different.

In some preferred embodiments all of $L^{5A}$, $L^{5B}$ and $L^{5C}$ are the same.

In some embodiments two of $L^{5A}$, $L^{5B}$ and $L^{5C}$ are the same

In some embodiments $L^{5A}$ and $L^{5B}$ are the same.

In some embodiments $L^{5A}$ and $L^{5C}$ are the same.

In some embodiments $L^{5B}$ and $L^{5C}$ are the same.

In certain embodiments, the effector molecule or the multi-targeted molecule comprises a monomer of structure:

MONOMER 13

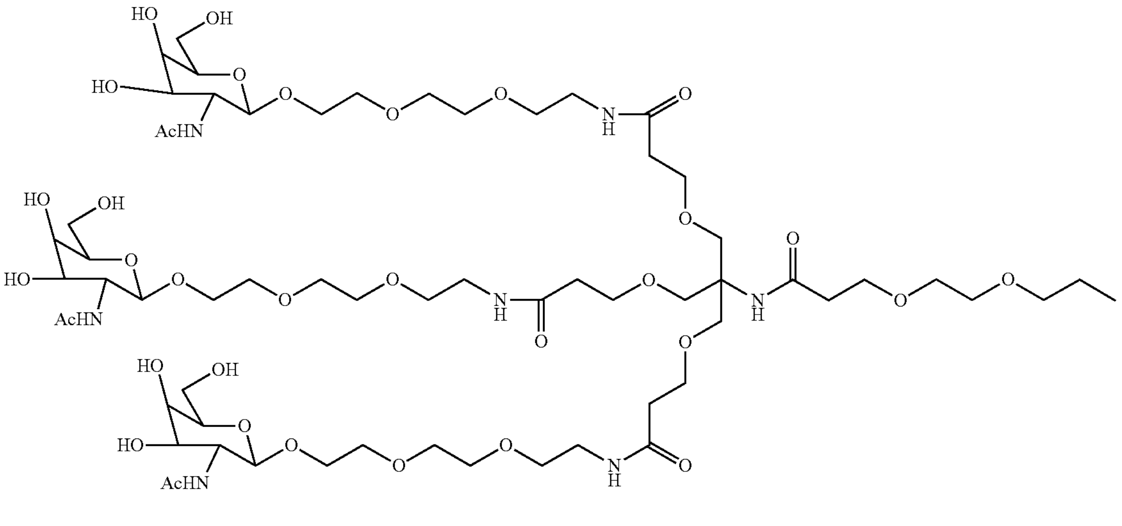

-continued

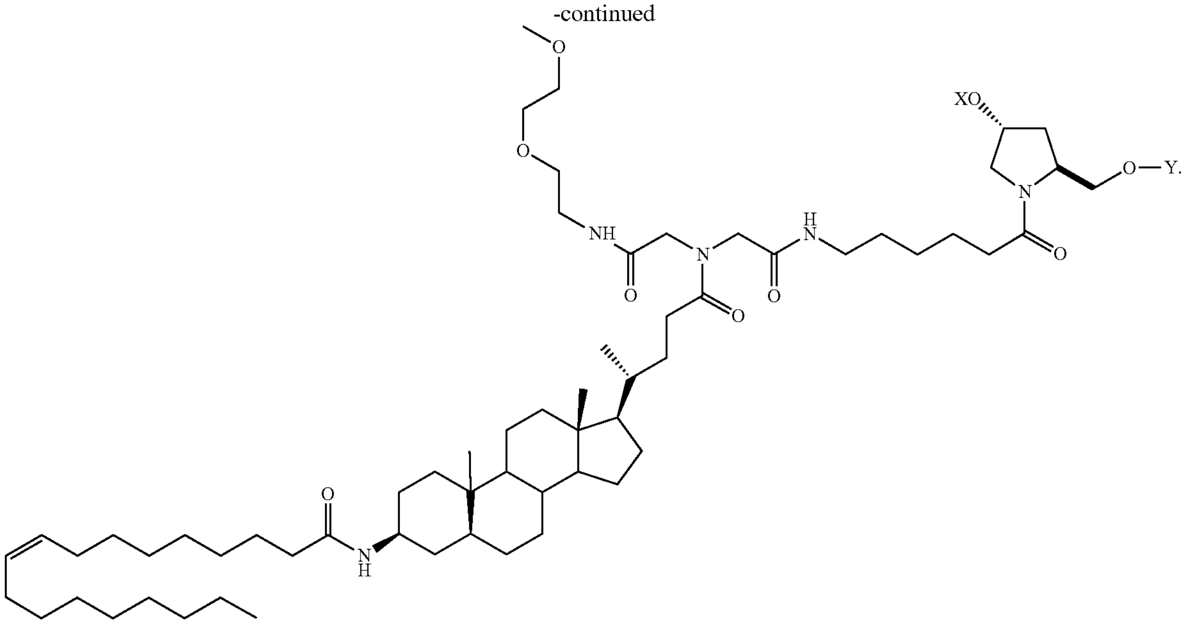

In certain embodiments, the effector molecule or the multi-targeted molecule comprises a monomer of structure:

MONOMER 14

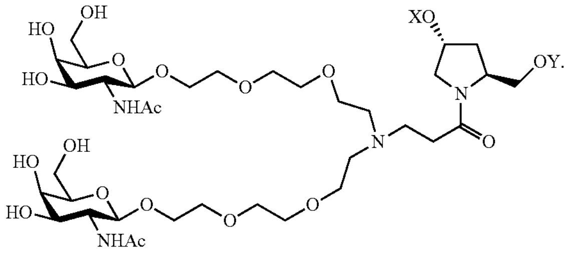

In certain embodiments, the effector molecule or the multi-targeted molecule comprises a monomer of structure:

MONOMER 15

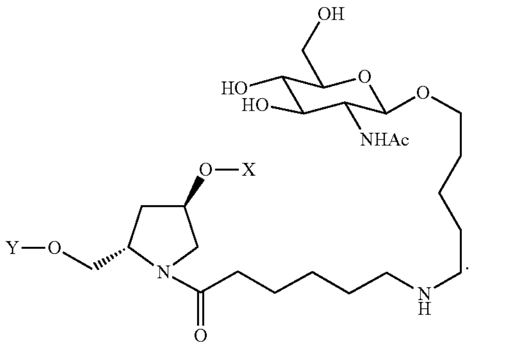

In certain embodiments, the effector molecule or the multi-targeted molecule comprises a monomer of structure:

MONOMER 16

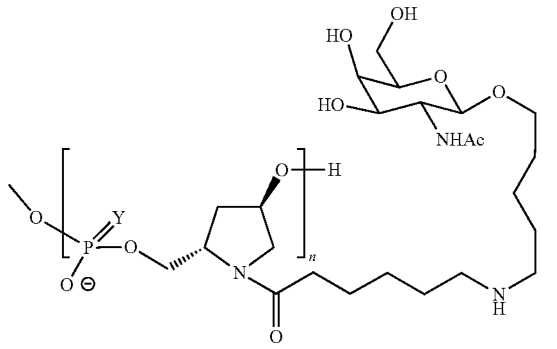

wherein Y is O or S and n is 1-6.

In certain embodiments, the effector molecule or the multi-targeted molecule comprises a monomer of structure:

MONOMER 17

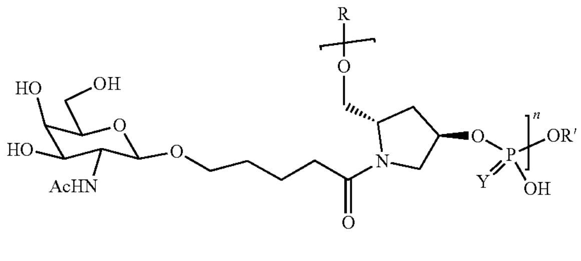

wherein Y=O or S. n is 1-6, R is hydrogen or nucleic acid, R' is nucleic acid.

In certain embodiments, the effector molecule or the multi-targeted molecule comprises a monomer of structure:

MONOMER 18
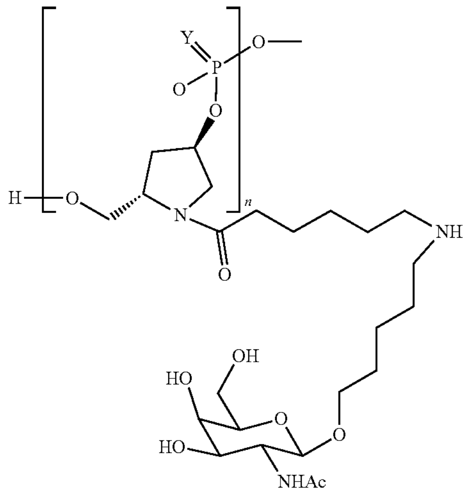
wherein Y is O or S and n is 1-6.
In certain embodiments, the effector molecule or the multi-targeted molecule comprises at least 1, 2, 3 or 4 monomer of structure:
MONOMER 19
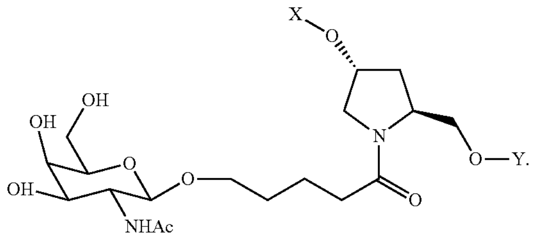
In certain embodiments, the effector molecule or the multi-targeted molecule comprises a monomer of structure:
MONOMER 20
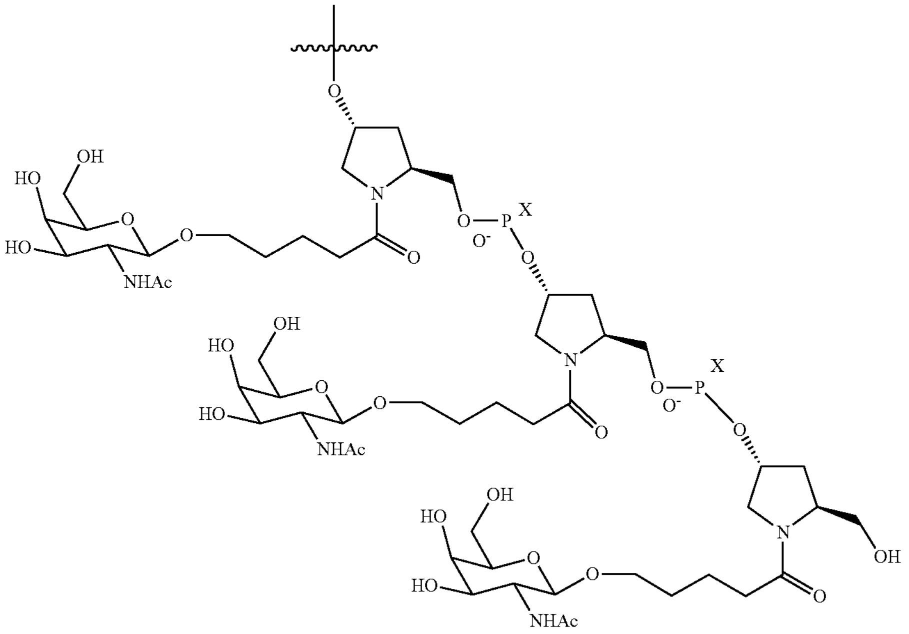
wherein X is O or S.

In certain embodiments, the effector molecule or the multi-targeted molecule comprises a monomer of structure:

MONOMER 21

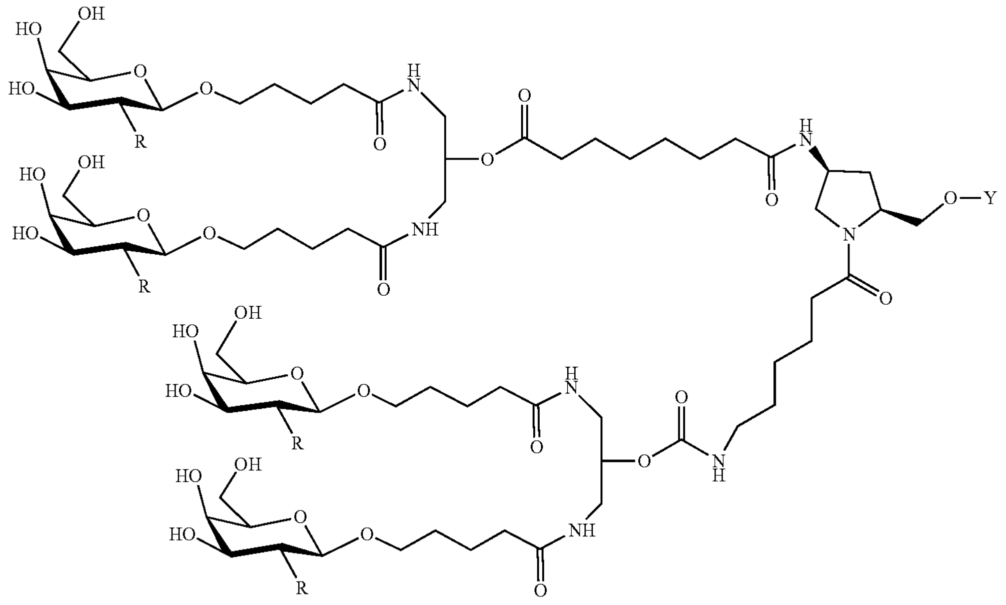

wherein R is OH or NHCOOH.

In certain embodiments, the effector molecule or the multi-targeted molecule comprises a monomer of structure:

MONOMER 22

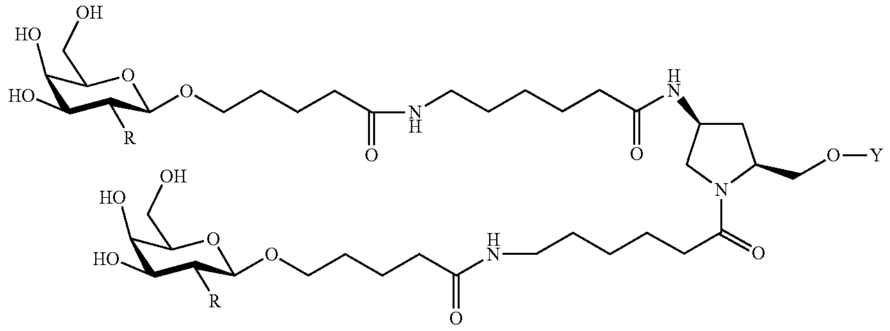

wherein R is OH or NHCOOH.

In certain embodiments, the effector molecule or the multi-targeted molecule comprises a monomer of structure:

Formula (VII)

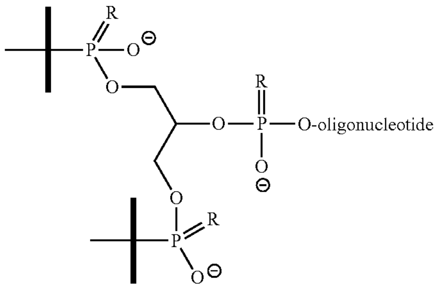

MONOMER 23 wherein R is O or S.

In certain embodiments, the effector molecule or the multi-targeted molecule comprises a monomer of structure:

MONOMER 24

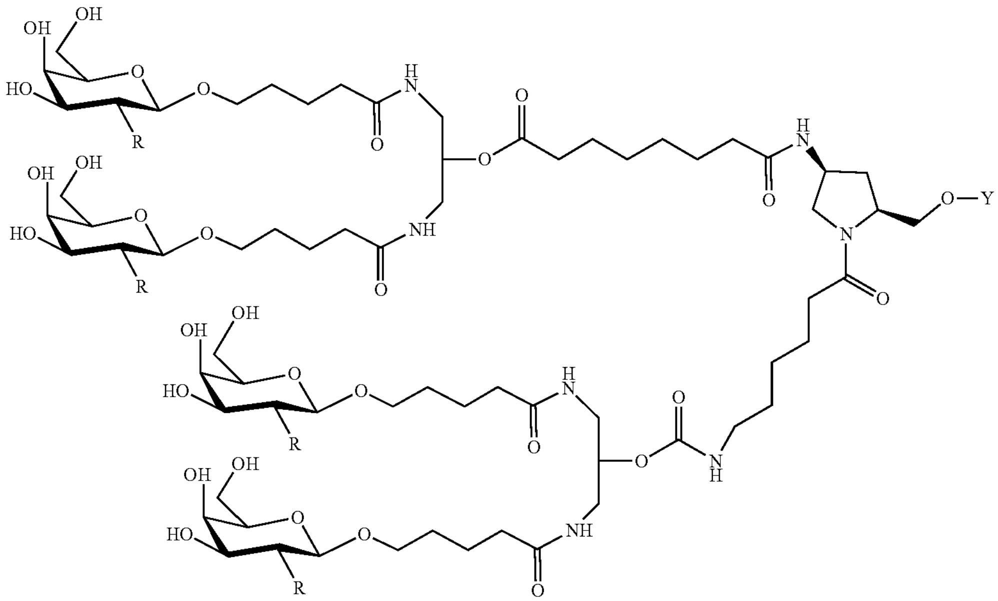

wherein R is OH or NHCOOH.

In certain embodiments, the effector molecule or the multi-targeted molecule comprises a monomer of structure:

MONOMER 25

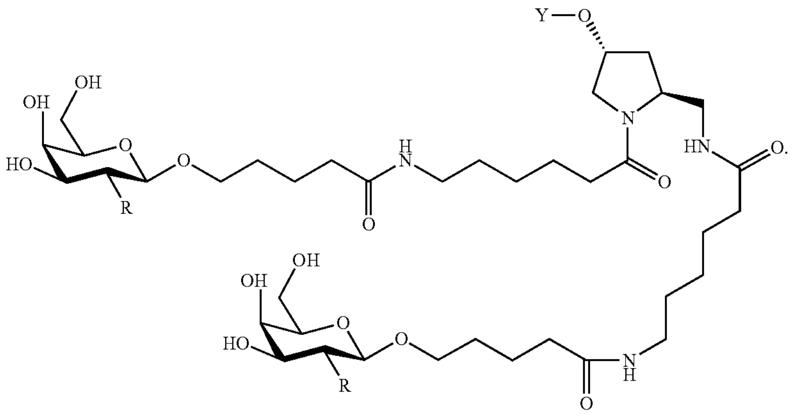

In certain embodiments, the multi-targeted molecule comprises a monomer of structure:

MONOMER 26

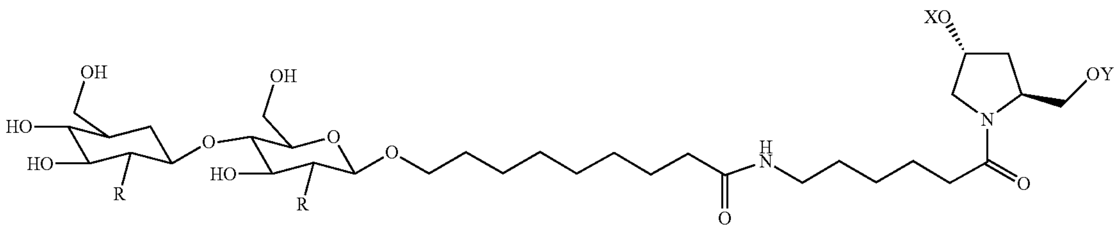

wherein R is OH or NHCOOH.

In certain embodiments, the effector molecule or the multi-targeted molecule comprises a monomer of structure:

MONOMER 27

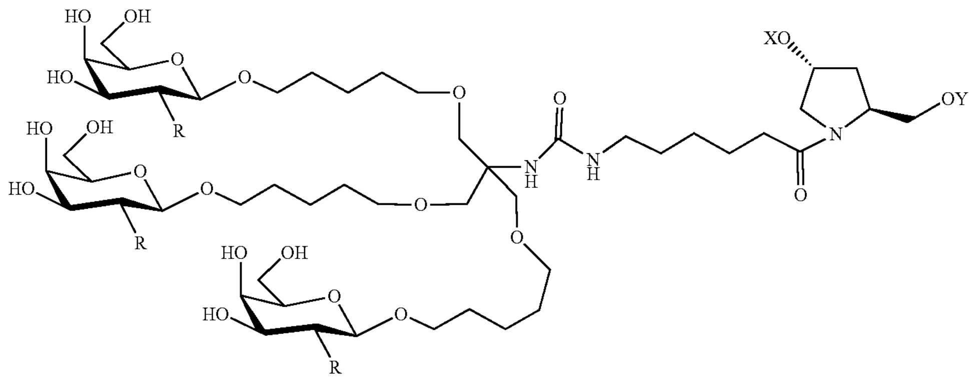

wherein R is OH or NHCOOH.

In certain embodiments, the effector molecule or the multi-targeted molecule comprises a monomer of structure:

MONOMER 28

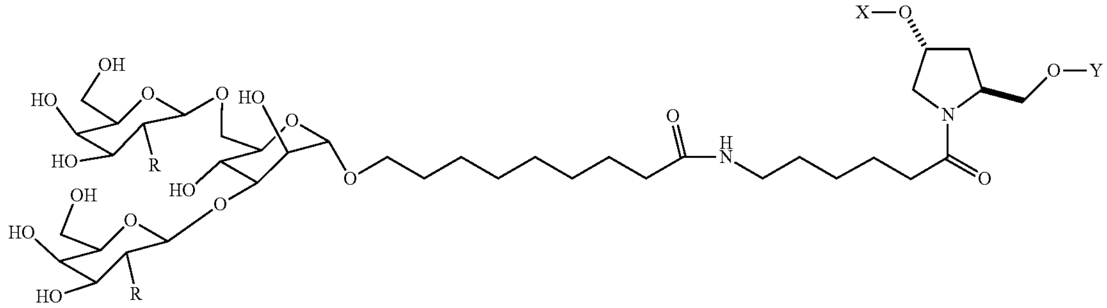

wherein R is OH or NHCOOH.

In certain embodiments, the multi-targeted molecule comprises a monomer of structure:

Monomer 29

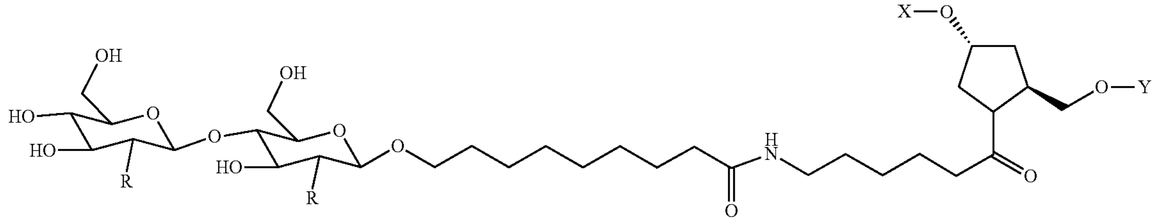

wherein R is OH or NHCOOH.

In certain embodiments, the effector molecule or the multi-targeted molecule comprises a monomer of structure:

Monomer 30

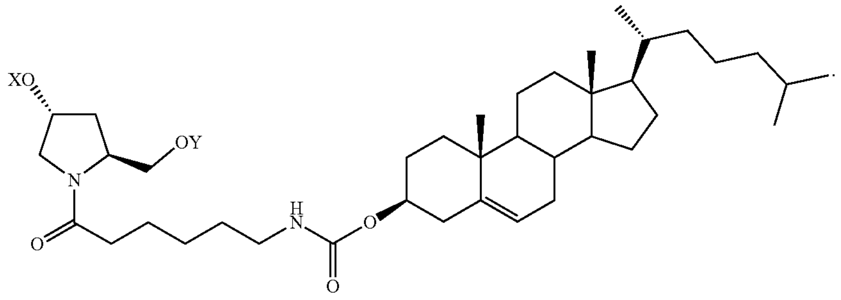

In the above described monomers, X and Y are each independently for each occurrence H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, a nucleotide, a nucleoside, or an oligonucleotide; and Z' and Z" are each independently for each occurrence O or S.

In some embodiments, the effector molecule linked with a ligand via a linker disclosed herein comprises a monomer selected from the group consisting of MONOMERS 1-30.

In some embodiments, the endosomal agent linked with ligand via a linker disclosed herein comprises a monomer selected from the group consisting of MONOMERS 1-30.

In certain embodiments, the effector molecule, the multi-targeted molecule or the endosomal agent is conjugated with a ligand of structure:

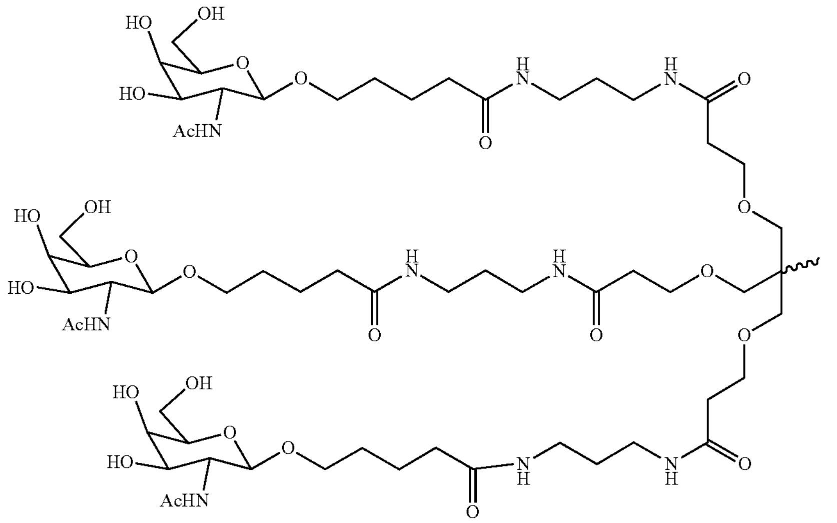

or

-continued
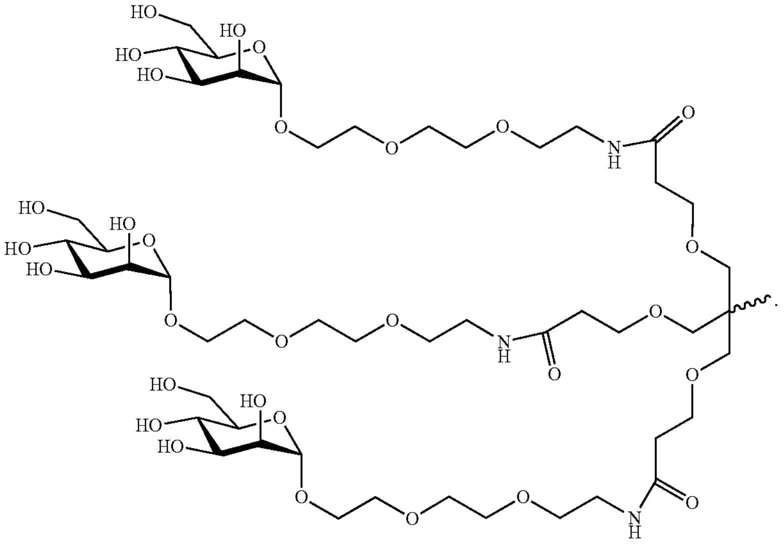
In certain embodiments, the effector molecule, the multi-targeted molecule or the endosomal agent is conjugated with a ligand of structure:
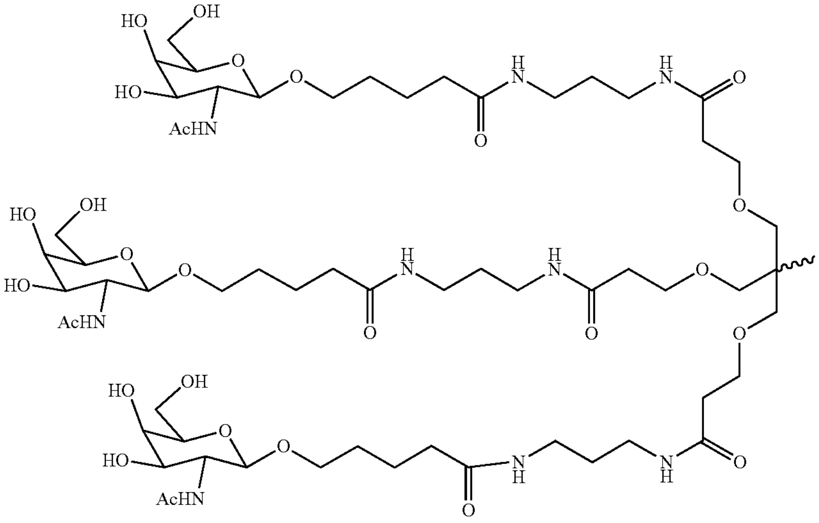
or -continued
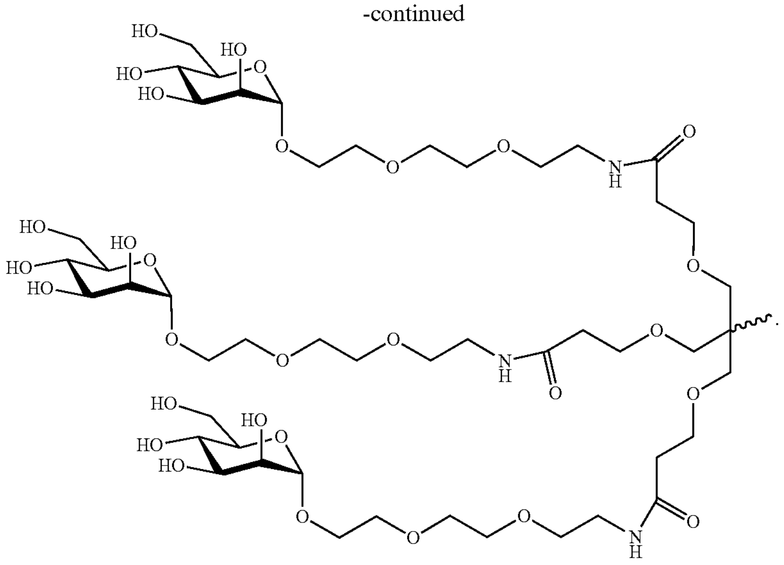
In certain embodiments, the effector molecule or the multi-targeted molecule comprises a monomer of structure:
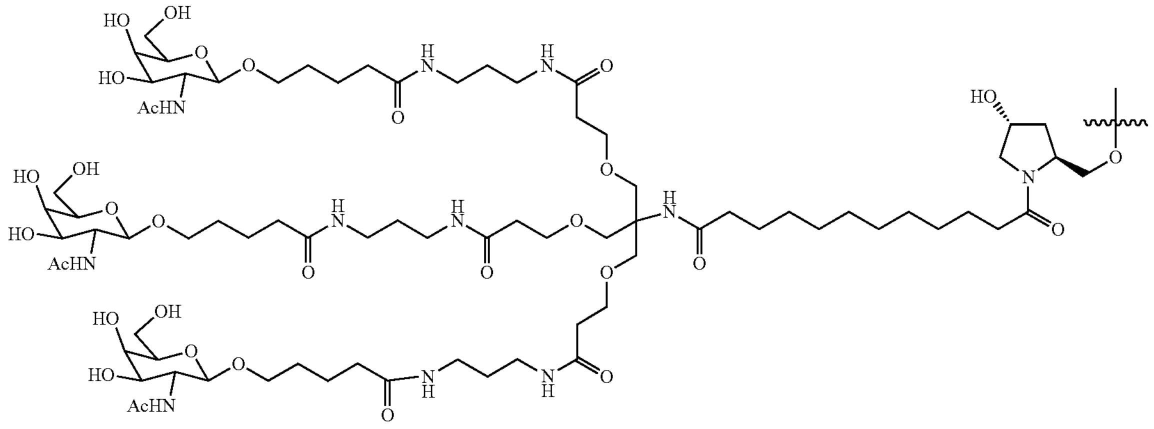
or
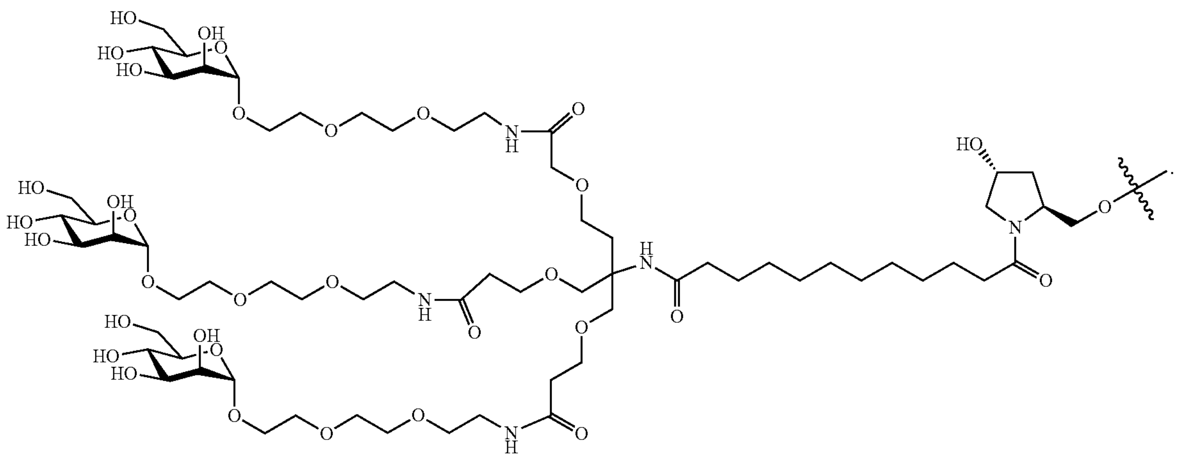

Synthesis of above described ligands and monomers is described, for example, in U.S. Pat. No. 8,106,022, content of which is incorporated herein by reference in its entirety.

Target Genes

Without limitations, target genes for the effector molecules include, but are not limited to genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Specific exemplary target genes for the effector molecules include, but are not limited to, PCSK-9, ApoC3, AT3, AGT, ALAS1, TMPR, HAO1, AGT, C5, CCR-5, PDGF beta gene; Erb-B gene, Src gene; CRK gene; GRB2 gene; RAS gene; MEKK gene; JNK gene; RAF gene; Erk1/2 gene; PCNA (p21) gene; MYB gene; c-MYC gene; JUN gene; FOS gene; BCL-2 gene; Cyclin D gene; VEGF gene; EGFR gene; Cyclin A gene; Cyclin E gene; WNT-1 gene; beta-catenin gene; c-MET gene; PKC gene; NFKB gene; STAT3 gene; survivin gene; Her2/Neu gene; topoisomerase I gene; topoisomerase II alpha gene; p73 gene; p21(WAF1/CIP1) gene, p27(KIP1) gene; PPM1D gene; caveolin I gene; MIB I gene; MTAI gene; M68 gene; tumor suppressor genes; p53 gene; DN-p63 gene; pRb tumor suppressor gene; APCI tumor suppressor gene; BRCA1 tumor suppressor gene; PTEN tumor suppressor gene; MLL fusion genes, e.g., MLL-AF9, BCR/ABL fusion gene; TEL/AML1 fusion gene; EWS/FLI1 fusion gene; TLS/FUS1 fusion gene; PAX3/FKHR fusion gene; AML1/ETO fusion gene; alpha v-integrin gene; Flt-1 receptor gene; tubulin gene; Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Varicella zoster virus gene, a gene that is required for Varicella zoster virus replication, adenovirus gene, a gene that is required for adenovirus replication, yellow fever virus gene, a gene that is required for yellow fever virus replication, poliovirus gene, a gene that is required for poliovirus replication, poxyirus gene, a gene that is required for poxyirus replication, *plasmodium* gene, a gene that is required for *plasmodium* gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, 1-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in loss of heterozygosity (LOH) cells, one allele gene of a polymorphic gene and combinations thereof.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in duploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific modulation of one allele of an essential gene with a composition of the invention.

Nucleic Acid Modifications

The effector molecule or the multi-targeted molecule can comprise comprises at least one nucleic acid modification described herein. For example, at least one modification selected from the group consisting of modified internucleoside linkage, modified nucleobase, modified sugar, and any combinations thereof. Without limitations, such a modification can be present anywhere in the effector molecule or the multi-targeted molecule. For example, the modification can be present in one of the effector molecules or a linker connecting two effector molecules of the multi-targeted molecule.

The naturally occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5'hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleoside backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The unmodified or natural nucleobases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the oligomer modifications described herein. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

As used herein, "unmodified" or "natural" nucleobases include the purine bases adenine (A) and guanine (G), and the pyrimidine bases thymine (T), cytosine (C) and uracil (U). Exemplary modified nucleobases include, but are not limited to, other synthetic and natural nucleobases such as inosine, xanthine, hypoxanthine, nubularine, isoguanisine, tubercidine, 2-(halo)adenine, 2-(alkyl)adenine, 2-(propyl) adenine, 2-(amino)adenine, 2-(aminoalkyl)adenine, 2-(aminopropyl)adenine, 2-(methylthio)-$N^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$,$N^6$-(dimethyl)adenine, 2-(alkyl)guanine,2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl) uracil, 5-(guanidiniumalkyl)uracil, 5-(1,3-diazole-1-alkyl) uracil, 5-(cyanoalkyl)uracil, 5-(dialkylaminoalkyl)uracil, 5-(dimethylaminoalkyl)uracil, 5-(halo)uracil, 5-(methoxy) uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, $N^3$-(methyl)uracil, 5-uracil (i.e., pseudouracil), 2-(thio)pseudouracil,4-(thio)pseudouracil,2,4-(dithio)pseudouracil,5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2(thio)-pseudouracil, 1-(aminocarbonylethylenyl)4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, pyrrolo-pyrimidin-2-on-3-yl, 6-phenyl-pyrrolopyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and “universal bases” can be employed.

As used herein, a universal nucleobase is any nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazole, 4-methylbenzimidazole, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, *Nucleic Acids Research,* 29, 2437-2447).

Further nucleobases include those disclosed in U.S. Pat. No. 3,687,808; those disclosed in International Application No. PCT/US09/038425, filed Mar. 26, 2009; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P.Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

The effector molecule or the multi-targeted molecule can comprise can comprise one or more (e.g., 1, 2, 3, 4, 5, 6, 7, 8, 9, 10, 11, 12, 13, 14, 15 or more) monomer, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a locked nucleic acid or bicyclic nucleic acid. In certain embodiments, oligomeric compounds comprise one or more (e.g., 1, 2, 3, 4, 5, 6, 7, 8, 9, 10, 11, 12, 13, 14, 15 or more) monomers that are LNA.

In some embodiments of a locked nucleic acid, the 2' position of furanosyl is connected to the 4' position by a linker selected independently from —$[C(R1)(R2)]_n$-, —$[C(R1)(R2)]_n$-O—, —$[C(R1)(R2)]_n$-N(R1)-, —$[C(R1)(R2)]_n$-N(R1)-O—, —$[C(R1R2)]_n$-O—N(R1)-, —C(R1)=C(R2)-O—, —C(R1)=N—, —C(R1)=N—O—, —C(=NR1)-, —C(=NR1)-O—, —C(=O)—, —C(=O)O—, —C(=S)—, —C(=S)O—, —C(=S)S—, —O—, —Si(R1)2-, —$S(=O)_x$— and —N(R1)-;

wherein:

x is 0, 1, or 2;

n is 1, 2, 3, or 4;

each R1 and R2 is, independently, H, a protecting group, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, heterocycle radical, substituted heterocycle radical, heteroaryl, substituted heteroaryl, C5-C7 alicyclic radical, substituted C5-C7 alicyclic radical, halogen, OJ1, NJ1J2, SJ1, N3, COOJ1, acyl (C(=O)—H), substituted acyl, CN, sulfonyl (S(=O)2-J1), or sulfoxyl (S(=O)-J1); and each J1 and J2 is, independently, H, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, acyl (C(=O)—H), substituted acyl, a heterocycle radical, a substituted heterocycle radical, C1-C12 aminoalkyl, substituted C1-C12 aminoalkyl or a protecting group.

In some embodiments, each of the linkers of the LNA compounds is, independently, —[C(R1)(R2)]n-, —[C(R1)(R2)]n-O—, —C(R1R2)-N(R1)-O— or —C(R1R2)-O—N(R1)-. In another embodiment, each of said linkers is, independently, 4'-$CH_2$-2', 4'-$(CH_2)$2-2', 4'-$(CH_2)$3-2', 4'-$CH_2$—O-2', 4'-$(CH_2)$2-O-2', 4'-$CH_2$—O—N(R1)-2' and 4'-$CH_2$—N(R1)-O-2'- wherein each R1 is, independently, H, a protecting group or C1-C12 alkyl.

Certain LNA’s have been prepared and disclosed in the patent literature as well as in scientific literature (Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039; Examples of issued US patents and published applications that disclose LNA s include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

Also provided herein are LNAs in which the 2'-hydroxyl group of the ribosyl sugar ring is linked to the 4' carbon atom of the sugar ring thereby forming a methyleneoxy (4'-$CH_2$—O-2') linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—$CH_2$—) group bridging the 2' oxygen atom and the 4' carbon atom, for which the term methyleneoxy (4'-$CH_2$—O-2') LNA is used for the bicyclic moiety; in the case of an ethylene group in this position, the term ethyleneoxy (4'-$CH_2CH_2$—O-2') LNA is used (Singh et al., Chem. Commun., 1998, 4, 455-456: Morita et al., Bioorganic Medicinal Chemistry, 2003, 11, 2211-2226). Methyleneoxy (4'-$CH_2$—O-2') LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., Proc. Natl. Acad. Sci. U.S.A., 2000, 97, 5633-5638).

An isomer of methyleneoxy (4'-$CH_2$—O-2') LNA that has also been discussed is alpha-L-methyleneoxy (4'-$CH_2$—O-2') LNA which has been shown to have superior stability against a 3'-exonuclease. The alpha-L-methyleneoxy (4'-$CH_2$—O-2') LNA's were incorporated into antisense gapmers and chimeras that showed potent antisense activity (Frieden et al., Nucleic Acids Research, 2003, 21, 6365-6372).

The synthesis and preparation of the methyleneoxy (4'-$CH_2$—O-2') LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). BNAs and preparation thereof are also described in WO 98/39352 and WO 99/14226.

Analogs of methyleneoxy (4'-$CH_2$—O-2') LNA, phosphorothioate-methyleneoxy (4'-$CH_2$—O-2') LNA and 2'-thio-LNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-LNA, a novel comformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Modified sugar moieties are well known and can be used to alter, typically increase, the affinity of the antisense compound for its target and/or increase nuclease resistance. A representative list of preferred modified sugars includes but is not limited to bicyclic modified sugars, including methyleneoxy (4'-$CH_2$—O-2') LNA and ethyleneoxy (4'-($CH_2$)2-O-2' bridge) ENA; substituted sugars, especially 2'-substituted sugars having a 2'-F, 2'-$OCH_3$ or a 2'-O($CH_2$)2-$OCH_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

Examples of "oxy"-2' hydroxyl group modifications include alkoxy or aryloxy (OR, e.g., R═H, alkyl, cycloalkyl, aryl, aralkyl, heteroaryl or sugar); polyethyleneglycols (PEG), $O(CH_2CH_2O)_nCH_2CH_2OR$, n=1-50: "locked" nucleic acids (LNA) in which the furanose portion of the nucleoside includes a bridge connecting two carbon atoms on the furanose ring, thereby forming a bicyclic ring system; O-AMINE or O—$(CH_2)_n$AMINE (n=1-10, AMINE=$NH_2$; alkylamino, dialkylamino, heterocyclyl, arylamino, diaryl amino, heteroaryl amino, diheteroaryl amino, ethylene diamine or polyamino); and O—$CH_2CH_2(NCH_2CH_2NMe_2)_2$.

"Deoxy" modifications include hydrogen (i.e. deoxyribose sugars, which are of particular relevance to the single-strand overhangs); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkyl-thio-alkyl; thioalkoxy; thioalkyl; alkyl; cycloalkyl; aryl; alkenyl and alkynyl, which can be optionally substituted with e.g., an amino functionality.

Other suitable 2'-modifications, e.g., modified MOE, are described in U.S. Patent Application Publication No. 20130130378, contents of which are herein incorporated by reference.

A modification at the 2' position can be present in the arabinose configuration The term "arabinose configuration" refers to the placement of a substituent on the C2' of ribose in the same configuration as the 2'-OH is in the arabinose.

The sugar can comprise two different modifications at the same carbon in the sugar, e.g., gem modification. The sugar group can also contain one or more carbons that possess the opposite stereochemical configuration than that of the corresponding carbon in ribose. Thus, an oligomeric compound can include one or more monomers containing e.g., arabinose, as the sugar. The monomer can have an alpha linkage at the 1' position on the sugar, e.g., alpha-nucleosides. The monomer can also have the opposite configuration at the 4'-position, e.g., C5' and H4' or substituents replacing them are interchanged with each other. When the C5' and H4' or substituents replacing them are interchanged with each other, the sugar is said to be modified at the 4' position.

The effector molecule or the multi-targeted molecule can also include abasic sugars, i.e., a sugar which lack a nucleobase at C-1' or has other chemical groups in place of a nucleobase at C1'. See for example U.S. Pat. No. 5,998,203, content of which is herein incorporated in its entirety. These abasic sugars can also be further containing modifications at one or more of the constituent sugar atoms. The effector molecule or the multi-targeted molecule can also contain one or more sugars that are the L isomer, e.g. L-nucleosides. Modification to the sugar group can also include replacement of the 4'-O with a sulfur, optionally substituted nitrogen or $CH_2$ group. In some embodiments, linkage between C1' and nucleobase is in a configuration.

Sugar modifications can also include acyclic nucleotides, wherein a C—C bonds between ribose carbons (e.g., C1'-C2', C2'-C3', C3'-C4', C4'-O4', C1'-O4') is absent and/or at least one of ribose carbons or oxygen (e.g., C1', C2', C3', C4' or O4') are independently or in combination absent from the nucleotide. In some embodiments, acyclic nucleotide is

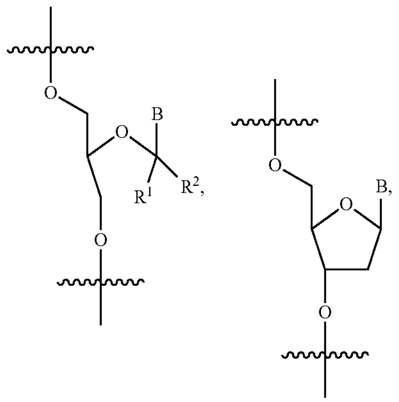

-continued

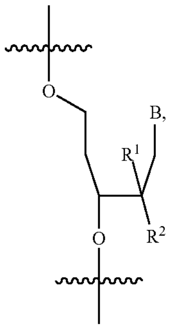

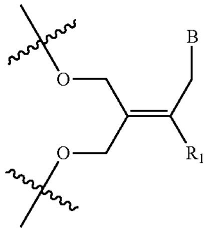

or

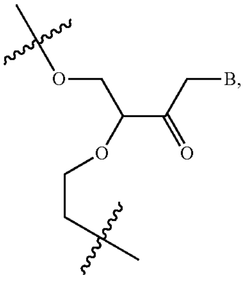

wherein B is a modified or unmodified nucleobase, $R_1$ and $R_2$ independently are H, halogen, $OR_3$, or alkyl; and $R_3$ is H, alkyl, cycloalkyl, aryl, aralkyl, heteroaryl or sugar).

In some embodiments, sugar modifications are selected from the group consisting of 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE) and gem 2'-OMe/2'F with 2'-O-Me in the arabinose configuration.

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position. A modification at the 3' position can be present in the xylose configuration The term "xylose configuration" refers to the placement of a substituent on the C3' of ribose in the same configuration as the 3'-OH is in the xylose sugar.

The hydrogen attached to C4' and/or C1' can be replaced by a straight- or branched-optionally substituted alkyl, optionally substituted alkenyl, optionally substituted alkynyl, wherein backbone of the alkyl, alkenyl and alkynyl can contain one or more of O, S, S(O), $SO_2$, N(R'), C(O), N(R')C(O)O, OC(O)N(R'), CH(Z'), phosphorous containing linkage, optionally substituted aryl, optionally substituted heteroaryl, optionally substituted heterocyclic or optionally substituted cycloalkyl, where R' is hydrogen, acyl or optionally substituted aliphatic. Z' is selected from the group consisting of $OR_{11}$, $COR_{11}$, $CO_2R_{11}$,

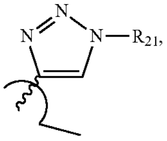

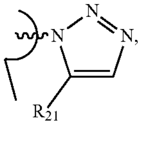

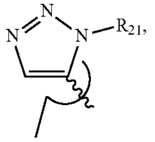

-continued

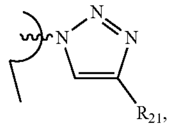

$NR_{21}R_{31}$, $CONR_{21}R_{31}$, $CON(H)NR_{21}R_{31}$, $ONR_{21}R_{31}$, $CON(H)N{=}CR_{41}R_{51}$, $N(R_{21})C({=}NR_{31})NR_{21}R_{31}$, $N(R_{21})C(O)NR_{21}R_{31}$, $N(R_{21})C(S)NR_{21}R_{31}$, $OC(O)NR_{21}R_{31}$, $SC(ONR_{21}R_{31}$, $N(R_{21})C(S)OR_{11}$, $N(R_{21})C(O)OR_{11}$, $N(R_{21})C(O)SR_{11}$, $N(R_{21})N{=}CR_{41}R_{51}$, $ON{=}CR_{41}R_{51}$, $SO_2R_{11}$, $SOR_{11}$, $SR_{11}$, and substituted or unsubstituted heterocyclic; $R_{21}$ and $R_{31}$ for each occurrence are independently hydrogen, acyl, unsubstituted or substituted aliphatic, aryl, heteroaryl, heterocycle, $OR_{11}$, $COR_{11}$, $CO_2R_{11}$, or $NR_{11}R_{11}'$; or $R_{21}$ and $R_{31}$, taken together with the atoms to which they are attached, form a heterocyclic ring; $R_{41}$ and $R_{51}$ for each occurrence are independently hydrogen, acyl, unsubstituted or substituted aliphatic, aryl, heteroaryl, heterocyclic, $OR_{11}$, $COR_{11}$, or $CO_2R_{11}$, or $NR_{11}R_{11}'$; and $R_{11}$ and $R_{11}'$ are independently hydrogen, aliphatic, substituted aliphatic, aryl, heteroaryl, or heterocyclic. In some embodiments, the hydrogen attached to the C4' of the 5' terminal nucleotide is replaced.

In some embodiments, C4' and C5' together form an optionally substituted heterocyclic, preferably comprising at least one —PX(Y)—, wherein X is H, OH, OM, SH, optionally substituted alkyl, optionally substituted alkoxy, optionally substituted alkylthio, optionally substituted alkylamino or optionally substituted dialkylamino, where M is independently for each occurrence an alki metal or transition metal with an overall charge of +1; and Y is O, S, or NR', where R' is hydrogen, optionally substituted aliphatic. Preferably this modification is at the 5 terminal of the oligonucleotide.

In certain embodiments, LNA's include bicyclic nucleoside having the formula:

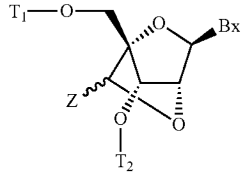

wherein:

Bx is a heterocyclic base moiety;

T1 is H or a hydroxyl protecting group;

T2 is H, a hydroxyl protecting group or a reactive phosphorus group;

Z is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, or substituted amide.

In some embodiments, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In certain such embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J, J2 and J3 is, independently, H, C1-C6 alkyl, or substituted C1-C6 alkyl and X is O or NJ 1.

In certain embodiments, the Z group is C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is C1-C6 alkyl substituted with one or more Xx, wherein each Xx is independently halo (e.g., fluoro), hydroxyl, alkoxy (e.g., CH3O—), substituted alkoxy or azido.

In certain embodiments, the Z group is —CH2Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is —$CH_2$Xx, wherein Xx is halo (e.g., fluoro), hydroxyl, alkoxy (e.g., CH3O—) or azido.

In certain such embodiments, the Z group is in the (R)-configuration:

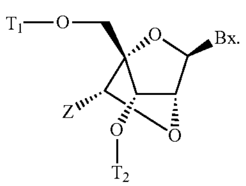

In certain such embodiments, the Z group is in the (S)-configuration:

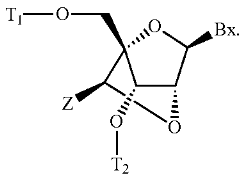

In certain embodiments, each T1 and T2 is a hydroxyl protecting group. A preferred list of hydroxyl protecting groups includes benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, T1 is a hydroxyl protecting group selected from acetyl, benzyl, t-butyldimethylsilyl, t-butyldiphenylsilyl and dimethoxytrityl wherein a more preferred hydroxyl protecting group is T1 is 4,4'-dimethoxytrityl.

In certain embodiments, T2 is a reactive phosphorus group wherein preferred reactive phosphorus groups include diisopropylcyanoethoxy phosphoramidite and H-phosphonate. In certain embodiments T1 is 4,4'-dimethoxytrityl and T2 is diisopropylcyanoethoxy phosphoramidite.

In certain embodiments, the multi-targeted molecules comprise at least one monomer of the formula:

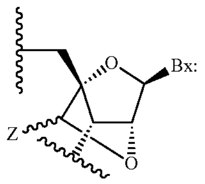

or of the formula

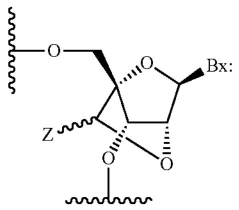

or of the formula

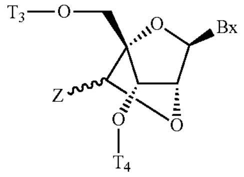

wherein

Bx is a heterocyclic base moiety;

T3 is H, a hydroxyl protecting group, a linked conjugate group or an internucleoside linking group attached to a nucleoside, a nucleotide, an oligonucleoside, an oligonucleotide, a monomeric subunit or an oligomeric compound;

T4 is H, a hydroxyl protecting group, a linked conjugate group or an internucleoside linking group attached to a nucleoside, a nucleotide, an oligonucleoside, an oligonucleotide, a monomeric subunit or an oligomeric compound;

wherein at least one of T3 and T4 is an internucleoside linking group attached to a nucleoside, a nucleotide, an oligonucleoside, an oligonucleotide, a monomeric subunit or an oligomeric compound; and Z is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, or substituted amide.

In some embodiments, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In some embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H or C1-C6 alkyl, and X is O or NJ1.

In certain such embodiments, at least one Z is C1-C6 alkyl or substituted C1-C6 alkyl. In certain embodiments, each Z is, independently, C1-C6 alkyl or substituted C1-C6 alkyl. In certain embodiments, at least one Z is C1-C6 alkyl. In certain embodiments, each Z is, independently, C1-C6 alkyl. In certain embodiments, at least one Z is methyl. In certain embodiments, each Z is methyl. In certain embodiments, at least one Z is ethyl. In certain embodiments, each Z is ethyl. In certain embodiments, at least one Z is substituted C1-C6 alkyl. In certain embodiments, each Z is, independently, substituted C1-C6 alkyl. In certain embodiments, at least one Z is substituted methyl. In certain embodiments, each Z is substituted methyl. In certain embodiments, at least one Z is substituted ethyl. In certain embodiments, each Z is substituted ethyl.

In certain embodiments, at least one substituent group is C1-C6 alkoxy (e.g., at least one Z is C1-C6 alkyl substituted with one or more C1-C6 alkoxy). In another embodiment, each substituent group is, independently. C1-C6 alkoxy (e.g., each Z is, independently. C1-C6 alkyl substituted with one or more C1-C6 alkoxy).

In certain embodiments, at least one C1-C6 alkoxy substituent group is CH3O— (e.g., at least one Z is $CH_3OCH_2$—). In another embodiment, each C1-C6 alkoxy substituent group is $CH_3O$— (e.g., each Z is $CH_3OCH_2$—).

In certain embodiments, at least one substituent group is halogen (e.g., at least one Z is C1-C6 alkyl substituted with one or more halogen). In certain embodiments, each substituent group is, independently, halogen (e.g., each Z is, independently, C1-C6 alkyl substituted with one or more halogen). In certain embodiments, at least one halogen substituent group is fluoro (e.g., at least one Z is $CH_2FCH_2$—, $CHF_2CH_2$— or $CF_3CH_2$—). In certain embodiments, each halo substituent group is fluoro (e.g., each Z is, independently, $CH_2FCH_2$—, $CHF_2CH_2$— or $CF_3CH_2$—).

In certain embodiments, at least one substituent group is hydroxyl (e.g., at least one Z is C1-C6 alkyl substituted with one or more hydroxyl). In certain embodiments, each substituent group is, independently, hydroxyl (e.g., each Z is, independently, C1-C6 alkyl substituted with one or more hydroxyl). In certain embodiments, at least one Z is $HOCH_2$—. In another embodiment, each Z is $HOCH_2$—.

In certain embodiments, at least one Z is $CH_3$—, $CH_3CH_2$—, $CH_2OCH_3$—, $CH_2F$— or $HOCH_2$—. In certain embodiments, each Z is, independently, $CH_3$—, $CH_3CH_2$—, $CH_2OCH_3$—, $CH_2F$— or $HOCH_2$—.

In certain embodiments, at least one Z group is C1-C6 alkyl substituted with one or more Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, at least one Z group is C1-C6 alkyl substituted with one or more Xx, wherein each Xx is, independently, halo (e.g., fluoro), hydroxyl, alkoxy (e.g., CH3O—) or azido.

In certain embodiments, each Z group is, independently, C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, C1-C6 alkyl substituted with one or more Xx, wherein each Xx is independently halo (e.g., fluoro), hydroxyl, alkoxy (e.g., CH3O—) or azido.

In certain embodiments, at least one Z group is —$CH_2$Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1 In certain embodiments, at least one Z group is —$CH_2$Xx, wherein Xx is halo (e.g., fluoro), hydroxyl, alkoxy (e.g., $CH_3O$—) or azido.

In certain embodiments, each Z group is, independently, —$CH_2$Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, —$CH_2$Xx, wherein each Xx is, independently, halo (e.g., fluoro), hydroxyl, alkoxy (e.g., $CH_3O$—) or azido.

In certain embodiments, at least one Z is $CH_3$—. In another embodiment, each Z is, $CH_3$—.

In certain embodiments, the Z group of at least one monomer is in the (R)-configuration represented by the formula:

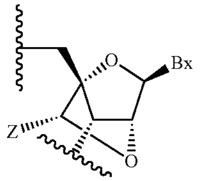

or the formula:

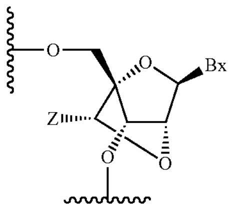

or the formula:

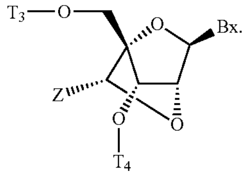

In certain embodiments, the Z group of each monomer of the formula is in the (R)-configuration.

In certain embodiments, the Z group of at least one monomer is in the (S)-configuration represented by the formula:

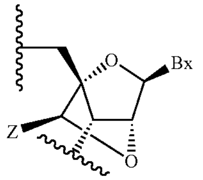

or the formula:

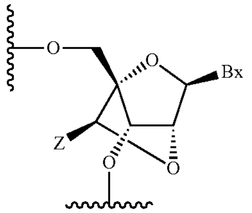

or the formula:

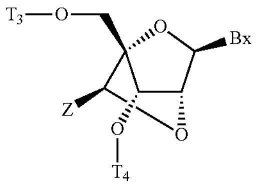

In certain embodiments, the Z group of each monomer of the formula is in the (S)-configuration.

In certain embodiments, T3 is H or a hydroxyl protecting group. In certain embodiments, T4 is H or a hydroxyl protecting group. In a further embodiment T3 is an internucleoside linking group attached to a nucleoside, a nucleotide or a monomeric subunit. In certain embodiments, T4 is an internucleoside linking group attached to a nucleoside, a nucleotide or a monomeric subunit. In certain embodiments, T3 is an internucleoside linking group attached to an oligonucleoside or an oligonucleotide. In certain embodiments, T4 is an internucleoside linking group attached to an oligonucleoside or an oligonucleotide. In certain embodiments. T3 is an internucleoside linking group attached to an oligomeric compound. In certain embodiments, T4 is an internucleoside linking group attached to an oligomeric compound. In certain embodiments, at least one of T3 and T4 comprises an internucleoside linking group selected from phosphodiester or phosphorothioate.

In certain embodiments, the effector molecule or the multi-targeted molecule can comprise at least one region of at least two contiguous monomers of the formula:

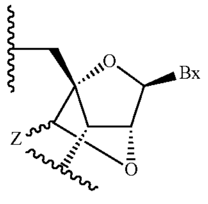

or of the formula:

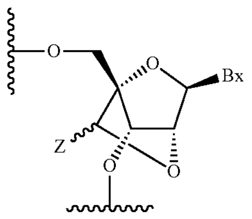

or of the formula:

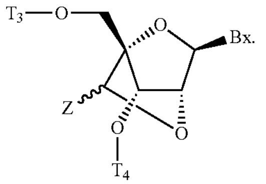

In certain such embodiments, LNAs include, but are not limited to, (A) α-L-Methyleneoxy (4'-CH2-O-2') LNA, (B) β-D-Methyleneoxy (4'-CH2-O-2') LNA, (C) Ethyleneoxy (4'-(CH2)2-O-2') LNA, (D) Aminooxy (4'-CH2-O—N(R)-2') LNA and (E) Oxyamino (4'-CH2-N(R)—O-2') LNA, as depicted below:

(A)

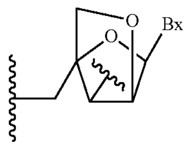

(B)

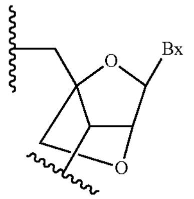

(C)

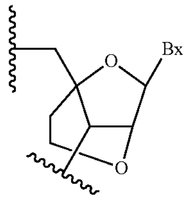

(D)

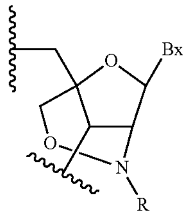

(E)

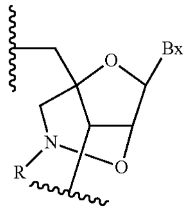

In certain embodiments, the effector molecule or the multi-targeted molecule can comprise at least two regions of at least two contiguous monomers of the above formula. In certain embodiments, the multi-targeted molecule comprises a gapped motif. In certain embodiments, the multi-targeted molecule comprises at least one region of from about 8 to about 14 contiguous β-D-2'-deoxyribofuranosyl nucleosides. In certain embodiments, the Multi-targeted molecule comprises at least one region of from about 9 to about 12 contiguous β-D-2'-deoxyribofuranosyl nucleosides.

In certain embodiments, the multi-targeted molecule comprises at least one (e.g., 1, 2, 3, 4, 5, 6, 7, 8, 9, 10, 11, 12, 13, 14, 15 or more) comprises at least one (S)-cEt monomer of the formula:

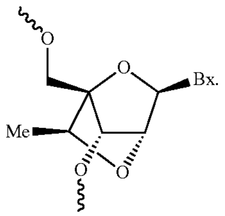

S-cEt (C)

wherein Bx IS heterocyclic base moiety.

In certain embodiments, monomers include sugar mimetics. In certain such embodiments, a mimetic is used in place of the sugar or sugar-internucleoside linkage combination, and the nucleobase is maintained for hybridization to a selected target. Representative examples of a sugar mimetics include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances, a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

Nucleic Acid Modifications (Intersugar Linkage)

Described herein are linking groups that link monomers (including, but not limited to, modified and unmodified nucleosides and nucleotides) together, thereby forming an oligomeric compound, e.g., an oligonucleotide. Such linking groups are also referred to as intersugar linkage. The two main classes of linking groups are defined by the presence or absence of a phosphorus atom. Representative phosphorus containing linkages include, but are not limited to, phosphodiesters (P═O), phosphotriesters, methylphosphonates, phosphoramidate, and phosphorothioates (P═S). Representative non-phosphorus containing linking groups include, but are not limited to, methylenemethylimino (—CH2-N(CH3)-O-CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Modified linkages, compared to natural phosphodiester linkages, can be used to alter, typically increase, nuclease resistance of the oligonucleotides. In certain embodiments, linkages having a chiral atom can be prepared as racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The phosphate group in the linking group can be modified by replacing one of the oxygens with a different substituent. One result of this modification can be increased resistance of the oligonucleotide to nucleolytic breakdown. Examples of modified phosphate groups include phosphorothioate, phosphoroselenates, borano phosphates, borano phosphate esters, hydrogen phosphonates, phosphoramidates, alkyl or aryl phosphonates and phosphotriesters. In some embodiments, one of the non-bridging phosphate oxygen atoms in the linkage can be replaced by any of the following: S, Se, $BR_3$ (R is hydrogen, alkyl, aryl), C (i.e. an alkyl group, an aryl group, etc. . . . ), H, $NR_2$ (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words, a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the sugar of the monomer), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker."

In certain embodiments, the phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-$CH_2$—C(═O)—N(H)-5') and amide-4 (3'-$CH_2$—N(H)—C(═O)-5')), hydroxylamino, siloxane (dialkylsiloxane), carboxamide, carbonate, carboxymethyl, carbamate, carboxylate ester, thioether, ethylene oxide linker, sulfide, sulfonate, sulfonamide, sulfonate ester, thioformacetal (3'-S—$CH_2$—O-5'), formacetal (3'-O—$CH_2$—O-5'), oxime, methyleneimino, methylenecarbonylamino, methylenemethylimino (MMI, 3'-$CH_2$—N($CH_3$)—O-5'), methylenehydrazo, methylenedimethylhydrazo, methyleneoxymethylimino, ethers (C3'-O—C5'), thioethers (C3'-S—C5'), thioacetamido (C3'-N(H)—C(═O)—$CH_2$—S—C5', C3'-O—P(O)—O—SS—C5', C3'—$CH_2$—NH—NH—C5', 3'-NHP(O)($OCH_3$)—O-5' and 3'-NHP(O)($OCH_3$)—O-5' and nonionic linkages containing mixed N, O, S and $CH_2$ component parts. See for example, Carbohydrate Modifications in Antisense Research; Y. S. Sanghvi and P. D. Cook Eds. ACS Symposium Series 580; Chapters 3 and 4, (pp.

40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phsophotriesters, aminoalkylphosphotrioesters, alkyl-phosphonaters (e.g., methylphosphonate), selenophosphates, phosphoramidates (e.g., N-alkylphosphoramidate), and boranophosphonates.

In some embodiments, the multi-targeted molecule comprises at least one (e.g., 1, 2, 3, 4, 5, 6, 7, 8, 9, 10, 11, 12, 13, 14, 15 or more and up to including all) modified or nonphosphodiester linkages. In some embodiments, effector molecule or the multi-targeted molecule can comprise at least one (e.g., 1, 2, 3, 4, 5, 6, 7, 8, 9, 10, 11, 12, 13, 14, 15 or more and up to including all) phosphorothioate linkages.

The effector molecule or the multi-targeted molecule can also be constructed wherein the phosphate linker and the sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backbone-extended pyrrolidine PNA (bepPNA) nucleoside surrogates. A preferred surrogate is a PNA surrogate.

The effector molecule or the multi-targeted molecule can comprise one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the multi-targeted molecules provided herein are all such possible isomers, as well as their racemic and optically pure forms.

Ends of the multi-targeted molecules or the effector molecules can be modified. Such modifications can be at one end or both ends. For example, the 3' and/or 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a double stranded oligomeric compound, this array can substitute for a hairpin loop in a hairpin-type oligomeric compound.

Terminal modifications useful for modulating activity include modification of the 5' end of oligonucleotides with phosphate or phosphate analogs. In certain embodiments, the 5'end of an oligonucleotide is phosphorylated or includes a phosphoryl analog. Exemplary 5'-phosphate modifications include those which are compatible with RISC mediated gene silencing. Modifications at the Y-terminal end can also be useful in stimulating or inhibiting the immune system of a subject. In some embodiments, the 5'-end of the oligomeric compound comprises the modification

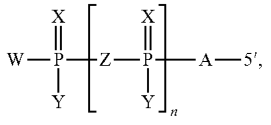

wherein W, X and Y are each independently selected from the group consisting of O, OR (R is hydrogen, alkyl, aryl), S, Se, $BR_3$ (R is hydrogen, alkyl, aryl), $BH_3^-$, C (i.e. an alkyl group, an aryl group, etc. . . . ), H, $NR_2$ (R is hydrogen, alkyl, aryl), or OR (R is hydrogen, alkyl or aryl); A and Z are each independently for each occurrence absent. O, S, $CH_2$, NR (R is hydrogen, alkyl, aryl), or optionally substituted alkylene, wherein backbone of the alkylene can comprise one or more of O, S, SS and NR (R is hydrogen, alkyl, aryl) internally and/or at the end; and n is 0-2. In some embodiments, n is 1 or 2. It is understood that A is replacing the oxygen linked to 5' carbon of sugar. When n is 0, W and Y together with the P to which they are attached can form an optionally substituted 5-8 membered heterocyclic, wherein W an Y are each independently O, S, NR' or alkylene. Preferably the heterocyclic is substituted with an aryl or heteroaryl. In some embodiments, one or both hydrogen on C5' of the 5'-terminal nucleotides are replaced with a halogen, e.g., F.

Exemplary 5'-modifications include, but are not limited to, 5'-monophosphate ($(HO)_2(O)P$—O-5'); 5'-diphosphate ($(HO)_2(O)P$—O—P(HO)(O)—O-5'); 5'-triphosphate ((HO) $_2$(O)P—O—(HO)(O)P—O—P(HO)(O)—O-5'); 5'-monothiophosphate (phosphorothioate; (HO)2(S)P—O-5'); 5'-monodithiophosphate (phosphorodithioate: (HO)(HS)(S) P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates ($(HO)_2(O)P$—NH-5', $(HO)(NH_2)(O)P$—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl ($CH_2OMe$), ethoxymethyl, etc. . . . ). Other exemplary 5'-modifications include where Z is optionally substituted alkyl at least once, e.g., $((HO)_2(X)P$—O[—$(CH_2)_a$—O—P(X)(OH)—O$]_b$-5', ((HO)2(X)P—O [—$(CH_2)_a$—P(X)(OH)—O$]_b$-5', ((HO)2(X)P—[—$(CH_2)_a$—O—P(X)(OH)—O$]_b$-5'; dialkyl terminal phosphates and phosphate mimics: HO[—$(CH_2)_a$—O—P(X) (OH)—O$]_b$-5', $H_2N$[—$(CH_2)_a$—O—P(X)(OH)—O$]_b$-5', H[—$(CH_2)_a$—O—P(X)(OH)—O$]_b$-5', $Me_2N$[—$(CH_2)_a$—O—P(X)(OH)—O$]_b$-5', HO[—$(CH_2)_a$—P(X)(OH)—O$]_b$-5', $H_2N$[—$(CH_2)_a$—P(X)(OH)—O$]_b$-5', H[—$(CH_2)_a$—P(X) (OH)—O$]_b$-5', $Me_2N$[—$(CH_2)_a$—P(X)(OH)—O$]_b$-5', wherein a and b are each independently 1-10. Other embodiments, include replacement of oxygen and/or sulfur with $BH_3$, $BH_3^-$ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

The effector molecules, such as siRNAs or dsRNA agents, can be optimized for RNA interference by increasing the propensity of the dsRNA duplex to disassociate or melt (decreasing the free energy of duplex association) by introducing a thermally destabilizing modification in the sense strand at a site opposite to the seed region of the antisense strand (i.e., at positions 2-8 of the 5'-end of the antisense strand). This modification can increase the propensity of the duplex to disassociate or melt in the seed region of the antisense strand.

The thermally destabilizing modifications can include abasic modification; mismatch with the opposing nucleotide in the opposing strand; and sugar modification such as 2'-deoxy modification or acyclic nucleotide, e.g., unlocked nucleic acids (UNA) or glycerol nucleic acid (GNA).

Exemplified abasic modifications are:

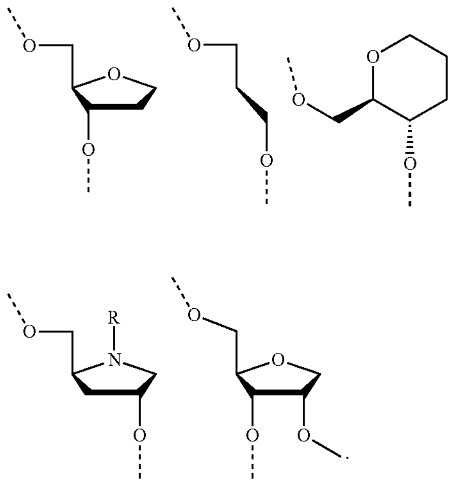

Exemplified sugar modifications are:

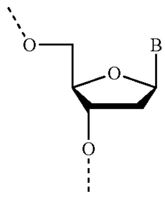

2'-deoxy

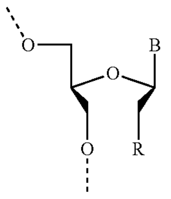

unlocked nucleic acid
R = H, OH, O-alkyl

-continued

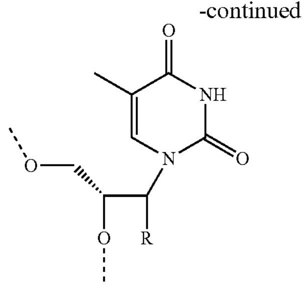

glycol nucleic acid
R = H, OH, O-alkyl

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent and/or at least one of ribose carbons or oxygen (e.g., C1', C2', C3', C4' or O4') are independently or in combination absent from the nucleotide. In some embodiments, acyclic nucleotide is

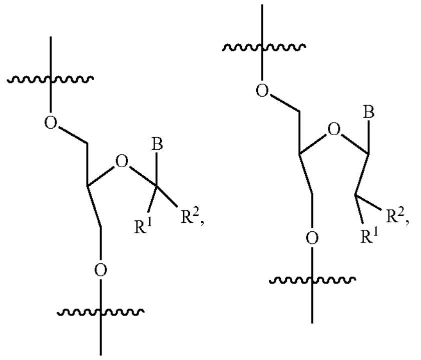

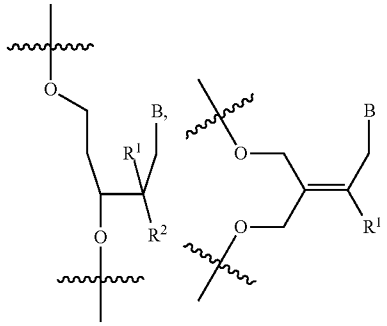

or

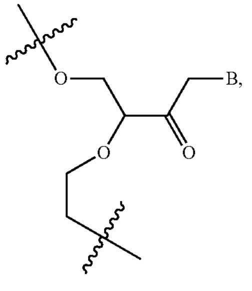

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

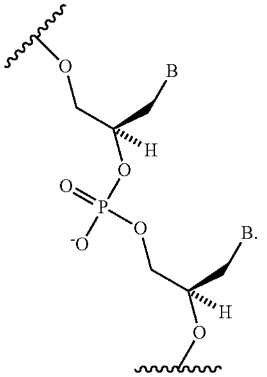

(R)-GNA

The thermally destabilizing modification can be mismatches (i.e., noncomplementary base pairs) between the thermally destabilizing nucleotide and the opposing nucleotide in the opposite strand within the dsRNA duplex. Exemplary mismatch basepairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the effector molecule, such as siRNA or dsRNA agent, contains at least one nucleobase in the mismatch pairing that is a 2'-deoxy nucleobase; e.g., the 2'-deoxy nucleobase is in the sense strand.

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

Nucleobase modifications with impaired or completely abolished capability to form hydrogen bonds with bases in the opposite strand have been evaluated for destabilization of the central region of the dsRNA duplex as described in WO 2010/0011895, which is herein incorporated by reference in its entirety. Exemplary nucleobase modifications are:

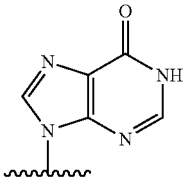

inosine

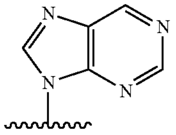

nebularine

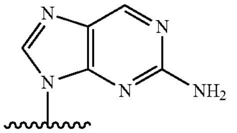

2-aminopurine

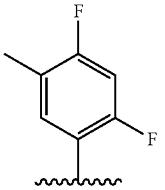

2,4-difluorotoluene

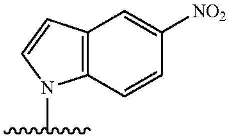

5-nitroindole

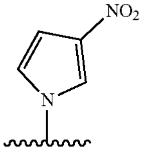

3-nitropyrrole

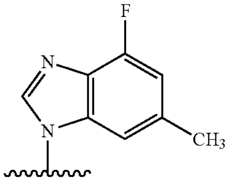

4-Fluoro-6-methybenzimidazole

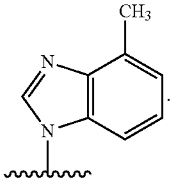

4-Methybenzimidazole

Exemplary phosphate modifications known to decrease the thermal stability of dsRNA duplexes compared to natural phosphodiester linkages are:

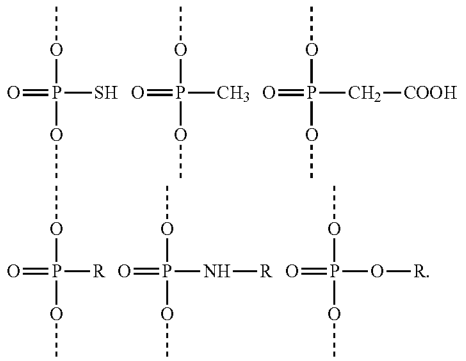

R = alkyl

In some embodiments, an effector molecule in the multi-targeted molecule can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, an effector molecule in the multi-targeted molecule can comprise L sugars (e.g., L ribose, L-arabinose with 2'-H, 2'-OH and 2'-OMe). For example, these L sugar modifications can be used to promote nuclease resistance or to inhibit binding of the sense to the antisense strand, or can be used at the 5' end of the sense strand to avoid sense strand activation by RISC.

In one embodiment the dsRNA agent of the invention is conjugated to a ligand via a carrier, wherein the carrier can be cyclic group or acyclic group: preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In some embodiments, at least one strand of at least one effector molecule in the multi-targeted molecules disclosed herein is 5' phosphorylated or includes a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate: (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), (OH)2(O)P-5'-$CH_2$—), 5'-alkyletherphosphonates (R=alkylether=methoxymethyl (MeOCH2-), ethoxymethyl, etc., e.g. RP(OH)(O)—O-5'-).

The present invention also includes effector molecules and multi-targeted molecules which are chimeric compounds. "Chimeric" compounds or "chimeras," in the context of this invention, are compounds which contain two or more chemically distinct regions, each made up of at least one monomer unit, e.g., a modified or unmodified nucleotide in the case of an oligonucleotide. Chimeric compounds can be described as having a particular motif. In some embodiments, the motifs include, but are not limited to, an alternating motif, a gapped motif, a hemimer motif, a uniformly fully modified motif and a positionally modified motif. As used herein, the phrase "chemically distinct region" refers to a region in the multi-targeted molecule which is different from other regions by having a modification that is not present elsewhere in the compound or by not having a modification that is present elsewhere in the compound. A multi-targeted molecule can comprise two or more chemically distinct regions. As used herein, a region that comprises no modifications is also considered chemically distinct.

A chemically distinct region can be repeated within a multi-targeted molecule compound. Thus, a pattern of chemically distinct regions in multi-targeted molecule can be realized such that a first chemically distinct region is followed by one or more second chemically distinct regions. This sequence of chemically distinct regions can be repeated one or more times. Preferably, the sequence is repeated more than one time. For example, both strands of a double-stranded effector molecule can comprise these sequences. Each chemically distinct region can actually comprise as little as single monomers, e.g., nucleotides. In some embodiments, each chemically distinct region comprises 1, 2, 3, 4, 5, 6, 7, 8, 9, 10, 11, 12, 13, 14, 15, 16, 17 or 18 monomers, e.g., nucleotides.

In some embodiments, alternating nucleotides comprise the same modification, e.g. all the odd number nucleotides in a strand have the same modification and/or all the even number nucleotides in a strand have the similar modification to the first strand. In some embodiments, all the odd number nucleotides in double-stranded effector molecule or the multi-targeted molecule have the same modification and all the even numbered nucleotides have a modification that is not present in the odd number nucleotides and vice versa.

When both strands of a double-stranded molecule comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other.

In some embodiments, the first strand has an alternating modification pattern wherein alternating nucleotides comprise a 2'-modification, e.g., 2'-O-Methyl modification. In some embodiments, the first strand comprises an alternating 2'-O-Methyl modification and the second strand comprises an alternating 2'-fluoro modification. In other embodiments, both strands of a double-stranded oligonucleotide comprise alternating 2'-O-methyl modifications.

When both strands of a double-stranded oligonucleotide comprise alternating 2'-O-methyl modifications, such 2'-modified nucleotides can be in complementary position in the duplex region. Alternatively, such 2'-modified nucleotides may not be in complementary positions in the duplex region.

In some embodiments, an oligonucleotide present in the multi-targeted molecule comprises two chemically distinct regions, wherein each region is 1, 2, 3, 4, 5, 6, 7, 8, 9 or 10 nucleotides in length.

In other embodiments, an oligonucleotide present in the multi-targeted molecule comprises three chemically distinct regions. The middle region is about 5-15, (e.g., 5, 6, 7, 8, 9, 10, 11, 12, 13, 14 or 15) nucleotide in length and each flanking or wing region is independently 1-10 (e.g., 1, 2, 3, 4, 5, 6, 7, 8, 9 or 10) nucleotides in length. All three regions can have different modifications or the wing regions can be similarly modified to each other. In some embodiments, the wing regions are of equal length, e.g. 1, 2, 3, 4, 5, 6, 7, 8, 9 or 10 nucleotides long.

As used herein the term "alternating motif" refers to compound comprising a contiguous sequence of linked monomer subunits wherein the monomer subunits have two different types of sugar groups that alternate for essentially the entire sequence of the compound. Oligonucleotides having an alternating motif can be described by the formula: 5'-A(-L-B-L-A)n(-L-B)m-3' where A and B are monomelic subunits that have different sugar groups, each L is an internucleoside linking group, n is from about 4 to about 12 and m is 0 or 1. This permits a compound with an alternating motif from about 9 to about 26 monomer subunits in length. This length range is not meant to be limiting as longer and shorter compounds are also amenable to the present invention. In some embodiments, one of A and B is a 2'-modified nucleoside as provided herein.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "type region" refers to a portion of a compound wherein the nucleosides and internucleoside linkages within the region all comprise the same type of modifications; and the nucleosides and/or the internucleoside linkages of any neighboring portions include at least one different type of modification. As used herein the term "uniformly fully modified motif" refers to an oligonucleotide comprising a contiguous sequence of linked monomer subunits that each have the same type of sugar group. In some embodiments, the uniformly fully modified motif includes a contiguous sequence of nucleosides of the invention. In some embodiments, one or both of the 3' and 5'-ends of the contiguous sequence of the nucleosides provided herein, comprise terminal groups such as one or more unmodified nucleosides.

In certain embodiments, the 5'-terminal monomer of a compound, e.g., multi-targeted molecule or an effector molecule, comprises a phosphorous moiety at the 5'-end. In certain embodiments the 5'-terminal monomer comprises a 2'-modification. In certain such embodiments, the 2'-modification of the 5'-terminal monomer is a cationic modification. In certain embodiments, the 5'-terminal monomer comprises a 5'-modification. In certain embodiments, the 5'-terminal monomer comprises a 2'-modification and a 5'-modification. In certain embodiments, the 5'-terminal monomer is a 5'-stabilizing nucleoside. In certain embodiments, the modifications of the 5'-terminal monomer stabilize the 5'-phosphate. In certain embodiments, compounds comprising modifications of the 5'-terminal monomer are resistant to exonucleases. In certain embodiments, compounds comprising modifications of the 5'-terminal monomer have improved gene expression modulating properties.

In certain embodiments, the 5'terminal monomer is attached to the rest of the compound via a modified linkage. In certain such embodiments, the 5'-terminal monomer is attached to the rest of the compound by a phosphorothioate linkage.

In certain embodiments, oligomeric compounds of the present invention comprise one or more regions of alternating modifications. In certain embodiments, oligomeric compounds comprise one or more regions of alternating nucleoside modifications. In certain embodiments, oligomeric compounds comprise one or more regions of alternating linkage modifications. In certain embodiments, oligomeric compounds comprise one or more regions of alternating nucleoside and linkage modifications.

In certain embodiments, oligomeric compounds of the present invention comprise one or more regions of alternating 2'-F modified nucleosides and 2'-OMe modified nucleosides. In certain such embodiments, such regions of alternating 2'F modified and 2'OMe modified nucleosides also comprise alternating linkages. In certain such embodiments, the linkages at the 3' end of the 2'-F modified nucleosides are phosphorothioate linkages. In certain such embodiments, the linkages at the 3'end of the 2'OMe nucleosides are phosphodiester linkages.

In certain embodiments, such alternating regions are:

(2'-F)—(PS)-(2'-OMe)-(PO)

In certain embodiments, oligomeric compounds comprise 2, 3, 4, 5, 6, 7, 8, 9, 10, or 11 such alternating regions. Such regions may be contiguous or may be interrupted by differently modified nucleosides or linkages.

In certain embodiments, one or more alternating regions in an alternating motif include more than a single nucleoside of a type. For example, oligomeric compounds of the present invention may include one or more regions of any of the following nucleoside motifs:

ABA;
ABBA;
AABA;
AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, LNA, DNA and MOE.

In certain embodiments, A is DNA. In certain embodiments B is DNA. In some embodiments, A is 4'-$CH_2$O-2'-LNA. In certain embodiments, B is 4'-$CH_2$O-2'-LNA. In certain embodiments, A is DNA and B is 4'-$CH_2$O-2'-LNA. In certain embodiments A is 4'-$CH_2$O-2'-LNA and B is DNA.

In certain embodiments, A is 2'-OMe. In certain embodiments B is 2'-OMe. In certain embodiments, A is 2'-OMe and B is 4'-$CH_2$O-2'-LNA. In certain embodiments A is 4'-$CH_2$O-2'-LNA and B is 2'-OMe. In certain embodiments, A is 2'-OMe and B is DNA. In certain embodiments A is DNA and B is 2'-OMe.

In certain embodiments, A is (S)-cEt. In some embodiments, B is (S)-cEt. In certain embodiments, A is 2'-OMe and B is (S)-cEt. In certain embodiments A is (S)-cEt and B is 2'-OMe. In certain embodiments, A is DNA and B is (S)-cEt. In certain embodiments A is (S)-cEt and B is DNA.

In certain embodiments, A is 2'-F. In certain embodiments B is 2'-F. In certain embodiments, A is 2'-F and B is 4'-$CH_2$O-2'-LNA. In certain embodiments A is 4'-$CH_2$O-2'-LNA and B is 2'-F. In certain embodiments, A is 2'-F and B is (S)-cEt. In certain embodiments A is (S)-cEt and B is 2'-F. In certain embodiments, A is 2'-F and B is DNA. In certain embodiments A is DNA and B is 2'-F. In certain embodiments, A is 2'-OMe and B is 2'-F. In certain embodiments, A is DNA and B is 2'-OMe. In certain embodiments, A is 2'-OMe and B is DNA.

In certain embodiments, oligomeric compounds having such an alternating motif also comprise a 5' terminal nucleoside comprising a phosphate stabilizing modification. In certain embodiments, oligomeric compounds having such an alternating motif also comprise a 5' terminal nucleoside comprising a 2'-cationic modification. In certain embodiments, oligomeric compounds having such an alternating motif also comprise a 5' terminal modification.

Two-Two-Three Motifs

In certain embodiments, an oligonucleotide in the multi-targeted molecule comprises a region having a 2-2-3 motif. Such regions comprises the following motif:

$$5'\text{-}(E)_w\text{-}(A)_2\text{-}(B)_x\text{-}(A)_2\text{-}(C)_y\text{-}(A)_3\text{-}(D)_z$$

wherein: A is a first type of modified nucleoside;

B, C, D, and E are nucleosides that are differently modified than A, however, B, C, D, and E may have the same or different modifications as one another;

w and z are from 0 to 15;

x and y are from 1 to 15.

In certain embodiments, A is a 2'-OMe modified nucleoside. In certain embodiments, B, C, D, and E are all 2'-F modified nucleosides. In certain embodiments, A is a 2'-OMe modified nucleoside and B, C, D, and E are all 2'-F modified nucleosides.

In certain embodiments, the linkages of a 2-2-3 motif are all modified linkages. In certain embodiments, the linkages are all phosphorothioate linkages. In certain embodiments, the linkages at the 3'-end of each modification of the first type are phosphodiester.

In certain embodiments, Z is 0. In such embodiments, the region of three nucleosides of the first type are at the 3'-end of the oligonucleotide. In certain embodiments, such region is at the 3'-end of the oligomeric compound, with no additional groups attached to the 3' end of the region of three nucleosides of the first type. In certain embodiments, an oligomeric compound comprising an oligonucleotide where Z is 0, may comprise a terminal group attached to the 3'-terminal nucleoside. Such terminal groups may include additional nucleosides. Such additional nucleosides are typically non-hybridizing nucleosides.

In certain embodiments, Z is 1-3. In certain embodiments, Z is 2. In certain embodiments, the nucleosides of Z are 2'-MOE nucleosides. In certain embodiments, Z represents non-hybridizing nucleosides. To avoid confusion, it is noted that such non-hybridizing nucleosides might also be described as a 3'-terminal group with Z=0.

Combination Motifs

It is to be understood, that certain of the above described motifs and modifications can be combined. Since a motif may comprise only a few nucleotides, a particular oligonucleotide can comprise two or more motifs. By way of non-limiting example, in certain embodiments, an oligonucleotide in the multi-targeted molecule can have two or more nucleotide motifs selected from LNAs, phosphorthioate linkages, 2'-OMe, conjugated ligand(s).

Without limitations, the multi-targeted molecules of the invention having any of the various nucleotide motifs described herein, can have also have any linkage motif. For example, in an oligonucleotide of present in the multi-targeted molecule, the first 1, 2, 3, 4 or 5 intersugar linkages at the 5'-end can be modified intersugar linkages and the first 4, 5, 6, 7 or 8 intersugar linkages at the 3'-end can be modified intersugar linkages. The central region of such modified oligonucleotides can have intersugar linkages based on any of the other motifs described herein, for example, uniform, alternating, hemimer, gapmer, and the like. In some embodiments, an oligonucleotide of present in the multi-targeted molecule comprises a phosphorothioate linkage between the first and second monomer at the 5'-terminus, alternating phosphorothioate/phosphodiester linkages in the central region and 6, 7, or 8 phosphorothioate linkages at the 3'-terminus.

It is to be noted that the lengths of the regions defined by a nucleotide motif and that of a linkage motif need not be the same.

In some embodiments, single-stranded oligonucleotides or at least one strand of a double-stranded oligonucleotide, includes at least one of the following motifs:

(a) 5'-phosphorothioate or 5'-phosphorodithioate;

(b) a cationic modification of nucleotides 1 and 2 on the 5' terminal, wherein the cationic modification is at C5 position of pyrimidines and C2, C6, C8, exocyclic N2 or exocyclic N6 of purines;

(c) at least one G-clamp nucleotide in the first two terminal nucleotides at the 5' end and the other nucleotide having a cationic modification, wherein the cationic modification is at C5 position of pyrimidines or C2, C6, C8, exocyclic N2 or exocyclic N6 position of purines;

(d) at least one 2'-F modified nucleotide comprising a nucleobase base modification;

(e) at least one gem-2'-O-methyl/2'-F modified nucleotide comprising a nucleobase modification, preferably the methyl substituent is in the up configuration, e.g. in the arabinose configuration;

(f) a 5'-PuPu-3' dinucleotide at the 3' terminal wherein both nucleotides comprise a modified MOE at 2'-position as described in U.S. Patent Application Publication No. 20130130378, content of which is incorporated herein by reference in its entirety, (g) a 5'-PuPu-3' dinucleotide at the 5' terminal wherein both nucleotides comprise a modified MOE at 2'-position as described in U.S. Patent Application Publication No. 20130130378;

(h) nucleotide at the 5' terminal having a modified MOE at 2-position as described in U.S. Patent Application Publication No. 20130130378;

(i) nucleotide at the 5' terminal having a 3'-F modification;

(j) 5' terminal nucleotide comprising a 4'-substituent;

(k) 5' terminal nucleotide comprising a O4' modification;

(l) 3' terminal nucleotide comprising a 4'-substituent; and (m) combinations thereof.

In some embodiments, both strands of a double-stranded oligonucleotide independently comprise at least one of the above described motifs. In some other embodiments, both strands of a double-stranded oligonucleotide comprise at least one at least one of the above described motifs, which motifs can be same or different or some combination of same and different.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of compounds, e.g., an oligonucleotide present in the multi-targeted molecule can be easily manipulated by lengthening or shortening one or more of the described regions, without disrupting the motif.

In some embodiments, an oligonucleotide in the effector molecule or the multi-targeted molecule comprises two or more chemically distinct regions and has a structure as described in International Application No. PCT/US09/038433, filed Mar. 26, 2009, contents of which are herein incorporated in their entirety.

Synthesis, Purification and Analysis

Oligomerization of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Nucleic acids, such as oligonucleotides, can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of synthesis.

Methods of purification and analysis of nucleic acids are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Nucleic acids, such as oligonucleotides, can also be prepared using solution-phase or solid-phase organic synthesis, or enzymatically by methods known in the art. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other nucleic acids, such as those comprising phosphorothioates, phosphorodithioates and alkylated derivatives of intersugar linkages. The double-stranded nucleic acids can be prepared using a two-step procedure. First, the individual strands of the double-stranded molecule are prepared separately. Then, the component strands are annealed.

Regardless of the method of synthesis, nucleic acids can be prepared in a solution (e.g., an aqueous and/or organic solution) that is appropriate for formulation. For example, the nucleic acid preparation can be precipitated and redissolved in pure double-distilled water, and lyophilized. The dried nucleic acid can then be resuspended in a solution appropriate for the intended formulation process.

Teachings regarding the synthesis of particular modified nucleic acids can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling: U.S. Pat. No. 5,457,191, drawn to modified nucleobases based on the 3-deazapurine ring system and methods of synthesis thereof: U.S. Pat. No. 5,459,255, drawn to modified nucleobases based on N-2 substituted purines; U.S. Pat. No. 5,521,302, drawn to processes for preparing oligonucleotides having chiral phosphorus linkages: U.S. Pat. No. 5,539,082, drawn to peptide nucleic acids; U.S. Pat. No. 5,554,746, drawn to oligonucleotides having beta-lactam backbones; U.S. Pat. No. 5,571,902, drawn to methods and materials for the synthesis of oligonucleotides: U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds: U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Compositions and Methods for Formulating Pharmaceutical Compositions

The effector molecule conjugated with a ligand or the multi-targeted molecules can be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

The effector molecule conjugated with a ligand or the multi-targeted molecules can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in some embodiments, employed in the methods described herein is a pharmaceutical composition comprising an effector molecule linked with a ligand via a linker disclosed herein and a pharmaceutically acceptable diluent. In some embodiments, employed in the methods described herein is a pharmaceutical composition comprising multi-targeted molecule and a pharmaceutically acceptable diluent. In certain embodiments, the pharmaceutically acceptable diluent is PBS.

Pharmaceutical compositions comprising Multi-targeted molecules encompass any pharmaceutically acceptable salts, esters, or salts of such esters. In certain embodiments, pharmaceutical compositions comprising Multi-targeted molecules comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a multi-targeted molecule which are cleaved by endogenous nucleases within the body, to form the active molecule.

The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer: intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The multi-targeted molecules can be delivered in a manner to target a particular tissue, such as the liver (e.g., the hepatocytes of the liver).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the multi-targeted molecules featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). Multi-targeted molecules featured in the invention may be encapsulated within liposomes or may form complexes thereto, in particular to cationic liposomes. Alternatively, the multi-targeted molecules may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, l-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Further advantages of liposomes include; liposomes obtained from natural phospholipids are biocompatible and biodegradable: liposomes can incorporate a wide range of water and lipid soluble drugs; liposomes can protect encapsulated drugs in their internal compartments from metabolism and degradation (Rosoff, in Pharmaceutical Dosage Forms, Lieberman. Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release. 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES)(Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029.91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Research Tools

In certain instances, oligonucleotides capable of modulating gene expression have been used as research tools. For example, researchers investigating the function of a particular gene product can design oligonucleotides to reduce the amount of that gene product present in a cell or an animal and observe phenotypic changes in the cell or animal. In certain embodiments, the present invention provides methods for reducing the amount of two different targets in a cell or animal. In some embodiments, the two different targets can be two different genes or gene products. In some embodiments, the two different targets can be the same gene or gene product. In certain embodiments, investigators can use such techniques to characterize proteins or untranslated nucleic acids. In certain embodiments, such experiments are used to investigate kinetics and/or turnover of gene products and/or certain cellular functions. In some embodiments, such experiments are used to investigate relationship or correlation between different genes or gene products.

Kits

In certain embodiments, the present invention provides kits comprising one or more multi-targeted molecules. In certain embodiments, such kits are intended for therapeutic application. In certain embodiments, such kits are intended for research use.

In certain embodiments, the present invention provides kits comprising at least one effector molecule conjugated with a ligand via a linker described herein. In certain embodiments, such kits are intended for therapeutic application. In certain embodiments, such kits are intended for research use.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Definitions

Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "target nucleic acid" refers to any nucleic acid molecule the expression or activity of which is capable of being modulated by an siRNA compound. Target nucleic acids include, but are not limited to, RNA (including, but not limited to pre-mRNA and mRNA or portions thereof) transcribed from DNA encoding a target protein, and also cDNA derived from such RNA, and miRNA. For example, the target nucleic acid can be a cellular gene (or mRNA transcribed from the gene) whose expression is associated with a particular disorder or disease state. In some embodiments, a target nucleic acid can be a nucleic acid molecule from an infectious agent.

As used herein, "gene silencing" by a RNA interference molecule refers to a decrease in the mRNA level in a cell for a target gene by at least about 5%, at least about 10%, at least about 20%, at least about 30%, at least about 40%, at least about 50%, at least about 60%, at least about 70%, at least about 80%, at least about 90%, at least about 95%, at least about 99% up to and including 100%, and any integer in between of the mRNA level found in the cell without the presence of the miRNA or RNA interference molecule. In one preferred embodiment, the mRNA levels are decreased by at least about 70%, at least about 80%, at least about 90%, at least about 95%, at least about 99%, up to and including 100% and any integer in between 5% and 100%."

As used herein the term "modulate gene expression" means that expression of the gene, or level of RNA molecule or equivalent RNA molecules encoding one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

As used herein, gene expression modulation happens when the expression of the gene, or level of RNA molecule or equivalent RNA molecules encoding one or more proteins or protein subunits is at least 5%, 10%, 20%, 30%, 40%, 50%, 60%, 70%, 80%, 90%, 100%, 2-fold, 3-fold. 4-fold, 5-fold or more different from that observed in the absence of the siRNA, e.g., RNAi agent. The % and/or fold difference can be calculated relative to the control or the non-control, for example, $$\%\ \text{difference} = \frac{[\text{expression with } siRNA - \text{expression without } siRNA}{\text{expression without } siRNA}$$

or $$\%\ \text{difference} = \frac{[\text{expression with } siRNA - \text{expression without } siRNA}{\text{expression without } siRNA}$$

As used herein, the term "inhibit", "down-regulate", or "reduce" in relation to gene expression, means that the expression of the gene, or level of RNA molecules or equivalent RNA molecules encoding one or more proteins or protein subunits, or activity of one or more proteins or protein subunits, is reduced below that observed in the absence of modulator. The gene expression is down-regulated when expression of the gene, or level of RNA molecules or equivalent RNA molecules encoding one or more proteins or protein subunits, or activity of one or more proteins or protein subunits, is reduced at least 10% lower relative to a corresponding non-modulated control, and preferably at least 10%, 20%, 30%, 40%, 50%, 60%, 70%, 80%, 90%, 95%, 98%, 99% or most preferably, 100% (i.e., no gene expression).

As used herein, the term "increase" or "up-regulate" in relation to gene expression means that the expression of the gene, or level of RNA molecules or equivalent RNA molecules encoding one or more proteins or protein subunits, or activity of one or more proteins or protein subunits, is increased above that observed in the absence of modulator. The gene expression is up-regulated when expression of the gene, or level of RNA molecules or equivalent RNA molecules encoding one or more proteins or protein subunits, or activity of one or more proteins or protein subunits, is increased at least 10% relative to a corresponding non-modulated control, and preferably at least 10%, 20%, 30%, 40%, 50%, 60%, 70%, 80%, 90%, 95%, 98%, 100%, 1.1-fold, 1.25-fold, 1.5-fold, 1.75-fold, 2-fold, 3-fold, 4-fold, 5-fold, 10-fold, 50-fold, 100-fold or more.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "reduced" or "reduce" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

By "specifically hybridizable" and "complementary" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987*, CSH Symp. Quant. Biol.* LII pp. 123-133; Frier et al., 1986, *Proc. Nat. Acad. Sci. USA* 83:9373-9377; Turner et al., 1987*, /. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

The term "off-target" and the phrase "off-target effects" refer to any instance in which an effector molecule against a given target causes an unintended affect by interacting either directly or indirectly with another target sequence, a DNA sequence or a cellular protein or other moiety. For example, an "off-target effect" may occur when there is a simultaneous degradation of other transcripts due to partial homology or complementarity between that other transcript and the sense and/or antisense strand of an siRNA.

As used herein, the term "nucleoside" means a glycosylamine comprising a nucleobase and a sugar. Nucleosides includes, but are not limited to, naturally occurring nucleosides, abasic nucleosides, modified nucleosides, and nucleosides having mimetic bases and/or sugar groups.

As used herein, the term "nucleotide" refers to a glycosomine comprising a nucleobase and a sugar having a phosphate group covalently linked to the sugar. Nucleotides may be modified with any of a variety of substituents.

As used herein, the term "nucleobase" refers to the base portion of a nucleoside or nucleotide. A nucleobase may comprise any atom or group of atoms capable of hydrogen bonding to a base of another nucleic acid.

As used herein, the term "heterocyclic base moiety" refers to a nucleobase comprising a heterocycle.

As used herein, the term "oligomeric compound" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antidote compounds. In certain embodiments, oligomeric compounds comprise conjugate groups.

As used herein "oligonucleoside" refers to an oligonucleotide in which the internucleoside linkages do not contain a phosphorus atom.

As used herein, the term "oligonucleotide" refers to an oligomeric compound comprising a plurality of linked nucleosides. In certain embodiment, one or more nucleotides of an oligonucleotide is modified. In certain embodiments, an oligonucleotide comprises ribonucleic acid (RNA) or deoxyribonucleic acid (DNA). In certain embodiments, oligonucleotides are composed of naturally- and/or non-naturally-occurring nucleobases, sugars and covalent internucleoside linkages, and can further include non-nucleic acid conjugates.

As used herein "internucleoside linkage" refers to a covalent linkage between adjacent nucleosides.

As used herein "naturally occurring internucleoside linkage" refers to a 3' to 5' phosphodiester linkage.

As used herein the term "detecting siRNA activity" or "measuring siRNA activity" means that a test for detecting or measuring siRNA activity is performed on a particular sample and compared to that of a control sample. Such detection and/or measuring can include values of zero. Thus, if a test for detection of siRNA activity results in a finding of no siRNA activity (siRNA activity of zero), the step of "detecting siRNA activity" has nevertheless been performed.

As used herein the term "control sample" refers to a sample that has not been contacted with a reporter oligomer compound.

As used herein, the term "motif" refers to the pattern of unmodified and modified nucleotides in an oligomeric compound.

As used herein, the term "chimeric oligomer" refers to an oligomeric compound, having at least one sugar, nucleobase or internucleoside linkage that is differentially modified as compared to at least on other sugar, nucleobase or internucleoside linkage within the same oligomeric compound. The remainder of the sugars, nucleobases and internucleoside linkages can be independently modified or unmodified, the same or different.

As used herein, the term "chimeric oligonucleotide" refers to an oligonucleotide, having at least one sugar, nucleobase or internucleoside linkage that is differentially modified as compared to at least on other sugar, nucleobase or internucleoside linkage within the same oligonucleotide. The remainder of the sugars, nucleobases and internucleoside linkages can be independently modified or unmodified, the same or different.

As used herein, the term "mixed-backbone oligomeric compound" refers to an oligomeric compound wherein at least one internucleoside linkage of the oligomeric compound is different from at least one other internucleoside linkage of the oligomeric compound.

As used herein, the term "target protein" refers to a protein, the modulation of which is desired.

As used herein, the term "target gene" refers to a gene encoding a target protein.

As used herein, the term "targeting" or "targeted to" refers to the association of antisense strand of an siRNA to a particular target nucleic acid molecule or a particular region of nucleotides within a target nucleic acid molecule.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an oligomeric compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are oligomeric compounds (e.g., siRNas, multi-targeted molecules and the like) that may comprise up to about 20% nucleotides that are mismatched (i.e., are not nucleobase complementary to the corresponding nucleotides of the target). Preferably the oligomeric compounds, such as siRNAs and multi-targeted molecules, contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" means the pairing of complementary oligomeric compounds (e.g., an antisense strand of an siRNA and its target nucleic acid or an antisense strand and sense strand of an siRNA). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, the antisense strand of an siRNA specifically hybridizes to more than one target site.

As used herein, "designing" or "designed to" refer to the process of designing an oligomeric compound that specifically hybridizes with a selected nucleic acid molecule.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

As used herein, "variant" refers to an alternative RNA transcript that can be produced from the same genomic region of DNA. Variants include, but are not limited to "pre-mRNA variants" which are transcripts produced from the same genomic DNA that differ from other transcripts produced from the same genomic DNA in either their start or stop position and contain both intronic and exonic sequence. Variants also include, but are not limited to, those with alternate splice junctions, or alternate initiation and termination codons.

As used herein, "high-affinity modified monomer" refers to a monomer having at least one modified nucleobase, internucleoside linkage or sugar moiety, when compared to naturally occurring monomers, such that the modification increases the affinity of an antisense compound comprising the high-affinity modified monomer to its target nucleic acid. High-affinity modifications include, but are not limited to, monomers (e.g., nucleosides and nucleotides) comprising 2'-modified sugars.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O—$C_1$-$C_{10}$ alkyl, —OCF3, O—$(CH_2)_2$—O—$CH_3$, 2'-$O(CH_2)_2SCH_3$, O—$(CH_2)_2$—O—N(Rm)(Rn), or O—$CH_2$—C(═O)—N(Rm)(Rn), where each Rm and Rn is, independently, H or substituted or unsubstituted $C_1$-$C_{10}$ alkyl. In certain embodiments, oligomeric compounds comprise a 2' modified monomer that does not have the formula 2'-$O(CH_2)_nH$, wherein n is one to six. In certain embodiments, oligomeric compounds comprise a 2' modified monomer that does not have the formula 2'-$OCH_3$. In certain embodiments, oligomeric compounds comprise a 2' modified monomer that does not have the formula or, in the alternative, 2'-$O(CH_2)_2OCH_3$.

As used herein, the term "locked nucleic acid" or "LNA" or "locked nucleoside" or "locked nucleotide" refers to a nucleoside or nucleotide wherein the furanose portion of the nucleoside includes a bridge connecting two carbon atoms on the furanose ring, thereby forming a bicyclic ring system. Locked nucleic acids are also referred to as bicyclic nucleic acids (BNA).

As used herein, unless otherwise indicated, the term "methyleneoxy LNA" alone refers to β-D-methyleneoxy LNA.

As used herein, the term "MOE" refers to a 2'-O-methoxyethyl substituent.

As used herein, the term "gapmer" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) in each wing are the same. In certain embodiments, the modification(s) in one wing are different from the modification(s) in the other wing. In certain embodiments, oligomeric compounds are gapmers having 2'-deoxynucleotides in the gap and nucleotides with high-affinity modifications in the wing.

As used herein, the term "prodrug" refers to a therapeutic agent that is prepared in an inactive form that is converted to an active form (i.e., drug) within the body or cells thereof by the action of endogenous enzymes or other chemicals and/or conditions.

As used herein, the term "pharmaceutically acceptable salts" refers to salts of active compounds that retain the desired biological activity of the active compound and do not impart undesired toxicological effects thereto.

As used herein, the term "cap structure" or "terminal cap moiety" refers to chemical modifications, which have been incorporated at either terminus of an antisense compound.

As used herein, the term "prevention" refers to delaying or forestalling the onset or development of a condition or disease for a period of time from hours to days, preferably weeks to months.

As used herein, the term "amelioration" refers to a lessening of at least one activity or one indicator of the severity of a condition or disease. The severity of indicators may be determined by subjective or objective measures which are known to those skilled in the art.

As used herein, the term "treatment" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "pharmaceutical agent" refers to a substance that provides a therapeutic benefit when administered to a subject. In certain embodiments, a pharmaceutical agent is an active pharmaceutical agent. In certain embodiments, a pharmaceutical agent is a prodrug.

As used herein, the term "therapeutically effective amount" refers to an amount of a pharmaceutical agent that provides a therapeutic benefit to an animal.

As used herein, "administering" means providing a pharmaceutical agent to an animal, and includes, but is not limited to administering by a medical professional and self-administering.

As used herein, the term "co-administering" means providing more than one pharmaceutical agent to an animal. In certain embodiments, such more than one pharmaceutical agents are administered together. In certain embodiments, such more than one pharmaceutical agents are administered separately. In certain embodiments, such more than one pharmaceutical agents are administered at the same time. In certain embodiments, such more than one pharmaceutical agents are administered at different times. In certain embodiments, such more than one pharmaceutical agents are administered through the same route of administration. In certain embodiments, such more than one pharmaceutical agents are administered through different routes of administration. In certain embodiments, such more than one pharmaceutical agents are contained in the same pharmaceutical formulation. In certain embodiments, such more than one pharmaceutical agents are in separate formulations.

As used herein, the term "pharmaceutical composition" refers to a mixture of substances suitable for administering to an individual. For example, a pharmaceutical composition may comprise an antisense oligonucleotide and a sterile aqueous solution. In certain embodiments, a pharmaceutical composition includes a pharmaceutical agent and a diluent and/or carrier.

As used herein, the term "in vitro" refers to events that occur in an artificial environment, e.g., in a test tube or reaction vessel, in cell culture, etc., rather than within an organism (e.g. animal or a plant). As used herein, the term "ex vivo" refers to cells which are removed from a living organism and cultured outside the organism (e.g., in a test tube). As used herein, the term "in vivo" refers to events that occur within an organism (e.g. animal, plant, and/or microbe).

As used herein, the term "subject" or "patient" refers to any organism to which a composition disclosed herein can be administered, e.g., for experimental, diagnostic, and/or therapeutic purposes. Typical subjects include animals (e.g., mammals such as mice, rats, rabbits, non-human primates, and humans) and/or plants. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to with domesticated animals and/or pets.

In some embodiments, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species. In some embodiments, the subject can be of European ancestry. In some embodiments, the subject can be of African American ancestry. In some embodiments, the subject can be of Asian ancestry.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, the term "dosage unit" refers to a form in which a pharmaceutical agent is provided. In certain embodiments, a dosage unit is a vial comprising lyophilized antisense oligonucleotide. In certain embodiments, a dosage unit is a vial comprising reconstituted antisense oligonucleotide.

As used herein, the term "active pharmaceutical ingredient" refers to the substance in a pharmaceutical composition that provides a desired effect.

As used herein, the term "side effects" refers to physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

As used herein, the term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C1-C12 alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, the term "alkenyl," as used herein, refers to a straight or branched hydrocarbon chain radical containing up to twenty-four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, the term "alkynyl," as used herein, refers to a straight or branched hydrocarbon radical containing up to twenty-four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

As used herein, the term "aminoalkyl" as used herein, refers to an amino substituted alkyl radical. This term is meant to include C1-C12 alkyl groups having an amino substituent at any position and wherein the alkyl group attaches the aminoalkyl group to the parent molecule. The alkyl and/or amino portions of the aminoalkyl group can be further substituted with substituent groups.

As used herein, the term "aliphatic," as used herein, refers to a straight or branched hydrocarbon radical containing up to twenty-four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

As used herein, the term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups. As used herein, the term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups. As used herein, the terms "halo" and "halogen," as used herein, refer to an atom selected from fluorine, chlorine, bromine and iodine.

As used herein, the terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, indenyl and the like. Preferred aryl ring systems have from about 5 to about 20 carbon atoms in one or more rings. Aryl groups as used herein may optionally include further substitutent groups.

As used herein, the terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

As used herein, the term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups. As used herein, the terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

As used herein, the term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

As used herein, the term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, the term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

As used herein, the term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, the terms "substituent" and "substituent group," as used herein, include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)Raa), carboxyl (—C(O)O-Raa), aliphatic groups, alicyclic groups, alkoxy, substituted oxo (—O—Raa), aryl, aralkyl, heterocyclic, heteroaryl, heteroarylalkyl, amino (—NRbbRcc), imino (=NRbb), amido (—C(O)N-RbbRcc or —N(Rbb)C(O)Raa), azido (—N3), nitro (—NO2), cyano (—CN), carbamido (—OC(O)NRbbRcc or —N(Rbb)C(O)ORaa), ureido (—N(Rbb)C(O)NRbbRcc), thioureido (—N(Rbb)C(S)NRbbRcc), guanidinyl (—N(Rbb)C(=NRbb)NRbbRcc), amidinyl (—C(=NRbb)-NRbbRcc or —N(Rbb)C(NRbb)Raa), thiol (—SRbb), sulfinyl (—S(O)Rbb), sulfonyl (—S(O)2Rbb), sulfonamidyl (—S(O)2NRbbRcc or —N(Rbb)S(O)2Rbb) and conjugate groups. Wherein each Raa, Rbb and Rcc is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

The terms "bis(siRNA)" and "bis-siRNA" are used interchangeably herein and refer to two siRNAs covalently or non-covalently linked to form a single chemical entity that can elicit RNAi activity in-vitro and/or in-vivo. The two linked siRNAs can target the same target gene at different sites or the two linked siRNAs can target can target the same site in the target gene to elicit RNAi-mediated gene silencing. In other aspects of the invention the two linked siRNA scan can target two different genes.

For clarification, one of the siRNAs in the bis(siRNA) can modulate gene expression of a first target nucleic acid and the other siRNA in the bis(siRNA) can modulate gene expression of a second target nucleic acid. In some embodiments, the first and second target nucleic acids are the same. In some further embodiments, the two siRNAs target the same nucleic acid sequence in the target nucleic acid.

In some other embodiments, one of the siRNAs in the bis(siRNA) can modulate gene expression of a first target nucleic acid and the other siRNA in the bis(siRNA) can modulate gene expression of a second target nucleic acid, wherein the first and the second target nucleic acids are different genes.

As used herein, “linker” or “linkers” includes nucleotide and non-nucleotide linkers or combinations thereof that connects two parts of a molecule, for example, one or both strands of two individual siRNA molecule to generate a bis(siRNA). In some embodiments mere electrostatic or stacking interaction between two individual siRNAs can represent a linker. The non-nucleotide linkers include tether or linker derived from monosaccharide, disaccharides, oligosaccharides and derivatives thereof, aliphatic, alicyclic, heterocyclic and combinations thereof.

Cleavable linkers are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linker by reduction; esterases; amidases: endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases. For example, the linker can be cleaved by a metabolic enzyme in vitro and/or in vivo. Exemplary metabolic enzymes include, but are not limited to classes of nucleases, proteases, peptidases, glycosylases, glycosydases, hydrolyses, oxidases, etc. . . .

EXAMPLES

Example 1: Synthesis of Bis(siRNA) with Cleavable Linkers Having Targeting Ligand Scheme 1

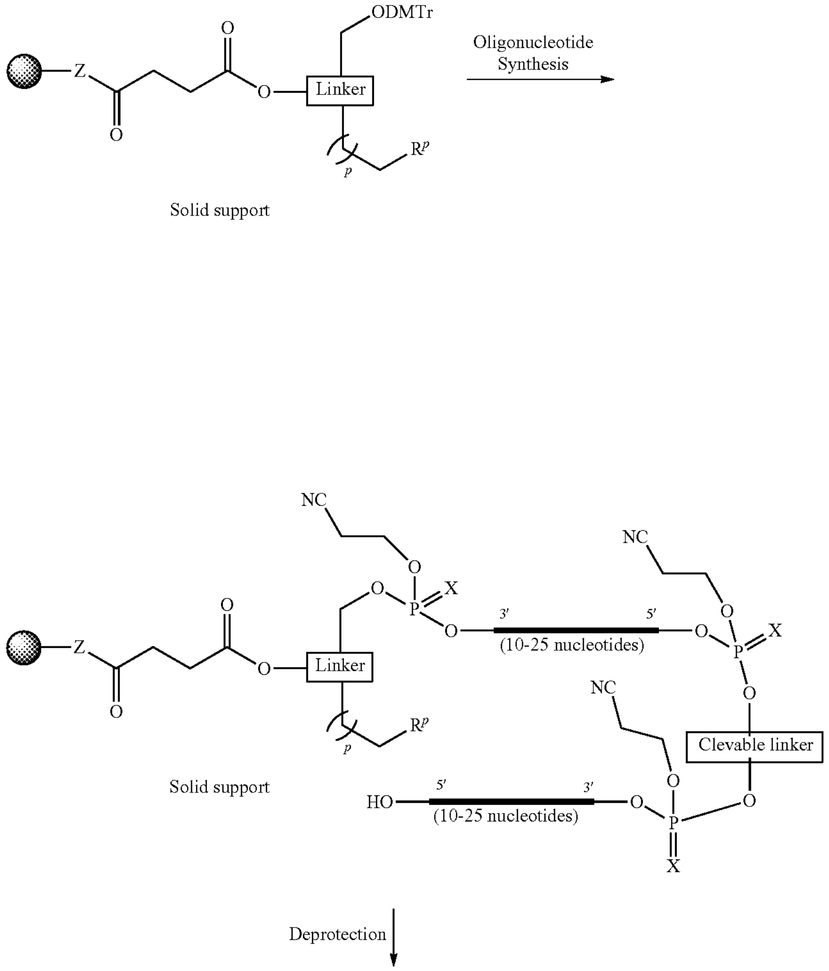

-continued

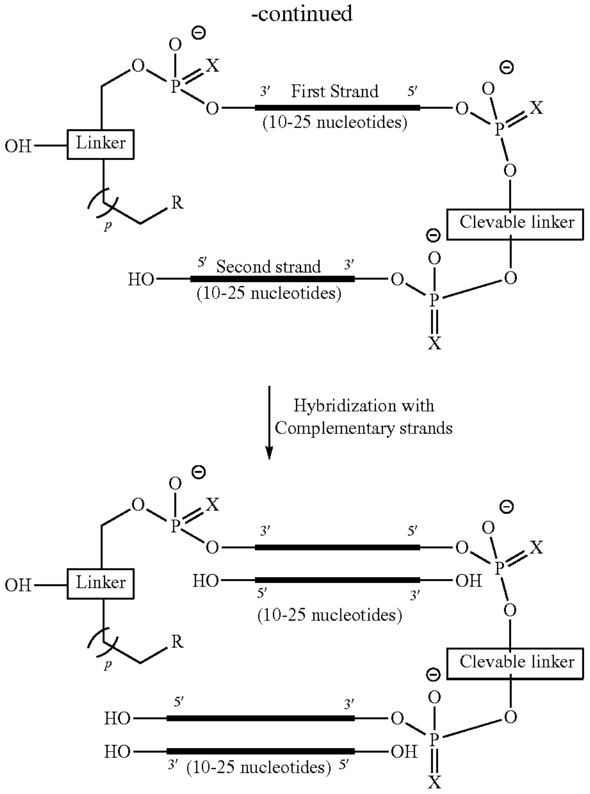

$R^P$ = Protected ligand, protected amine, protected disulfide, protected SH, maleimide moiety, protected carboxyl, alkyne moeity; R = Ligand, $NH_2$, SH, maleimide moiety, COOH, activated carboxyl or activated disulfide, alkyne moiety, azide; R′ = $NH_2$, SH, maleimide moiety, COOH, activated carboxyl or activated disulfide, alkyne moiety, azide;
X = O or S; Y = —C(O)NH— , —NHC(O)— , —S—S— , thioether, triazolide (click adduct); Z = O or NH; p, q = 1-10

Cleavable linker = Bio-cleavable linker contains one or more carbohydrate (saccharide) moiety or a peptide linker connecting two siRNA units or siRNA and a ligand or a ligand and endosomal cleavable agent. Bio-cleavable carbohydrate linker having i. Saccharide units will have at least one anomeric linkage connecting two siRNA units
ii. This linker may contain 1 to 10 saccharide units
iii. When two or more saccharides are present, these units were linked via 1-3, 1-4, or 1-6 sugar linkages
iv. When two or more saccharides are present, these units were also may be linked via alkyl chains The bis(siRNA) is synthesized on the solid support or post-synthetic with cleavable linker and followed by hybridization to complementary strands as shown in the Scheme 1.

Example 2: SiRNA or Endosomal Agents with Cleavable Linkers Having Targeting Ligand Scheme 2

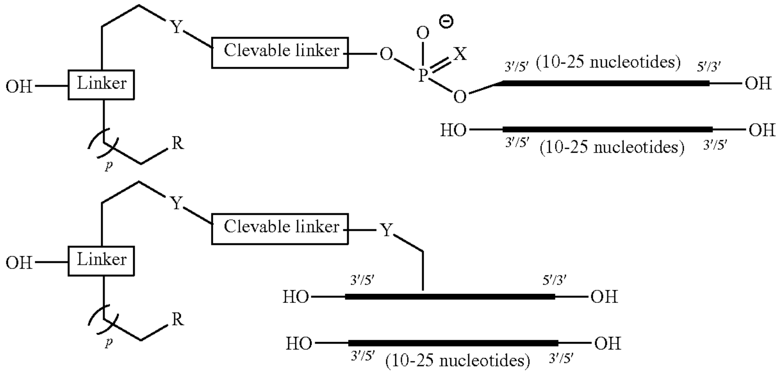

-continued

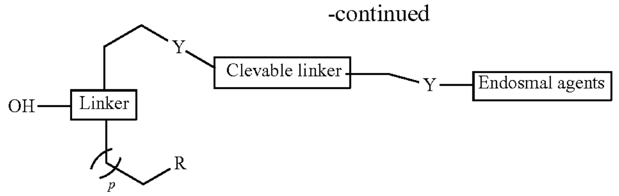

R = Ligand, $NH_2$, SH, maleimide moiety, COOH, activated carboxyl or activated disulfide, alkyne moiety, azide; R′ = $NH_2$, SH, maleimide moiety, COOH, activated carboxyl or activated disulfide, alkyne moiety, azide; X = O or S; Y = O, —C(O)NH—, —NHC(O)—, —S—S—, thioether, triazolide (click adduct), carbamate.

Example 3. Synthesis of siRNA-ASO with Cleavable Linkers Having Targeting Ligand Scheme 3

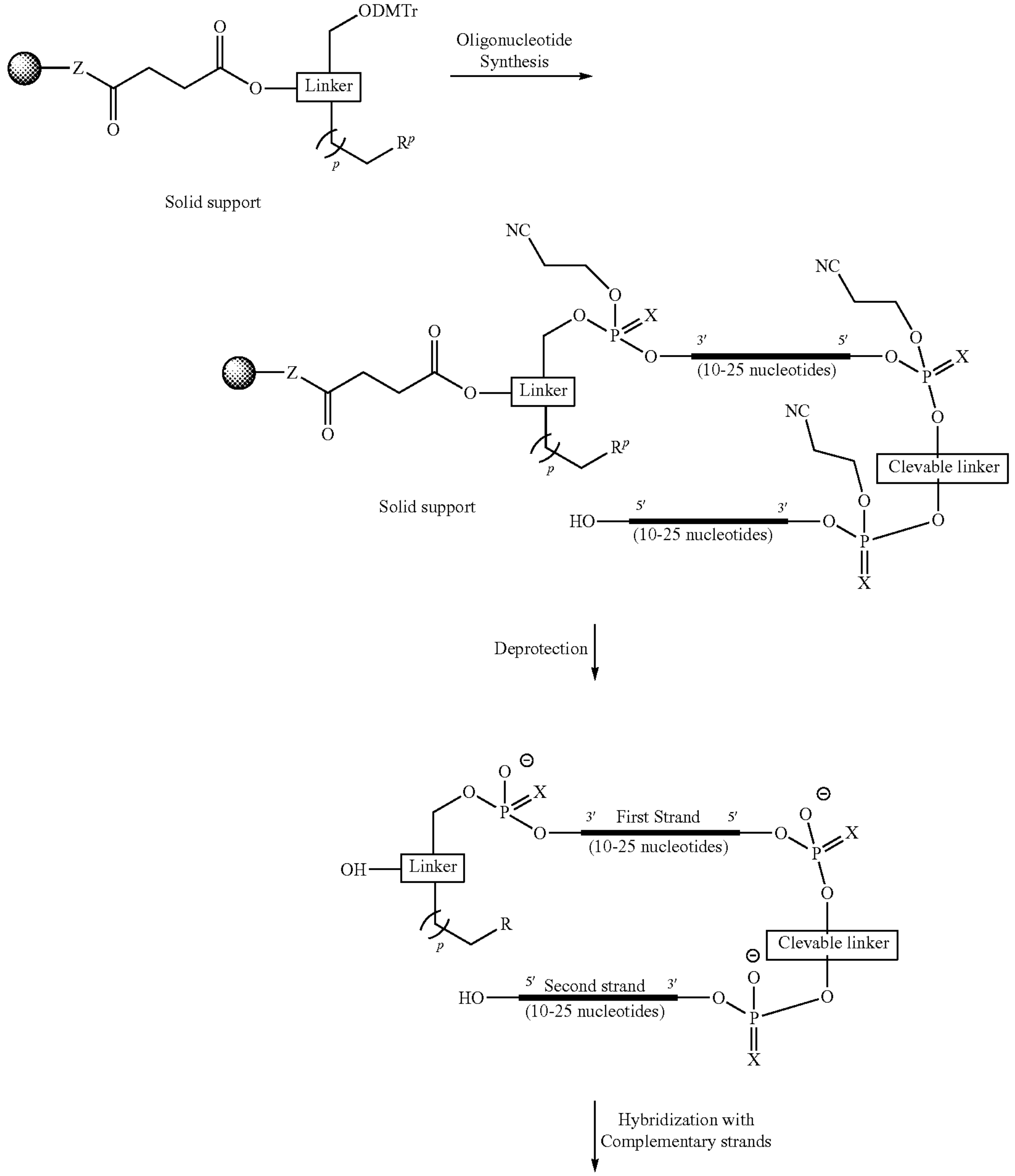

-continued

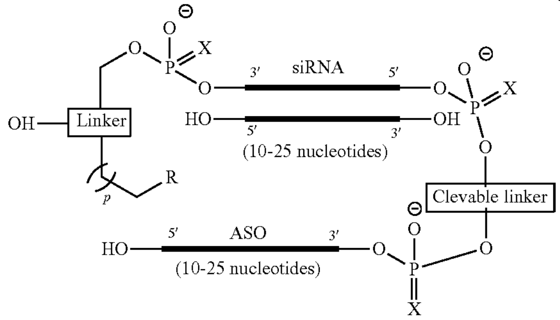

or

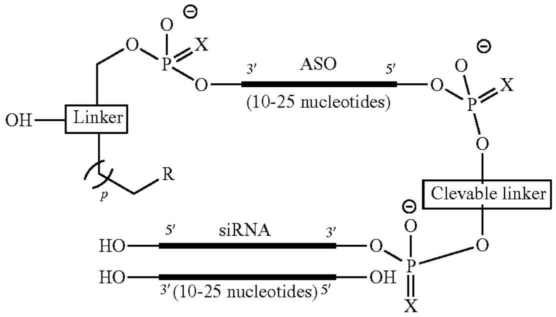

$R^P$ = Protected ligand, protected amine, protected disulfide, protected SH, maleimide moiety, protected carboxyl, alkyne moeity; R = Ligand, $NH_2$, SH, maleimide moiety, COOH, activated carboxyl or activated disulfide, alkyne moiety, azide; R′ = $NH_2$, SH, maleimide moiety, COOH, activated carboxyl or activated disulfide, alkyne moiety, azide; X = O or S; Y = —C(O)NH—, —NHC(O)—, —S—S—, thioether, triazolide (click adduct); Z = O or NH; p, q = 1-10.

The siRNA-ASO or ASO-siRNA is synthesized on the solid support or post-synthetic with cleavable linker and followed by hybridization to complementary strand as shown in the Scheme 3.

Example 4. Synthesis of siRNA-Anti-miRs with Cleavable Linkers Having Targeting Ligand Scheme 4

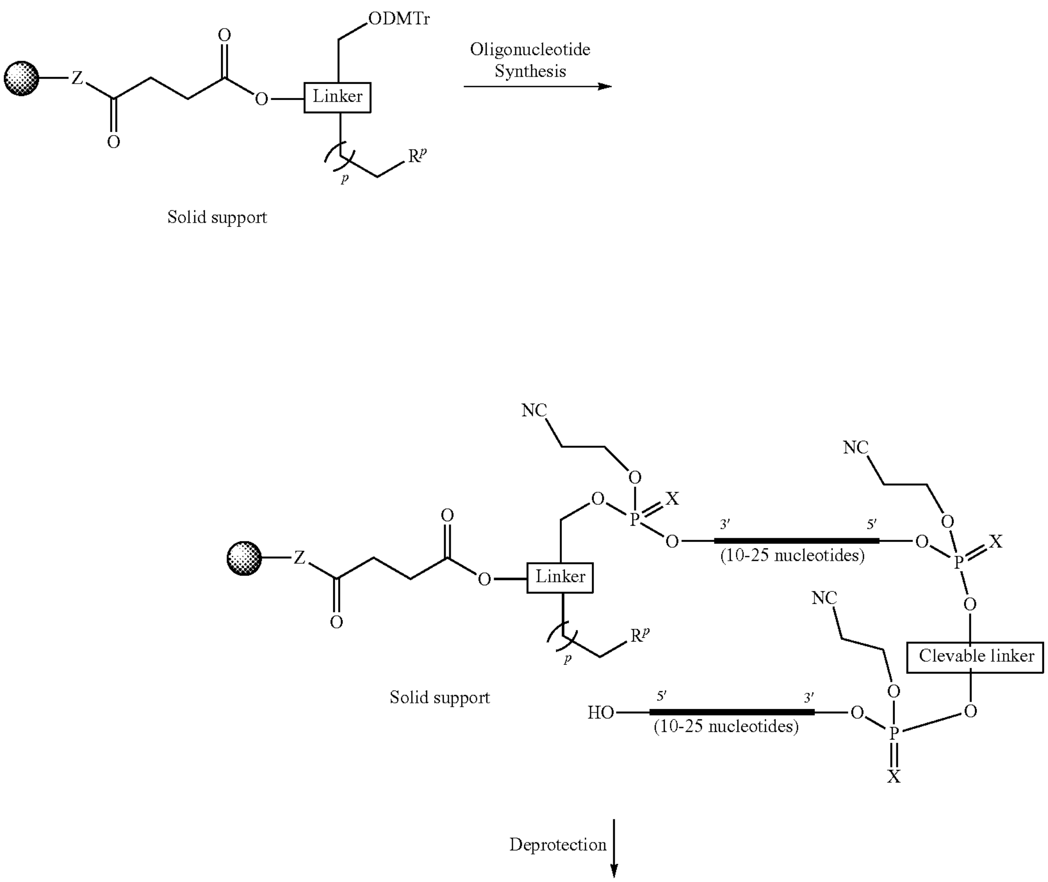

-continued

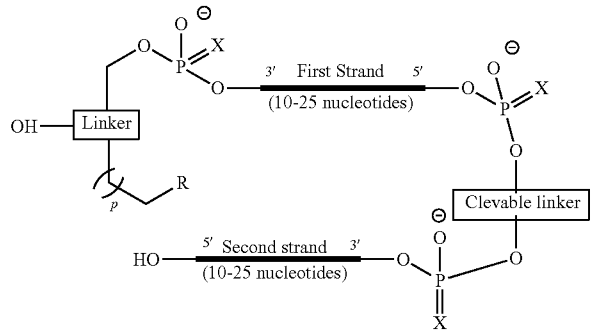

Hybridization with
Complementary strands

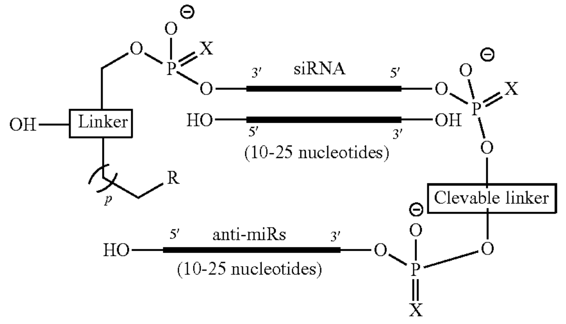

or

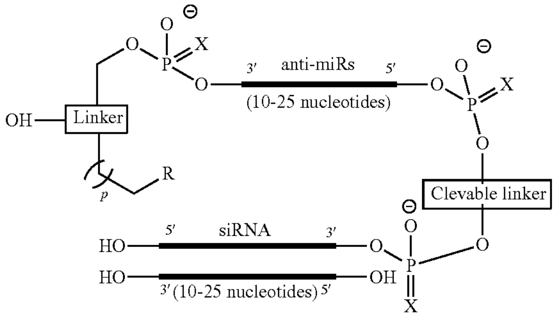

$R^P$ = Protected ligand, protected amine, protected disulfide, protected SH, maleimide moiety, protected carboxyl, alkyne moeity; R = Ligand, $NH_2$, SH, maleimide moiety, COOH, activated carboxyl or activated disulfide, alkyne moiety, azide; R′ = $NH_2$, SH, maleimide moiety, COOH, activated carboxyl or activated disulfide, alkyne moiety, azide; X = O or S; Y = —C(O)NH— , —NHC(O)— , —S—S— , thioether, triazolide (click adduct); Z = O or NH; p, q = 1-10.

The siRNA-anti-miR or anti-miR-siRNA is synthesized on the solid support or post-synthetic with cleavable linker and followed by hybridization to complementary strand as shown in the Scheme 4.

Example 5. Synthesis of Bis(ASO) with Cleavable Linkers Having Targeting Ligand Scheme 5

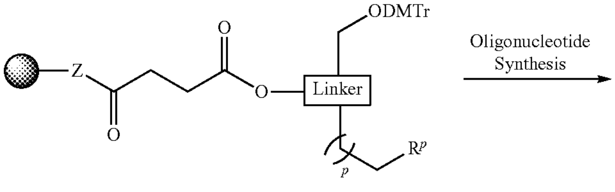

Solid support

-continued

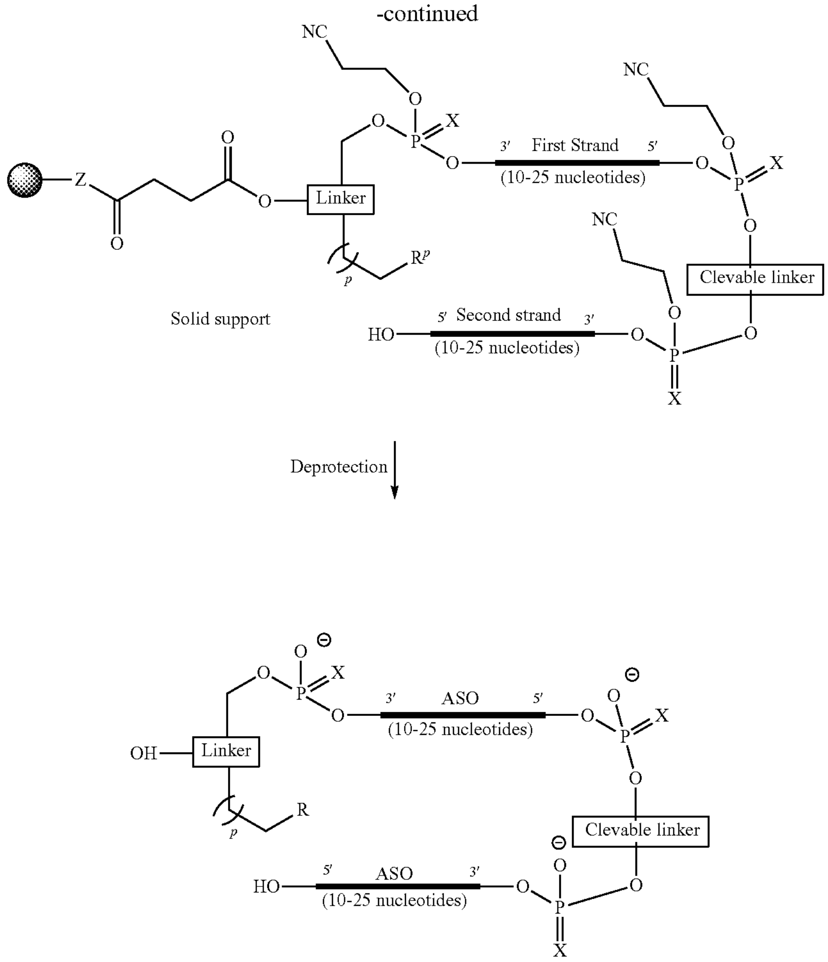

$R^P$ = Protected ligand, protected amine, protected disulfide, protected SH, maleimide moiety, protected carboxyl, alkyne moeity; R = Ligand, $NH_2$, SH, maleimide moiety, COOH, activated carboxyl or activated disulfide, alkyne moiety, azide; R′ = $NH_2$, SH, maleimide moiety, COOH, activated carboxyl or activated disulfide, alkyne moiety, azide; X = O or S; Y = —C(O)NH— , —NHC(O)— , —S—S— , thioether, triazolide (click adduct); Z = O or NH; p, q = 1-10.

The bis(ASO) is synthesized on the solid support or post-synthetic with cleavable linker and followed by hybridization to complementary strand as shown in the Scheme 5.

Example 6. Synthesis of Bis(Anti-miR) with Cleavable Linkers Having Targeting Ligand Scheme 6

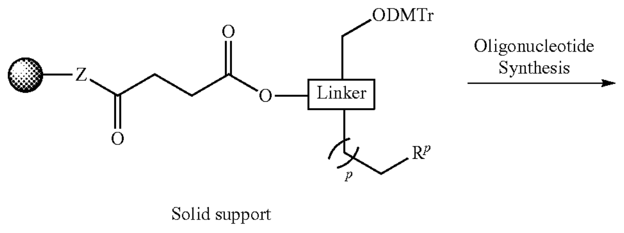

-continued

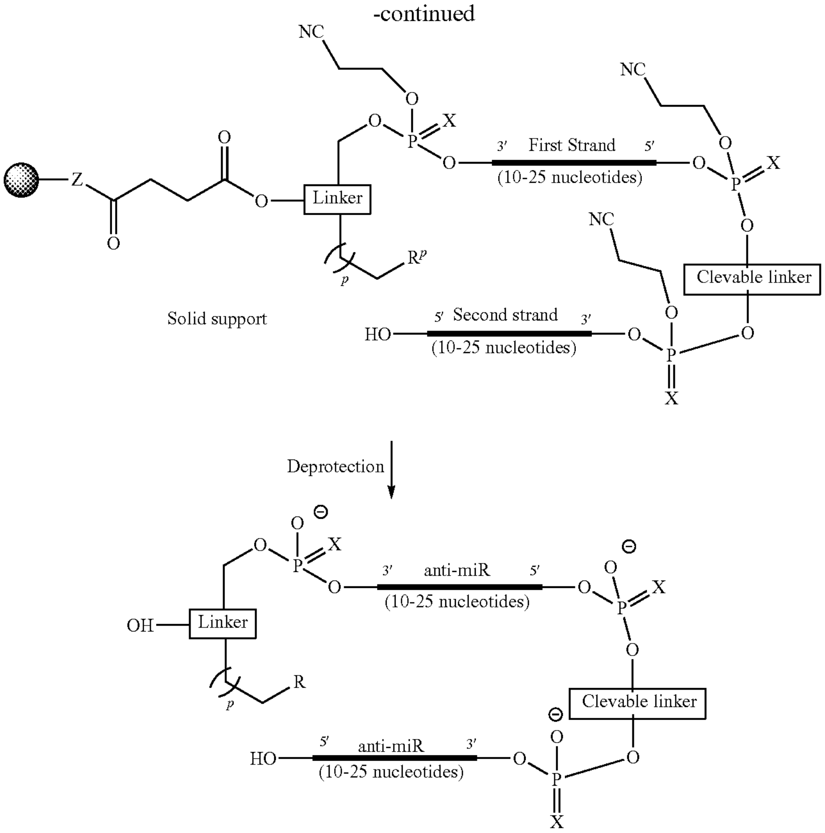

$R^P$ = Protected ligand, protected amine, protected disulfide, protected SH, maleimide moiety, protected carboxyl, alkyne moeity; R = Ligand, $NH_2$, SH, maleimide moiety, COOH, activated carboxyl or activated disulfide, alkyne moiety, azide; R′ = $NH_2$, SH, maleimide moiety, COOH, activated carboxyl or activated disulfide, alkyne moiety, azide; X = O or S; Y = —C(O)NH—, —NHC(O)—, —S—S—, thioether, triazolide (click adduct); Z = O or NH; p, q = 1-10.

The bis(anti-miR) is synthesized on the solid support or post-synthetic with cleavable linker and followed by hybridization to complementary strand as shown in the Scheme 6.

Example 7. Functionalized Cleavable Linkers and Phosphoramidites

Scheme 7

6001

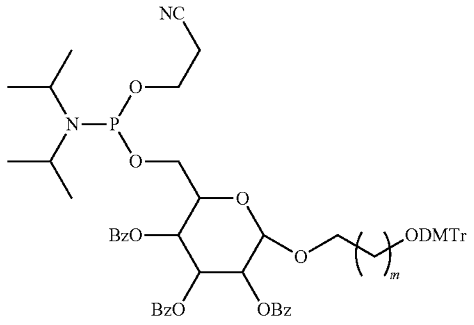

-continued

6002

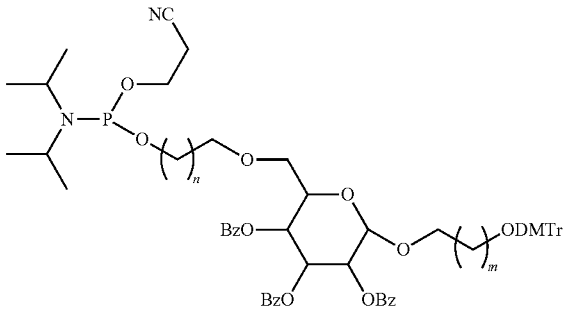

6003

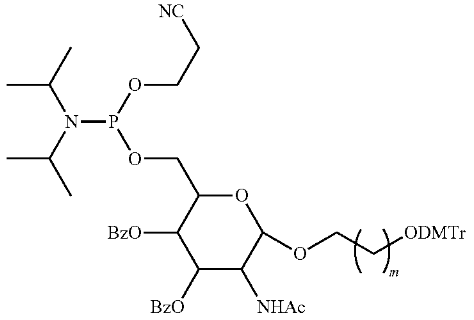

-continued
6004
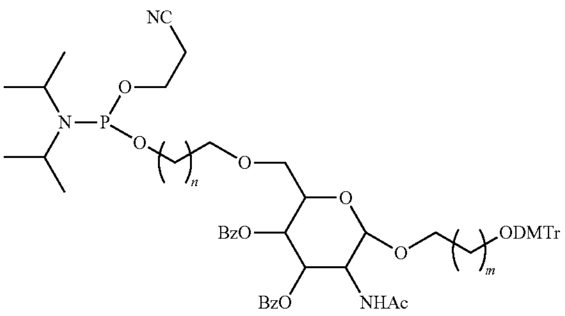
6005
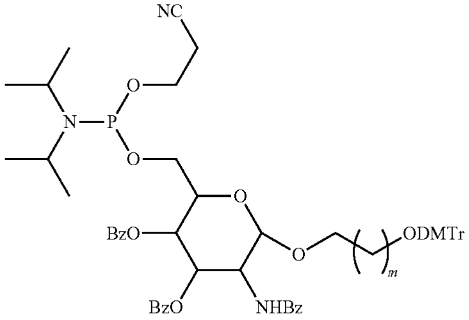
6006
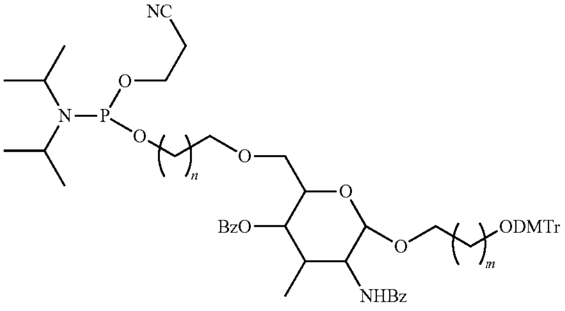
6007
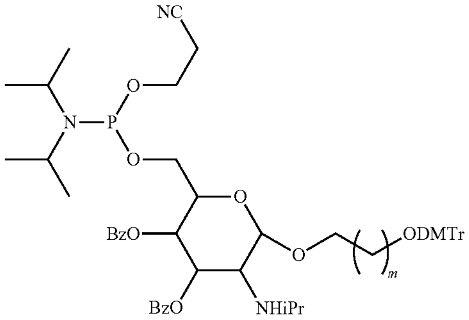
6008
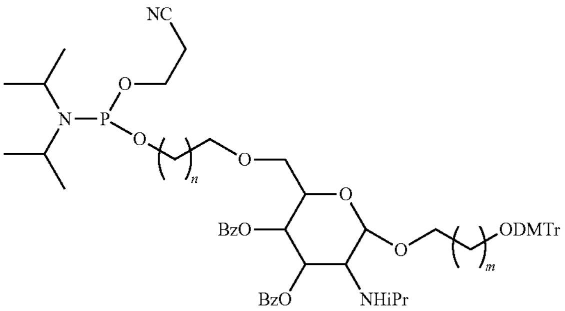
-continued
6009
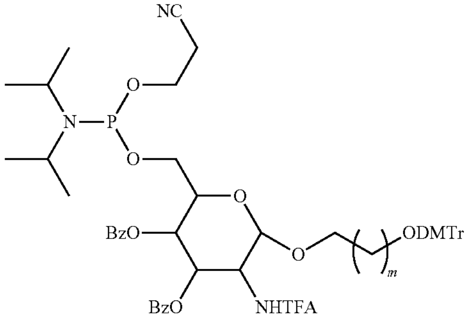
6010
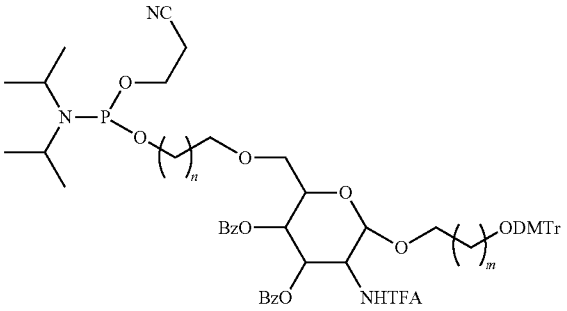
6011
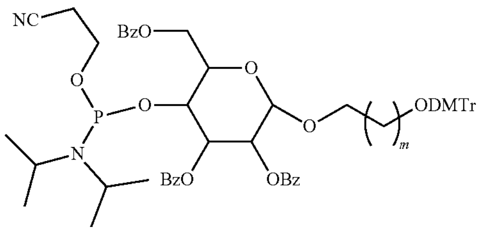
6012
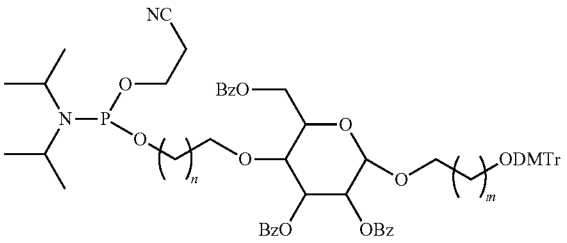
6013
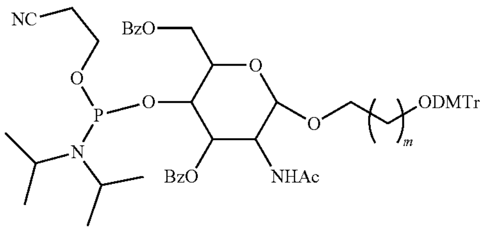

6014
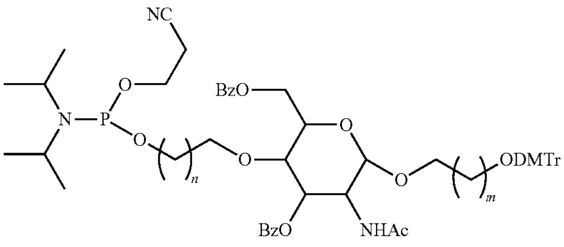
6015
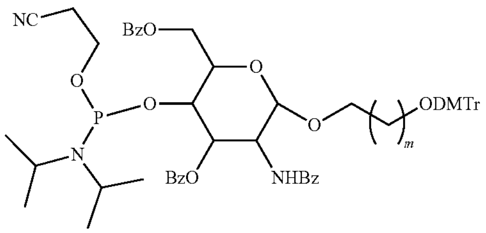
6016
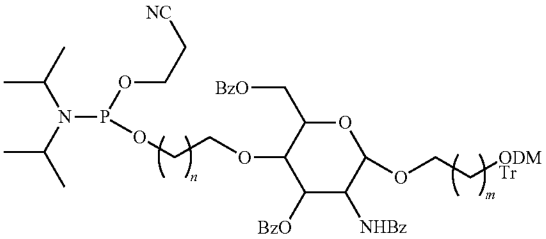
6017
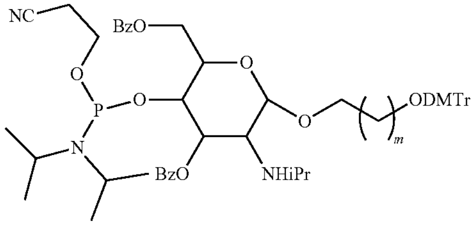
6018
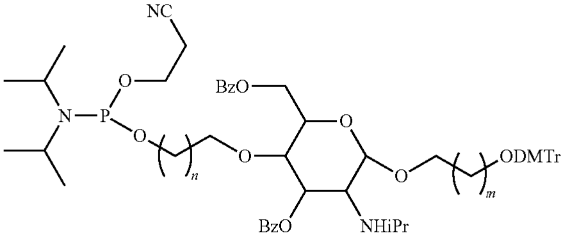
6019
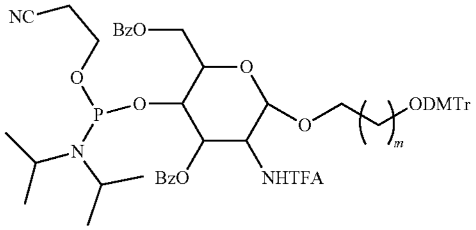
6020
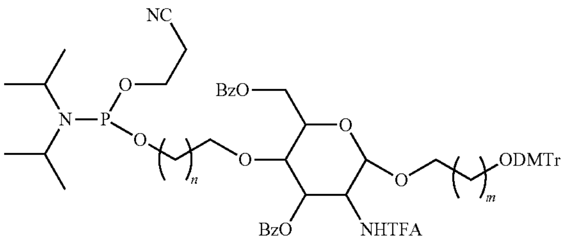
6021
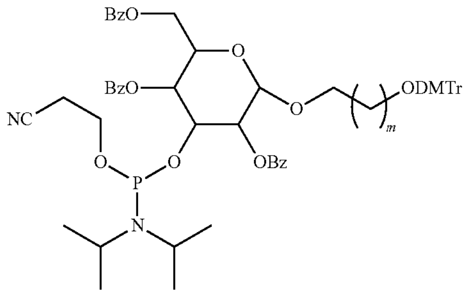
6022
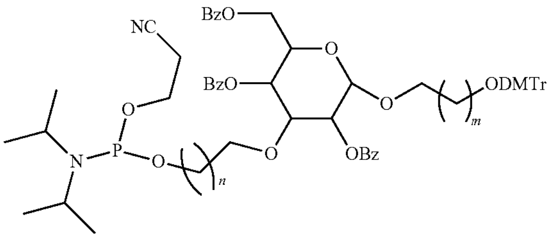
6023
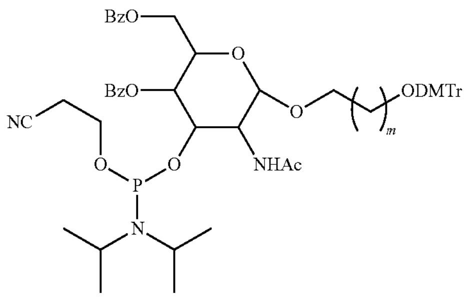
6024
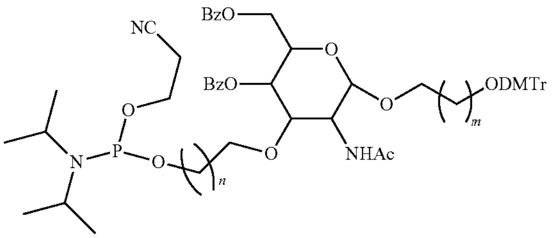

-continued

6025

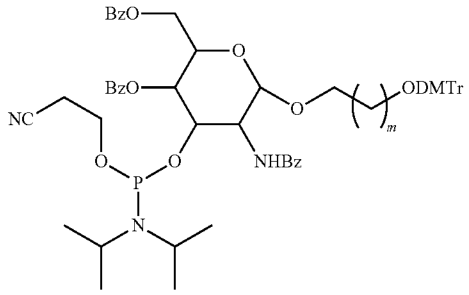

6026

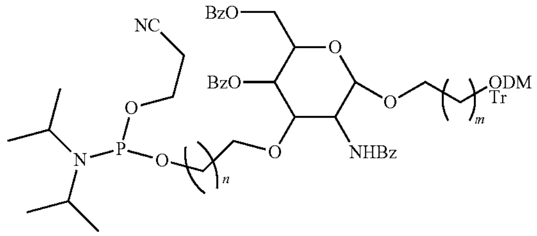

6027

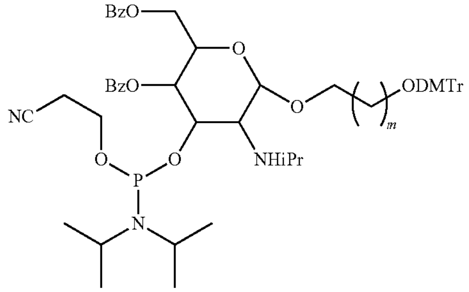

6028

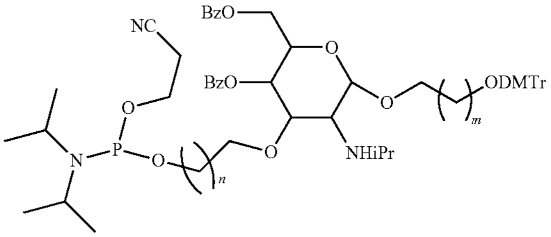

6029

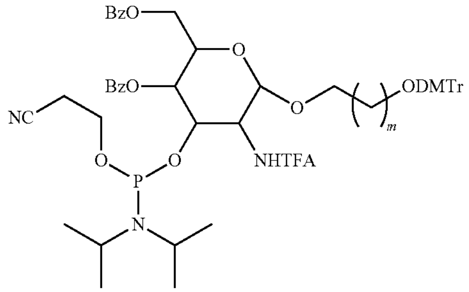

-continued

6030

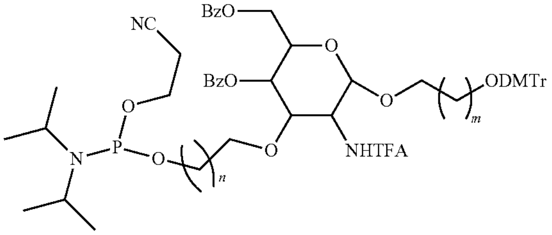

n = 1-12 and m = 1-12, various carbohydrates (Galactose, Galactosamine, Glucose, Glucosamine, Mannose, Mannosamine derivatives or pentose derivatives).

The bis(siRNA) is synthesized on the solid support with consecutive addition of one or more of these cleavable linkers and followed by hybridization to complementary strands as shown in the Example 1 (Scheme 1)

Example 8. Functionalized Cleavable Linkers and Phosphoramidites

Scheme 8

6031

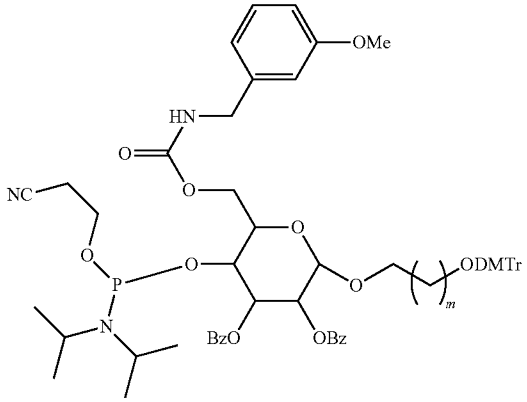

6032

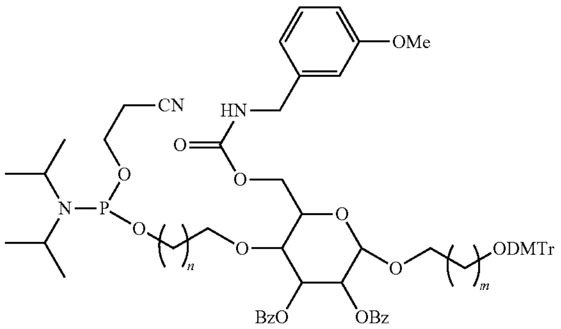

-continued
6033
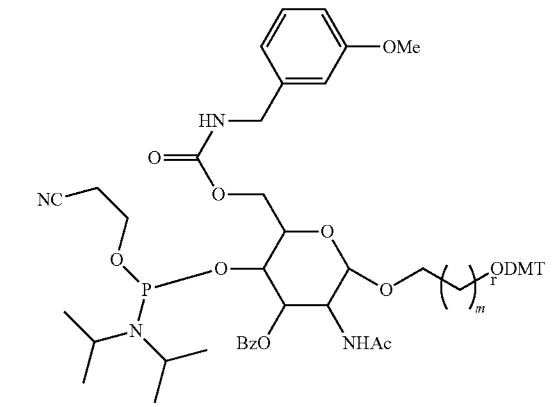
6034
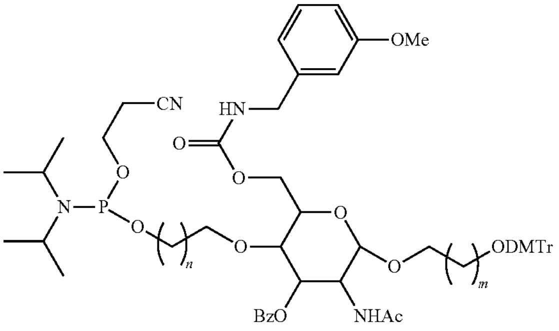
6035
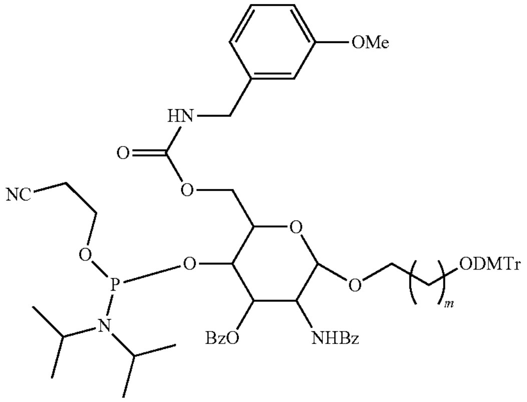
6036
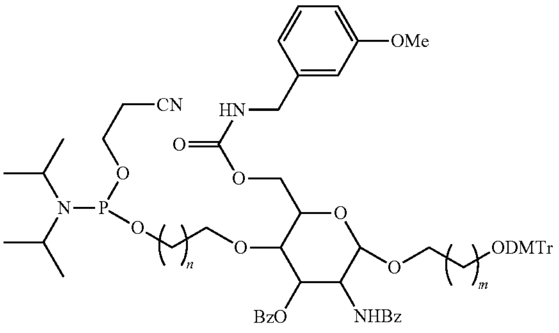
-continued
6037
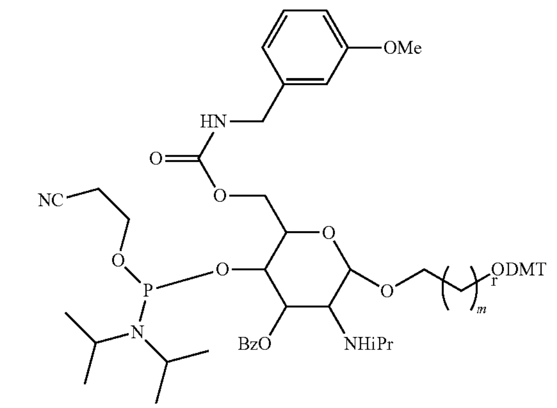
6038
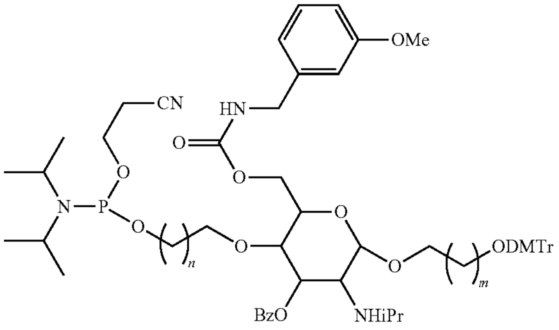
6039
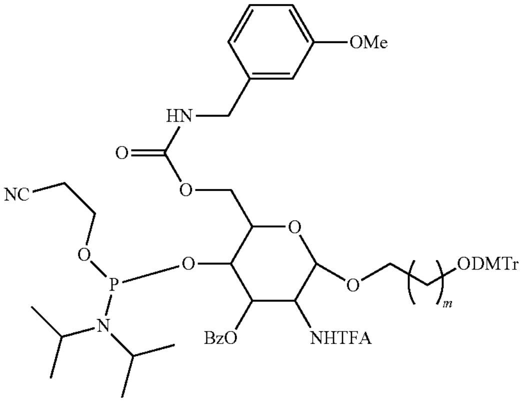
6040
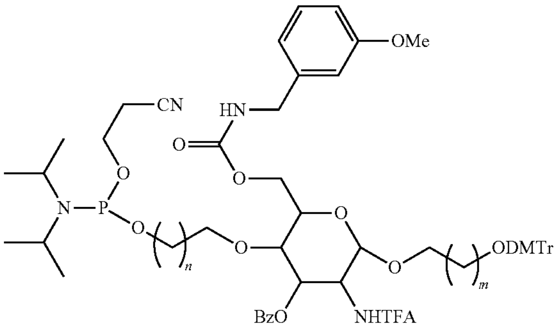

-continued
6041
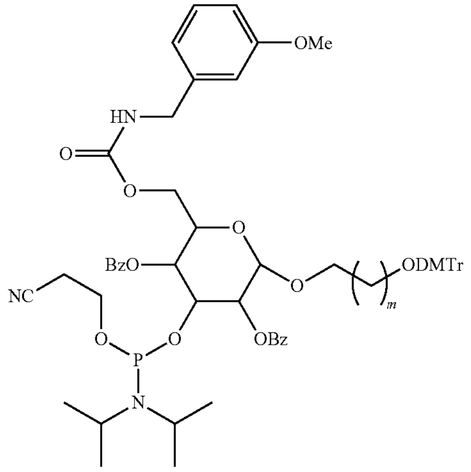
6042
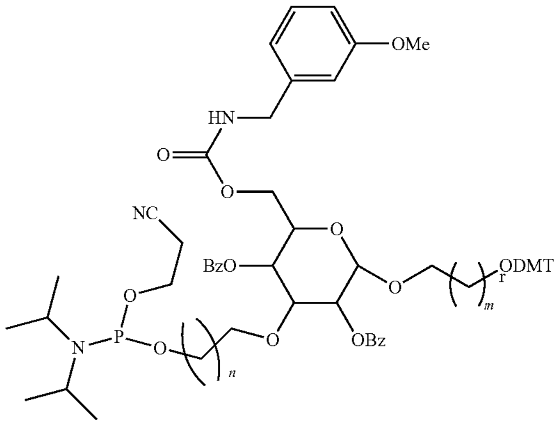
6043
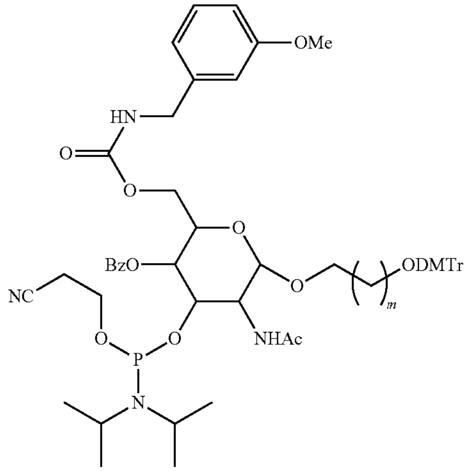
-continued
6044
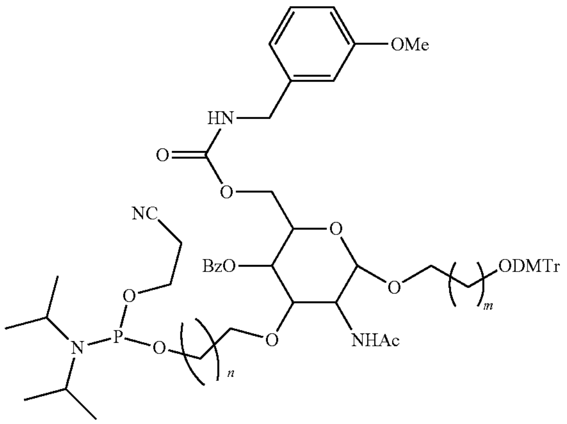
6045
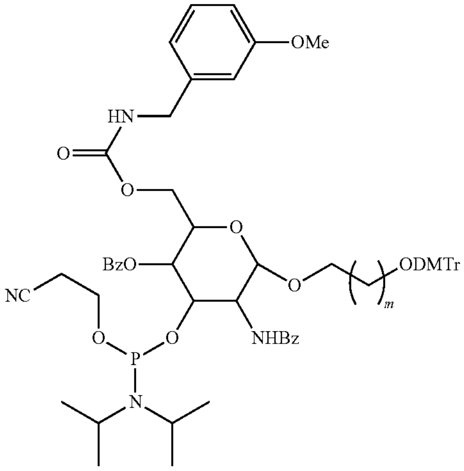
6046
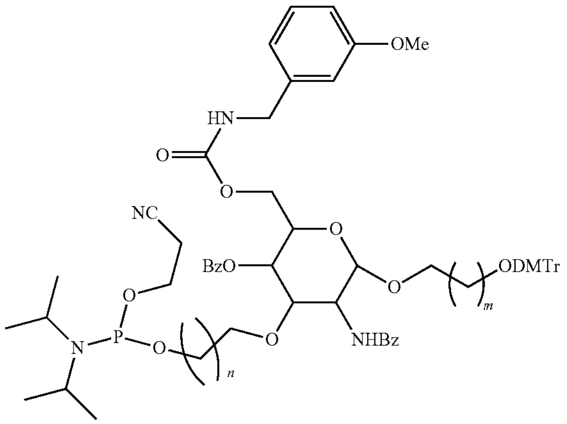

-continued

6047

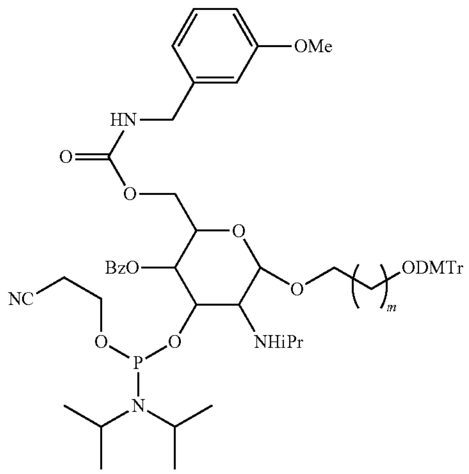

6048

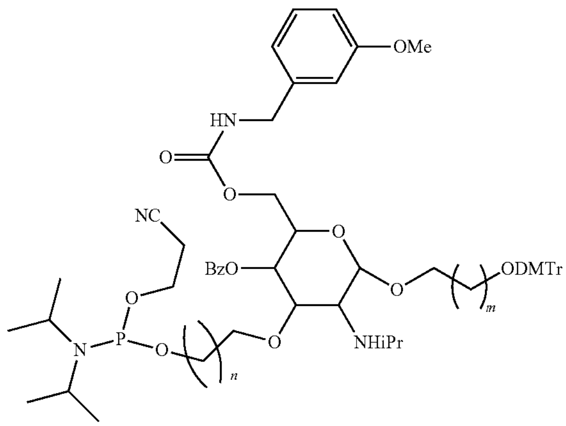

-continued

6049

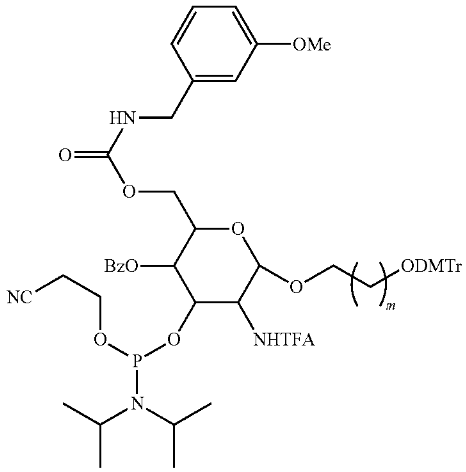

6050

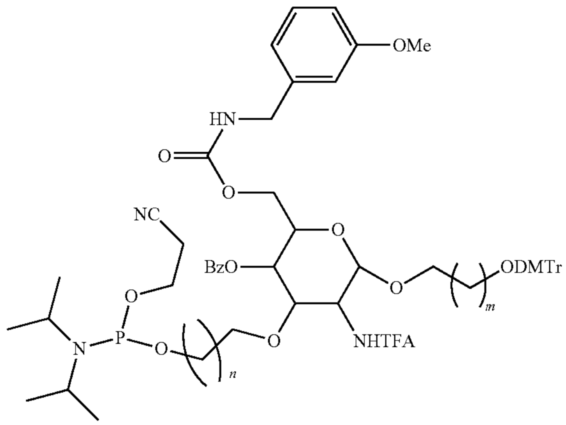

n = 1-12 and m = 1-12, various modified carbohydrates (Glactose, Galactosamine, Glucose, Glucosamine, Mannose, Mannosamine derivatives or pentose derivatives).

The bis(siRNA) is synthesized on the solid support with consecutive addition of one or more of these cleavable linkers and followed by hybridization to complementary strands as shown in the Example 1 (Scheme 1)

Example 9. Functionalized Cleavable Linkers and Phosphoramidites

Scheme 9

6051

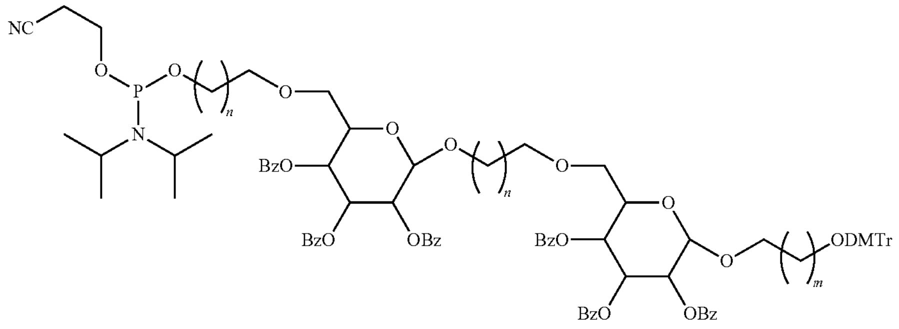

-continued

6052

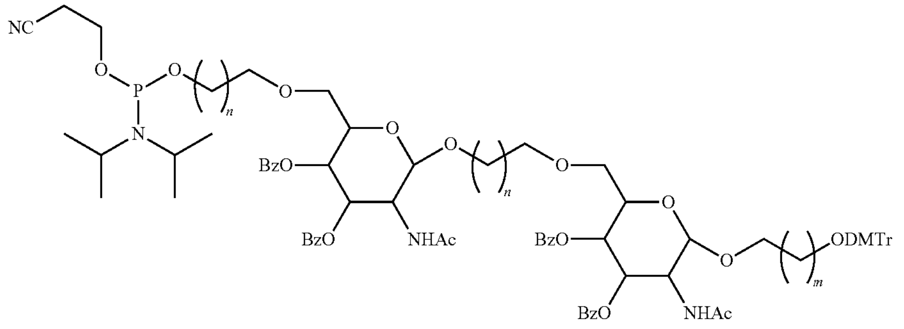

6053

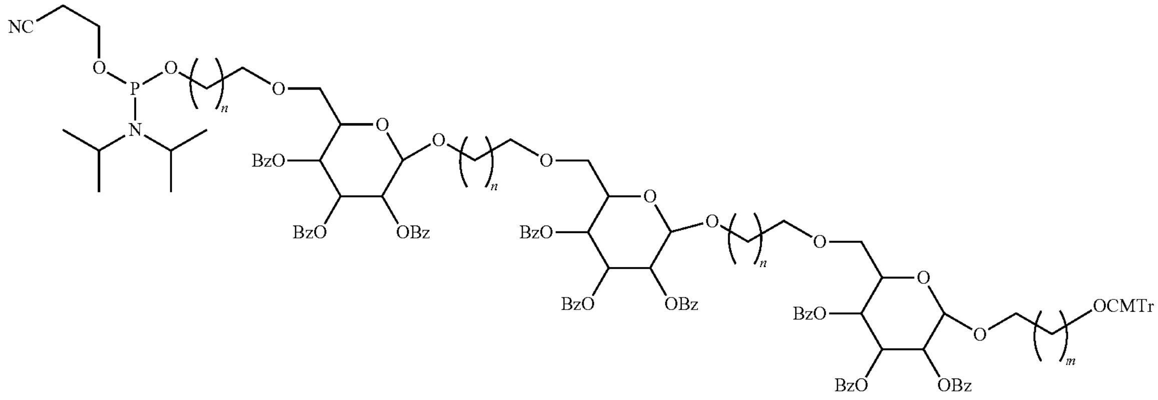

6054

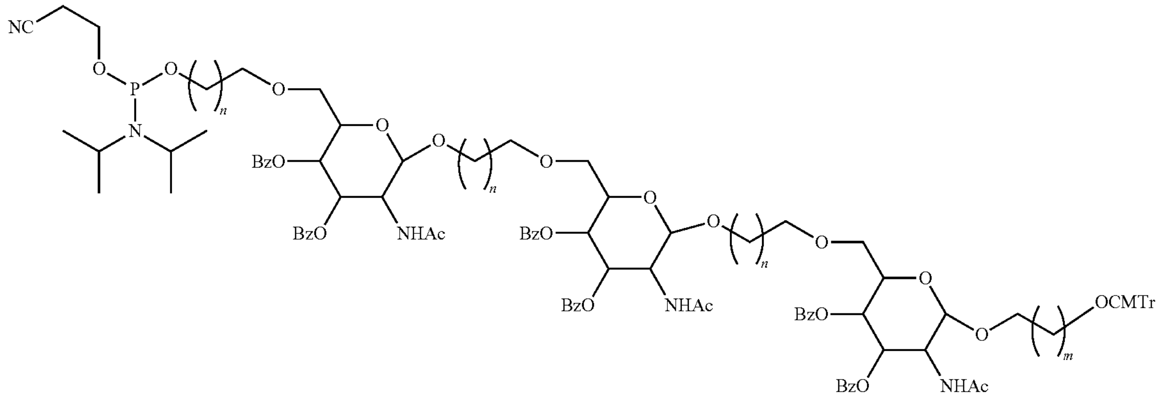

n = 1-12 and m = 1-12, various modified carbohydrates (di or tri saccharides of Galactose, Galactosamine, Glucose, Glucosamine, Mannose, Mannosamine derivatives).

The bis(siRNA) is synthesized on the solid support with consecutive addition of one or more of these cleavable linkers and followed by hybridization to complementary strands as shown in the Example 1 (Scheme 1).

Example 10. Functionalized Cleavable Linkers and Phosphoramidites
Scheme 10
6055
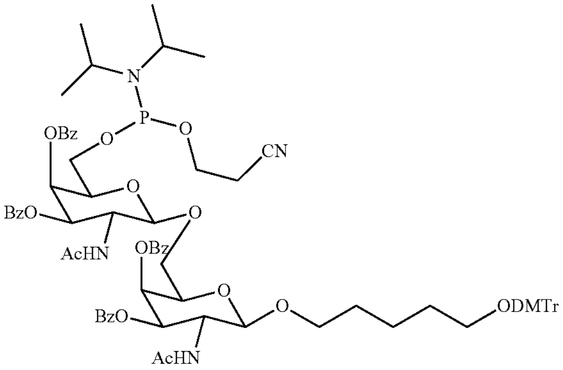
6056
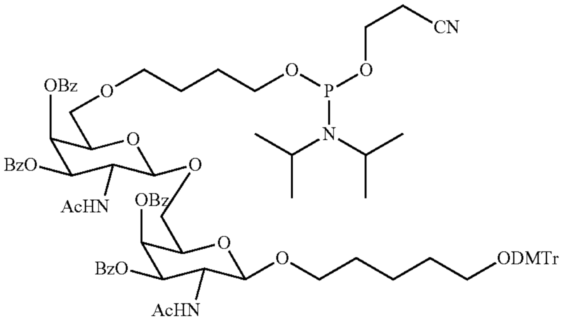
6057
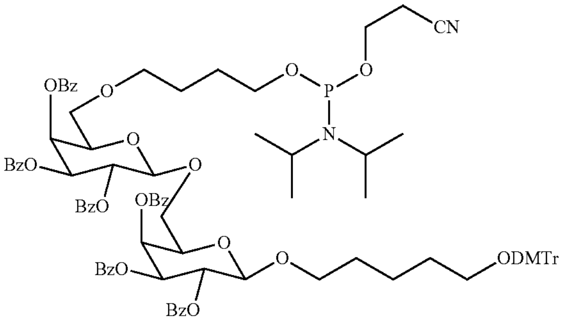
6058
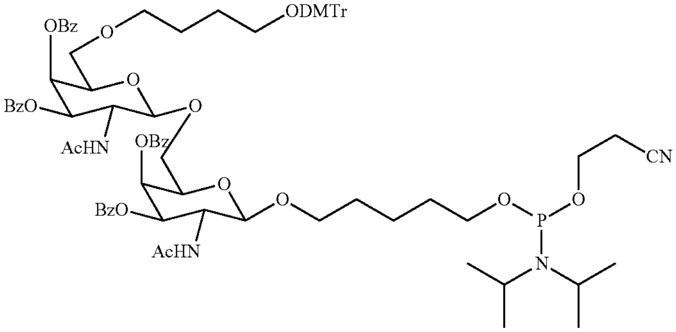

-continued
6059
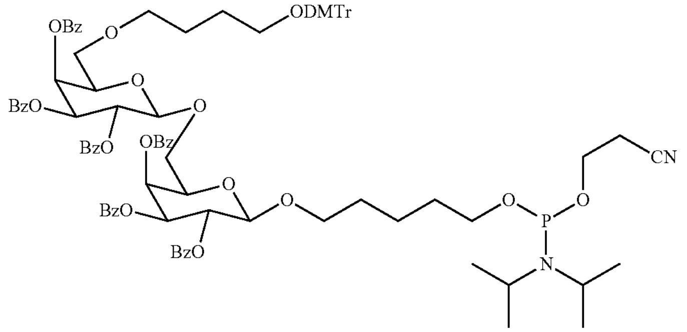
6060
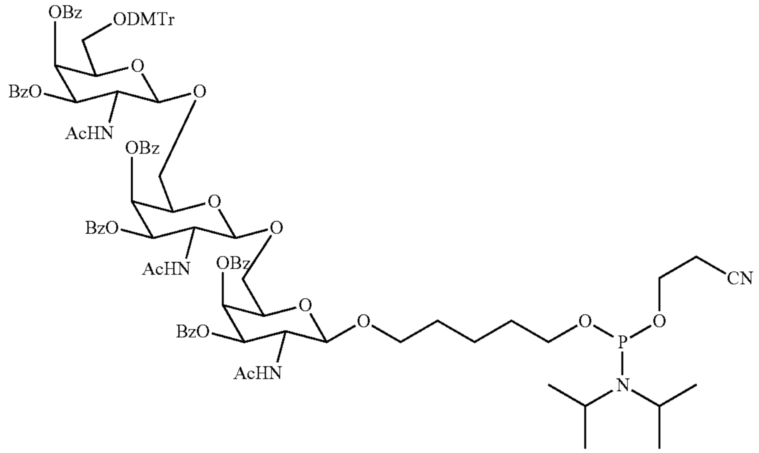
6061
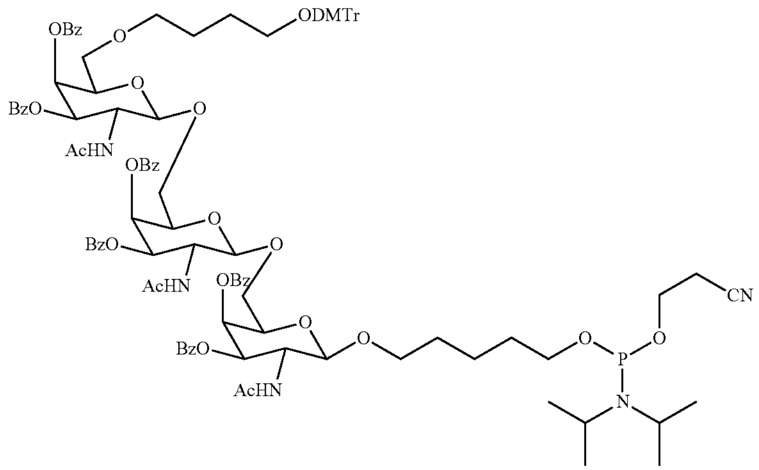

-continued
6062
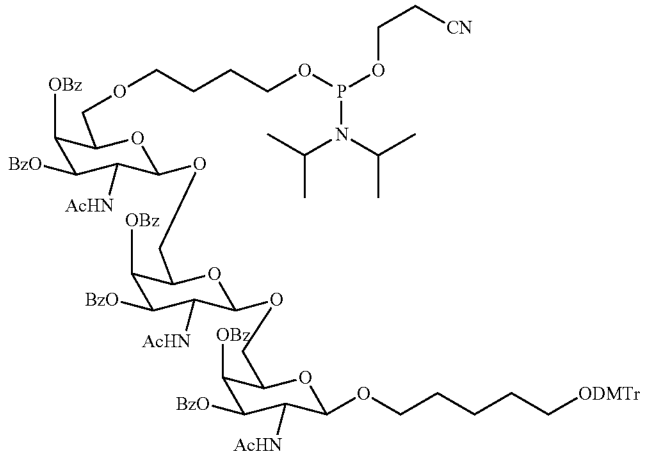
6063
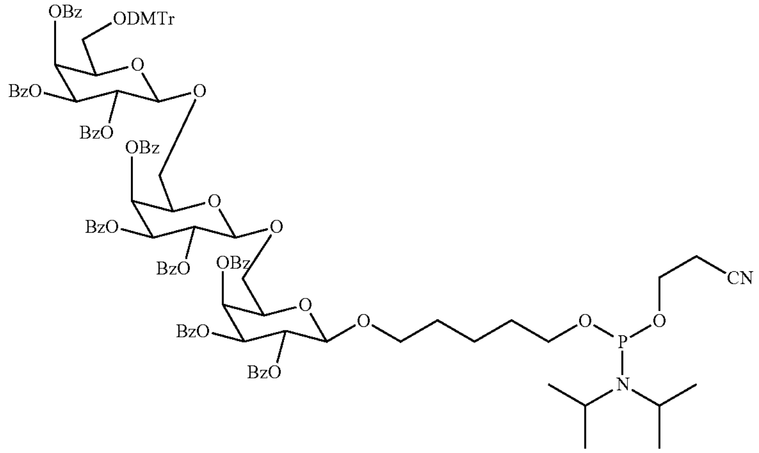
6064
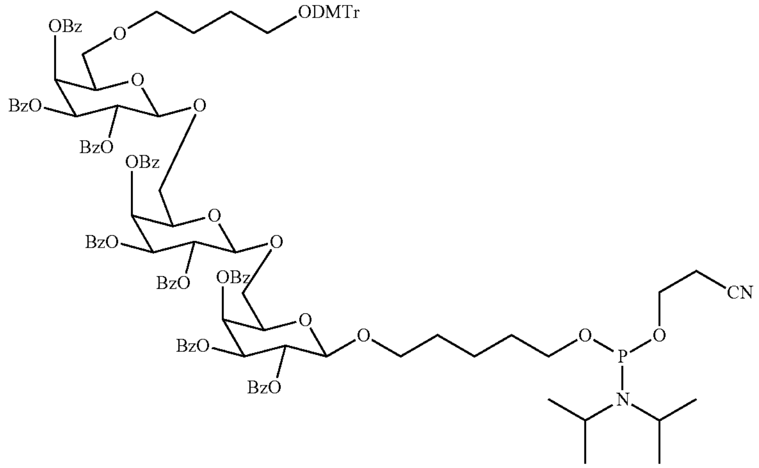

-continued
6065
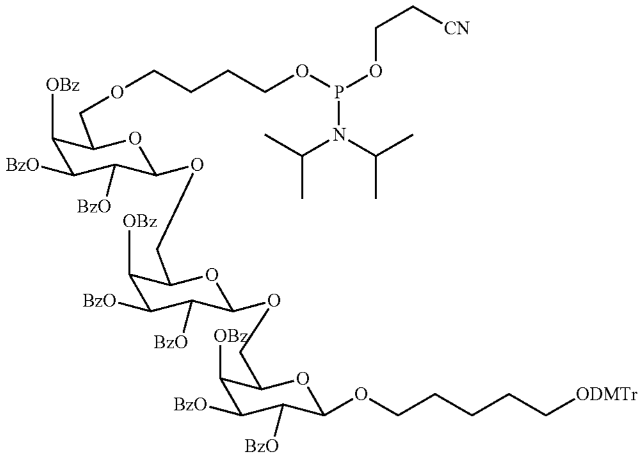
6066
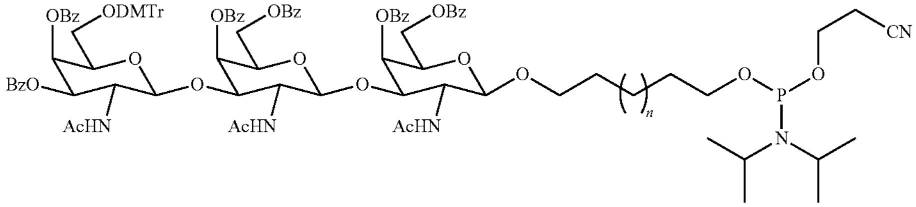
6067
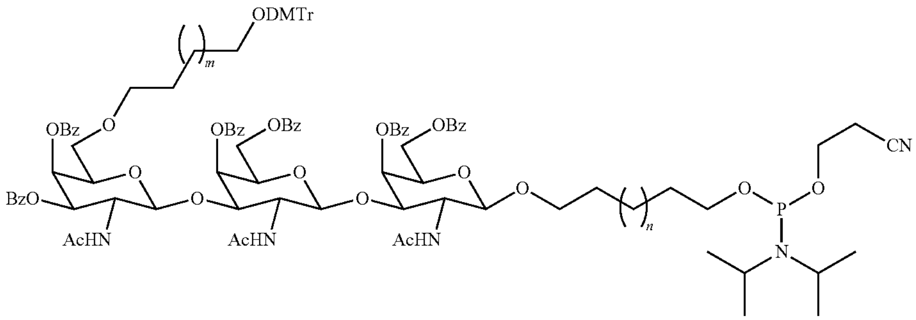
6068
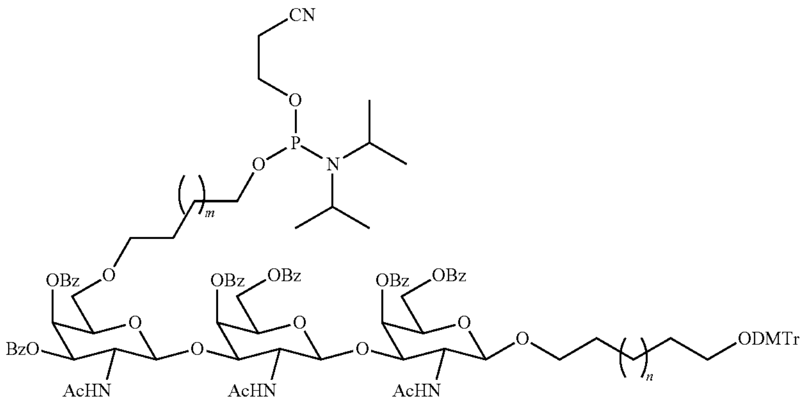
6069
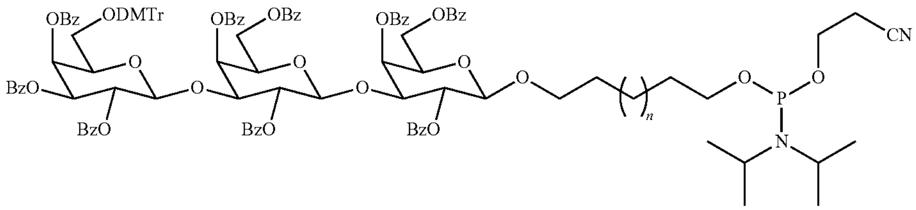

-continued
6070
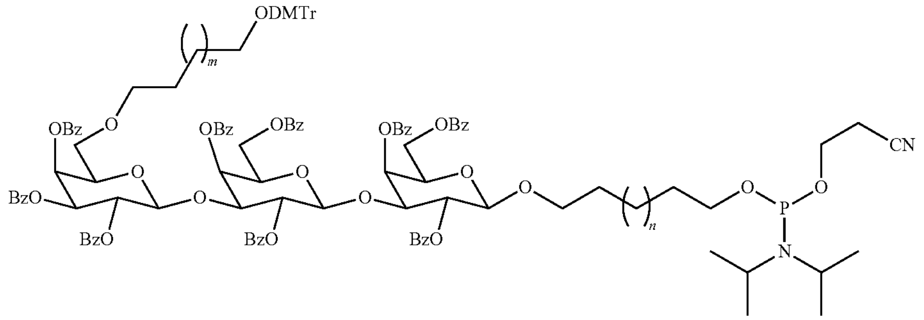
6071
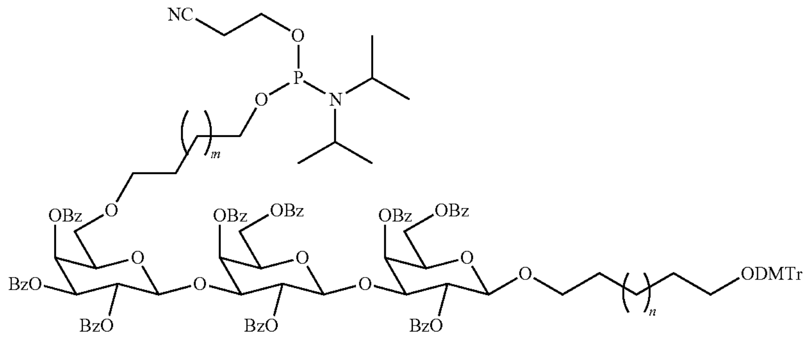
6072
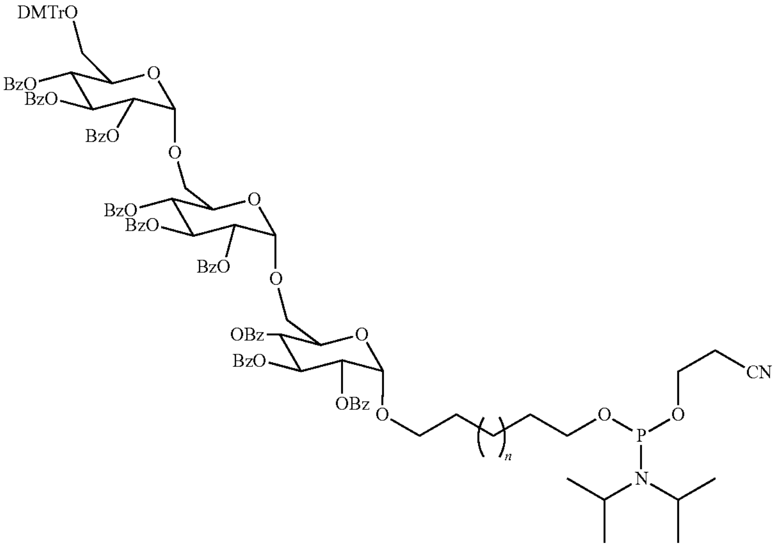

-continued

6073

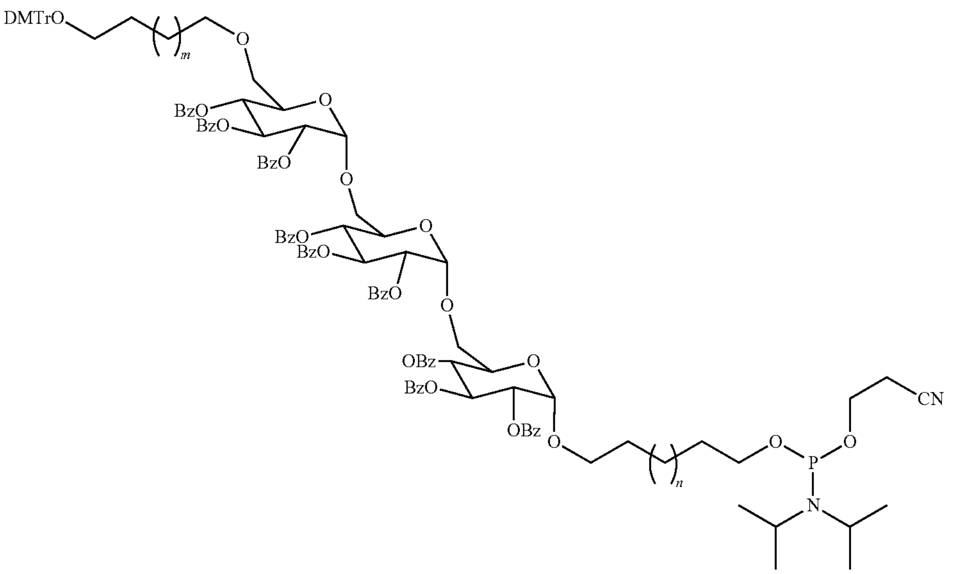

6074

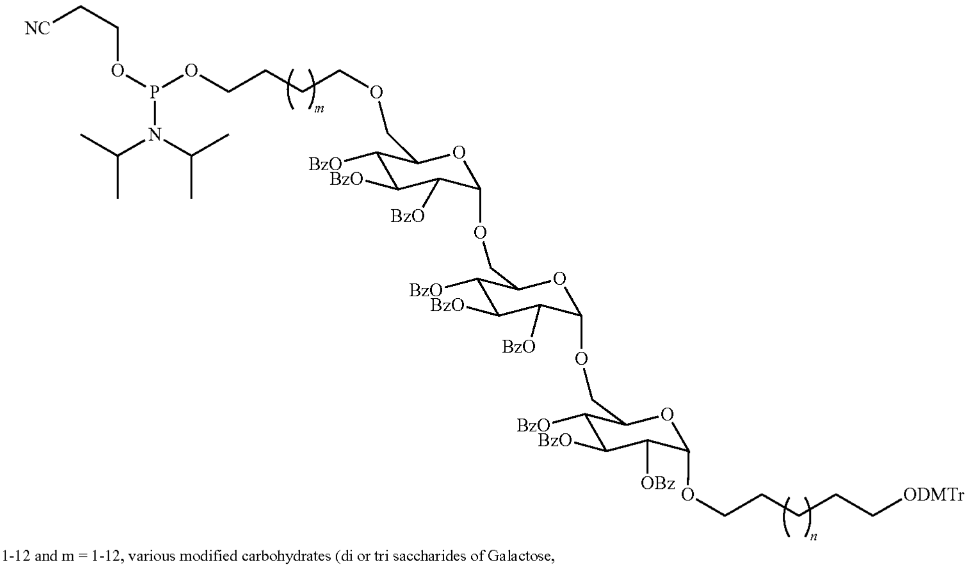

n = 1-12 and m = 1-12, various modified carbohydrates (di or tri saccharides of Galactose, Galactosamine, Glucose, Glucosamine, Mannose, Mannosamine derivatives).

The bis(siRNA) is synthesized on the solid support with consecutive addition of one or more of these cleavable linkers and followed by hybridization to complementary strands as shown in the Example 1 (Scheme 1)

Example 11. Functionalized Protease Cleavable Linkers and Phosphoramidites

Scheme 11
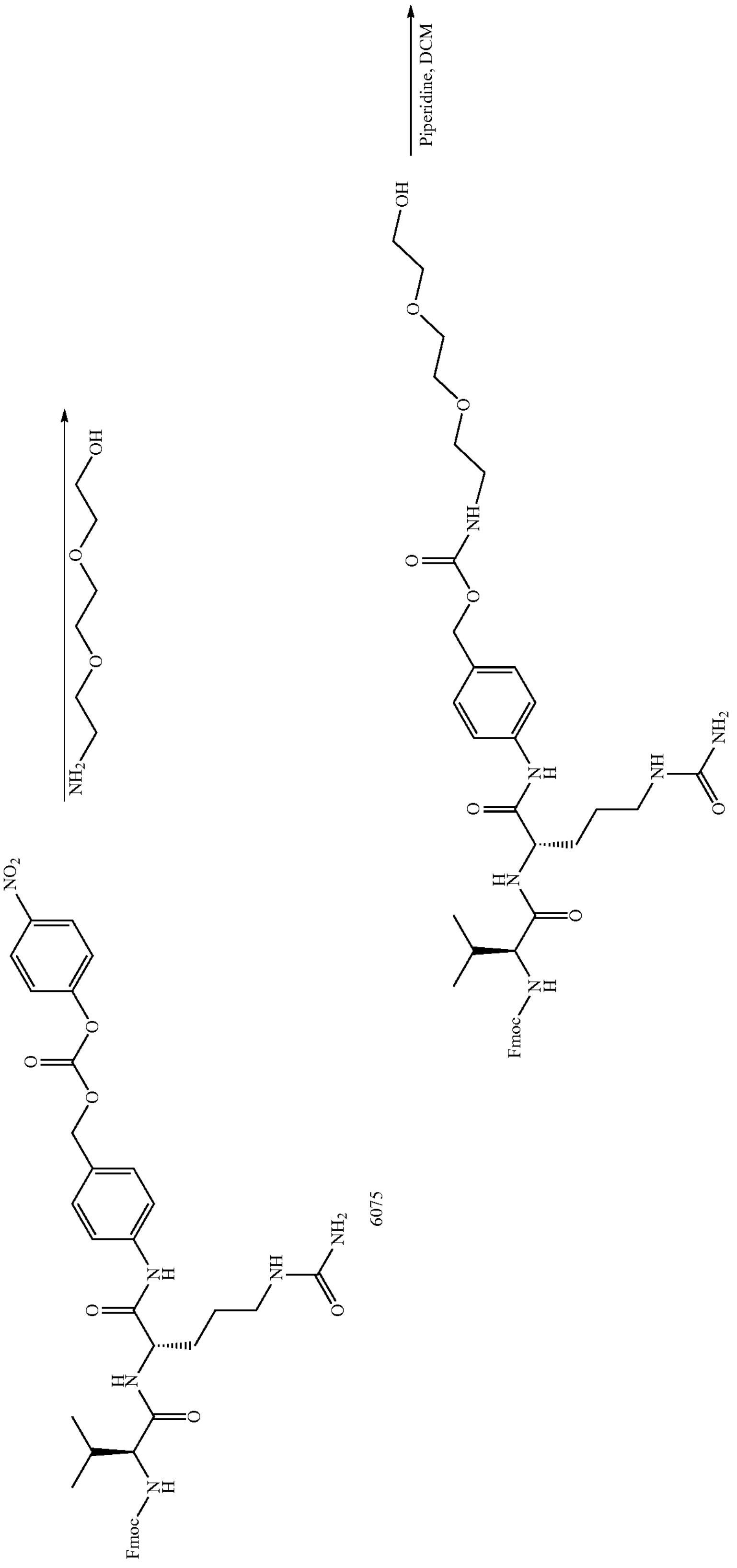
6075
6076

-continued
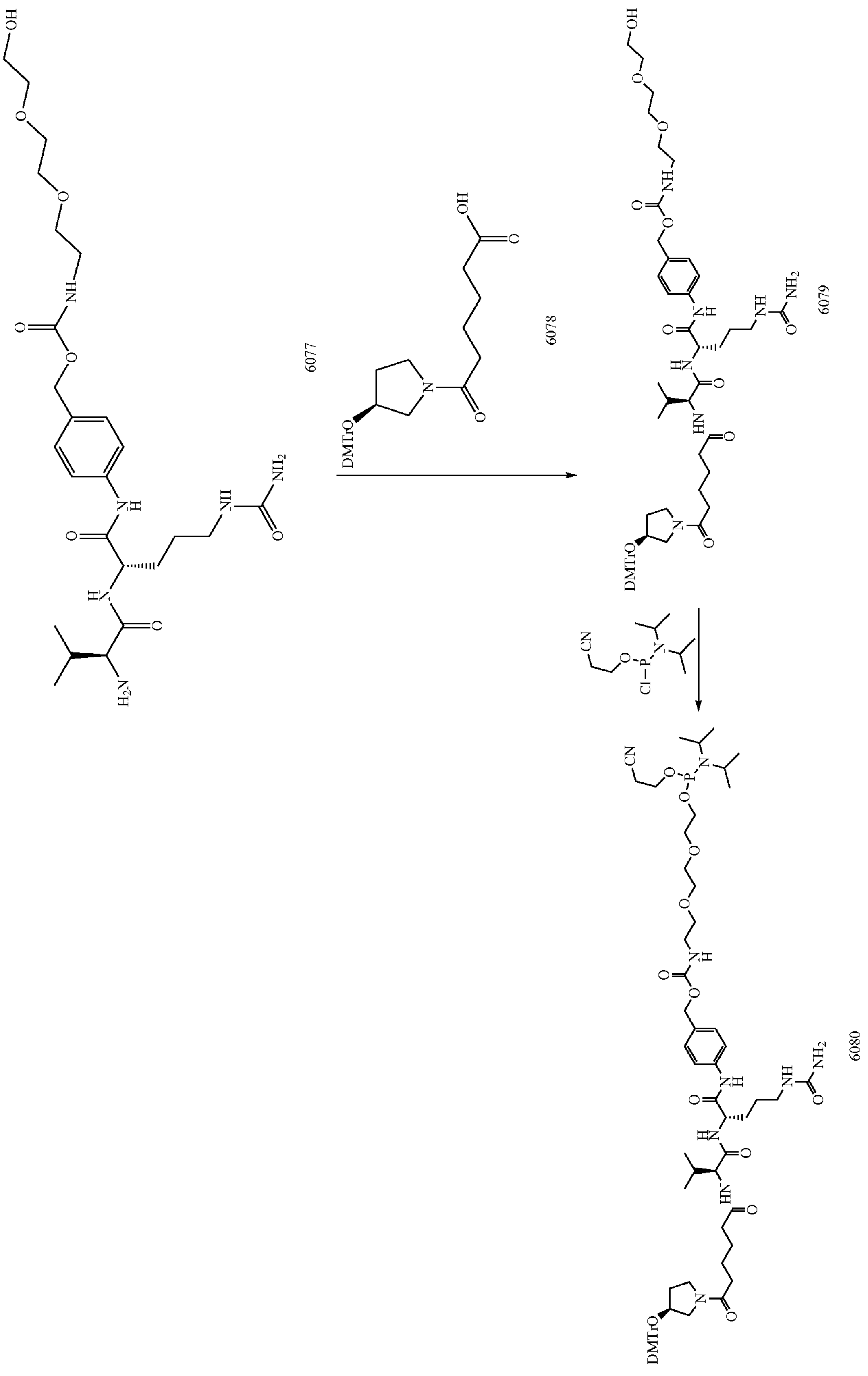
6077
6078
6079
6080

-continued
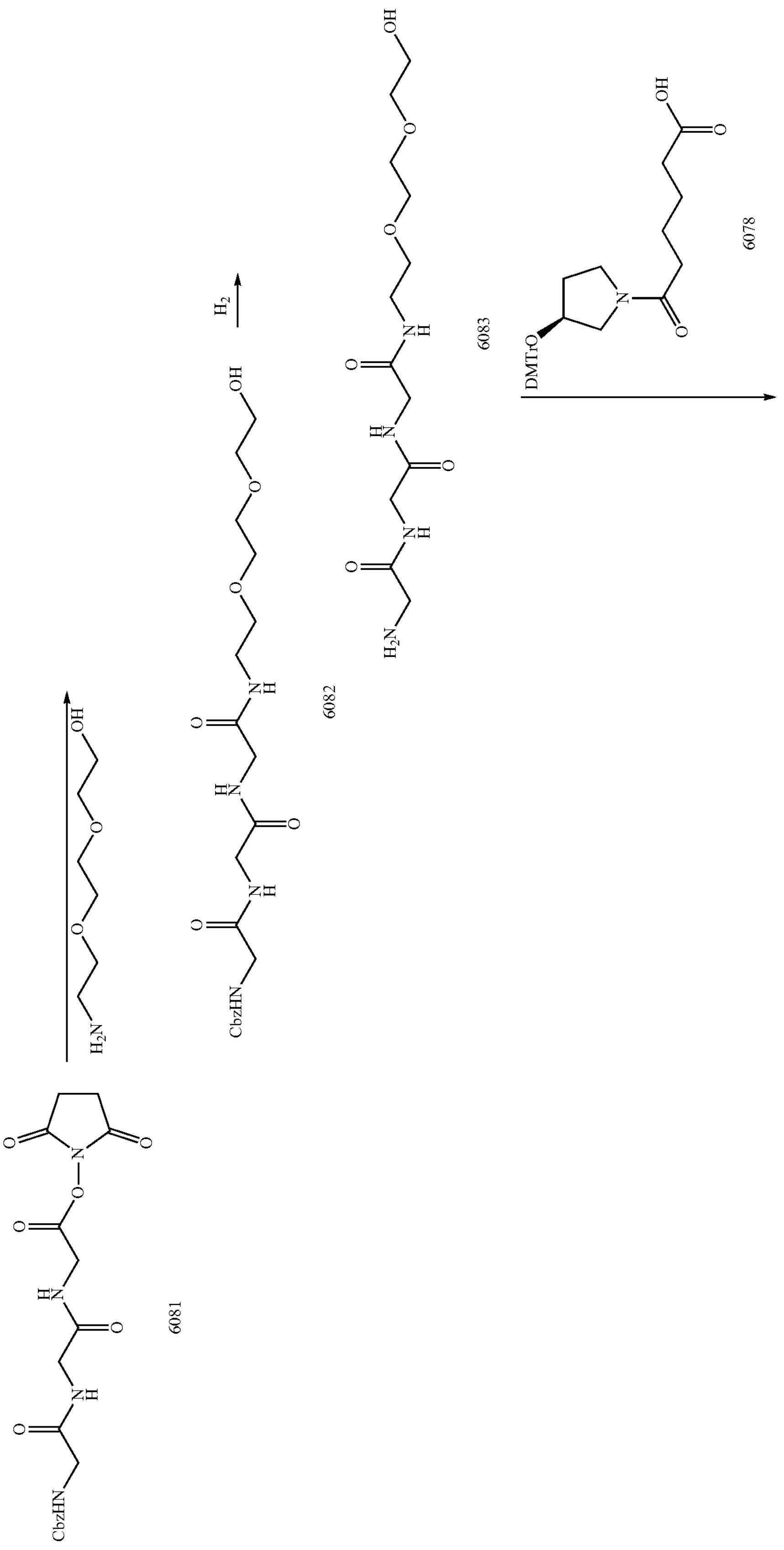
6081
6082
6083
6078

-continued
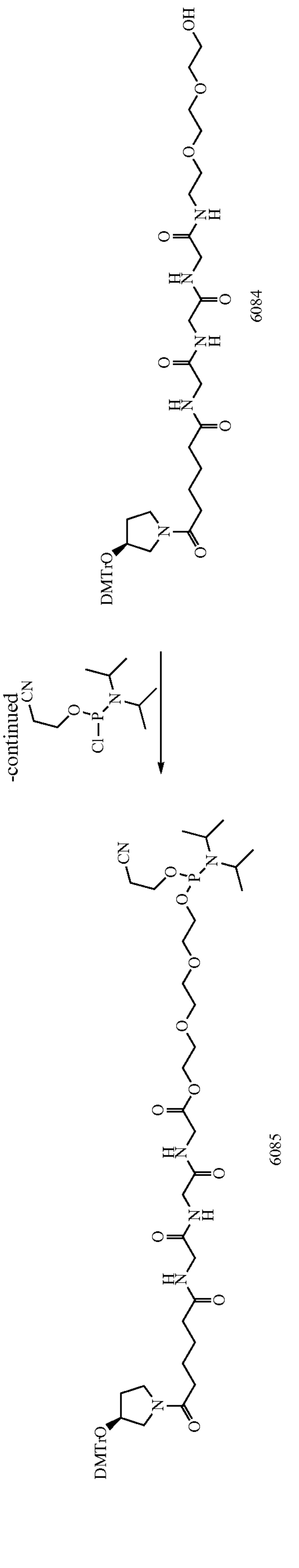
6084
6085

The bis(siRNA) is synthesized on the solid support with consecutive addition of one or more of these cleavable linkers and followed by hybridization to complementary strands as shown in the Example 1 (Scheme 1)

Example 12. Synthesis of Phosphoramidite 106

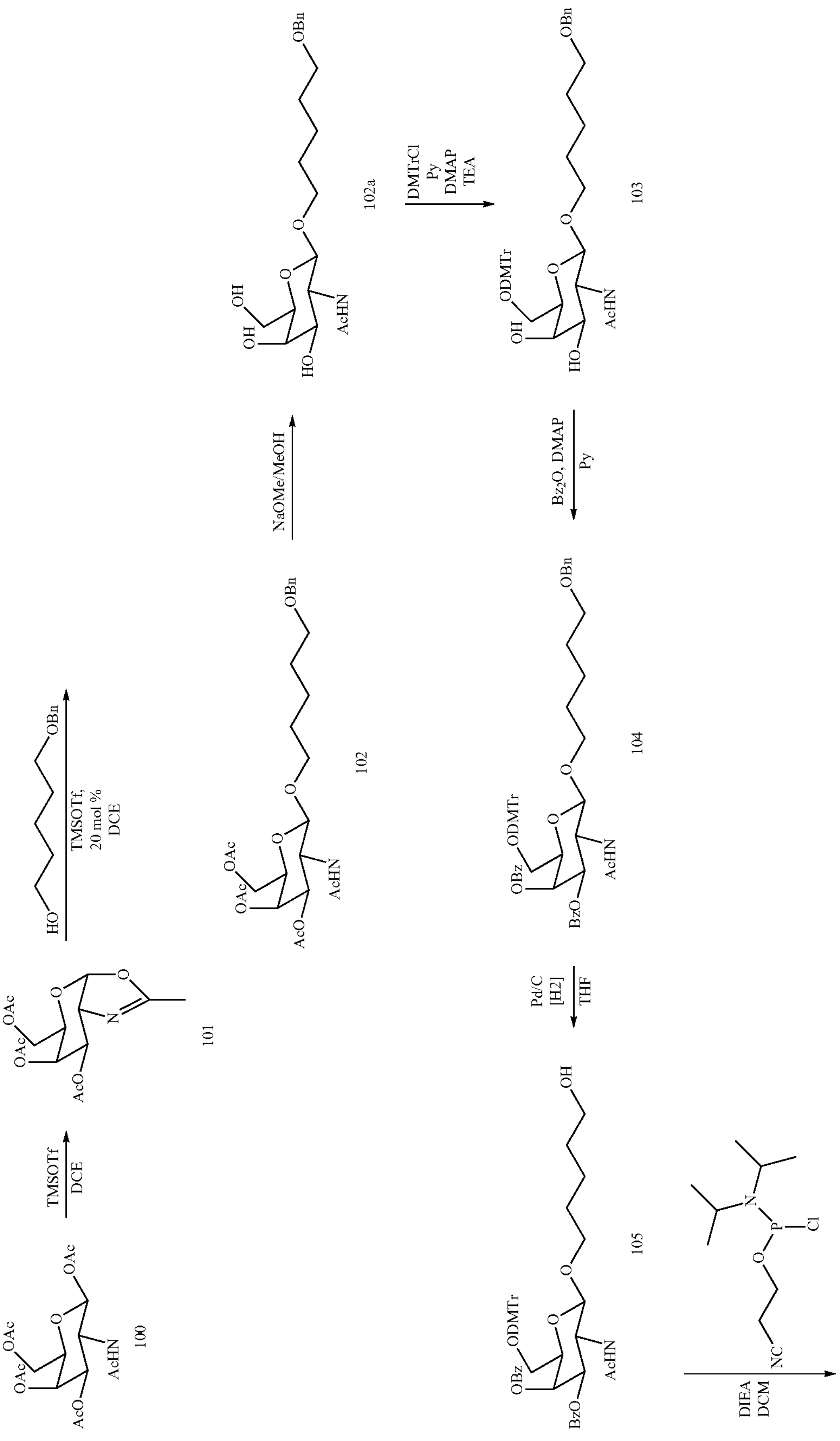
100 101 102 102a 103 104 105

-continued
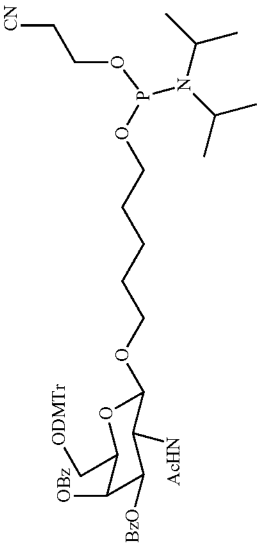
106

Compound (101)—Compound 100 (20 g, 51.4 mmol) was suspended in anhydrous dichloroethane (DCE) (200 mL). The reaction flash was evacuated and purged with argon. Trimethylsilyl trifluoromethanesulfonate (11.16 ml, 61.7 mmol) was added dropwise via syringe. Reaction was heated to 45° C. utilizing water bath and stirred overnight resulting in a clear solution. Reaction was checked by TLC (5% MeOH/DCM) and developed using Hanessian stain. Reaction was complete and cooled reaction with ice bath. Took sodium bicarbonate (12.95 g, 154.2 ml) and dissolved in 100 ml of water. Sodium bicarbonate solution was SLOWLY to reaction mixture and effervescence occurred. Reaction was left to stir for 20 minutes to completely neutralize. The mixture was added to separation funnel and organic layer was separated and aqueous layer was washed with dichloromethane. The organic layers were combined and washed with a brine solution. The organic layer was separated and dried with sodium sulfate. The solid was filtered off and the mother liquor was concentrated and put on hi vacuum to yield (16.64 g) of 101. $^1$H NMR (400 MHz, DMSO-d6) δ 6.04 (d, J=7.0 Hz, 1H), 5.23 (dd, J=3.9, 2.8 Hz, 1H), 4.87 (dd, J=6.9, 3.9 Hz, 1H), 4.25 (ddd, J=7.5, 5.0, 2.8 Hz, 1H), 4.10 (dd, J=11.6, 7.2 Hz, 1H), 4.02 (dd, J=11.5, 5.0 Hz, 1H), 3.94 (tq, J=6.9, 1.4 Hz, 1H), 3.89 (s, 1H), 2.06 (s, 3H), 2.00 (d, J=3.6 Hz, 6H), 1.94 (d, J=1.4 Hz, 3H). Mass calc. for C14H19NO8: 329.31, found: 330.1 (M+H).

Compound (102)—Compound 101 (5 g, 15.19 mmol) and 5-Benzyloxy-1-pentanol (3.21 ml, 16.71 mmol) was dissolved with dry dichloroethane (DCE) (60 ml). The reaction flash was evacuated, purged with argon and cooled in ice bath. Trimethylsilyl trifluoromethanesulfonate (0.550 ml, 3.04 mmol) was added via syringe. Reaction was checked after 3.5 hours by TLC (5% MeOH/DCM) and developed using Hanessian stain. Reaction was complete. Sodium bicarbonate (383 mg, 4.56 mmol) was dissolved in 100 mL and cooled in ice bath. The reaction mixture was added dropwise to the stirring sodium bicarbonate solution. The reaction was left to stir for 20 minutes to completely neutralize. The mixture was added to separation funnel and organic layer was separated and aqueous layer was washed with dichloromethane. The organic layers were combined and washed with a brine solution. The organic layer was separated and dried with sodium sulfate. The solid was filtered off and the mother liquor was concentrated and put on hi vacuum to yield (8.88 g) of 102. $^1$H NMR (400 MHz, DMSO-d6) δ 7.81 (d, J=9.2 Hz, 1H), 7.38-7.21 (m, 6H), 5.20 (d, J=3.4 Hz, 1H), 4.94 (dd, J=11.3, 3.4 Hz, 1H), 4.47 (d, J=8.5 Hz, 1H), 4.08-3.93 (m, 3H), 3.89 (s, 2H), 3.89-3.80 (m, 1H), 3.69 (dt, J=9.9, 6.1 Hz, 1H), 3.45-3.34 (m, 5H), 3.33 (s, 3H), 2.09 (s, 3H), 1.98 (s, 3H), 1.88 (s, 3H), 1.73 (s, 2H), 1.58-1.24 (m, 8H).

Compound (102a)—Compound 102 (7.95 g, 15.19 mmol) was dissolved in 150 ml of anhydrous methanol. The reaction flash was evacuated and purged with argon. Sodium methoxide in methanol (0.5M, 3.04 ml, 6.07 mmol) was added via syringe. Reaction was allowed to stir at room temperature overnight. Reaction was checked by TLC (10% MeOH/DCM) and developed using Hanessian stain. Glacial acetic acid was added to the reaction to lower the pH to 7 and the reaction mixture was concentrated under reduced pressure. The residue was suspended in 100 ml of dichloromethane with minimal methanol to dissolve crude. The product was precipitated by adding this crude solution to a 50/50 ether/hexane (500 ml) solution drop wise. A precipitate formed, stirred for another 10 minutes, product filtered off and dried under high vacuum to yield (5.26 g) of 102a. $^1$H NMR (400 MHz, DMSO-d6) δ 7.62 (d, J=9.0 Hz, 1H), 7.38-7.21 (m, 5H), 4.62 (s, 3H), 4.42 (s, 2H), 4.20 (d, J=8.4 Hz, 1H), 3.75-3.60 (m, 3H), 3.57-3.43 (m, 3H), 3.39 (q, J=6.5, 5.3 Hz, 4H), 3.31 (d, J=6.5 Hz, 8H), 3.26 (t, J=6.2 Hz, 1H), 1.75 (s, 3H), 1.47 (dq, J=28.9, 6.9, 6.5 Hz, 4H), 1.37-1.26 (m, 2H). Mass calc. for C20H31NO7: 397.47, found: 420.2 (M+Na).

Compound (103)—Compound 102a (5.20 g, 13.09 mmol) and 50 ml of anhydrous pyridine was added to a reaction flask. Pyridine was stripped off under reduced pressure. This was repeated for three times and dried under high vacuum overnight. The next day 4-(Dimethylamino)pyridine (0.160 g, 1.31 mmol), triethylamine (1.78 ml, 13.09 mmol), and anhydrous pyridine was added to the reaction flask. The reaction was cooled to 0° C. using an ice bath. The reaction flash was evacuated and purged with argon. 4,4'-Dimethoxytrityl Chloride (4.92 g, 14.53 mmol) was dissolved in anhydrous pyridine and resulting solution was added via syringe to the reaction flask. The reaction was allowed to come up to room temperature and stirred overnight. The reaction was checked by TLC (100% EtOAc) and developed using Hanessian stain. Methanol was added to quench the reaction and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated and put on hi vacuum to yield (8.70 g) of 103. Compound 103 $^1$H NMR (400 MHz, DMSO-d6) δ 7.63 (d, J=9.0 Hz, 1H), 7.44-7.37 (m, 3H), 7.36-7.15 (m, 17H), 7.09-7.01 (m, 1H), 6.92-6.78 (m, 7H), 4.62 (d, J=6.0 Hz, 1H), 4.52 (d, J=4.3 Hz, 1H), 4.39 (s, 2H), 4.27 (d, J=8.4 Hz, 1H), 3.69 (d, J=7.1 Hz, 11H), 3.67-3.62 (m, 1H), 3.59 (t, J=3.8 Hz, 1H), 3.52 (t, J=5.8 Hz, 1H), 3.43 (ddd, J=9.9, 6.1, 3.0 Hz, 2H), 3.37 (t, J=6.5 Hz, 3H), 3.33 (s, 5H), 3.18 (dd, J=9.3, 7.0 Hz, 1H), 3.00 (dd, J=9.3, 4.8 Hz, 1H), 2.92 (d, J=12.9 Hz, 2H), 1.77 (s, 3H), 1.54-1.45 (m, 4H), 1.39-1.28 (m, 2H). Mass calc. for C41H49NO9: 699.84, found: 722.3 (M+Na).

Compound (104)—Compound 103 (8.70 g, 12.44 mmol) and 4-(Dimethylamino)pyridine (1.52 g, 12.44 mmol) were added to a reaction flask. The reaction flash was evacuated and purged with argon. Anhydrous pyridine (230 ml) was added via syringe. A pyridine solution of benzoic anhydride (7.03 g, 31.1 mmol) was added to the reaction mixture via syringe and the reaction was stirred at room temperature overnight. The reaction was checked by TLC (30% EtOAc/Hexane) and developed using Hanessian stain. After the reaction was complete, water was added to quench the reaction and stirred for 10 minutes. Solvent was removed under reduced pressure. EtOAc and water were added and put into a separation funnel. The organic layer was separated and washed with saturated sodium bicarbonate. The organic layer was separated and washed with a brine solution. The organic layer was separated and dried with sodium sulfate. The solid was filtered off and the mother liquor was concentrated and put on hi vacuum to yield (8.35 g) of 104. $^1$H NMR (400 MHz, DMSO-d6) δ 8.01-7.88 (m, 2H), 7.73 (ddd, J=8.2, 3.9, 1.4 Hz, 4H), 7.71-7.55 (m, 3H), 7.45 (dt, J=39.3, 7.8 Hz, 5H), 7.37-7.20 (m, 8H), 7.20-7.04 (m, 8H), 6.76-6.58 (m, 5H), 5.84 (d, J=3.3 Hz, 1H), 5.33 (dd, J=11.1, 3.4 Hz, 1H), 4.64 (d, J=8.5 Hz, 1H), 4.41 (s, 2H), 4.31 (dd, J=8.6, 5.9 Hz, 1H), 4.16 (dt, J=11.0, 8.9 Hz, 1H), 3.79-3.66 (m, 2H), 3.64 (s, 7H), 3.44 (dt, J=9.8, 6.5 Hz, 1H), 3.37 (t, J=6.4 Hz, 2H), 3.33 (s, 1H), 3.16 (dd, J=8.5, 5.4 Hz, 1H), 2.95 (t, J=8.6 Hz, 1H), 1.65 (s, 3H), 1.50 (ddt, J=14.9, 10.6, 6.5 Hz, 4H), 1.32 (qd, J=10.5, 9.3, 6.3 Hz, 2H). Mass calc. for C55H57NO11: 908.06, found: 930.3 (M+Na).

Compound (105)—Compound 104 (3.74 g, 4.12 mmol) was added to a reaction flask. The reaction flash was evacuated and purged with argon three times. The starting material was dissolved by adding anhydrous tetrahydrofuran via syringe. Then 10% palladium on carbon, deguessa type, (374 mg, 10% by weight) was added. The reaction flash was evacuated and purged with argon three times. Then the reaction flask was evacuated and purged with hydrogen from a balloon two times. The reaction was left to stir at room temperature overnight. The reaction was checked by TLC (50/50 EtOAc/Hexane) and developed using phosphomolybdic acid. After the reaction complete, the flask was evacuated and purged with argon three times. The reaction mixture was filtered through celite to remove palladium on carbon, and was washed with methanol. The mother liquor was concentrated under reduced pressure. The residue was purified by flash chromatography on silica gel (10% to 100% EtOAc/Hexane) and the product fractions combined and concentrated on reduced pressure to yield (2.00 g 59%) of 105. $^1$H NMR (400 MHz, DMSO-d6) δ 8.04-7.85 (m, 1H), 7.79-7.64 (m, 4H), 7.64-7.54 (m, 1H), 7.51 (t, J=7.7 Hz, 2H), 7.40 (t, J=7.7 Hz, 2H), 7.34-7.21 (m, 2H), 7.22-7.01 (m, 6H), 6.75-6.59 (m, 4H), 5.84 (d, J=3.2 Hz, 1H), 5.33 (dd, J=11.1, 3.3 Hz, 1H), 4.64 (d, J=8.5 Hz, 1H), 4.32 (dt, J=9.7, 5.6 Hz, 2H), 3.71 (dt, J=9.7, 6.2 Hz, 1H), 3.61 (s, 5H), 3.43 (dt, J=10.0, 6.6 Hz, 1H), 3.39-3.29 (m, 2H), 3.16 (dd, J=8.6, 5.4 Hz, 1H), 2.94 (t, J=8.6 Hz, 1H), 1.67 (s, 3H), 1.55-1.43 (m, 2H), 1.38 (dt, J=13.0, 5.8 Hz, 2H), 1.28 (q, J=7.6 Hz, 2H). Mass calc. for C48H51NO11: 817.93, found: 840.3 (M+Na).

Compound (106)—Compound 105 is added to the reaction flask which is evacuated and purged with argon. The starting material is dissolved in dichloromethane, and diisopropyl amine is added and the reaction is stirred at room temperature for 1 to 2 hours. After checking the TLC for completeness, the reaction is worked up using standard extraction conditions. The crude residue is purified on silica gel to yield compound 106.

Example 13. Synthesis of Phosphoramidite 113

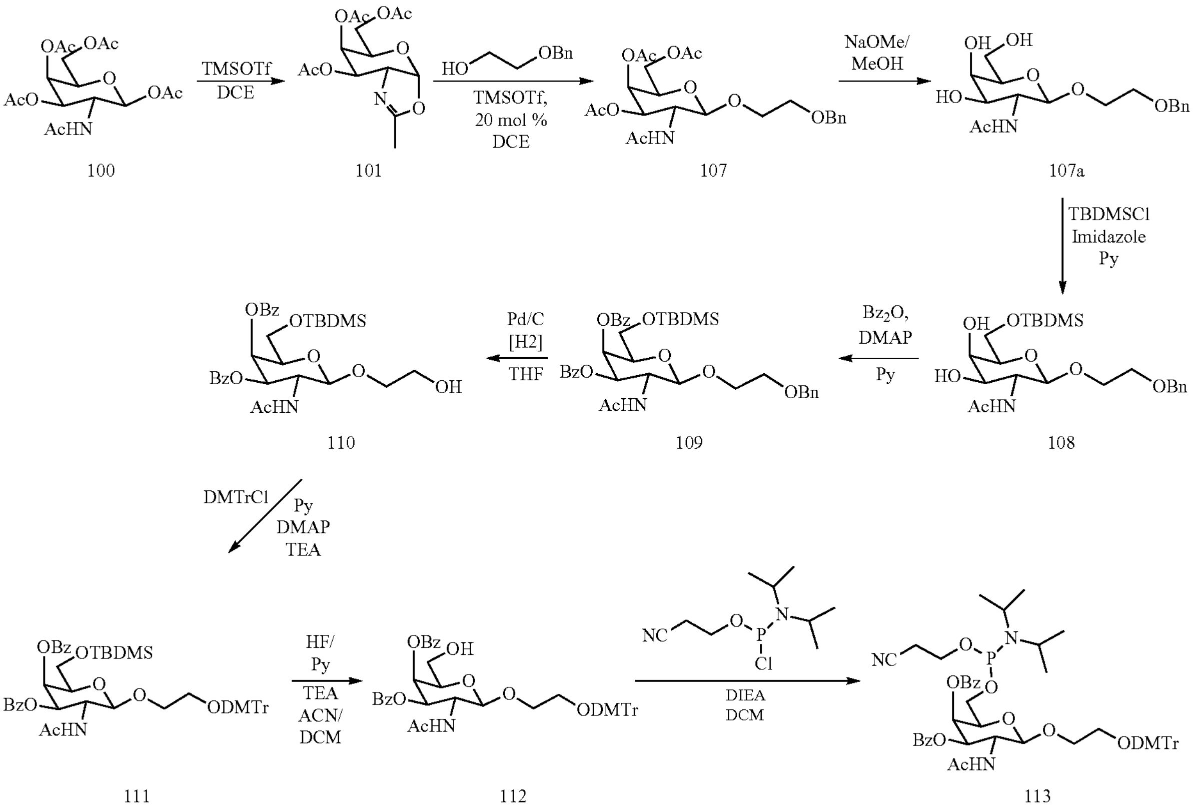

Compound (107): Compound 101 (5.0 g, 15.19 mmol) and 2-(Benzyloxy)ethanol (2.80 ml, 19.75 mmol) was dissolved with dry dichloroethane (DCE) (60 ml). The reaction flash was evacuated, purged with argon and cooled in ice bath. Trimethylsilyl trifluoromethanesulfonate (0.550 ml, 3.04 mmol) was added via syringe. Reaction was checked after 3.5 hours by TLC (5% MeOH/DCM) and developed using Hanessian stain. Reaction was complete. Sodium bicarbonate (383 mg, 4.56 mmol) was dissolved in 100 mL and cooled in ice bath. The reaction mixture was added dropwise to the stirring sodium bicarbonate solution. The reaction was left to stir for 20 minutes to completely neutralize. The mixture was added to separation funnel and organic layer was separated and aqueous layer was washed with dichloromethane. The organic layers were combined and washed with a brine solution. The organic layer was separated and dried with sodium sulfate. The solid was filtered off and the mother liquor was concentrated and put on hi vacuum to yield (8.64 g) of 107. $^1$H NMR (400 MHz, DMSO-d6) δ 7.38-7.22 (m, 4H), 5.21 (d, J=3.4 Hz, 1H), 4.97 (dd, J=11.2, 3.4 Hz, 1H), 4.56 (d, J=8.5 Hz, 1H), 4.47

(d, J=1.4 Hz, 2H), 4.09-3.95 (m, 2H), 3.89 (s, 1H), 3.84 (ddd, J=14.7, 7.5, 3.4 Hz, 1H), 3.63 (ddd, J=10.8, 6.4, 3.6 Hz, 1H), 3.54 (dq, J=10.7, 5.2 Hz, 2H), 3.44 (t, J=5.1 Hz, 1H), 2.09 (d, J=4.4 Hz, 2H), 1.98 (s, 2H), 1.88 (s, 2H), 1.73 (s, 1H).

Compound (107a)—Compound 107 (7.31 g, 15.19 mmol) was dissolved in 150 ml of anhydrous methanol. The reaction flash was evacuated and purged with argon. Sodium methoxide in methanol (0.5M, 2.275 ml, 4.55 mmol) was added via syringe. Reaction was allowed to stir at room temperature overnight. Reaction was checked by TLC (10% MeOH/DCM) and developed using Hanessian stain. After the reaction was complete, glacial acetic acid was added to the reaction to lower the pH to 7 and the reaction mixture was concentrated under reduced pressure. The residue was suspended in 100 ml of dichloromethane with minimal methanol to dissolve crude. The product was precipitated by adding this crude solution to a 50/50 ether/hexane (500 ml) solution dropwise. A precipitate formed, stirred for another 10 minutes, product filtered off and dried under high vacuum to yield (5.05 g) of 107a. $^1$H NMR (400 MHz, DMSO-d6) δ 7.65 (d, J=8.9 Hz, 1H), 7.38-7.21 (m, 5H), 4.63 (d, J=11.5 Hz, 2H), 4.47 (s, 2H), 4.28 (d, J=8.4 Hz, 1H), 3.83 (dt, J=9.1, 3.4 Hz, 1H), 3.72 (dt, J=10.7, 8.7 Hz, 1H), 3.64 (s, 1H), 3.62-3.45 (m, 6H), 3.41 (d, J=10.5 Hz, 2H), 3.36-3.25 (m, 7H), 1.90-1.78 (m, 1H), 1.75 (s, 2H).

Compound (108): Compound 107a (5.0 g, 14.08 mmol) and imidazole (2.88 g, 42.24 mmol) was added to a reaction flask. The reaction flash was evacuated and purged with argon. Anhydrous pyridine was added via syringe and starting materials dissolved. Reaction was stirred at room temperature for 10 minutes then a solution of tert-Butyldimethylsilyl chloride (3.18 g, 21.12 mmol) in pyridine was added via syringe. Reaction was stirred overnight at room temperature. The reaction was checked by TLC (100% EtOAc) and developed using Hanessian stain. After the reaction was complete; methanol was added to quench the reaction and stirred for 10 minutes. The reaction mixture was concentrated under reduced pressure and added dichloromethane and water. The mixture was added to separation funnel and organic layer was separated and aqueous layer was washed with dichloromethane. The organic layer was combined and washed with saturated sodium bicarbonate. The organic layer was separated and washed with a brine solution. The organic layer was separated and dried with sodium sulfate. The solid was filtered off and the mother liquor was concentrated to yield (8.80 g) of 108. This was used as crude for the next reaction.

Compound (109): Compound 108 (6.61 g, 14.09 mmol) and 4-(Dimethylamino)pyridine (1.72 g, 14.09 mmol) were added to a reaction flask. The reaction flash was evacuated and purged with argon. Anhydrous pyridine (200 ml) was added via syringe. A pyridine solution of benzoic anhydride (11.15 g, 49.31 mmol) was added to the reaction mixture via syringe and the reaction was stirred at room temperature overnight. The reaction was checked by TLC (50% EtOAc/Hexane) and developed using Hanessian stain. After the reaction was complete; water was added to quench the reaction and stirred for 10 minutes. Solvent was removed under reduced pressure. EtOAc and water were added and put into a separation funnel. The organic layer was separated and washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 100% EtOAc/Hexane) and the product fractions combined and concentrated on reduced pressure to yield (4.22 g 44%) of 109. $^1$H NMR (400 MHz, DMSO-$d_6$) δ 7.97 (d, J=9.2 Hz, 1H), 7.94-7.86 (m, 2H), 7.75-7.63 (m, 3H), 7.56 (dt, J=15.1, 7.5 Hz, 4H), 7.44-7.35 (m, 2H), 7.33 (d, J=3.5 Hz, 4H), 7.30-7.23 (m, 1H), 5.67 (d, J=3.3 Hz, 1H), 5.27 (dd, J=11.1, 3.3 Hz, 1H), 4.73 (d, J=8.5 Hz, 1H), 4.51 (s, 2H), 4.35-4.16 (m, 1H), 4.08 (t, J=7.3 Hz, 1H), 3.97-3.85 (m, 1H), 3.76-3.67 (m, 2H), 3.67-3.53 (m, 4H), 1.65 (s, 3H), 0.89-0.77 (m, 2H), 0.76 (s, 8H), 0.64 (s, 1H), −0.06 (s, 3H), −0.14 (s, 3H). Mass calc. for C37H47NO9Si: 677.87, found: 678.3 (M+H), 700.3 (M+Na).

Compound (110): Compound 109 (3.0 g, 4.43 mmol) was added to a reaction flask. The reaction flash was evacuated and purged with argon three times. The starting material was dissolved by adding anhydrous methanol via syringe. Then 10% palladium on carbon, deguessa type, (300 mg, 10% by weight) was added. The reaction flash was evacuated and purged with argon three times. Then the reaction flask was evacuated and purged with hydrogen from a balloon two times. The reaction was left to stir at room temperature overnight. The reaction was checked by TLC (60% EtOAc/Hexane) and developed using Hanessian stain. After the reaction was complete: the flash was evacuated and purged with argon three times. The reaction mixture was filtered through celite to remove palladium on carbon, and was washed with methanol. The mother liquor was concentrated under reduced pressure to yield (2.75 g) of 110. Mass calc. for C30H41NO9Si: 587.74, found: 588.3 (M+H), 610.3 (M+Na).

Compound (111): Compound 110 (2.60 g, 4.43 mmol) and 50 ml of anhydrous pyridine was added to a reaction flask. Pyridine was stripped off under reduced pressure. The residue was co-evaporated with pyridine three times and dried under high vacuum overnight. The next day 4-(Dimethylamino)pyridine (0.054 g, 0.443 mmol), triethylamine (0.604 ml, 4.43 mmol), and anhydrous pyridine was added to the reaction flask. The reaction was cooled to 0° C. using an ice bath. The reaction flash was evacuated and purged with argon. 4,4'-Dimethoxytrityl Chloride (1.67 g, 4.92 mmol) was dissolved in anhydrous pyridine and resulting solution was added via syringe to the reaction flask. The reaction was allowed to come up to room temperature and stirred overnight. The reaction was checked by TLC (60% EtOAc/Hexane) and developed using Hanessian stain. After the reaction was complete; methanol was added to quench the reaction and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/Hexane) and the product fractions combined and concentrated on reduced pressure to yield (1.96 g, 49.7%) of 111. $^1$H NMR (400 MHz, DMSO-d6) δ 8.04 (d, J=9.4 Hz, 1H), 7.95-7.85 (m, 2H), 7.76-7.71 (m, 2H), 7.71-7.63 (m, 1H), 7.63-7.56 (m, 1H), 7.53 (t, J=7.7 Hz, 2H), 7.45-7.36 (m, 4H), 7.34-7.23 (m, 6H), 7.23-7.15 (m, 1H), 6.91-6.83 (m, 4H), 5.70 (d, J=4.3 Hz, 1H), 5.30 (dd, J=11.1, 3.4 Hz, 1H), 4.75 (d, J=8.5 Hz, 1H), 4.41-4.28 (m, 1H), 4.11 (s, 1H), 3.77-3.67 (m, 7H), 3.67-3.56 (m, 2H), 3.33 (s, 1H), 3.20 (s, 1H), 2.98-2.91 (m, 1H), 1.60 (s, 3H), 0.84 (d, J=14.5 Hz, 1H), 0.76 (s, 8H), 0.73-0.64 (m, 1H), −0.07 (s, 3H), −0.15 (s, 3H). Mass calc. for C51H59NO11Si: 890.11, found: 912.4 (M+Na).

Compound (112): Compound 111 (1.86 g, 2.09 mmol) was added to a plastic reaction vessel. dichloromethane (18.3 ml) was added to dissolve starting material. Acetonitrile (55.8 ml), pyridine (37.2 ml), and trimethylamine (9.3 ml) were added. The reaction vessel was purged and cooled in an ice bath. The reaction was stirred and then hydrogen fluoride pyridine complex (9.3 ml) was added carefully. Reaction was stirred and warmed up to room temperature over 5 hours. The reaction was checked by TLC (35% EtOAc/Hexane) and developed using phosphomolybdic acid. The reaction was 90% complete. 200 ml of saturated sodium bicarbonate was cooled in an ice bath and stirred. The reaction mixture was slowly added to the cooled bicarbonate solution to quench reaction. There was some effervescence and stirred mixture for another ½ hour. Dichloromethane was added and transferred the mixture to a separation funnel. The organic layer was separated and was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 100% EtOAc/Hexane) and the product fractions combined and concentrated on reduced pressure to yield (1.13 g, 69%) of 112. $^1$H NMR (400 MHz, DMSO-d6) δ 8.01 (d, J=9.4 Hz, 1H), 7.95-7.83 (m, 2H), 7.79-7.72 (m, 1H), 7.72-7.55 (m, 3H), 7.52 (d, J=7.7 Hz, 2H), 7.47-7.35 (m, 4H), 7.35-7.24 (m, 6H), 7.24-7.14 (m, 1H), 6.96-6.79 (m, 4H), 5.70 (d, J=3.6 Hz, 1H), 5.27 (dd, J=11.1, 3.3 Hz, 1H), 4.93 (dd, J=6.4, 4.3 Hz, 1H), 4.74 (d, J=8.5 Hz, 1H), 4.34 (dt, J=11.1, 8.9 Hz, 1H), 3.99 (dq, J=20.8, 6.8 Hz, 3H), 3.72 (d, J=1.1 Hz, 6H), 3.59-3.37 (m, 2H), 3.20 (ddd, J=11.0, 7.8, 3.6 Hz, 1H), 2.95 (dt, J=10.2, 4.1 Hz, 1H), 1.98 (s, 2H), 1.60 (s, 3H), 1.16 (t, J=7.1 Hz, 2H). Mass calc. for C45H45NO11: 775.85, found: 798.3 (M+Na).

Compound (113)—Compound 112 is added to the reaction flask which is evacuated and purged with argon. The starting material is dissolved in dichloromethane, and diisopropylamine is added via syringe. 2-Cyanoethyl N,N-diisopropylchlorophosphoramidite is added and the reaction is stirred at room temperature for 1 to 2 hours. After checking the TLC for completeness, the reaction is worked up using standard extraction conditions. The crude residue is purified on silica gel to yield compound 113.

Example 14. Synthesis of Phosphoramidite 508

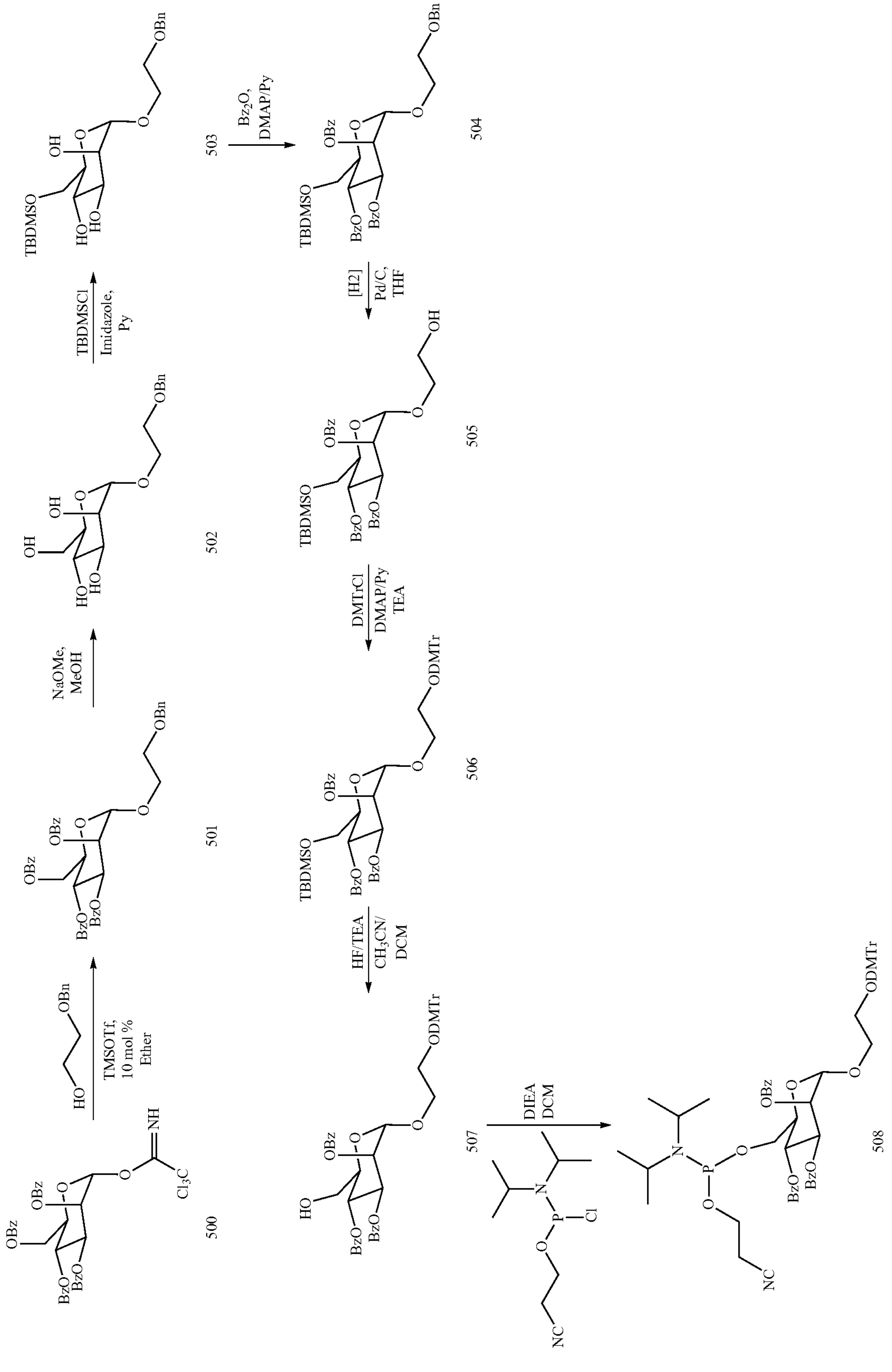
500 501 502 503 504 505 506 507 508

Compound (501): Compound 500 (6 g, 7.70 mmol) and 2-(Benzyloxy)ethanol (1.20 ml, 8.117 mmol) was added into a reaction flask and dissolved with anhydrous toluene. The solvent was stripped off under reduced pressure. This was repeated three times and put on high vacuum to dry overnight. The next day a stirrer bar and molecular sieves were added and was evacuated and purged with argon three times. Anhydrous ether was added via syringe and the reaction was cooled to 0° C. with an ice bath. It was stirred for 10 minutes, then trimethylsilyl trifluoromethanesulfonate (0.139 ml, 0.77 mmol) was added via syringe. The reaction was allowed to stir for 3 hours then checked by TLC (20% EtOAc/Hexane) and developed using Hanessian stain. The reaction was complete and it was quenched with trimethylamine. The solution was diluted with ethyl acetate and molecular sieves were filtered off. The solution was added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/Hexane) and the product fractions combined and concentrated on reduced pressure to yield (5.87 g) of 501. Mass calc. for C43H38O11: 730.77, found: 753.2 (M+Na).

Compound (502): Compound 501 (5.62 g, 7.70 mmol) was dissolved in 150 ml of anhydrous methanol. The reaction flash was evacuated and purged with argon. Sodium methoxide in methanol (0.5M, 6.16 ml, 3.08 mmol) was added via syringe. Reaction was allowed to stir at room temperature overnight. Reaction was checked by TLC (5% MeOH/DCM) and developed using Hanessian stain. After the reaction was complete it was neutralized to pH 7 by adding 20 drops of glacial acetic acid. The solvent was stripped under reduced vacuum to yield (3.63 g) of 502. Mass calc. for $C_{15}H_{22}O_7$: 314.33. found: 337.1 (M+Na).

Compound (503): Compound 502 (2.42 g, 7.70 mmol) and imidazole (1.57 g, 23.1 mmol) was added to a reaction flask. The reaction flash was evacuated and purged with argon. Anhydrous pyridine was added via syringe and starting materials dissolved. Reaction was stirred at room temperature for 10 minutes then a solution of tert-Butyldimethylsilyl chloride (1.74 g, 11.55 mmol) in pyridine was added via syringe. Reaction was stirred overnight at room temperature. The reaction was checked by TLC (100% EtOAc) and developed using Hanessian stain. After the reaction was complete methanol was added to quench the reaction and stirred for 10 minutes. The reaction mixture was concentrated under reduced pressure and added dichloromethane and water. The mixture was added to separation funnel and organic layer was separated and aqueous layer was washed with dichloromethane. The organic layer was combined and washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 100% EtOAc/Hexane) and the product fractions combined and concentrated on reduced pressure to yield (2.57 g, 78.1%) of 503. $^1H$ NMR (400 MHz, DMSO-d6) δ 7.40-7.16 (m, 2H), 4.74 (dd, J=5.8, 4.8 Hz, 1H), 4.67-4.54 (m, 1H), 4.48 (s, 1H), 3.78-3.67 (m, 1H), 3.65-3.48 (m, 2H), 3.45 (ddd, J=9.3, 6.1, 3.4 Hz, 1H), 3.42-3.23 (m, 1H), 0.84 (s, 4H), 0.02 (s, 3H). Mass calc. for $C_{21}H_{36}O_7Si$: 428.60, found: 451.2 (M+Na).

Compound (504): Compound 503 (2.50 g, 5.84 mmol) and 4-(Dimethylamino)pyridine (0.714 g, 5.84 mmol) were added to a reaction flask. The reaction flash was evacuated and purged with argon. Anhydrous pyridine (100 ml) was added via syringe. A pyridine solution of benzoic anhydride (5.28 g, 23.36 mmol) was added to the reaction mixture via syringe and the reaction was stirred at room temperature overnight. The reaction was checked by TLC (20% EtOAc/Hexane) and developed using Hanessian stain. After the reaction was complete water was added to quench the reaction and stirred for 10 minutes. Solvent was removed under reduced pressure. EtOAc and water were added and put into a separation funnel. The organic layer was separated and washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/Hexane) and the product fractions combined and concentrated on reduced pressure to yield (3.78 g, 87.5%) of 504. $^1H$ NMR (400 MHz, DMSO-d6) δ 8.09-7.89 (m, 2H), 7.91-7.78 (m, 2H), 7.78-7.65 (m, 3H), 7.65-7.51 (m, 4H), 7.46 (q, J=7.7 Hz, 2H), 7.41-7.31 (m, 6H), 7.31-7.21 (m, 1H), 5.96 (t, J=10.1 Hz, 1H), 5.70-5.53 (m, 2H), 5.20 (d, J=1.8 Hz, 1H), 4.58 (s, 2H), 4.21 (dt, J=10.1, 2.5 Hz, 1H), 3.96-3.75 (m, 2H), 3.75-3.60 (m, 4H), 0.86 (s, 8H), −0.12 (s, 5H). Mass calc. for $C_{42}H_{48}O_{10}Si$: 740.92, found: 763.3 (M+Na).

Compound (505): Compound 504 (2.32 g, 3.13 mmol) was added to a reaction flask. The reaction flash was evacuated and purged with argon three times. The starting material was dissolved by adding anhydrous tetrahydrofuran via syringe. Then 10% palladium on carbon, deguessa type, (278 mg, 10% by weight) was added. The reaction flash was evacuated and purged with argon three times. Then the reaction flask was evacuated and purged with hydrogen from a balloon two times. The reaction was left to stir at room temperature overnight. The reaction was checked by TLC (30% EtOAc/Hexane) and developed using Hanessian stain. After the reaction was complete, reaction mixture was evacuated and purged with argon three times. The reaction mixture was filtered through celite to remove palladium on carbon, and was washed with methanol. The mother liquor was concentrated under reduced pressure. The residue was purified by flash chromatography on silica gel (0% to 40% EtOAc/Hexane) and the product fractions combined and concentrated on reduced pressure to yield (1.20 g, 59.1%) of 505. $^1H$ NMR (400 MHz, DMSO-d6) δ 8.06-7.95 (m, 2H), 7.95-7.82 (m, 2H), 7.79-7.63 (m, 2H), 7.64-7.50 (m, 3H), 7.45 (t, J=7.8 Hz, 2H), 7.36 (t, J=7.8 Hz, 2H), 5.96 (t, J=10.1 Hz, 1H), 5.67 (dd, J=10.2, 3.3 Hz, 1H), 5.60 (dd, J=3.3, 1.8 Hz, 1H), 5.16 (d, J=1.9 Hz, 1H), 4.85 (t, J=5.3 Hz, 1H), 4.23 (dt, J=10.1, 2.5 Hz, 1H), 3.80 (d, J=2.5 Hz, 3H), 3.71-3.54 (m, 3H), 0.87 (s, 7H), −0.09 (s, 4H). Mass calc. for $C_{35}H_{42}O_{10}Si$: 650.80, found: 673.3 (M+Na).

Compound (506): Compound 505 (1.20 g, 1.84 mmol) and 50 ml of anhydrous pyridine was added to a reaction flask. Pyridine was stripped off under reduced pressure and was repeated three times and the residue was dried under high vacuum overnight. The next day 4-(Dimethylamino)pyridine (0.022 g, 0.184 mmol), triethylamine (0.251 ml, 1.84 mmol), and anhydrous pyridine was added to the reaction flask. The reaction was cooled to 0° C. using an ice bath. The reaction flash was evacuated and purged with argon. 4,4'-Dimethoxytrityl Chloride (0.691 g, 2.04 mmol) was dissolved in anhydrous pyridine and resulting solution was added via syringe to the reaction flask. The reaction was allowed to come up to room temperature and stirred overnight. The reaction was checked by TLC (20% EtOAc/Hexane) and developed using Hanessian stain. Reaction complete. Methanol was added to quench the reaction and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 30% EtOAc/Hexane) and the product fractions combined and concentrated on reduced pressure to yield (1.68 g, 96%) of (2S,3S,4S,5R,6R)-2-(2-(bis(4-methoxyphenyl)(phenyl)methoxy)ethoxy)-6-(((tert-butyldimethylsilyl)oxy)methyl)tetrahydro-2H-pyran-3,4,5-triyl tribenzoate 506. $^{1}$H NMR (400 MHz, DMSO-d6) δ 8.07-7.92 (m, 2H), 7.81-7.62 (m, 5H), 7.56 (tdd, J=7.6, 7.0, 6.3, 1.8 Hz, 4H), 7.50-7.41 (m, 2H), 7.41-7.27 (m, 10H), 7.28-7.19 (m, 2H), 6.98-6.86 (m, 4H), 5.98 (t, J=10.1 Hz, 1H), 5.76 (dd, J=10.2, 3.3 Hz, 1H), 5.64 (dd, J=3.3, 1.8 Hz, 1H), 5.22 (d, J=1.8 Hz, 1H), 4.36 (dt, J=10.2, 2.4 Hz, 1H), 4.01 (q, J=7.1 Hz, 1H), 3.93 (td, J=7.6, 7.1, 3.7 Hz, 1H), 3.79 (td, J=10.6, 9.3, 2.7 Hz, 3H), 3.71 (s, 7H), 3.31-3.16 (m, 2H), 1.16 (t, J=7.1 Hz, 1H), 0.88 (s, 9H), −0.08 (s, 5H). Mass calc. for $C_{56}H_{60}O_{12}Si$: 953.17, found: 975.4 (M+Na).

Compound (507): Compound 506 (1.60 g, 1.68 mmol) was added to a plastic reaction vessel. Dichloromethane (16 ml) was added to dissolve starting material. Acetonitrile (48 ml), pyridine (32 ml), and trimethylamine (8 ml) were added. The reaction vessel was purged and cooled in an ice bath. The reaction was stirred and then Hydrogen fluoride pyridine complex (8 ml) was added carefully. Reaction was stirred and warmed up to room temperature over 5 hours. The reaction was checked by TLC (30% EtOAc/Hexane) and developed using phosphomolybdic acid. 200 ml of saturated sodium bicarbonate was cooled in an ice bath and stirred. The reaction mixture was slowly added to the cooled bicarbonate solution to quench reaction. There was some effervescence, so be careful. This was stirred for ½ hour. The solution was concentrated under reduced pressure. Dichloromethane was added and was added to separation funnel. The organic layer was separated and was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 40% EtOAc/Hexane) and the product fractions combined and concentrated on reduced pressure to yield (1.29 g, 91.4%) of 507. $^{1}$H NMR (400 MHz, DMSO-d6) δ 8.05-7.98 (m, 2H), 7.73 (dtt, J=8.6, 3.7, 1.5 Hz, 5H), 7.66-7.51 (m, 4H), 7.51-7.44 (m, 2H), 7.44-7.30 (m, 10H), 7.28-7.19 (m, 1H), 6.97-6.88 (m, 4H), 5.90-5.75 (m, 2H), 5.66 (dd, J=3.2, 1.8 Hz, 1H), 5.22 (d, J=1.7 Hz, 1H), 5.06 (t, J=5.7 Hz, 1H), 4.31 (ddd, J=9.6, 4.4, 2.3 Hz, 1H), 4.02 (q, J=7.1 Hz, 1H), 3.95 (ddd, J=10.0, 6.8, 2.5 Hz, 1H), 3.75 (ddd, J=10.8, 5.3, 2.5 Hz, 1H), 3.68-3.55 (m, 2H), 3.32-3.15 (m, 2H), 1.98 (s, 1H), 1.16 (t, J=7.1 Hz, 1H). Mass calc. for $C_{50}H_{46}O_{12}$: 838.91, found: 861.3 (M+Na).

Compound (508): Compound 507 is added to the reaction flask which is evacuated and purged with argon. The starting material is dissolved in dichloromethane, and diisopropylamine is added via syringe. 2-Cyanoethyl N,N-diisopropylchlorophosphoramidite is added and the reaction mixture stir at room temperature for 1 to 2 hours. After checking the TLC for completeness, the reaction is worked up using standard extraction conditions. The crude residue is purified on silica gel to yield compound 508.

Example 15. Synthesis of Phosphoramidite 106

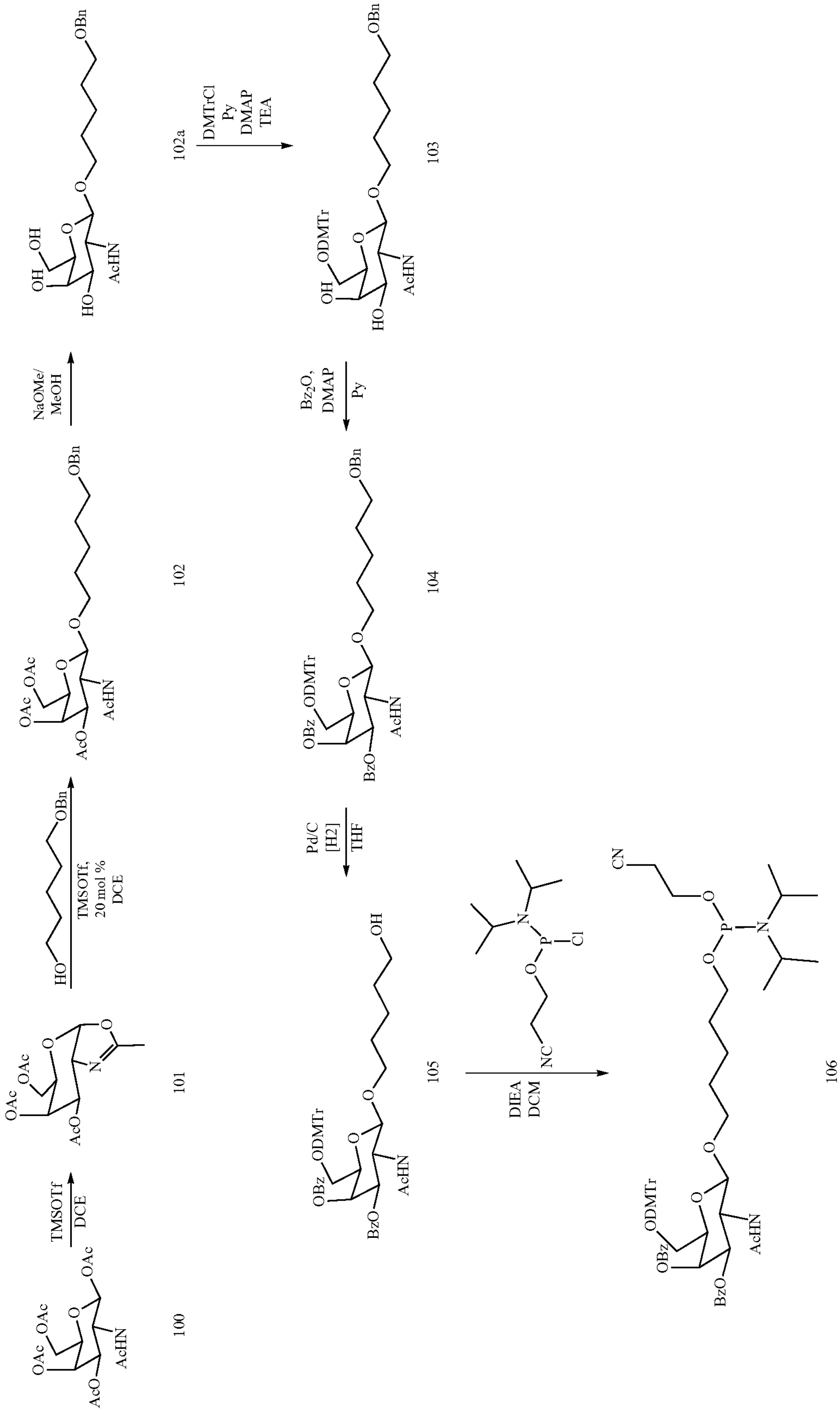
100 101 102 102a 103 104 105 106

Compound 101: Compound 100 (20 g& 51.4 mmol) was suspended in anhydrous dichloroethane (DCE) (200 mL). The reaction flash was evacuated and purged with argon. Trimethylsilyl trifluoromethanesulfonate (11.16 mL, 61.7 mmol) was added dropwise via syringe. Reaction was heated to 45° C. utilizing water bath and stirred overnight resulting in a clear solution. Reaction was checked by TLC (5% MeOH/DCM) and developed using Hanessian stain. Reaction was complete and cooled reaction with ice bath. Took sodium bicarbonate (12.95 g, 154.2 mL) and dissolved in 100 mL of water. Sodium bicarbonate solution was added slowly to reaction mixture and effervescence occurred. Reaction was left to stir for 20 minutes to completely neutralize. The mixture was added to separation funnel and organic layer was separated and aqueous layer was washed with dichloromethane. The organic layers were combined and washed with a brine solution. The organic layer was separated and dried with sodium sulfate. The solid was filtered off and the mother liquor was concentrated and put on high vacuum to yield 16.64 g of 101. $^1$H NMR (400 MHz, DMSO-$d_6$): δ 6.04 (d, J=7.0 Hz, 1H), 5.23 (dd, J=3.9, 2.8 Hz, 1H), 4.87 (dd, J=6.9, 3.9 Hz, 1H). 4.25 (m, 1H), 4.10 (dd, J=11.6, 7.2 Hz, 1H), 4.02 (dd, J=11.5, 5.0 Hz, 1H), 3.94 (m, 1H), 3.89 (s, 1H), 2.06 (s, 3H), 2.00 (d, J=3.6 Hz, 6H), 1.94 (d, J=1.4 Hz, 3H). Mass calc. for $C_{14}H_{19}NO_8$: 329.31, found: 330.1 (M+H).

Compound 102: Compound 101 (5 g, 15.19 mmol) and 5-Benzyloxy-1-pentanol (3.21 mL, 16.71 mmol) was dissolved with dry dichloroethane (DCE) (60 mL). The reaction flash was evacuated, purged with argon and cooled in ice bath. Trimethylsilyl trifluoromethanesulfonate (0.550 mL, 3.04 mmol) was added via syringe. Reaction was checked after 3.5 hours by TLC (5% MeOH/DCM) and developed using Hanessian stain. Reaction was complete. Sodium bicarbonate (383 mg, 4.56 mmol) was dissolved in 100 mL and cooled in ice bath. The reaction mixture was added dropwise to the stirring sodium bicarbonate solution. The reaction was left to stir for 20 minutes to completely neutralize. The mixture was added to separation funnel and organic layer was separated and aqueous layer was washed with dichloromethane. The organic layers were combined and washed with a brine solution. The organic layer was separated and dried with sodium sulfate. The solid was filtered off and the mother liquor was concentrated and put on high vacuum to yield 8.88 g of 102. $^1$H NMR (400 MHz, DMSO-$d_6$): δ 7.81 (d, J=9.2 Hz, 1H), 7.38-7.21 (m, 6H), 5.20 (d, J=3.4 Hz, 1H), 4.94 (dd, J=11.3, 3.4 Hz, 1H), 4.47 (d, J=8.5 Hz, 1H), 4.08-3.93 (m, 3H), 3.89 (s, 2H), 3.89-3.80 (m, 1H), 3.69 (m, 1H), 3.45-3.34 (m, 5H), 3.33 (s, 3H), 2.09 (s, 3H), 1.98 (s, 3H), 1.88 (s, 3H), 1.73 (s, 2H), 1.58-1.24 (m, 8H).

Compound 102a: Compound 102 (7.95 g, 15.19 mmol) was dissolved in 150 mL of anhydrous methanol. The reaction flash was evacuated and purged with argon. Sodium methoxide in methanol (0.5M, 3.04 mL, 6.07 mmol) was added via syringe. Reaction was allowed to stir at room temperature overnight. Reaction was checked by TLC (10% MeOH/DCM) and developed using Hanessian stain. Glacial acetic acid was added to the reaction to lower the pH to 7 and the reaction mixture was concentrated under reduced pressure. The residue was suspended in 100 mL of dichloromethane with minimal methanol to dissolve crude. The product was precipitated by adding this crude solution to a 50/50 ether/hexane (500 mL) solution drop wise. A precipitate formed, stirred for another 10 minutes, product filtered off and dried under high vacuum to yield 5.26 g of 102a. $^1$H NMR (400 MHz, DMSO-$d_6$): δ 7.62 (d, J=9.0 Hz, 1H), 7.38-7.21 (m, 5H), 4.62 (s, 3H), 4.42 (s, 2H), 4.20 (d, J=8.4 Hz, 1H), 3.75-3.60 (m, 3H), 3.57-3.43 (m, 3H), 3.39 (q, J=6.5, 5.3 Hz, 4H), 3.31 (d, J=6.5 Hz, 8H), 3.26 (t, J=6.2 Hz, 1H), 1.75 (s, 3H), 1.47 (m, 4H), 1.37-1.26 (m, 2H). Mass calc. for $C_{20}H_{31}NO_7$: 397.47, found: 420.2 (M+Na).

Compound 103: Compound 102a (5.20 g, 13.09 mmol) and 50 mL of anhydrous pyridine was added to a reaction flask. Pyridine was stripped off under reduced pressure. This was repeated for three times and dried under high vacuum overnight. The next day 4-(dimethylamino)pyridine (0.160 g, 1.31 mmol), triethylamine (1.78 mL, 13.09 mmol), and anhydrous pyridine was added to the reaction flask. The reaction was cooled to 0° C. using an ice bath. The reaction flash was evacuated and purged with argon. 4,4'-Dimethoxytrityl Chloride (4.92 g, 14.53 mmol) was dissolved in anhydrous pyridine and resulting solution was added via syringe to the reaction flask. The reaction was allowed to come up to room temperature and stirred overnight. The reaction was checked by TLC (100% EtOAc) and developed using Hanessian stain. Methanol was added to quench the reaction and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated and put on high vacuum to yield compound 103 (8.70 g). $^1$H NMR (400 MHz, DMSO-$d_6$): δ 7.63 (d, J=9.0 Hz, 1H), 7.44-7.37 (m, 3H), 7.36-7.15 (m, 17H), 7.09-7.01 (m, 1H), 6.92-6.78 (m, 7H), 4.62 (d, J=6.0 Hz, 1H), 4.52 (d, J=4.3 Hz, 1H), 4.39 (s, 2H), 4.27 (d, J=8.4 Hz, 1H), 3.69 (d, J=7.1 Hz, 11H), 3.67-3.62 (m, 1H), 3.59 (t, J=3.8 Hz, 1H), 3.52 (t, J=5.8 Hz, 1H), 3.43 (mm, 2H), 3.37 (t, J=6.5 Hz, 3H), 3.33 (s, 5H), 3.18 (dd, J=9.3, 7.0 Hz, 1H), 3.00 (dd, J=9.3, 4.8 Hz, 1H), 2.92 (d, J=12.9 Hz, 2H), 1.77 (s, 3H), 1.54-1.45 (m, 4H), 1.39-1.28 (m, 2H). Mass calc. for $C_{41}H_{49}NO_9$: 699.84, found: 722.3 (M+Na).

Compound 104: Compound 103 (8.70 g, 12.44 mmol) and 4-(dimethylamino)pyridine (1.52 g, 12.44 mmol) were added to a reaction flask. The reaction flash was evacuated and purged with argon. Anhydrous pyridine (230 mL) was added via syringe. A pyridine solution of benzoic anhydride (7.03 g, 31.1 mmol) was added to the reaction mixture via syringe and the reaction was stirred at room temperature overnight. The reaction was checked by TLC (30% EtOAc/hexanes) and developed using Hanessian stain. After the reaction was complete, water was added to quench the reaction and stirred for 10 minutes. Solvent was removed under reduced pressure. EtOAc and water were added and put into a separation funnel. The organic layer was separated and washed with saturated sodium bicarbonate. The organic layer was separated and washed with a brine solution. The organic layer was separated and dried with sodium sulfate. The solid was filtered off and the mother liquor was concentrated and put on high vacuum to yield 8.35 g of 104. $^1$H NMR (400 MHz, DMSO-$d_6$): δ 8.01-7.88 (m, 2H), 7.73 (m, 4H), 7.71-7.55 (m, 3H), 7.45 (m, 5H), 7.37-7.20 (m, 8H), 7.20-7.04 (m, 8H), 6.76-6.58 (m, 5H), 5.84 (d, J=3.3 Hz, 1H), 5.33 (dd, J=11.1, 3.4 Hz, 1H), 4.64 (d, J=8.5 Hz, 1H), 4.41 (s, 2H), 4.31 (dd, J=8.6, 5.9 Hz, 1H), 4.16 (m, 3.79-3.66 (m, 2H), 3.64 (s, 7H), 3.44 (m, 3.37 (t, J=6.4 Hz, 2H), 3.33 (s, 1H), 3.16 (dd, J=8.5, 5.4 Hz, 1H), 2.95 (t, J=8.6 Hz, 1H), 1.65 (s, 3H), 1.50 (m, 4H), 1.32 (m, 2H). Mass calc. for $C_{55}H_{57}NO_{11}$: 908.06, found: 930.3 (M+Na).

Compound 105: Compound 104 (3.74 g, 4.12 mmol) was added to a reaction flask. The reaction flash was evacuated and purged with argon three times. The starting material was dissolved by adding anhydrous tetrahydrofuran via syringe. Then 10% palladium on carbon, deguessa type, (374 mg, 10% by weight) was added. The reaction flash was evacuated and purged with argon three times. Then the reaction flask was evacuated and purged with hydrogen from a balloon two times. The reaction was left to stir at room temperature overnight. The reaction was checked by TLC (50/50 EtOAc/hexanes) and developed using phosphomolybdic acid. After the reaction complete, the flask was evacuated and purged with argon three times. The reaction mixture was filtered through celite to remove palladium on carbon, and was washed with methanol. The mother liquor was concentrated under reduced pressure. The residue was purified by flash chromatography on silica gel (10% to 100% EtOAc/hexanes) and the product fractions combined and concentrated on reduced pressure to yield 2.00 g (59%) of 105. $^1$H NMR (400 MHz, DMSO-d$_6$): δ 8.04-7.85 (m, 1H), 7.79-7.64 (m, 4H), 7.64-7.54 (m, 1H), 7.51 (t, J=7.7 Hz, 2H), 7.40 (t, J=7.7 Hz, 2H), 7.34-7.21 (m, 2H), 7.22-7.01 (m, 6H), 6.75-6.59 (m, 4H), 5.84 (d, J=3.2 Hz, 1H), 5.33 (dd, J=11.1, 3.3 Hz, 1H), 4.64 (d, J=8.5 Hz, 1H), 4.32 (m, 3.71 (m, 1H), 3.61 (s, 5H), 3.43 (m, 1H), 3.39-3.29 (m, 2H), 3.16 (dd, J=8.6, 5.4 Hz, 1H), 2.94 (t, J=8.6 Hz, 1H), 1.67 (s, 3H), 1.55-1.43 (m, 2H), 1.38 (m, 1.28 (q, J=7.6 Hz, 2H). Mass calc. for $C_{48}H_{51}NO_{11}$: 817.93, found: 840.3 (M+Na).

Compound 106: Compound 105 (1.50 g, 1.84 mmol) was added to the reaction flask. The reaction flask was evacuated and purged with argon. The starting material was dissolved in dichloromethane, and diisopropylethylamine (0.641 mL, 3.68 mmol) was added via syringe. 2-Cyanoethyl N,N-diisopropylchlorophosphoramidite (0.491 mL, 2.21 mmol) was added and stirred at room temperature for 1 hour. The reaction was checked by TLC (50/50 EtOAc/hexanes) and the reaction was concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was dissolved in minimal dichloromethane, and added dropwise to a solution of 90/10 hexanes/ether. An oily precipitate formed and was stirred for 10 minutes. The solvent was decanted off and remaining residue was dissolved in dichloromethane and transferred to flask. Solvent was removed by reduced pressure to yield compound 1.62 g, (87%) of 106. $^1$H NMR (500 MHz, Acetonitrile-d$_3$): δ 7.79 (m, J=8.4, 1.7 Hz, 4H), 7.69-7.62 (m, 1H), 7.62-7.49 (m, 2H), 7.47 (d, J=8.0 Hz, 2H), 7.41-7.31 (m, 4H), 7.24-7.10 (m, 7H), 6.74-6.59 (m, 4H), 5.89 (d, J=3.3 Hz, 1H), 5.41 (dd, J=11.2, 3.4 Hz, 1H), 4.70 (d, J=8.4 Hz, 1H), 4.23-4.13 (m, 2H), 3.85-3.72 (m, 3H), 3.66 (t, J=10.4 Hz, 8H), 3.57 (m, 2.9 Hz, 3H), 3.29 (dd, J=8.8, 5.6 Hz, 1H), 3.01 (t, J=8.5 Hz, 1H), 2.67-2.59 (m, 2H), 1.74 (s, 3H), 1.58 (m, 4H), 1.45-1.37 (m, 2H), 1.23 (t, J=6.8 Hz, 3H), 1.16 (t, J=7.1 Hz, 11H). $^{31}$P NMR (202 MHz, Chloroform-d): δ 147.93, 147.68.

Example 16. Synthesis of Phosphoramidite 113

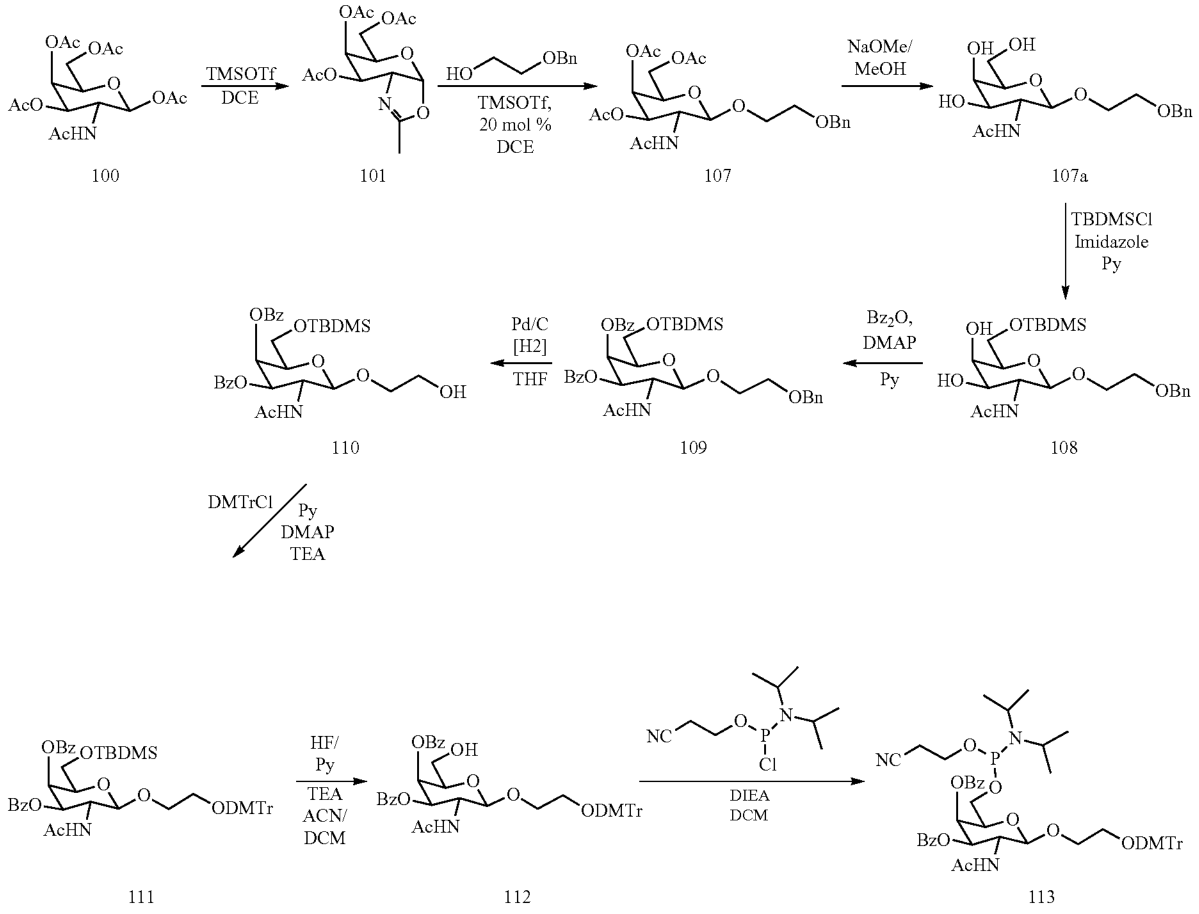

Compound 107: Compound 101 (5.0 g, 15.19 mmol) and 2-(benzyloxy)ethanol (2.80 mL, 19.75 mmol) was dissolved with dry dichloroethane (DCE) (60 mL). The reaction flash was evacuated, purged with argon and cooled in ice bath. Trimethylsilyl trifluoromethanesulfonate (0.550 mL, 3.04 mmol) was added via syringe. Reaction was checked after 3.5 hours by TLC (5% MeOH/DCM) and developed using Hanessian stain. Reaction was complete. Sodium bicarbonate (383 mg, 4.56 mmol) was dissolved in 100 mL and cooled in ice bath. The reaction mixture was added dropwise to the stirring sodium bicarbonate solution. The reaction was left to stir for 20 minutes to completely neutralize. The mixture was added to separation funnel and organic layer was separated and aqueous layer was washed with dichloromethane. The organic layers were combined and washed with a brine solution. The organic layer was separated and dried with sodium sulfate. The solid was filtered off and the mother liquor was concentrated and put on high vacuum to yield 8.64 g of 107. $^1H$ NMR (400 MHz, DMSO-$d_6$): δ 7.38-7.22 (m, 4H), 5.21 (d, J=3.4 Hz, 1H), 4.97 (dd, J=11.2, 3.4 Hz, 1H), 4.56 (d, J=8.5 Hz, 1H), 4.47 (d, J=1.4 Hz, 2H), 4.09-3.95 (m, 2H), 3.89 (s, 1H), 3.84 (m, 1H), 3.63 (m, 1H), 3.54 (m, 2H), 3.44 (t, J=5.1 Hz, 1H), 2.09 (d, J=4.4 Hz, 2H), 1.98 (s, 2H), 1.88 (s, 2H), 1.73 (s, 1H).

Compound 107a: Compound 107 (7.31 g, 15.19 mmol) was dissolved in 150 mL of anhydrous methanol. The reaction flash was evacuated and purged with argon. Sodium methoxide in methanol (0.5M, 2.275 mL, 4.55 mmol) was added via syringe. Reaction was allowed to stir at room temperature overnight. Reaction was checked by TLC (10% MeOH/DCM) and developed using Hanessian stain. After the reaction was complete, glacial acetic acid was added to the reaction to lower the pH to 7 and the reaction mixture was concentrated under reduced pressure. The residue was suspended in 100 mL of dichloromethane with minimal methanol to dissolve crude. The product was precipitated by adding this crude solution to a 50/50 ether/hexanes (500 mL) solution dropwise. A precipitate formed, stirred for another 10 minutes, product filtered off and dried under high vacuum to yield 5.05 g of 107a. $^1H$ NMR (400 MHz, DMSO-$d_6$): δ 7.65 (d, J=8.9 Hz, 1H), 7.38-7.21 (m, 5H), 4.63 (d, J=11.5 Hz, 2H), 4.47 (s, 2H), 4.28 (d, J=8.4 Hz, 1H), 3.83 (m, 1H), 3.72 (m, 1H), 3.64 (s, 1H), 3.62-3.45 (m, 6H), 3.41 (d, J=10.5 Hz, 2H), 3.36-3.25 (m, 7H), 1.90-1.78 (m, 1H), 1.75 (s, 2H).

Compound 108: Compound 107a (5.0 g, 14.08 mmol) and imidazole (2.88 g, 42.24 mmol) was added to a reaction flask. The reaction flash was evacuated and purged with argon. Anhydrous pyridine was added via syringe and starting materials dissolved. Reaction was stirred at room temperature for 10 minutes then a solution of tert-butyldimethylsilyl chloride (3.18 g, 21.12 mmol) in pyridine was added via syringe. Reaction was stirred overnight at room temperature. The reaction was checked by TLC (100% EtOAc) and developed using Hanessian stain. After the reaction was complete, methanol was added to quench the reaction and stirred for 10 minutes. The reaction mixture was concentrated under reduced pressure and added dichloromethane and water. The mixture was added to separation funnel and organic layer was separated and aqueous layer was washed with dichloromethane. The organic layer was combined and washed with saturated sodium bicarbonate. The organic layer was separated and washed with a brine solution. The organic layer was separated and dried with sodium sulfate. The solid was filtered off and the mother liquor was concentrated to yield 8.80 g of 108. This was used as crude for the next reaction.

Compound 109: Compound 108 (6.61 g, 14.09 mmol) and 4-(dimethylamino)pyridine (1.72 g, 14.09 mmol) were added to a reaction flask. The reaction flash was evacuated and purged with argon. Anhydrous pyridine (200 mL) was added via syringe. A pyridine solution of benzoic anhydride (11.15 g, 49.31 mmol) was added to the reaction mixture via syringe and the reaction was stirred at room temperature overnight. The reaction was checked by TLC (50% EtOAc/hexanes) and developed using Hanessian stain. After the reaction was complete; water was added to quench the reaction and stirred for 10 minutes. Solvent was removed under reduced pressure. EtOAc and water were added and put into a separation funnel. The organic layer was separated and washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 100% EtOAc/hexanes) and the product fractions combined and concentrated on reduced pressure to yield 4.22 g (44%) of 109. $^1H$ NMR (400 MHz, DMSO-$d_6$): δ 7.97 (d, J=9.2 Hz, 1H), 7.94-7.86 (m, 2H), 7.75-7.63 (m, 3H), 7.56 (m, 4H), 7.44-7.35 (m, 2H), 7.33 (d, J=3.5 Hz, 4H), 7.30-7.23 (m, 1H), 5.67 (d, J=3.3 Hz, 1H), 5.27 (dd, J=11.1, 3.3 Hz, 1H), 4.73 (d, J=8.5 Hz, 1H), 4.51 (s, 2H), 4.35-4.16 (m, 1H), 4.08 (t, J=7.3 Hz, 1H), 3.97-3.85 (m, 1H), 3.76-3.67 (m, 2H), 3.67-3.53 (m, 4H), 1.65 (s, 3H), 0.89-0.77 (m, 2H), 0.76 (s, 8H), 0.64 (s, 1H), −0.06 (s, 3H), −0.14 (s, 3H). Mass calc. for $C_{37}H_{47}NO_9Si$: 677.87, found: 678.3 (M+H), 700.3 (M+Na).

Compound 110: Compound 109 (3.0 g, 4.43 mmol) was added to a reaction flask. The reaction flash was evacuated and purged with argon three times. The starting material was dissolved by adding anhydrous methanol via syringe. Then 10% palladium on carbon, deguessa type, (300 mg, 10% by weight) was added. The reaction flash was evacuated and purged with argon three times. Then the reaction flask was evacuated and purged with hydrogen from a balloon two times. The reaction was left to stir at room temperature overnight. The reaction was checked by TLC (60% EtOAc/hexanes) and developed using Hanessian stain. After the reaction was complete; the flash was evacuated and purged with argon three times. The reaction mixture was filtered through celite to remove palladium on carbon, and was washed with methanol. The mother liquor was concentrated under reduced pressure to yield 2.75 g of 110. Mass calc. for $C_{30}H_{41}NO_9Si$: 587.74, found: 588.3 (M+H), 610.3 (M+Na).

Compound 111: Compound 110 (2.60 g, 4.43 mmol) and 50 mL of anhydrous pyridine was added to a reaction flask. Pyridine was stripped off under reduced pressure. The residue was co-evaporated with pyridine three times and dried under high vacuum overnight. The next day 4-(dimethylamino)pyridine (0.054 g, 0.443 mmol), triethylamine (0.604 mL, 4.43 mmol), and anhydrous pyridine was added to the reaction flask. The reaction was cooled to 0° C. using an ice bath. The reaction flash was evacuated and purged with argon. 4,4'-Dimethoxytrityl chloride (1.67 g, 4.92 mmol) was dissolved in anhydrous pyridine and resulting solution was added via syringe to the reaction flask. The reaction was allowed to come up to room temperature and stirred overnight. The reaction was checked by TLC (60% EtOAc/hexanes) and developed using Hanessian stain. After the reaction was complete; methanol was added to quench the reaction and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/hexanes) and the product fractions combined and concentrated on reduced pressure to yield 1.96 g (49.7%) of 111. $^1$H NMR (400 MHz, DMSO-$d_6$): δ 8.04 (d, J=9.4 Hz, 1H), 7.95-7.85 (m, 2H), 7.76-7.71 (m, 2H), 7.71-7.63 (m, 1H), 7.63-7.56 (m, 1H), 7.53 (t, J=7.7 Hz, 2H), 7.45-7.36 (m, 4H), 7.34-7.23 (m, 6H), 7.23-7.15 (m, 1H), 6.91-6.83 (m, 4H), 5.70 (d, J=4.3 Hz, 1H), 5.30 (dd, J=11.1, 3.4 Hz, 1H), 4.75 (d, J=8.5 Hz, 1H), 4.41-4.28 (m, 1H), 4.11 (s, 1H), 3.77-3.67 (m, 7H), 3.67-3.56 (m, 2H), 3.33 (s, 1H), 3.20 (s, 1H), 2.98-2.91 (m, 1H), 1.60 (s, 3H), 0.84 (d, J=14.5 Hz, 1H), 0.76 (s, 8H), 0.73-0.64 (m, 1H), −0.07 (s, 3H), −0.15 (s, 3H). Mass calc. for $C_{51}H_{59}NO_{11}Si$: 890.11, found: 912.4 (M+Na).

Compound 112: Compound 111 (1.86 g, 2.09 mmol) was added to a plastic reaction vessel. dichloromethane (18.3 mL) was added to dissolve starting material. Acetonitrile (55.8 mL), pyridine (37.2 mL), and trimethylamine (9.3 mL) were added. The reaction vessel was purged and cooled in an ice bath. The reaction was stirred and then hydrogen fluoride pyridine complex (9.3 mL) was added carefully. Reaction was stirred and warmed up to room temperature over 5 hours. The reaction was checked by TLC (35% EtOAc/hexanes) and developed using phosphomolybdic acid. The reaction was 90% complete. 200 mL of saturated sodium bicarbonate was cooled in an ice bath and stirred. The reaction mixture was slowly added to the cooled bicarbonate solution to quench reaction. There was some effervescence and stirred mixture for another ½ hour. Dichloromethane was added and transferred the mixture to a separation funnel. The organic layer was separated and was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 100% EtOAc/hexanes) and the product fractions combined and concentrated on reduced pressure to yield 1.13 g (69%) of 112. $^1$H NMR (400 MHz, DMSO-$d_6$): δ 8.01 (d, J=9.4 Hz, 1H), 7.95-7.83 (m, 2H), 7.79-7.72 (m, 1H), 7.72-7.55 (m, 3H), 7.52 (d, J=7.7 Hz, 2H), 7.47-7.35 (m, 4H), 7.35-7.24 (m, 6H), 7.24-7.14 (m, 1H), 6.96-6.79 (m, 4H), 5.70 (d, J=3.6 Hz, 1H), 5.27 (dd, J=11.1, 3.3 Hz, 1H), 4.93 (dd, J=6.4, 4.3 Hz, 1H), 4.74 (d, J=8.5 Hz, 1H), 4.34 (m, 1H), 3.99 (m, 3H), 3.72 (d, J=1.1 Hz, 6H), 3.59-3.37 (m, 2H), 3.20 (m, 1H), 2.95 (m, 1H), 1.98 (s, 2H), 1.60 (s, 3H), 1.16 (t, J=7.1 Hz, 2H). Mass calc. for $C_{45}H_{45}NO_{11}$: 775.85, found: 798.3 (M+Na).

Compound 113:—Compound 112 (1.13 g, 1.46 mmol) was added to the reaction flask. The reaction flask was evacuated and purged with argon. The starting material was dissolved in dichloromethane, and diisopropylethylamine (0.509 mL, 2.92 mmol) was added via syringe. 2-Cyanoethyl N,N-diisopropylchlorophosphoramidite (0.389 mL, 1.75 mmol) was added and stirred at room temperature for 1 hour. The reaction was checked by TLC (50/50 EtOAc/hexanes) and the reaction was concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was dissolved in minimal dichloromethane, and added dropwise to a solution of 90/10 hexanes/ether. An oily precipitate formed and was stirred for 10 minutes. The solvent was decanted off and remaining residue was dissolved in dichloromethane and transferred to flask. Solvent was removed by reduced pressure to yield 1.1 g (77%) of 113. $^1$H NMR (500 MHz, Acetonitrile-$d_3$): δ 7.98 (m, 2H), 7.83-7.77 (m, 2H), 7.66 (m, 1H), 7.60-7.46 (m, 5H), 7.42-7.28 (m, 8H), 7.22 (t, J=7.3 Hz, 1H), 6.88 (d, J=8.8 Hz, 4H), 5.80 (dd, J=5.7, 3.4 Hz, 1H), 5.47-5.36 (m, 1H), 4.83 (d, J=8.5 Hz, 1H), 4.40 (m, 1H), 4.16 (q, J=7.3 Hz, 1H), 3.99 (m, 1H), 3.85-3.77 (m, 1H), 3.76 (s, 6H), 3.75-3.63 (m, 4H), 3.54 (m, 2H), 3.30 (m, 1H), 3.11-3.03 (m, 1H), 2.59-2.44 (m, 1H), 1.65 (s, 3H), 1.23 (t, J=6.7 Hz, 1H), 1.11 (dd, J=6.7, 2.2 Hz, 9H), 1.03 (d, J=6.7 Hz, 2H). $^{31}$P NMR (202 MHz, Acetonitrile-$d_3$): δ 150.06, 149.61, 15.13 (d, J=1.9 Hz).

Example 17. Synthesis of Phosphoramidite 508

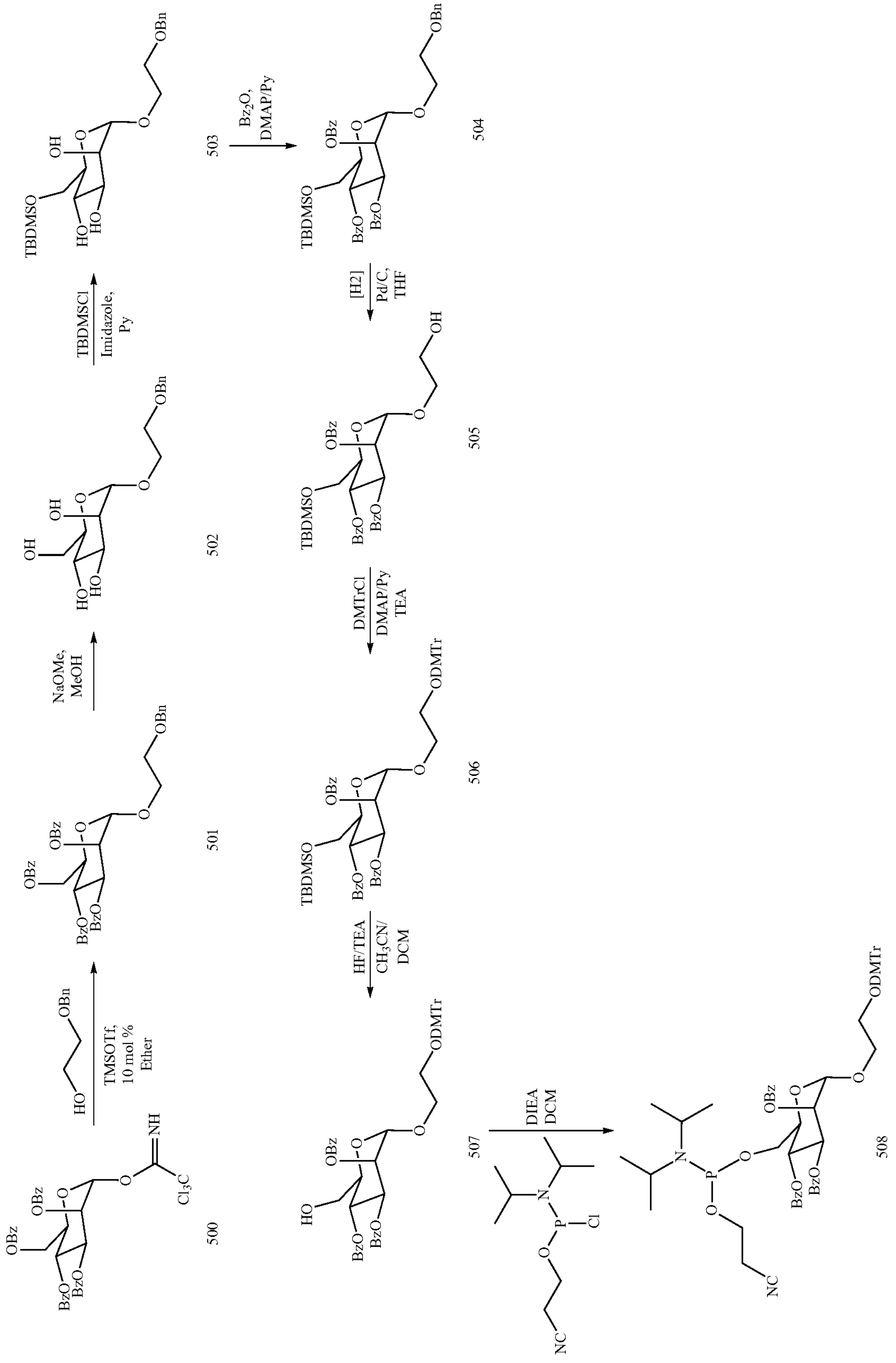
500 501 502 503 504 505 506 507 508

Compound 501: Compound 500 (6 g, 7.70 mmol) and 2-(benzyloxy)ethanol (1.20 mL, 8.117 mmol) was added into a reaction flask and dissolved with anhydrous toluene. The solvent was stripped off under reduced pressure. This was repeated three times and put on high vacuum to dry overnight. The next day a stirrer bar and molecular sieves were added and was evacuated and purged with argon three times. Anhydrous ether was added via syringe and the reaction was cooled to 0° C. with an ice bath. It was stirred for 10 minutes, then trimethylsilyl trifluoromethanesulfonate (0.139 mL, 0.77 mmol) was added via syringe. The reaction was allowed to stir for 3 hours then checked by TLC (20% EtOAc/hexanes) and developed using Hanessian stain. The reaction was complete and it was quenched with trimethylamine. The solution was diluted with ethyl acetate and molecular sieves were filtered off. The solution was added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/hexanes) and the product fractions combined and concentrated on reduced pressure to yield 5.87 g of 501. Mass calc. for $C_{43}H_{38}O_{11}$: 730.77, found: 753.2 (M+Na).

Compound 502: Compound 501 (5.62 g, 7.70 mmol) was dissolved in 150 mL of anhydrous methanol. The reaction flash was evacuated and purged with argon. Sodium methoxide in methanol (0.5M, 6.16 mL, 3.08 mmol) was added via syringe. Reaction was allowed to stir at room temperature overnight. Reaction was checked by TLC (5% MeOH/DCM) and developed using Hanessian stain. After the reaction was complete it was neutralized to pH 7 by adding 20 drops of glacial acetic acid. The solvent was stripped under reduced vacuum to yield 3.63 g of 502. Mass calc. for $C_{15}H_{22}O_7$: 314.33, found: 337.1 (M+Na).

Compound 503: Compound 502 (2.42 g, 7.70 mmol) and imidazole (1.57 g, 23.1 mmol) was added to a reaction flask. The reaction flash was evacuated and purged with argon. Anhydrous pyridine was added via syringe and starting materials dissolved. Reaction was stirred at room temperature for 10 minutes then a solution of tert-butyldimethylsilyl chloride (1.74 g, 11.55 mmol) in pyridine was added via syringe. Reaction was stirred overnight at room temperature. The reaction was checked by TLC (100% EtOAc) and developed using Hanessian stain. After the reaction was complete methanol was added to quench the reaction and stirred for 10 minutes. The reaction mixture was concentrated under reduced pressure and added dichloromethane and water. The mixture was added to separation funnel and organic layer was separated and aqueous layer was washed with dichloromethane. The organic layer was combined and washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 100% EtOAc/hexanes) and the product fractions combined and concentrated on reduced pressure to yield 2.57 g (78.1%) of 503. $^1$H NMR (400 MHz, DMSO-$d_6$): δ 7.40-7.16 (m, 2H), 4.74 (dd, J=5.8, 4.8 Hz, 1H), 4.67-4.54 (m, 1H), 4.48 (s, 1H), 3.78-3.67 (m, 1H), 3.65-3.48 (m, 2H), 3.45 (m, 1H), 3.42-3.23 (m, 1H), 0.84 (s, 4H), 0.02 (s, 3H). Mass calc. for $C_{21}H_{36}O_7Si$: 428.60, found: 451.2 (M+Na).

Compound 504: Compound 503 (2.50 g, 5.84 mmol) and 4-(dimethylamino)pyridine (0.714 g, 5.84 mmol) were added to a reaction flask. The reaction flash was evacuated and purged with argon. Anhydrous pyridine (100 mL) was added via syringe. A pyridine solution of benzoic anhydride (5.28 g, 23.36 mmol) was added to the reaction mixture via syringe and the reaction was stirred at room temperature overnight. The reaction was checked by TLC (20% EtOAc/hexanes) and developed using Hanessian stain. After the reaction was complete water was added to quench the reaction and stirred for 10 minutes. Solvent was removed under reduced pressure. EtOAc and water were added and put into a separation funnel. The organic layer was separated and washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/hexanes) and the product fractions combined and concentrated on reduced pressure to yield 3.78 g (87.5%) of 504. $^1$H NMR (400 MHz, DMSO-$d_6$): δ 8.09-7.89 (m, 2H), 7.91-7.78 (m, 2H), 7.78-7.65 (m, 3H), 7.65-7.51 (m, 4H), 7.46 (q, J=7.7 Hz, 2H), 7.41-7.31 (m, 6H), 7.31-7.21 (m, 1H), 5.96 (t, J=10.1 Hz, 1H), 5.70-5.53 (m, 2H), 5.20 (d, J=1.8 Hz, 1H), 4.58 (s, 2H), 4.21 (m, 1H), 3.96-3.75 (m, 2H), 3.75-3.60 (m, 4H), 0.86 (s, 8H), −0.12 (s, 5H). Mass calc. for $C_{42}H_{48}O_{10}Si$: 740.92, found: 763.3 (M+Na).

Compound 505: Compound 504 (2.32 g, 3.13 mmol) was added to a reaction flask. The reaction flash was evacuated and purged with argon three times. The starting material was dissolved by adding anhydrous tetrahydrofuran via syringe. Then 10% palladium on carbon, deguessa type, (278 mg, 10% by weight) was added. The reaction flash was evacuated and purged with argon three times. Then the reaction flask was evacuated and purged with hydrogen from a balloon two times. The reaction was left to stir at room temperature overnight. The reaction was checked by TLC (30% EtOAc/hexanes) and developed using Hanessian stain. After the reaction was complete, reaction mixture was evacuated and purged with argon three times. The reaction mixture was filtered through celite to remove palladium on carbon, and was washed with methanol. The mother liquor was concentrated under reduced pressure. The residue was purified by flash chromatography on silica gel (0% to 40% EtOAc/hexanes) and the product fractions combined and concentrated on reduced pressure to yield 1.20 g (59.1%) of 505. $^1$H NMR (400 MHz, DMSO-$d_6$): δ 8.06-7.95 (m, 2H), 7.95-7.82 (m, 2H), 7.79-7.63 (m, 2H), 7.64-7.50 (m, 3H), 7.45 (t, J=7.8 Hz, 2H), 7.36 (t, J=7.8 Hz, 2H), 5.96 (t, J=10.1 Hz, 1H), 5.67 (dd, J=10.2, 3.3 Hz, 1H), 5.60 (dd, J=3.3, 1.8 Hz, 1H), 5.16 (d, J=1.9 Hz, 1H), 4.85 (t, J=5.3 Hz, 1H), 4.23 (m, 1H), 3.80 (d, J=2.5 Hz, 3H), 3.71-3.54 (m, 3H), 0.87 (s, 7H), −0.09 (s, 4H). Mass calc. for $C_{35}H_{42}O_{10}Si$: 650.80, found: 673.3 (M+Na).

Compound 506: Compound 505 (1.20 g, 1.84 mmol) and 50 mL of anhydrous pyridine was added to a reaction flask. Pyridine was stripped off under reduced pressure and was repeated three times and the residue was dried under high vacuum overnight. The next day 4-(dimethylamino)pyridine (0.022 g, 0.184 mmol), triethylamine (0.251 mL, 1.84 mmol), and anhydrous pyridine was added to the reaction flask. The reaction was cooled to 0° C. using an ice bath. The reaction flash was evacuated and purged with argon. 4,4'-Dimethoxytrityl chloride (0.691 g, 2.04 mmol) was dissolved in anhydrous pyridine and resulting solution was added via syringe to the reaction flask. The reaction was allowed to come up to room temperature and stirred overnight. The reaction was checked by TLC (20% EtOAc/hexanes) and developed using Hanessian stain. Reaction complete. Methanol was added to quench the reaction and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 30% EtOAc/hexanes) and the product fractions combined and concentrated on reduced pressure to yield 1.68 g (96%) of 506. $^1$H NMR (400 MHz, DMSO-$d_6$): δ 8.07-7.92 (m, 2H), 7.81-7.62 (m, 5H), 7.56 (m, 4H), 7.50-7.41 (m, 2H), 7.41-7.27 (m, 10H), 7.28-7.19 (m, 2H), 6.98-6.86 (m, 4H), 5.98 (t, J=10.1 Hz, 1H), 5.76 (dd, J=10.2, 3.3 Hz, 1H), 5.64 (dd, J=3.3, 1.8 Hz, 1H), 5.22 (d, J=1.8 Hz, 1H), 4.36 (m, 1H), 4.01 (q, J=7.1 Hz, 1H), 3.93 (m, 1H), 3.79 (m, 3H), 3.71 (s, 7H), 3.31-3.16 (m, 2H), 1.16 (t, J=7.1 Hz, 1H), 0.88 (s, 9H), −0.08 (s, 5H). Mass calc. for $C_{56}H_{60}O_{12}Si$: 953.17, found: 975.4 (M+Na).

Compound 507: Compound 506 (1.60 g, 1.68 mmol) was added to a plastic reaction vessel. Dichloromethane (16 mL) was added to dissolve starting material. Acetonitrile (48 mL), pyridine (32 mL), and trimethylamine (8 mL) were added. The reaction vessel was purged and cooled in an ice bath. The reaction was stirred and then Hydrogen fluoride pyridine complex (8 mL) was added carefully. Reaction was stirred and warmed up to room temperature over 5 hours. The reaction was checked by TLC (30% EtOAc/hexanes) and developed using phosphomolybdic acid. 200 mL of saturated sodium bicarbonate was cooled in an ice bath and stirred. The reaction mixture was slowly added to the cooled bicarbonate solution to quench reaction. There was some effervescence, so be careful. This was stirred for ½ hour. The solution was concentrated under reduced pressure. Dichloromethane was added and was added to separation funnel. The organic layer was separated and was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 40% EtOAc/hexanes) and the product fractions combined and concentrated on reduced pressure to yield 1.29 g (91.4%) of 507. $^1$H NMR (400 MHz, DMSO-$d_6$): δ 8.05-7.98 (m, 2H), 7.73 (m, 5H), 7.66-7.51 (m, 4H), 7.51-7.44 (m, 2H), 7.44-7.30 (m, 10H), 7.28-7.19 (m, 1H), 6.97-6.88 (m, 4H), 5.90-5.75 (m, 2H), 5.66 (dd, J=3.2, 1.8 Hz, 1H), 5.22 (d, J=1.7 Hz, 1H), 5.06 (t, J=5.7 Hz, 1H), 4.31 (m, 1H), 4.02 (q, J=7.1 Hz, 1H), 3.95 (m, 1H), 3.75 (m, 1H), 3.68-3.55 (m, 2H), 3.32-3.15 (m, 2H), 1.98 (s, 1H), 1.16 (t, J=7.1 Hz, 1H). Mass calc. for $C_{50}H_{49}O_{12}$: 838.91, found: 861.3 (M+Na).

Compound 508: Compound 507 (1.19 g, 1.42 mmol) was added to the reaction flask. The reaction flask was evacuated and purged with argon. The starting material was dissolved in dichloromethane, and diisopropylethylamine (0.495 mL, 2.84 mmol) was added via syringe. 2-Cyanoethyl N,N-diisopropylchlorophosphoramidite (0.378 mL, 1.70 mmol) was added and stirred at room temperature for 1 hour. The reaction was checked by TLC (35% EtOAc/hexanes) and the reaction was concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/hexanes) and the product fractions combined and concentrated on reduced pressure to yield 0.427 g (29%) of 508. $^1$H NMR (500 MHz, Acetonitrile-$d_3$): δ 8.06 (m, 2H), 7.81-7.73 (m, 3H), 7.70 (t, J=7.8 Hz, 1H), 7.60-7.48 (m, 5H), 7.43 (m, 4H), 7.39-7.30 (m, 5H), 7.28-7.21 (m, 1H), 6.96-6.89 (m, 3H), 5.98-5.81 (m, 2H), 4.56 (m, 1H), 4.04 (m, 1H), 3.97-3.76 (m, 4H), 3.74 (d, J=3.0 Hz, 6H), 3.61 (m, 2H), 3.37 (m, 1H), 3.28 (m, 1H), 2.53 (m, 2H), 2.14 (s, 7H), 1.18-1.11 (m, 7H), 1.10 (d, J=6.7 Hz, 3H). $^1$H NMR (202 MHz, Acetonitrile-$d_3$): δ 149.85, 149.56.

Example 18. Synthesis of Phosphoramidite 515

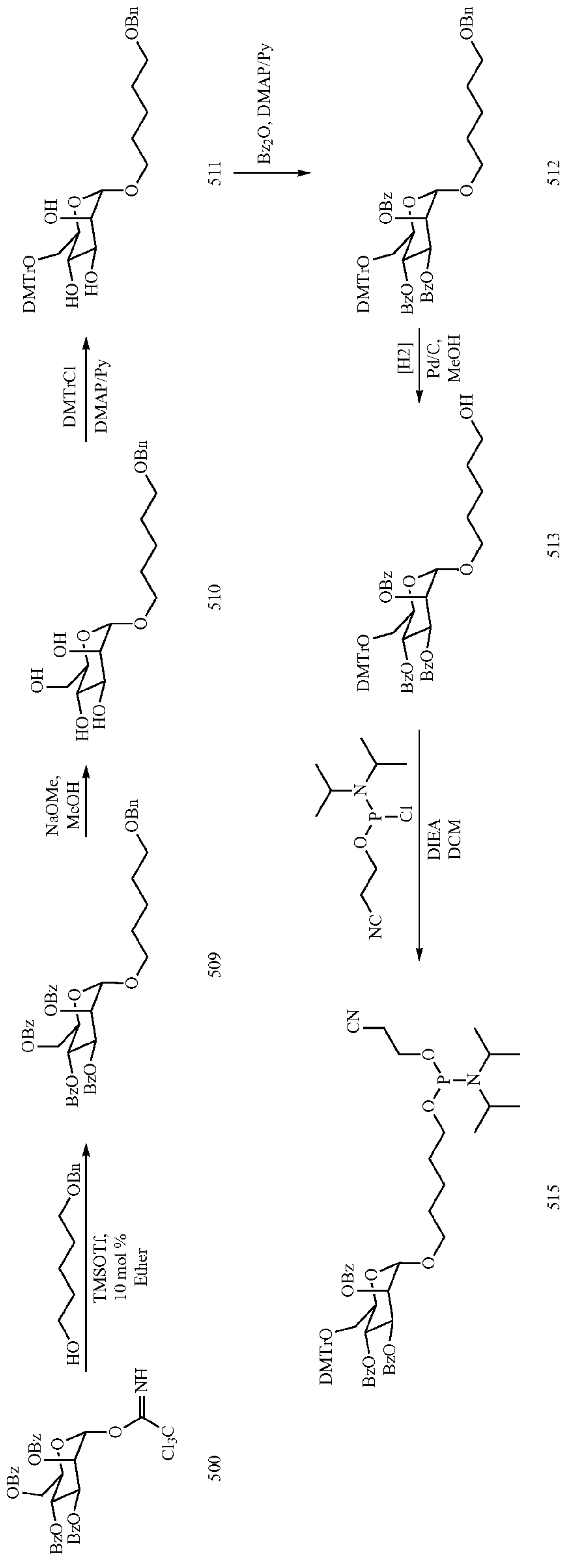
500
509
510
511
512
513
515

Compound 509: Compound 500 (6.0 g, 8.12 mmol) and 5-benzyloxy-1-pentanol (2.03 mL, 10.55 mmol) was added to a reaction flask and dissolved with anhydrous toluene. The solvent was stripped off under reduced pressure. This was repeated three times and put on high vacuum to dry overnight. The next day a stirrer bar and molecular sieves were added and was evacuated and purged with argon three times. Anhydrous ether was added via syringe and the reaction was cooled to 0° C. with an ice bath. The reaction was stirred for 10 minutes, then trimethylsilyl trifluoromethanesulfonate (0.293 mL, 1.62 mmol) was added via syringe. The reaction was allowed to stir for 4 hours then checked by TLC (30% EtOAc/hexanes) and developed using Hanessian stain. The reaction was complete and quenched with trimethylamine. The solution was diluted with ethyl acetate and molecule sieves were filtered off. The solution was added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 50% EtOAc/hexanes) and the product fractions combined and concentrated on reduced pressure to yield 5.46 g (87%) of 509. $^1$H NMR (400 MHz, DMSO-$d_6$): δ 8.36 (d, J=45.3 Hz, 2H), 8.04 (dd, J=8.3, 1.4 Hz, 2H), 7.92 (m, 4H), 7.78-7.63 (m, 4H), 7.63-7.37 (m, 8H), 7.34 (dd, J=15.6, 6.1 Hz, 6H), 5.98 (t, J=10.2 Hz, 1H), 5.71 (dd, J=10.1, 3.2 Hz, 1H), 5.61 (dd, J=3.3, 1.8 Hz, 1H), 5.20 (d, J=1.8 Hz, 1H), 4.72-4.56 (m, 1H), 4.55-4.40 (m, 4H), 3.80 (m, 1H), 3.58 (m, 1H), 3.44 (t, J=6.3 Hz, 2H), 1.97 (s, 1H), 1.76-1.51 (m, 4H), 1.45 (m, 2H), 1.15 (t, J=7.1 Hz, 1H). Mass calc. for $C_{46}H_{44}O_{11}$: 772.85, found: 795.3 (M+Na).

Compound 510: Compound 509 (6.39 g, 8.27 mmol) was dissolved in 150 mL of dry methanol. The reaction flash was evacuated and purged with argon. Sodium methoxide in methanol (0.5M, 6.62 mL, 3.31 mmol) was added via syringe. Reaction was allowed to stir at room temperature overnight. Reaction was checked by TLC (5% MeOH/DCM) and developed using Hanessian stain. The reaction was neutralized to pH 7 by adding 20 drops of glacial acetic acid and the solvent was concentrated under reduced vacuum to yield 2.95 g (100%) of 510. $^1$H NMR (400 MHz, DMSO-$d_6$): δ 8.00-7.92 (m, 4H), 7.65 (t, J=7.4 Hz, 2H), 7.52 (dd, J=8.4, 7.1 Hz, 4H), 7.38-7.21 (m, 4H), 4.57 (d, J=1.7 Hz, 1H), 4.43 (s, 2H), 3.84 (s, 7H), 3.67-3.53 (m, 3H), 3.48-3.33 (m, 5H), 3.27 (m, 2H), 1.67 (s, 1H), 1.51 (m, 4H), 1.41-1.28 (m, 2H). Mass calc. for $C_{18}H_{28}O_7$: 356.42, found: 379.2 (M+Na).

Compound 511: Compound 510 (2.95 g, 8.28 mmol) and anhydrous pyridine was added to a reaction flask. Pyridine was stripped off under reduced pressure. This was carried out 3× and put on high vacuum overnight. The next day 4-(dimethylamino)pyridine (0.101 g, 0.828 mmol), trimethylamine (1.13 mL, 8.28 mmol) and anhydrous pyridine were added to the reaction flask. The reaction flash was evacuated, purged with argon and cooled to 0° C. using an ice bath. 4,4'-Dimethoxytrityl chloride (3.09 g, 9.11 mmol) was dissolved in anhydrous pyridine and added via syringe to the reaction flask. The reaction was allowed to come up to room temperature and stirred overnight. The reaction was checked by TLC (3% MeOH/DCM) and developed using Hanessian stain. Methanol was added to quench the reaction and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 5% MeOH/DCM) and the product fractions combined and concentrated on reduced pressure and put on high vacuum to yield 3.0 g (55%) of 511. $^1$H NMR (400 MHz, DMSO-$d_6$): δ 7.44-7.37 (m, 2H), 7.33-7.21 (m, 10H), 7.20-7.13 (m, 1H), 6.90-6.81 (m, 4H), 4.73 (d, J=4.4 Hz, 1H), 4.69-4.60 (m, 2H), 4.55 (d, J=6.1 Hz, 1H), 4.42 (s, 2H), 3.81 (m, 1H), 3.71 (s, 6H), 3.67-3.56 (m, 2H), 3.51-3.39 (m, 4H), 3.31 (s, 1H), 3.30-3.16 (m, 2H), 1.62 (m, 4H), 1.53-1.38 (m, 2H). Mass calc. for $C_{39}H_{46}O_9$: 658.79, found: 681.3 (M+Na).

Compound 512: Compound 511 (3.0 g, 4.56 mmol) and 4-(dimethylamino)pyridine (0.557 g, 4.56 mmol) were added to a reaction flask. The reaction flash was evacuated and purged with argon. Anhydrous pyridine was added via syringe. A pyridine solution of benzoic anhydride (4.13 g, 18.24 mmol) was added to the reaction mixture via syringe and the reaction was stirred at room temperature overnight. The reaction was checked by TLC (20% EtOAc/hexanes) and developed using Hanessian stain. Water was added to quench the reaction and stirred for 10 minutes. Solvent was removed under reduced pressure. The residue was dissolved in ethyl acetate, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated under reduced pressure to yield compound 512. $^1$H NMR (400 MHz, DMSO-$d_6$): δ 8.11-8.04 (m, 2H), 7.77 (t, J=7.4 Hz, 1H), 7.71 (m, 4H), 7.66-7.49 (m, 4H), 7.43-7.34 (m, 6H), 7.29 (d, J=4.4 Hz, 4H), 7.25-7.08 (m, 8H), 6.73-6.61 (m, 4H), 5.64-5.56 (m, 2H), 5.24 (d, J=1.5 Hz, 1H), 4.43 (s, 2H), 4.24 (m, 1H), 3.77 (m, 1H), 3.60 (s, 7H), 3.44 (t, J=6.3 Hz, 2H), 3.37-3.29 (m, 2H), 3.08 (dd, J=10.6, 3.6 Hz, 1H), 1.74-1.54 (m, 4H), 1.52-1.39 (m, 2H). Mass calc. for $C_{60}H_{58}O_{12}$: 971.11, found: 993.4 (M+Na).

Compound 513: Compound 512 (1.5 g, 1.55 mmol) was added to a reaction flask. The reaction flash was evacuated and purged with argon three times. The starting material was dissolved by adding anhydrous tetrahydrofuran via syringe. Then 10% palladium on carbon (150 mg, 10% by weight), deguessa type, was added. The reaction flash was evacuated and purged with argon three times. Then the reaction flask was evacuated and purged with hydrogen from a balloon two times. The reaction was stirred at room temperature overnight. The reaction was checked by TLC (30% EtOAc/hexanes) and developed using phosphomolybdic acid. The reaction flash was evacuated and purged with argon three times. The reaction mixture was filtered through celite to remove palladium on carbon, and was washed with methanol. The mother liquor was concentrated under reduced pressure and purified by flash chromatography on silica gel (10% to 100% EtOAc/hexanes). The product fractions were combined and concentrated on reduced pressure to yield 0.779 g (57%) of 513. $^1$H NMR (400 MHz, DMSO-$d_6$): δ 8.05 (m, 3H), 7.96-7.88 (m, 1H), 7.84-7.76 (m, 2H), 7.72 (m, 5H), 7.66-7.51 (m, 6H), 7.49 (t, J=7.8 Hz, 1H), 7.45-7.33 (m, 7H), 7.26-7.08 (m, 7H), 6.74-6.60 (m, 4H), 5.78 (d, J=6.5 Hz, 1H), 5.64-5.53 (m, 2H), 5.24 (d, J=1.5 Hz, 1H), 4.57 (dd, J=11.9, 4.8 Hz, 1H), 4.37 (m, 2H), 4.29-4.11 (m, 2H), 4.01 (m, 1H), 3.74 (m, 6.7 Hz, 2H), 3.60 (s, 7H), 3.56-3.48 (m, 1H), 3.50-3.38 (m, 3H), 3.38-3.29 (m, 2H), 3.08 (dd, J=10.6, 3.7 Hz, 1H), 1.64 (m, 3H), 1.54-1.33 (m, 6H). Mass calc. for $C_{53}H_{52}O_{12}$: 880.99, found: 903.3 (M+Na).

Compound 515: Compound 513 (0.776 g, 0.882 mmol) was added to the reaction flask, evacuated and purged with argon. The starting material was dissolved in dichloromethane, and diisopropylethylamine (0.307 mL, 1.76 mmol) added via syringe. 2-Cyanoethyl N,N-diisopropylchlorophosphoramidite (0.236 mL, 1.06 mmol) was added and the reaction stirred at room temperature for 1 hours. The reaction was checked by TLC and concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (0% to 100% EtOAc/hexanes) and the product fractions combined and concentrated on reduced pressure to yield 0.324 g (34%) of 515. $^1$H NMR (500 MHz, Acetonitrile-$d_3$): δ 8.15-8.07 (m, 3H), 8.04-7.88 (m, 2H), 7.81-7.74 (m, 4H), 7.69 (m, 2H), 7.60-7.54 (m, 4H), 7.54-7.49 (m, 2H), 7.49-7.42 (m, 3H), 7.40 (q, J=8.0 Hz, 3H), 7.33 (t, J=7.7 Hz, 2H), 7.28 (t, J=8.8 Hz, 4H), 7.18 (m, 3H), 6.73-6.63 (m, 4H), 6.11 (t, J=10.5 Hz, 1H), 5.69-5.62 (m, 2H), 5.15 (d, J=1.6 Hz, 1H), 4.32-4.25 (m, 1H), 3.90-3.79 (m, 2H), 3.80-3.68 (m, 4H), 3.66 (d, J=2.8 Hz, 7H), 3.64-3.48 (m, 6H), 3.44-3.33 (m, 1H), 3.14 (dd, J=10.6, 3.9 Hz, 1H), 2.61 (t, J=5.9 Hz, 2H), 2.13 (s, 1H), 1.80-1.59 (m, 6H), 1.59-1.43 (m, 3H), 1.20-1.12 (m, 16H), 1.10 (d, J=6.8 Hz, 1H), 1.00 (dd, J=6.8, 4.3 Hz, 2H), 0.92 (d, J=6.7 Hz, 1H). $^{31}$P NMR (202 MHz, Acetonitrile-$d_3$): δ 152.55, 151.90, 148.36.

Example 19. Synthesis of Phosphoramidite 610

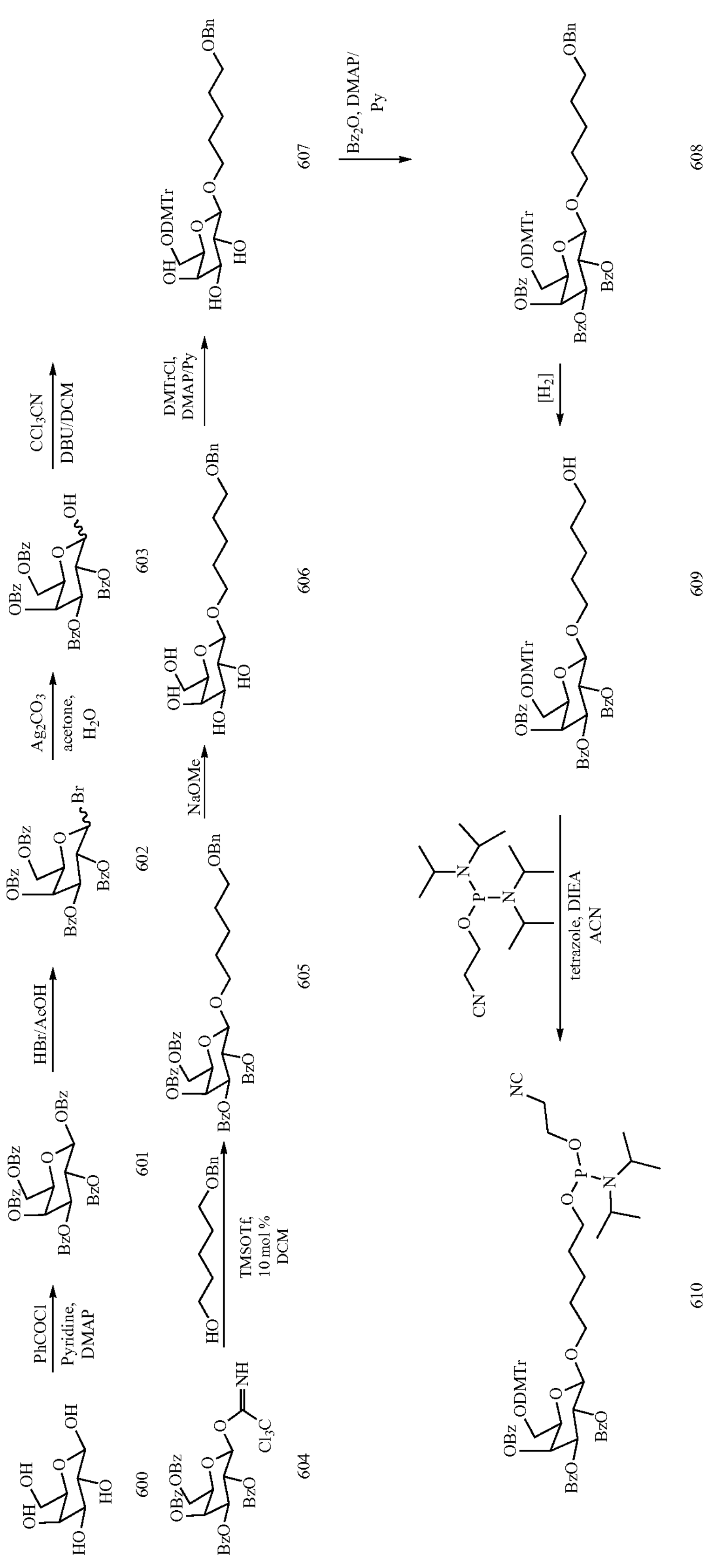
600 601 602 603
604 605 606 607
608 609 610

Compound 610: Starting compound 609 (1.5 g, 1.7 mmol) was added to the reaction flask, evacuated and purged with argon. The starting material was dissolved in acetonitrile, diisopropylethylamine (0.326 mL, 1.87 mmol) and 2-cyanoethyl N,N,N',N'-tetraisopropylphosphorodiamidite (0.844 mL, 2.56 mmol) was added via syringe. A solution of 1H-tetrazole (4.16 mL, 1.87 mmol, 0.45M) was added and stirred at room temperature for ½ hour. The reaction was checked by TLC (60% EtOAc/hexanes) and concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (10% to 100% EtOAc/hexanes) and the product fractions combined and concentrated on reduced pressure to yield 1.33 g (72%) of 610. $^{1}$H NMR (400 MHz, Chloroform-d): δ 7.97-7.87 (m, 3H), 7.83-7.76 (m, 2H), 7.62-7.46 (m, 2H), 7.46-7.32 (m, 6H), 7.30-7.07 (m, 8H), 6.72-6.61 (m, 3H), 6.06 (dd, J=2.9, 1.2 Hz, 1H), 5.69-5.56 (m, 2H), 4.72 (d, J=7.0 Hz, 1H), 4.08 (dd, J=8.3, 5.6 Hz, 1H), 3.93 (m, 1H), 3.84-3.74 (m, 2H), 3.69 (d, J=7.7 Hz, 5H), 3.62-3.49 (m, 3H), 3.49-3.39 (m, 2H), 3.39-3.22 (m, 2H), 2.59 (t, J=6.5 Hz. 2H), 1.51-1.37 (m, 2H), 1.23 (d, J=21.3 Hz, 2H), 1.14 (dd, J=16.6, 6.8 Hz, 9H). $^{31}$P NMR (202 MHz, Chloroform-d): δ 147.80, 147.78

Example 20. Synthesis of Phosphoramidite 618

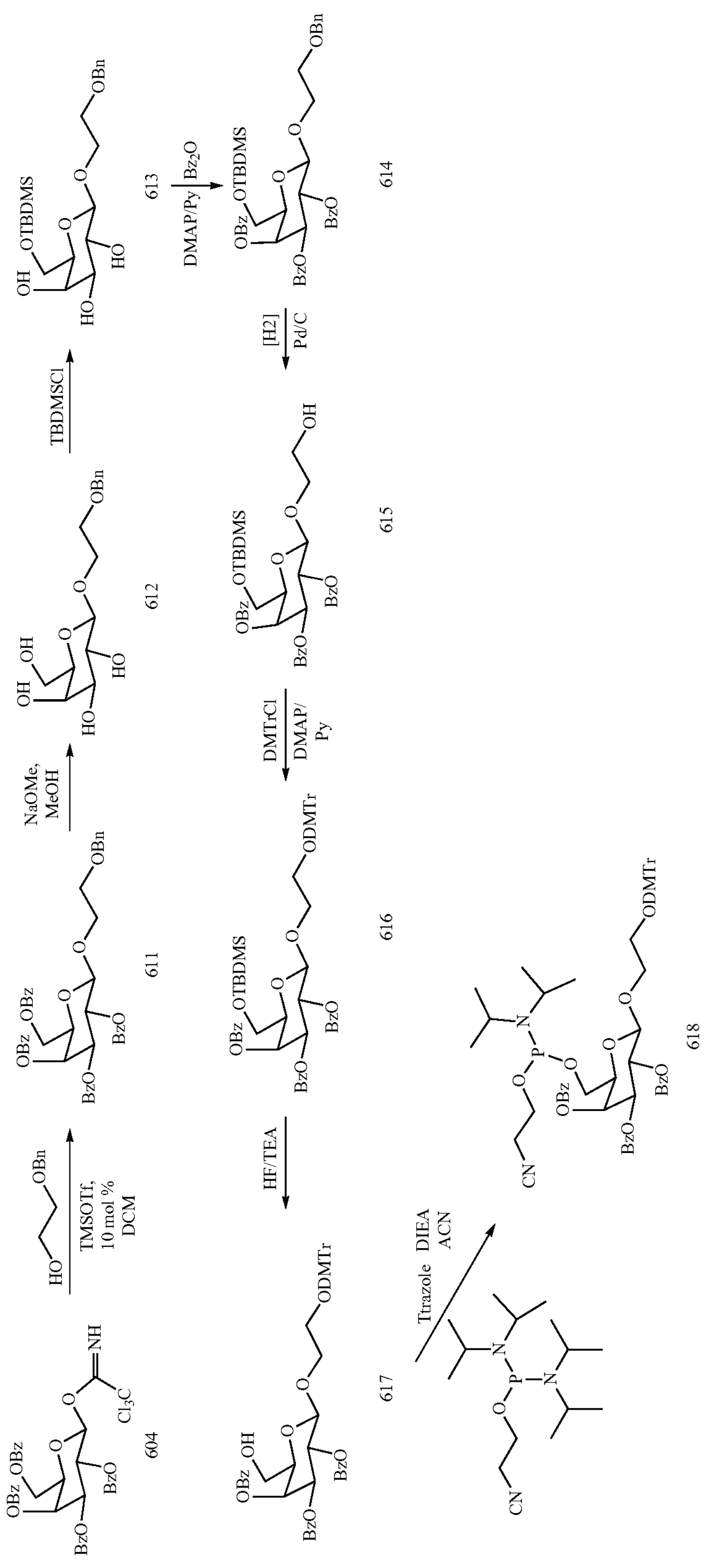
TMSOTf,
10 mol %
DCM
NaOMe,
MeOH
TBDMSCl
DMAP/Py
$Bz_2O$
[H2]
Pd/C
DMTrCl
DMAP/
Py
HF/TEA
Ttrazole
DIEA
ACN
604
611
612
613
614
615
616
617
618

Compound 618: Starting compound 617 (1.5 g, 1.79 mmol) was added to the reaction flask, evacuated and purged with argon. The starting material was dissolved in acetonitrile, diisopropylethylamine (0.343 mL, 1.97 mmol) and 2-cyanoethyl N,N,N',N'-tetraisopropylphosphorodiamidite (0.887 mL, 2.69 mmol) was added via syringe. A solution of 1H-tetrazole (4.37 mL, 1.97 mmol, 0.45 M) was added and stirred at room temperature for ½ hour. The reaction was checked by TLC (60% EtOAc/hexanes) and concentrated under reduced pressure. The residue was dissolved in dichloromethane, added to separation funnel and organic layer was washed with saturated sodium bicarbonate solution. The organic layer was separated and washed with abrine solution. The organic layer was separated and dried with sodium sulfate. The solid was filtered off and the mother liquor was concentrated. The residue was purified by flash chromatography on silica gel (10% to 100% EtOAc/hexanes) and the product fractions combined and concentrated on reduced pressure to yield 1.54 g (83%) of compound 617. $^1$H NMR (400 MHz, Chloroform-d): δ 8.11-8.03 (m, 2H), 7.92-7.84 (m, 2H), 7.83-7.75 (m, 2H), 7.65-7.55 (m, 1H), 7.50-7.39 (m, 4H), 7.36 (m, 2H), 7.29-7.12 (m, 1H), 6.78-6.68 (m, 4H), 5.96 (m, 1H), 5.81 (m, 1H), 5.60 (m, 1H), 4.96 (dd, J=8.0, 5.4 Hz, 1H), 4.17 (m, 1H), 4.08-3.99 (m, 1H), 3.97-3.87 (m, 1H), 3.87-3.79 (m, 2H), 3.76 (s, 8H), 3.73-3.68 (m, 1H), 3.54 (m, 2H), 3.33 (m, 1H), 3.13 (dd, J=10.2, 4.7 Hz, 1H), 2.62 (m, 1H), 2.50 (m, 1H), 1.13 (dd, J=6.8, 1.4 Hz, 8H), 1.06 (d, J=6.8 Hz, 2H). $^{31}$P NMR (202 MHz, Chloroform-d): δ 149.71, 149.53.

Example 21. Synthesis of Phosphoramidite 629

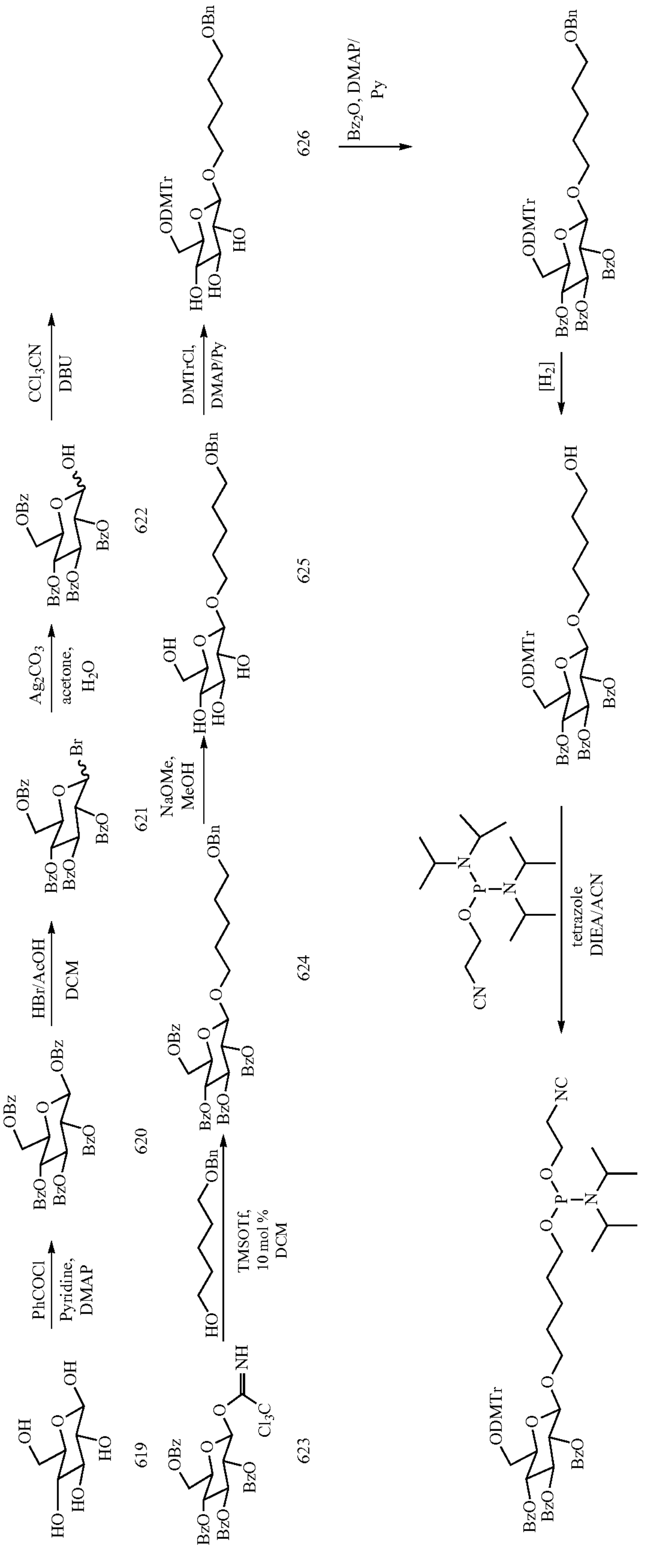
619 620 621 622 623 624 625 626 627 628 629
619
PhCOCl
Pyridine,
DMAP
620
HBr/AcOH
DCM
621
$Ag_2CO_3$
acetone,
$H_2O$
622
$CCl_3CN$
DBU
623
TMSOTf,
10 mol %
DCM
624
NaOMe,
MeOH
625
DMTrCl,
DMAP/Py
626
$Bz_2O$, DMAP/
Py
627
$[H_2]$
628
tetrazole
DIEA/ACN
629

Compound 629: Starting compound 628 (1.5 g, 1.7 mmol) was added to the reaction flask, evacuated and purged with argon. The starting material was dissolved in acetonitrile, diisopropylethylamine (0.326 mL, 1.87 mmol) and 2-cyanoethyl N,N,N',N'-tetraisopropylphosphorodiamidite (0.845 mL, 2.56 mmol) was added via syringe. A solution of 1H-tetrazole (4.15 mL, 1.87 mmol, 0.45 M) was added and stirred at room temperature for ½ hour. The reaction was checked by TLC (70% EtOAc/hexanes) and concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (10% to 100% EtOAc/hexanes) and the product fractions combined and concentrated on reduced pressure to yield 1.21 g, (66%) of 629. $^1$H NMR (400 MHz, Chloroform-d): δ 8.00-7.92 (m, 2H), 7.87-7.79 (m, 2H), 7.75-7.68 (m, 2H), 7.56-7.46 (m, 2H), 7.46-7.36 (m, 5H), 7.30 (m, 8H), 7.23-7.07 (m, 3H), 6.73-6.63 (m, 4H), 5.78 (t, J=9.6 Hz, 1H), 5.64 (q, J=9.7, 9.1 Hz, 1H), 5.52 (dd, J=9.7, 7.8 Hz, 1H), 4.80 (d, J=7.8 Hz, 1H), 4.00 (m, 1H), 3.86 (m, 1H), 3.77 (m, 6.4, 2.3, 1.7 Hz, 2H), 3.70 (d, J=3.7 Hz, 6H), 3.66-3.45 (m, 4H), 3.42 (t, J=8.9 Hz, 1H), 3.34 (dd, J=10.6, 2.5 Hz, 1H), 3.25 (dd, J=10.5, 4.9 Hz, 1H), 2.63-2.51 (m, 2H), 1.73-1.59 (m, 3H), 1.58 (s, 3H), 1.36 (s, 1H), 1.15 (dd, J=13.5, 6.8 Hz, 12H). $^{31}$P NMR (202 MHz, Chloroform-d): δ 147.78.

Example 22. Synthesis of Phosphoramidite 637

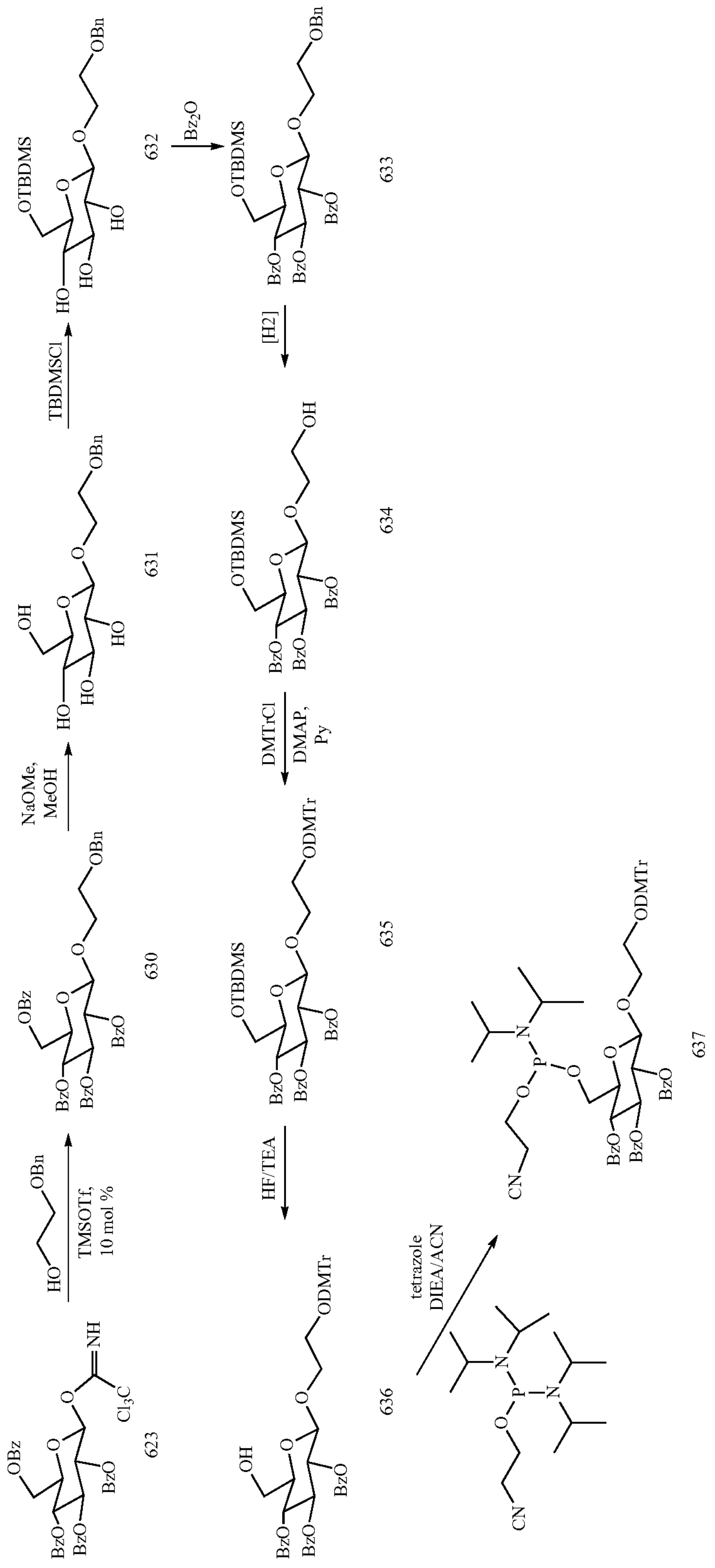
623
TMSOTf,
10 mol %
630
NaOMe,
MeOH
631
TBDMSCl
632
$Bz_2O$
633
[H2]
634
DMTrCl
DMAP,
Py
635
HF/TEA
636
tetrazole
DIEA/ACN
637

Compound 637: The phosphoramidite precursor 636 was prepared from the protected sugar 623 as described in the Scheme above. Compound 636 (1.5 g, 1.79 mmol) was added to the reaction flask, evacuated and purged with argon. The starting material was dissolved in acetonitrile, diisopropylethylamine (0.343 mL, 1.97 mmol) and 2-Cyanoethyl N,N,N',N'-tetraisopropylphosphordiamidite (0.887 mL, 2.69 mmol) was added via syringe. A solution of 1H-tetrazole (4.38 mL, 1.97 mmol, 0.45 M) was added and stirred at room temperature for ½ hour. The reaction was checked by TLC (70% EtOAc/hexanes) and concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (10% to 100% EtOAc/hexanes) and the product fractions combined and concentrated on reduced pressure to yield 1.57 g, (84%) of 637. $^{1}$H NMR (400 MHz, Chloroform-d): δ 7.93 (m, 2H), 7.91-7.79 (m, 4H), 7.60-7.48 (m, 1H), 7.48-7.37 (m, 4H), 7.37-7.32 (m, 2H), 7.32-7.10 (m, 11H), 6.77-6.66 (m, 4H), 5.88 (m, 1H), 5.63-5.45 (m, 2H), 4.99-4.85 (m, 1H), 4.08-3.84 (m, 3H), 3.84-3.69 (m, 10H), 3.55 (m, 2H), 3.36-3.24 (m, 1H), 3.14-3.03 (m, 1H), 2.52 (m, 2H), 1.26 (s, 1H), 1.18-1.05 (m, 10H), 1.05-0.91 (m, 1H). $^{31}$P NMR (202 MHz, Chloroform-d): δ 151.94, 151.76, 149.62.

Example 23. Synthesis of Phosphoramidite 645

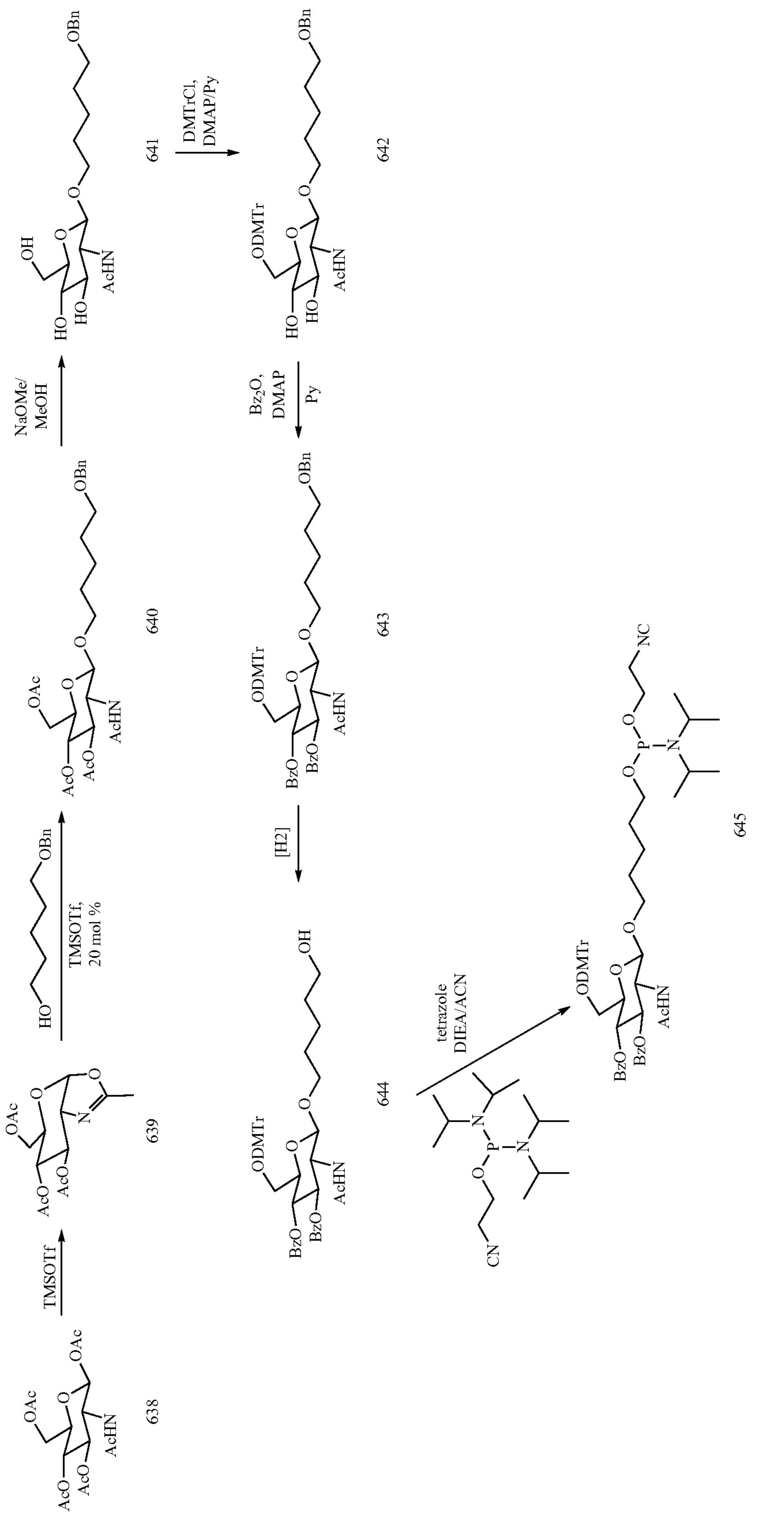
638 639 640 641 642 643 644 645

Compound 645: The phosphoramidite precursor 644 was prepared from the protected sugar 638 as described in the Scheme above. Compound 644 (1.5 g, 1.84 mmol) was added to the reaction flask, evacuated and purged with argon. The starting material was dissolved in acetonitrile, diisopropylethylamine (0.352 mL, 2.02 mmol) and 2-Cyanoethyl N,N,N',N'-tetraisopropylphosphordiamidite (0.910 mL, 2.76 mmol) was added via syringe. A solution of 1H-tetrazole (4.49 mL, 2.02 mmol, 0.45 M) was added and stirred at room temperature for ½ hour. The reaction was checked by TLC (60% EtOAc/hexanes) and concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (10% to 100% EtOAc/hexanes) and the product fractions combined and concentrated on reduced pressure to yield 0.951 g, (51%) of 645. $^1$H NMR (400 MHz, Chloroform-d): δ 7.97-7.89 (m, 2H), 7.72-7.65 (m, 2H), 7.53-7.39 (m, 4H), 7.36 (t, J=7.7 Hz, 2H), 7.32-7.23 (m, 6H), 7.22-7.05 (m, 3H), 6.71-6.61 (m, 4H), 5.79 (dd, J=15.9, 9.0 Hz, 1H), 5.63-5.53 (m, 2H), 4.77 (d, J=8.2 Hz, 1H), 4.25-4.13 (m, 1H), 4.05-3.94 (m, 1H), 3.88-3.72 (m, 3H), 3.69 (d, J=3.7 Hz, 7H), 3.59 (m, 4H), 3.31 (dd, J=10.5, 2.4 Hz, 1H), 3.17 (dd, J=10.5, 4.8 Hz, 1H), 2.59 (q, J=6.6 Hz, 2H), 1.89 (d, J=1.3 Hz, 3H), 1.78-1.61 (m, 6H), 1.49 (q, J=7.7 Hz, 2H), 1.17 (dd, J=6.8, 4.4 Hz, 11H). $^{31}$P NMR (202 MHz, Chloroform-d): δ 147.82, 147.66

Example 24. Synthesis of Phosphoramidite 653

Compound 653—The phosphoramidite precursor 652 was prepared from the protected sugar 638 as described in the Scheme above. Compound 652 (1.5 g, 1.93 mmol) was added to the reaction flask, evacuated and purged with argon. The starting material was dissolved in acetonitrile, diisopropylethylamine (0.369 mL, 2.12 mmol) and 2-Cyanoethyl N,N,N',N'-tetraisopropylphosphorodiamidite (0.953 mL, 2.89 mmol) was added via syringe. A solution of 1H-tetrazole (4.71 mL, 2.12 mmol, 0.45 M) was added and stirred at room temperature for ½ hour. The reaction was checked by TLC (70% EtOAc/hexanes) and concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The crude residue was dissolved in minimal dichloromethane, and added dropwise to a solution of 90/10 hexanes/ether. An oily precipitate formed, stirred for 10 minutes and the solvent decanted off. The remaining residue was dissolved in dichloromethane and transferred to flask which was concentrated under reduced pressure to yield compound 1.68 g, (89%) of 653. $^1$H NMR (500 MHz, Chloroform-d): δ 7.91 (m, 4H), 7.54-7.47 (m, 2H), 7.47-7.38 (m, 3H), 7.38-7.32 (m, 7H), 7.32-7.24 (m, 3H), 6.89-6.79 (m, 4H), 5.61 (m, 1H), 5.57-5.42 (m, 2H), 4.83 (dd, J=8.3, 3.2 Hz, 1H), 4.31-4.15 (m, 2H), 4.08-3.98 (m, 1H), 3.94-3.81 (m, 2H), 3.82-3.72 (m, 11H), 3.60-3.45 (m, 3H), 3.38 (m, 1H), 3.22-3.14 (m, 1H), 2.57-2.45 (m, 2H), 1.69 (d, J=2.9 Hz, 4H), 1.36-1.20 (m, 6H), 1.20-1.05 (m, 12H), 0.88 (t, J=7.1 Hz, 2H). $^{31}$P NMR (202 MHz, Chloroform-d): δ 149.73, 149.54.

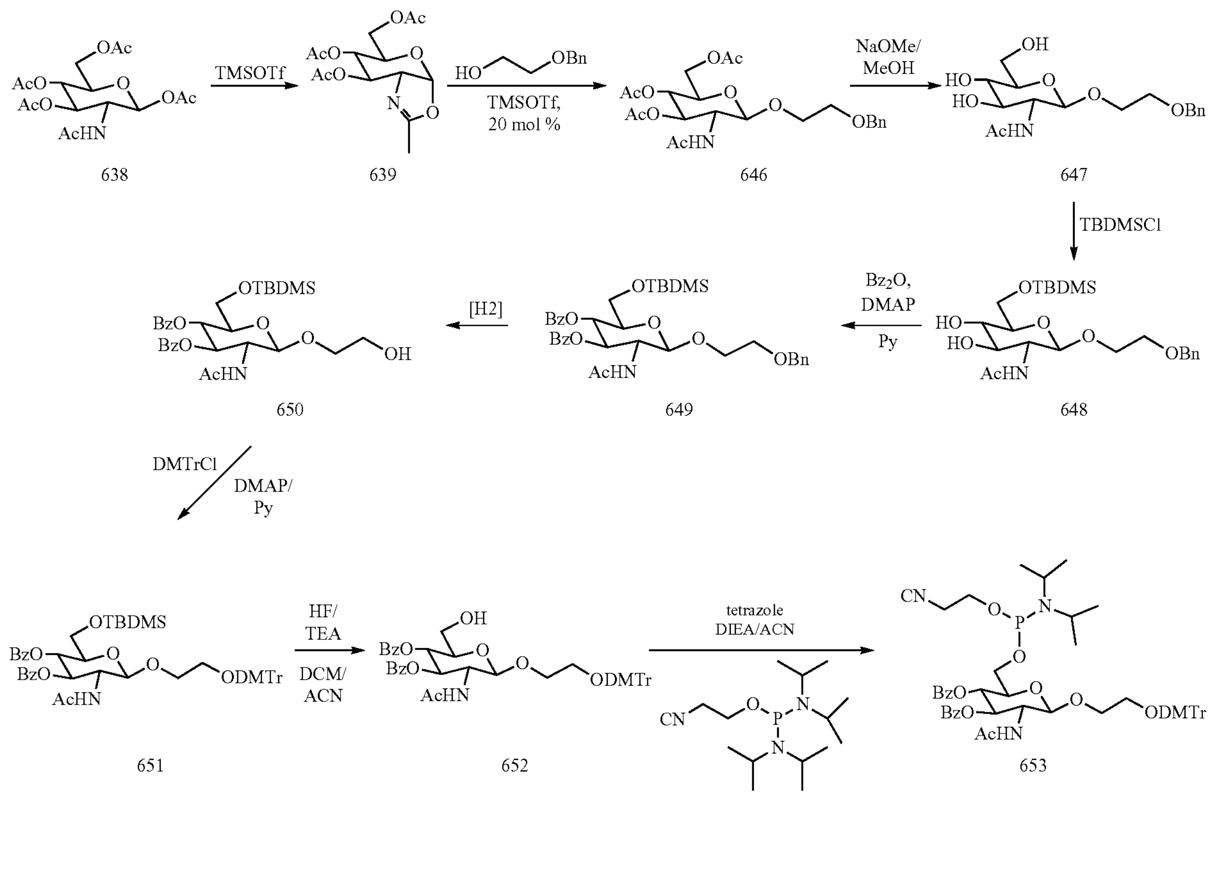

Example 25. Synthesis of Phosphoramidite 659

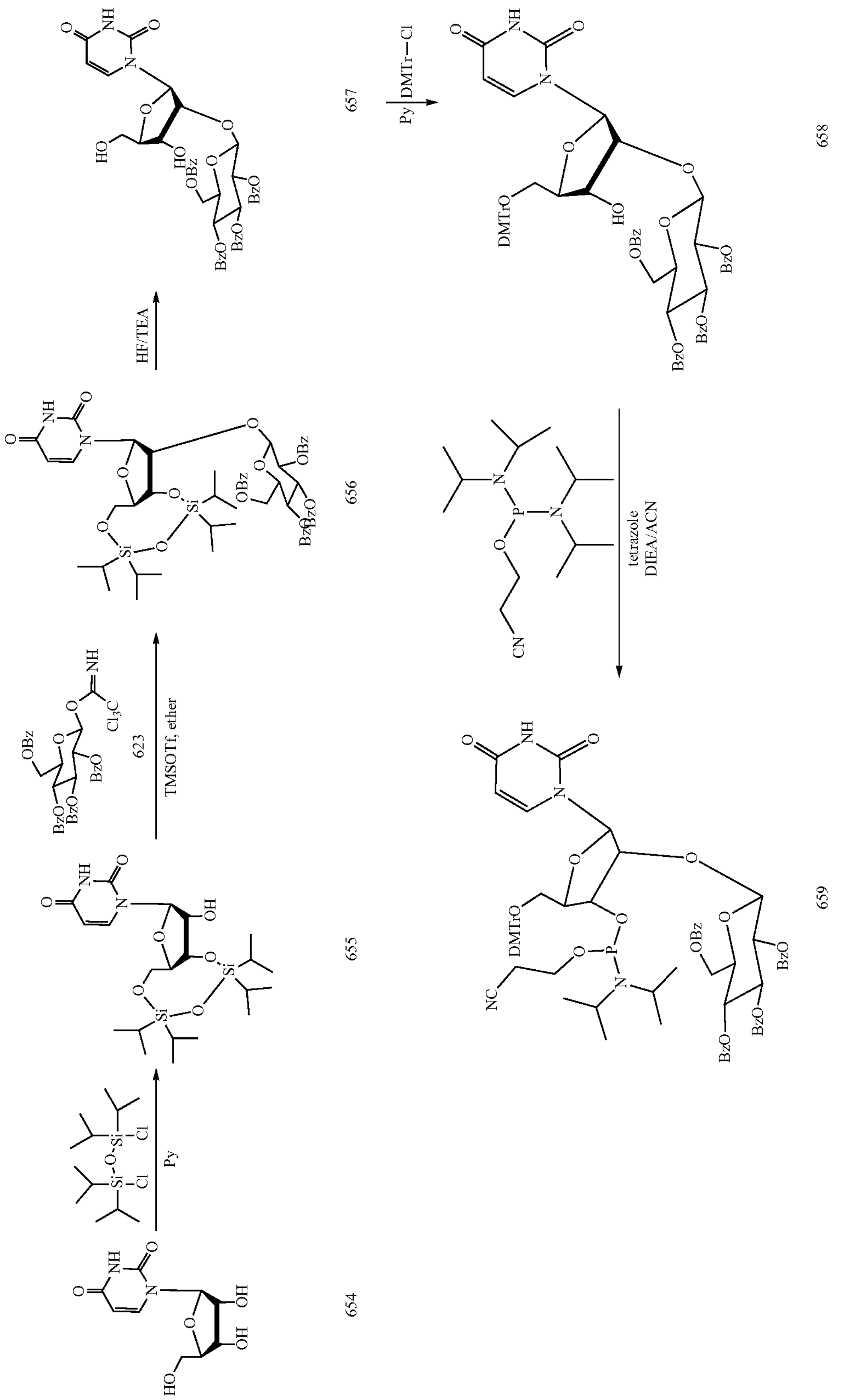
654
655
623
656
657
658
659

Compound 659: Starting material 654 is treated with isopropyl silyl derivative to get compound 655. This is further reacted with glucose trichloroacetimidate followed by silyl deprotection and introduction of DMTr give compound 658. Amidite is synthesized from this using normal protocol described earlier in example 21.

Example 26. Synthesis of Phosphoramidite 1009

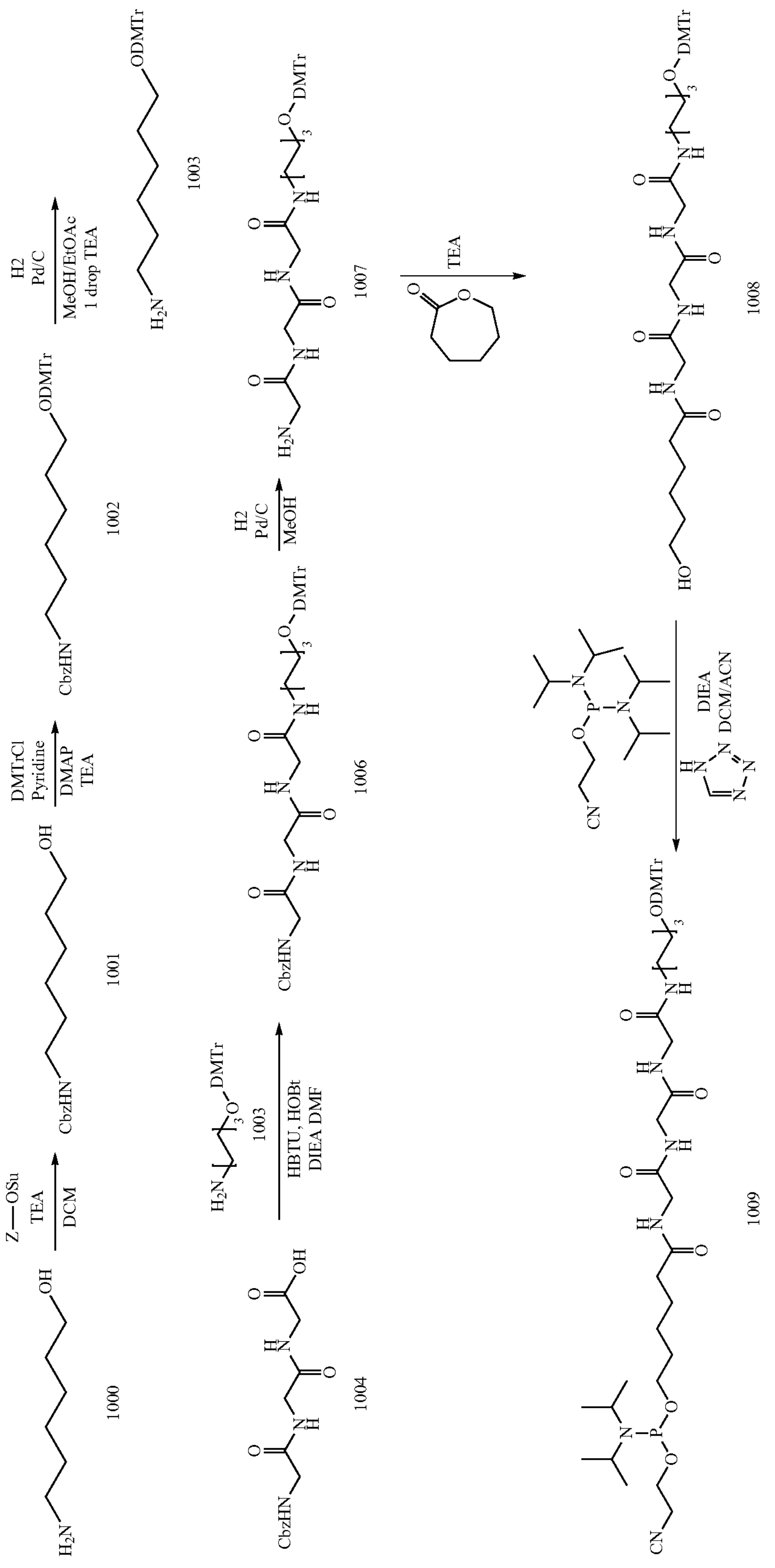
1000
Z—OSu
TEA
DCM
1001
DMTrCl
Pyridine
DMAP
TEA
1002
H2
Pd/C
MeOH/EtOAc
1 drop TEA
1003
1004
1003
HBTU, HOBt
DIEA DMF
1006
H2
Pd/C
MeOH
1007
TEA
1008
DIEA
DCM/ACN
1009

Compound 1001—Starting compound 1000 (10 g, 85.38 mmol) was added to the reaction flask, evacuated and purged with argon. The starting material was dissolved in dichloromethane and triethylamine (23.79 mL, 170.7 mmol) was added via syringe. N-(Benzyloxycarbonyloxy)succinimide (31.9 g, 128 mmol) was dissolved in anhydrous dichloromethane and then added to the reaction mixture via syringe. The reaction was stirred at room temperature for 1 hour. The reaction was checked by TLC (50% EtOAc/hexanes) and the reaction was concentrated under reduced pressure. The residue was dissolved in dichloromethane, added to separation funnel and organic layer was washed with 10% citric acid solution. The organic layer was separated and washed with a brine solution. The organic layer was separated and dried with sodium sulfate. The solid was filtered off and the mother liquor was concentrated. The residue was purified by flash chromatography on silica gel (10% to 100% EtOAc/hexanes) and the product fractions combined and concentrated on reduced pressure to yield 17.9 g, (83%) of 1001. $^1$H NMR (400 MHz, DMSO-$d_6$): δ 7.40-7.25 (m, 4H), 7.21 (t, J=5.7 Hz, 1H), 4.99 (s, 2H), 4.31 (t, J=5.1 Hz, 1H), 3.36 (m, 2H), 2.96 (q, J=6.7 Hz, 2H), 1.38 (m, 4H), 1.32-1.17 (m, J=5.2, 4.6 Hz, 4H).

Compound 1002—Compound 1001 (17.5 g, 69.7 mmol) and 50 mL of anhydrous pyridine was added to a reaction flask. Pyridine was stripped off under reduced pressure. This was repeated for three times and dried under high vacuum overnight. The next day 4-(dimethylamino)pyridine (0.851 g, 6.97 mmol), triethylamine (9.71 mL, 69.7 mmol), and anhydrous pyridine were added to the reaction flask. The reaction was cooled to 0° C. using an ice bath. The reaction flash was evacuated and purged with argon. 4,4'-Dimethoxytrityl chloride (26.2 g, 77.4 mmol) was dissolved in anhydrous pyridine and resulting solution was added via syringe to the reaction flask. The reaction was allowed to come up to room temperature and stirred overnight. The reaction was checked by TLC (30% EtOAc/hexanes) and the reaction was concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (10% to 50% EtOAc/hexanes) and the product fractions combined and concentrated on reduced pressure to yield 37.2 g, (96%) of 1002. $^1$H NMR (400 MHz, DMSO-$d_6$): δ 7.41-7.26 (m, 9H), 7.21 (dd, J=8.7, 6.7 Hz, 7H), 6.91-6.79 (m, 5H), 4.98 (s, 2H), 3.72 (s, 7H), 2.93 (m, 4H), 1.51 (m, 2H), 1.36 (m, 2H), 1.29 (t, J=7.9 Hz, 2H)

Compound 1003—Compound 1002 (36 g, 65.07 mmol) was added to a reaction flask. The reaction flash was evacuated and purged with argon three times. The starting material was dissolved by adding anhydrous methanol, ethyl acetate, and one drop of trimethylamine. Then 10% palladium on carbon, deguessa type, (3.6 g, 10% by weight) was added. The reaction flash was evacuated and purged with argon three times. Then the reaction flask was evacuated and purged with hydrogen from a balloon two times. The reaction was left to stir at room temperature for 3 hours. The reaction was checked by TLC (30% EtOAc/hexanes) and evacuated and purged with argon three times. The reaction mixture was filtered through celite to remove palladium on carbon, and was washed with methanol. The mother liquor was concentrated under reduced pressure to yield 27.3 g, (100%) of 1003. $^1$H NMR (400 MHz, DMSO-$d_6$): δ 7.39-7.32 (m, 2H), 7.29 (t, J=7.7 Hz, 2H), 7.26-7.16 (m, 5H), 6.91-6.84 (m, 4H), 3.72 (s, 6H), 2.93 (t, J=6.5 Hz, 3H), 2.46 (d, J=6.7 Hz, 2H), 1.52 (m, 2H), 1.29 (m, 3H), 1.21 (d, J=13.8 Hz, 2H).

Compound 1006—Starting compound 1004 (5 g, 15.47 mmol), N,N,N',N'-tetramethyl-O-(1H-benzotriazol-1-yl) uronium hexafluorophosphate (6.16 g, 16.24 mmol), and 1-hydroxybenzotriazole hydrate (2.09 g, 15.47 mmol) were added to the reaction flask, evacuated and purged with argon. Compound 1003 (6.81 g, 16.24 mmol) was added to a separate flask and dissolved in dimethylformamide. The reaction was preactivated by adding diisopropylethylamine (8.08 mL, 46.41 mmol) via syringe and the reaction turned yellow. Let stir at room temp for 5 minutes, then added the solution of compound 1003 via syringe. The reaction was stirred at room temperature overnight. The reaction was checked by TLC (5% MeOH/DCM) and precipitated in water. The precipitate was filtered off and washed with water. The solid was dried under high vacuum overnight. The residue was preloaded onto silica by dissolving the residue in MeOH/DCM and adding silica gel. This slurry was concentrated under reduced pressure and dried on high vacuum. This was purified by flash chromatography on silica gel (0% to 10% MeOH/DCM) and the product fractions combined and concentrated on reduced pressure to yield 8.9 g, (79%) of 1006. 1H NMR (400 MHz, DMSO-$d_6$): δ 8.16 (d, J=5.6 Hz, 1H), 8.08 (t, J=5.9 Hz, 1H), 7.69 (t, J=5.7 Hz, 1H), 7.48 (t, J=6.0 Hz, 1H), 7.38-7.26 (m, 9H), 7.25-7.16 (m, 5H), 6.92-6.83 (m, 4H), 5.02 (s, 2H), 3.72 (s, 8H), 3.65 (dd, J=7.9, 5.4 Hz, 4H), 3.00 (q, J=6.7 Hz, 2H), 2.92 (t, J=6.5 Hz, 2H), 1.51 (t, J=7.2 Hz, 2H), 1.37 (q, J=7.2 Hz, 2H), 1.33-1.24 (m, 2H), 1.24-1.13 (m, 2H).

Compound 1007—Compound 1006 (7.87 g, 10.86 mmol) was added to a reaction flask. The reaction flash was evacuated and purged with argon three times. The starting material was dissolved by adding anhydrous methanol. Then 10% palladium on carbon, deguessa type, (0.787 g, 10% by weight) was added. The reaction flash was evacuated and purged with argon three times. Then the reaction flask was evacuated and purged with hydrogen from a balloon two times. The reaction was left to stir at room temperature for 3 hours. The reaction was checked by TLC (5% MeOH/DCM) and evacuated and purged with argon three times. The reaction mixture was filtered through celite to remove palladium on carbon, and was washed with methanol. The mother liquor was concentrated under reduced pressure. The residue was purified by flash chromatography on silica gel (0% to 10% MeOH/DCM) and the product fractions combined and concentrated on reduced pressure 5.20 g, (81%) of 1007. $^1$H NMR (400 MHz, DMSO-$d_6$): δ 8.10 (t, J=5.9 Hz, 1H), 7.69 (t, J=5.6 Hz, 1H), 7.38-7.33 (m, 1H), 7.30 (t, J=7.7 Hz, 1H), 7.25-7.17 (m, 2H), 6.92-6.83 (m, 2H), 3.72 (s, 4H), 3.64 (d, J=5.9 Hz, 1H), 3.12 (s, 1H), 3.01 (q, J=6.7 Hz, 1H), 2.93 (t, J=6.5 Hz, 1H), 2.41 (q, J=7.1 Hz, 11H), 1.85 (s, 11H), 1.52 (m, 11H), 1.36 (m, 11H), 1.29 (t, J=7.8 Hz, 1H), 1.19 (m, 1H), 0.92 (t, J=7.1 Hz, 1H).

Compound 1008—Compound 1007 (1.58 g, 2.68 mmol) was added to the reaction flask. Caprolactone was added to dissolve the starting material and a drop of trimethylamine was added to keep the reaction basic. The reaction was heated at 40° C. for 4 days. The reaction was checked by TLC (15% MeOH/DCM) and was concentrated under reduced pressure. The residue was precipitated in ether and the slurry was stirred for ½ hour to get a nice solid. The precipitate was filtered off, washed with ether and dried on high vacuum to yield 1.38 g, (73%) of 1008. $^1$H NMR (400 MHz, Methanol-$d_4$): δ 7.45-7.37 (m, 2H), 7.32-7.23 (m, 6H), 7.22-7.14 (m, 1H), 6.88-6.79 (m, 4H), 3.93-3.81 (m, 7H), 3.77 (s, 6H), 3.54 (t, J=6.5 Hz, 2H), 3.17 (t, J=7.1 Hz, 2H), 3.04 (t, J=6.4 Hz, 2H), 2.28 (t, J=7.6 Hz, 2H), 1.71 (t, J=5.9 Hz, 2H), 1.68-1.45 (m, 9H), 1.39 (m, 4H), 1.34-1.22 (m, 2H).

Compound 1009—Compound 1008 (1.38 g, 1.96 mmol) was added to the reaction flask, evacuated and purged with argon. The starting material was dissolved in a mixture of DCM and acetonitrile, diisopropylethylamine (0.375 mL, 2.15 mmol), and 2-cyanoethyl N,N,N',N'-tetraisopropylphosphorodiamidite (0.969 mL, 2.94 mmol) were added via syringe. A solution of 1H-tetrazole (4.78 mL, 2.15 mmol, 0.45 M) was added and stirred at room temperature for ½ hour. The reaction was checked by TLC (10% MeOH/DCM) and concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was dissolved in minimal DCM and precipitated with ether. The product was filtered off, washed with ether and dried on high vacuum to yield compound 1.77 g, (100%) of 1009. $^1$H NMR (500 MHz, Chloroform-d): δ 7.50 (t, J=5.2 Hz, 1H), 7.41 (d, J=7.7 Hz, 2H), 7.30 (d, J=8.4 Hz, 5H), 7.26 (d, J=8.2 Hz, 4H), 7.22-7.15 (m, 2H), 6.88 (t, J=6.0 Hz, 1H), 6.81 (d, J=8.4 Hz, 4H), 6.70 (s, 1H), 4.08-3.98 (m, 6H), 3.78 (s, 6H), 3.69-3.52 (m, 4H), 3.21 (q, J=6.8 Hz, 2H), 3.02 (t, J=6.5 Hz, 2H), 2.62 (t, J=6.4 Hz, 2H), 2.27 (t, J=7.7 Hz, 2H), 1.66 (d, J=16.6 Hz, 15H), 1.50 (m, 3H), 1.39 (m, 5H), 1.28 (dd, J=15.7, 8.4 Hz, 4H), 1.16 (t, J=6.5 Hz, 10H). $^{31}$P NMR (202 MHz, Chloroform-d): δ 147.90, 148.29.

Example 27. Synthesis of Phosphoramidite 1017

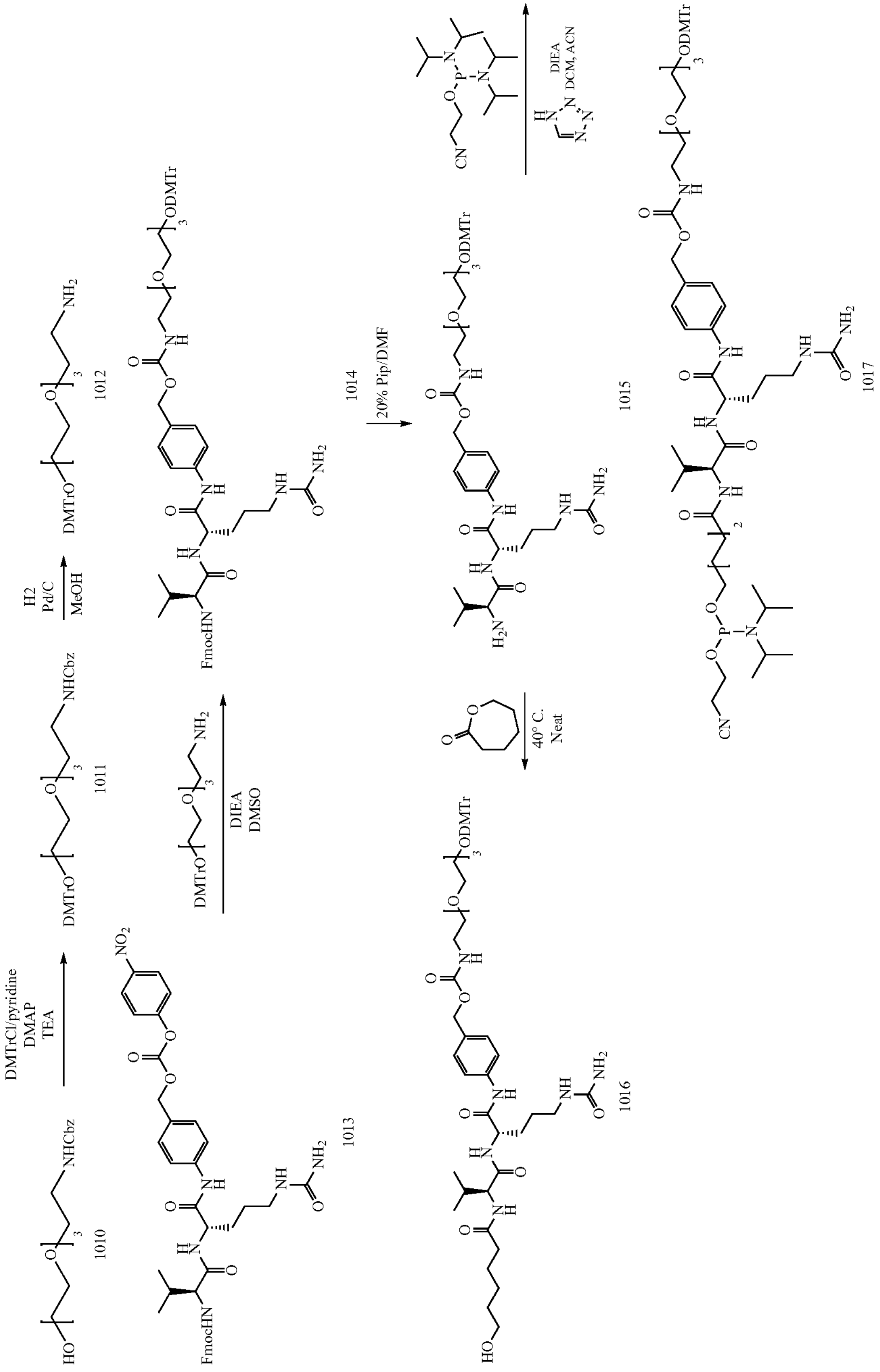
1010, 1011, 1012, 1013, 1014, 1015, 1016, 1017

Compound 1011—Starting material 1010 (5 g, 15.3 mmol) and 50 mL of anhydrous pyridine was added to a reaction flask. Pyridine was stripped off under reduced pressure. This was repeated for three times and dried under high vacuum overnight. The next day 4-(dimethylamino) pyridine (0.187 g, 1.53 mmol), triethylamine (2.13 mL, 15.3 mmol), and anhydrous pyridine was added to the reaction flask. The reaction was cooled to 0° C. using an ice bath. The reaction flash was evacuated and purged with argon. 4,4'-dimethoxytrityl chloride (5.76 g, 17 mmol) was dissolved in anhydrous pyridine and resulting solution was added via syringe to the reaction flask. The reaction was allowed to come up to room temperature and stirred overnight. The reaction was checked by TLC (30% EtOAc/hexanes) and concentrated under reduced pressure. The residue was dissolved in dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (10% to 100% EtOAc/hexanes) and the product fractions combined and concentrated on reduced pressure to yield 6.61 g, (69%) of 1011. $^1$H NMR (400 MHz, DMSO-$d_6$): δ 7.43-7.15 (m, 14H), 6.91-6.83 (m, 4H), 4.99 (s, 2H), 3.72 (s, 6H), 3.52 (q, J=7.8, 6.9 Hz, 10H), 3.39 (t, J=5.9 Hz, 2H), 3.12 (q, J=5.9 Hz, 2H), 3.04 (t, J=5.0 Hz, 2H).

Compound 1012—Compound 1011 (6.61 g, 10.5 mmol) was added to a reaction flask. The reaction flash was evacuated and purged with argon three times. The starting material was dissolved by adding anhydrous methanol. Then 10% palladium on carbon, deguessa type, (661 mg, 10% by weight) was added. The reaction flash was evacuated and purged with argon three times. Then the reaction flask was evacuated and purged with hydrogen from a balloon two times. The reaction was left to stir at room temperature for 3 hours. The reaction was checked by TLC (10% MeOH/DCM) and the reaction flash was evacuated and purged with argon three times. The reaction mixture was filtered through celite to remove palladium on carbon, and was washed with methanol. The mother liquor was concentrated under reduced pressure. The residue was purified by flash chromatography on silica gel (0% to 10% MeOH/DCM) and the product fractions combined and concentrated on reduced pressure to yield 4.4 g, (85%) of 1012. $^1$H NMR (400 MHz, DMSO-$d_6$): δ 7.43-7.35 (m, 2H), 7.34-7.16 (m, 7H), 6.92-6.83 (m, 4H), 3.72 (s, 6H), 3.55 (d, J=7.8 Hz, 8H), 3.51-3.44 (m, 2H), 3.04 (t, J=4.9 Hz, 2H), 2.61 (t, J=5.8 Hz, 2H).

Compound 1014—Starting compound 1013 (2 g, 2.61 mmol) and compound 1012 (1.36 g, 2.74 mmol) were added to the reaction flask. The reaction was evacuated and purged with argon three times. The starting material was dissolved by adding dimethyl sulfoxide, then N,N-diisopropylethylamine (0.909 mL, 5.22 mmol) was added via syringe. The reaction was stirred at room temperature overnight. The reaction was checked by TLC (10% MeOH/DCM) and the reaction was diluted with dichloromethane, added to separation funnel and organic layer was washed with saturated sodium bicarbonate. The organic layer was separated and washed with a brine solution. The organic layer was separated and dried with sodium sulfate. The solid was filtered off and the mother liquor was concentrated on reduced pressure to yield 2.91 g, (99%) of 1014. $^1$H NMR (400 MHz, DMSO-$d_6$): δ 10.12 (s, 1H), 7.94-7.80 (m, 2H), 7.57 (d, J=8.4 Hz, 1H), 7.45-7.34 (m, 3H), 7.27 (m, 10H), 6.91-6.82 (m, 4H), 6.42 (d, J=9.0 Hz, 1H), 6.27 (s, 1H), 5.41 (s, 1H), 4.91 (s, 1H), 3.72 (d, J=2.5 Hz, 6H), 3.59-3.45 (m, 12H), 3.10 (m, J=5.9 Hz, 2H), 3.06-2.86 (m, 5H), 2.53 (s, 37H), 1.22 (s, 1H), 0.87 (d, J=6.9 Hz, 2H), 0.76 (d, J=6.8 Hz, 2H).

Compound 1015—Compound 1014 (2.91 g, 2.59 mmol) was added to the reaction flask. The reaction was evacuated and purged with argon three times. The starting material was dissolved by adding anhydrous dimethylformamide, and piperidine (20% v/v) was also added via syringe. The reaction was stirred at room temperature overnight. The reaction was checked by MS and the reaction was concentrated by reduced pressure. The residue was dissolved with ethyl acetate, added to separation funnel and organic layer was washed with saturated sodium bicarbonate. The organic layer was separated and washed with a brine solution. The organic layer was separated and dried with sodium sulfate. The solid was filtered off and the mother liquor was concentrated on reduced pressure and precipitated in ether to yield 1.67 g, (72%) of 1015. $^1$H NMR (400 MHz, DMSO-$d_6$): δ 10.11 (s, 1H), 8.13 (d, J=7.8 Hz, 1H), 8.06-7.97 (m, 1H), 7.57 (d, J=8.4 Hz, 2H), 7.38 (d, J=7.1 Hz, 3H), 7.35-7.15 (m, 12H), 6.87 (dd, J=9.0, 2.5 Hz, 5H), 6.74-6.65 (m, 1H), 5.96 (t, J=5.9 Hz, 1H), 5.39 (s, 2H), 4.92 (s, 2H), 4.46 (d, J=7.1 Hz, 1H), 3.72 (d, J=2.7 Hz, 7H), 3.59-3.53 (m, 6H), 3.53-3.42 (m, 7H), 3.38 (t, J=6.0 Hz, 2H), 3.11 (q, J=5.9 Hz, 2H), 3.03 (m, 4H), 3.01-2.86 (m, 2H), 1.91 (m, 1H), 1.66 (d, J=9.0 Hz, 1H), 1.57 (dd, J=9.2, 4.9 Hz, 1H), 1.36 (m, 2H), 0.82 (dd, J=39.2, 6.8 Hz, 5H). Mass calc. for $C_{48}H_{64}N_6O_{11}$: 901.07, found: 923.3 (M+Na).

Compound 1016—Compound 1015 (1.67 g, 1.85 mmol) was added to the reaction flask. Caprolactone was added to dissolve the starting material and a drop of trimethylamine was added to keep the reaction basic. The reaction was heated at 40° C. for 4 days. The reaction was checked by TLC (15% MeOH/DCM) and was concentrated under reduced pressure. The residue was precipitated in ether and the slurry was stirred for ½ hour to get a nice solid. The precipitate was filtered off, washed with ether and dried on high vacuum to yield 1.22 g, (65%) of 1016. $^1$H NMR (400 MHz, DMSO-$d_6$): δ 9.98 (s, 1H), 8.07 (d, J=7.5 Hz, 1H), 7.80 (d, J=8.6 Hz, 1H), 7.58 (d, J=8.2 Hz, 2H), 7.38 (d, J=7.3 Hz, 2H), 7.33-7.16 (m, 10H), 6.91-6.83 (m, 4H), 5.97 (t, J=5.8 Hz, 1H), 5.40 (s, 2H), 4.92 (s, 2H), 4.34 (m, 2H), 4.23-4.14 (m, 1H), 3.72 (s, 6H), 3.52 (q, J=8.7, 7.5 Hz, 10H), 3.37 (m, 7H), 3.11 (q, J=5.9 Hz, 2H), 3.04 (t, J=5.2 Hz, 2H), 2.95 (m, 2H), 2.28-2.06 (m, 2H), 1.96 (m, 1H), 1.69 (s, 1H). 1.54-1.30 (m, 6H), 1.30-1.20 (m, 2H), 0.83 (dd, J=11.4, 6.7 Hz, 5H).

Compound 1017—Compound 1016 is added to the reaction flask which is evacuated and purged with argon. The starting material is dissolved in a mixture of DCM and acetonitrile, diisopropylethylamine and 2-Cyanoethyl N,N,N',N'-tetraisopropylphosphordiamidite is added via syringe. A solution of 1H-tetrazole is added and stirred at room temperature for ½ hour. The reaction is checked by TLC (10% MeOH/DCM) and the reaction is worked up using standard extraction conditions. The residue is dissolved in minimal DCM and precipitated with ether. The product is filtered off, washed with ether and dried on high vacuum to yield compound 1017.

Example 28. Bis(siRNA) Qualitative Stability Using EMSA in Rat Plasma, Liver Cytosol and Liver Tritosomes Bis(siRNA) multiplexes were evaluated for stability of linkers via an electrophoretic mobility shift assay in non-denaturing 10% Criterion TBE gels. Bis-siRNA samples were prepared at 2 μM in PBS and then diluted to 0.1 μM in matrix. Matrices were either: (a) Sprague Dawley (S.D.) Rat or Cynomolgous Monkey Plasma (in lithium heparin, Bioreclamation)(b) Mixed Gender Rat Liver Tritosomes (Xenotech), diluted 1:2 in 20 mM NaCitrate buffer pH 4.5, or (c) Female S.D. Rat Liver Cytosol or mixed gender Cynomolgous Monkey Liver Cytosol (supplied as 10 mg/mL, Xenotech), diluted 1:10 in 50 mM Tris, 5 mM $MgCl_2$, pH 7.4. To the bis-siRNA/matrix mixture, two units of heparin were added. Samples were then incubated at 37° C. for 0 or 24 hours. At end of incubation, 25 mM EDTA was added to quench reaction. Samples were store in −80° C.

Prior to loading gel, Bis-siRNA samples were thawed at RT and Trackit 6× Cyan/Orange Loading Buffer (Life Technologies) was added to samples in 1:6 ratio. Ladder was prepared with 1:1:10 ratio of 10 bp ladder (Life Technologies, Cat #10488-019), BlueJuice™ Gel Loading Buffer (Life Technologies), and DI water. Ladder and bis-siRNA samples were loaded onto a 10% TBE gel run at 100 Volts for 2 hours at 4° C. Gels were stained in 10% TBE and SYBR Gold (10,000× stock) for 10 minutes at RT. Images were read using a Gel Doc™ XR+ Imaging System with Image Lab software.

Materials:

- Gels: 10% TBE, *Criterion*, Cat. #345-0053
- *Recently switched to 10% TBE, *Novex*, Cat. #EC62755BOX
- Rat Plasma (lithium heparin), *Bioreclamation*, Cat. #RATLLIHP
- Sprague Dawley (SD) Rat Liver Tritosomes, *Xenotech*, Cat. #R0610.LT, tyloxapol-treated, mixed gender, pool of 60
- Rat Liver Cytosol, Female, IGS Sprague Dawley, Pool of 115, *Xenotech*, Cat. #R1500.C, supplied as 1 mL at 10 mg/mL
- 10×PBS buffer pH7.4, *Ambion*, Cat. #AM9625 (diluted to 1×)
- Heparin 1000 U/mL, *Sagent*
- EDTA 500 mM (diluted to 50 mM)
- 10 bp DNA ladder, *Life Technologies*, Cat. #10488-019
- BlueJuice™ Gel Loading Buffer (10×)—bromophenol blue, *Life Technologies*, Cat. #10816-015
  - Composed of 54% (w/v) sucrose, 10 mM Tris-HCl (pH6.5), 10 mM EDTA, 0.3% (w/v) bromophenol blue
- 10×TBE (Tris/Boric Acid/EDTA), *BioRad Labs*, Cat. #171-0070
- TrackIt 6× Cyan/Orange Loading Buffer, *Life Technologies*. Cat. #10482-028
  - Composed of 30% (w/v) glycerol, 60 mM Tris-HCl (pH7.5), 60 mM EDTA, 0.36% (w/v) XCFF, and 2.4% (w/v) Orange G
- SYBR Gold, *Life Technologies*, Cat. #S11494, 10,000× stock
- Gel Doc™ XR+ Imaging System with Image Lab software, *BioRad*

Controls: PBS (matrix only, no sample)

- AD-77748.1 (duplex of dA and dT 20mers)
- Mixture of two duplexes: FVII (AD-68269) and TTR (AD-69228)

Procedure:

1. Dilute samples to 2 μM in 1×PBS.
2. In PCR tubes, add 1 μL siRNA to 19 μL matrix.
   a. For tritosomes, first dilute 1:2 in 20 mM NaCitrate buffer pH4.5
   b. For cytosol, first dilute 10× in 50 mM Tris, 5 mM $MgCl_2$, pH7.4
3. Add 2 μL heparin.
   a. Can omit this step for plasma (heparin already in prep)
4. Incubate at 37° C. for 0 h, 4 h or 24 h.
5. At end of incubation, add 20 μL of 50 mM EDTA.
6. Add 8.6 μL cyan/orange loading dye to tubes.
7. Prepare ladder. Dilute 4 μL of 10 bp ladder, 4 μL BlueJuice, and 41 μL DI H2O.
8. Spin down diluted samples.
9. Run on 10% TBE gel (100V, 2 h @4° C.).
   a. Load 5 μL for ladder.
   b. Load 12 μL for each bis(siRNA) sample.
10. Stain in 50 mL of 1×TBE and 5 μL SYBR gold for 10 mins @RT.
11. Wash in 1×TBE and read.

The cleavage rate for each bis(siRNA) is compared with untreated sample or sample at 0 h. From this approximate rate of cleavage is calculated. The bis(siRNA) design for evaluating exemplary cleavable linkers are shown in Table 1. Results are shown in FIGS. 7A-10 and summarized in Table 2.

Figure 7A:
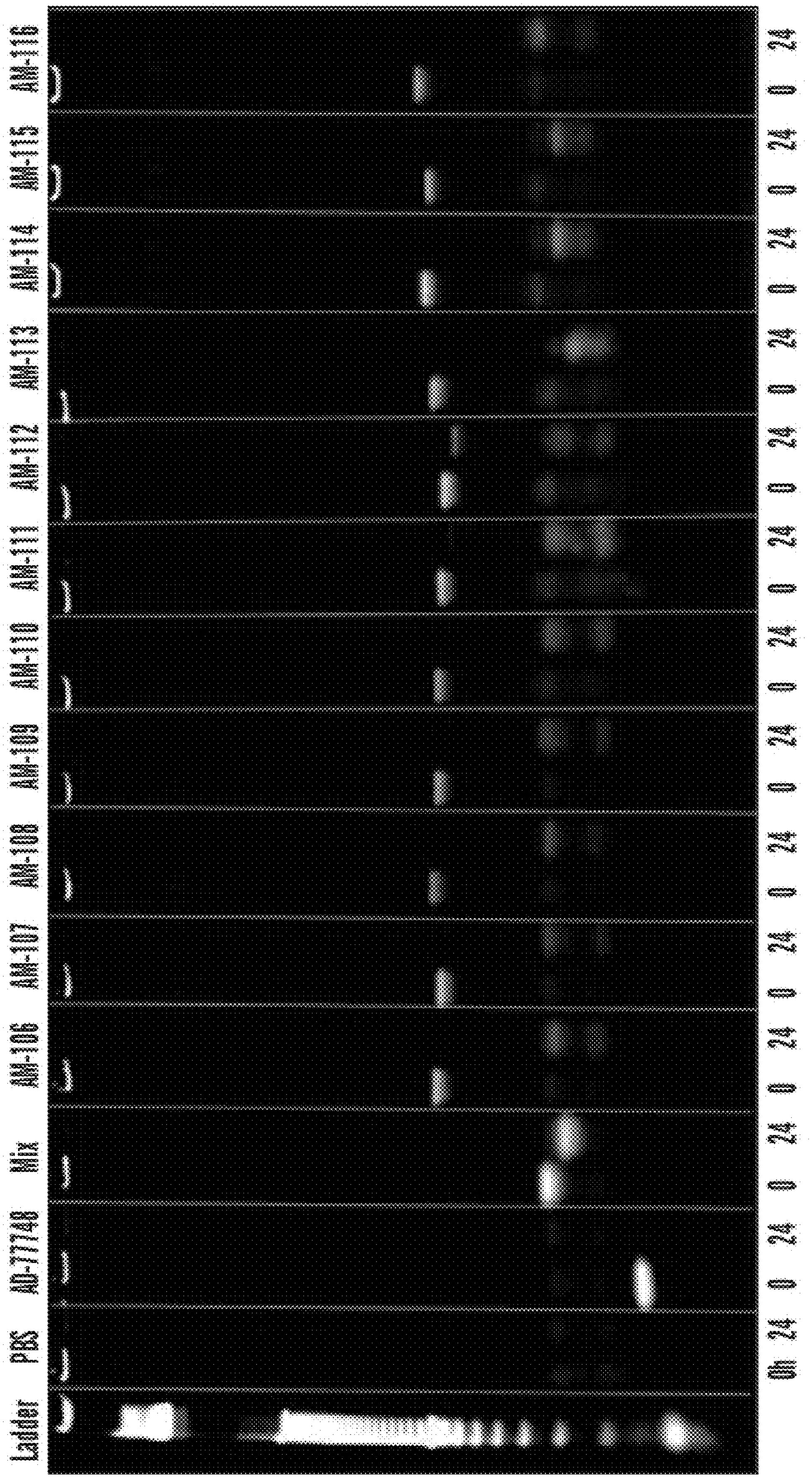
FIGS. 7A-10 are photographs of gel mobility assays showing degradation of bis(siRNA)s comprising exemplary linkers in rat. The bis(siRNA) compounds are AM-106-AM-129 (FIGS. 7A-7B), AM-130-AM-147 (FIGS. 8A-8B), AM-148-AM-154 (FIG. 9), and AM-155-AM-161 (FIG. 10).
Figure 7B:
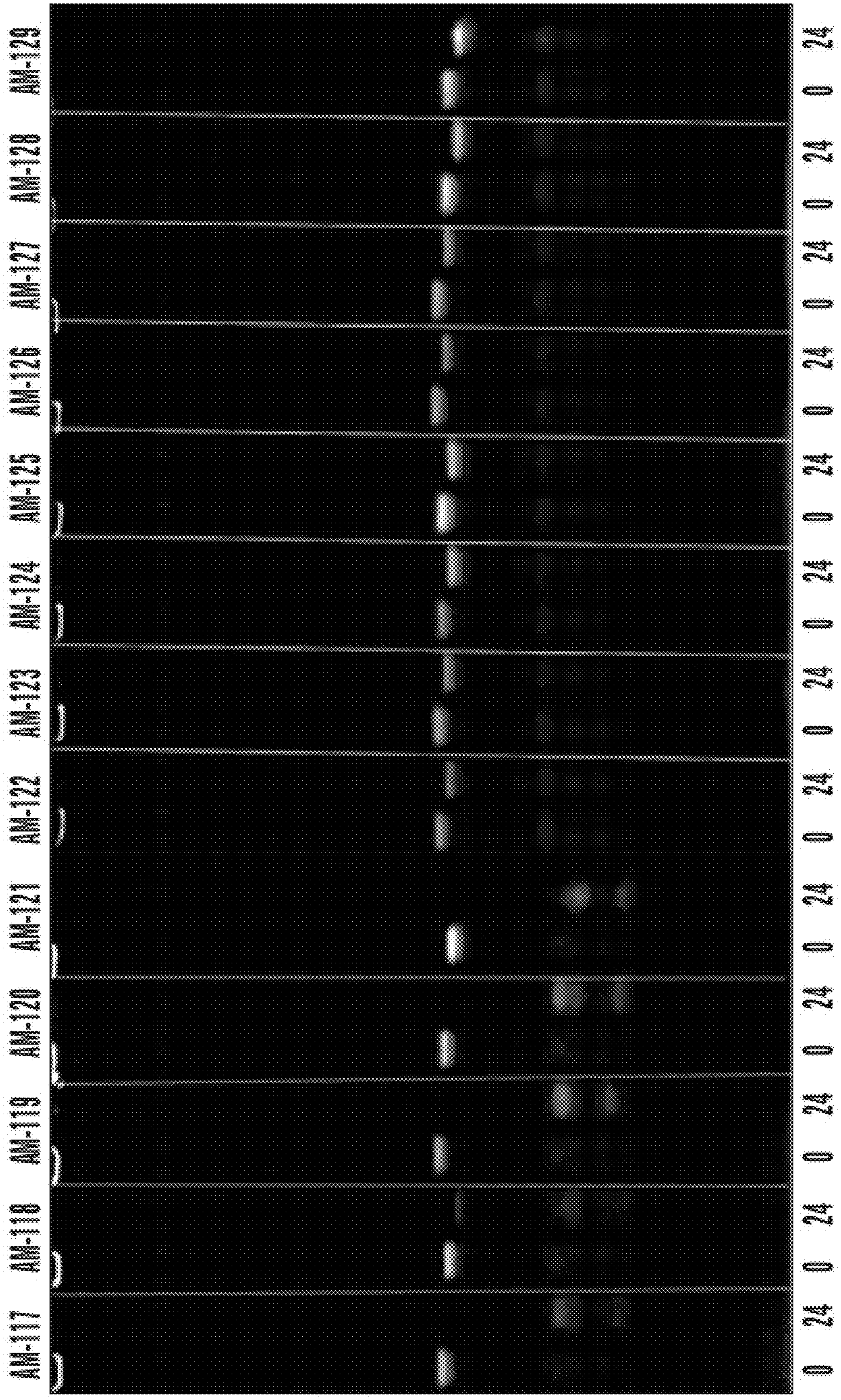

FIGS. 7A-7B shows degradation of bis(siRNA) designs AM-106 to AM-129 in rat tritosome after 24 h of incubation. Compounds were incubated with rat tritosomes and the products were analyzed by gel electrophoresis to determine cleavability of the likers as described above. All sugar combinations underwent degradation in 24 h. Less shown for AM-112 (2xQ303 flanked by Q48s) and AM-118 (Q198+2xQ303). DNA and 2'-fluoro constructs showed no degradation in 24 h.

Figure 8A:
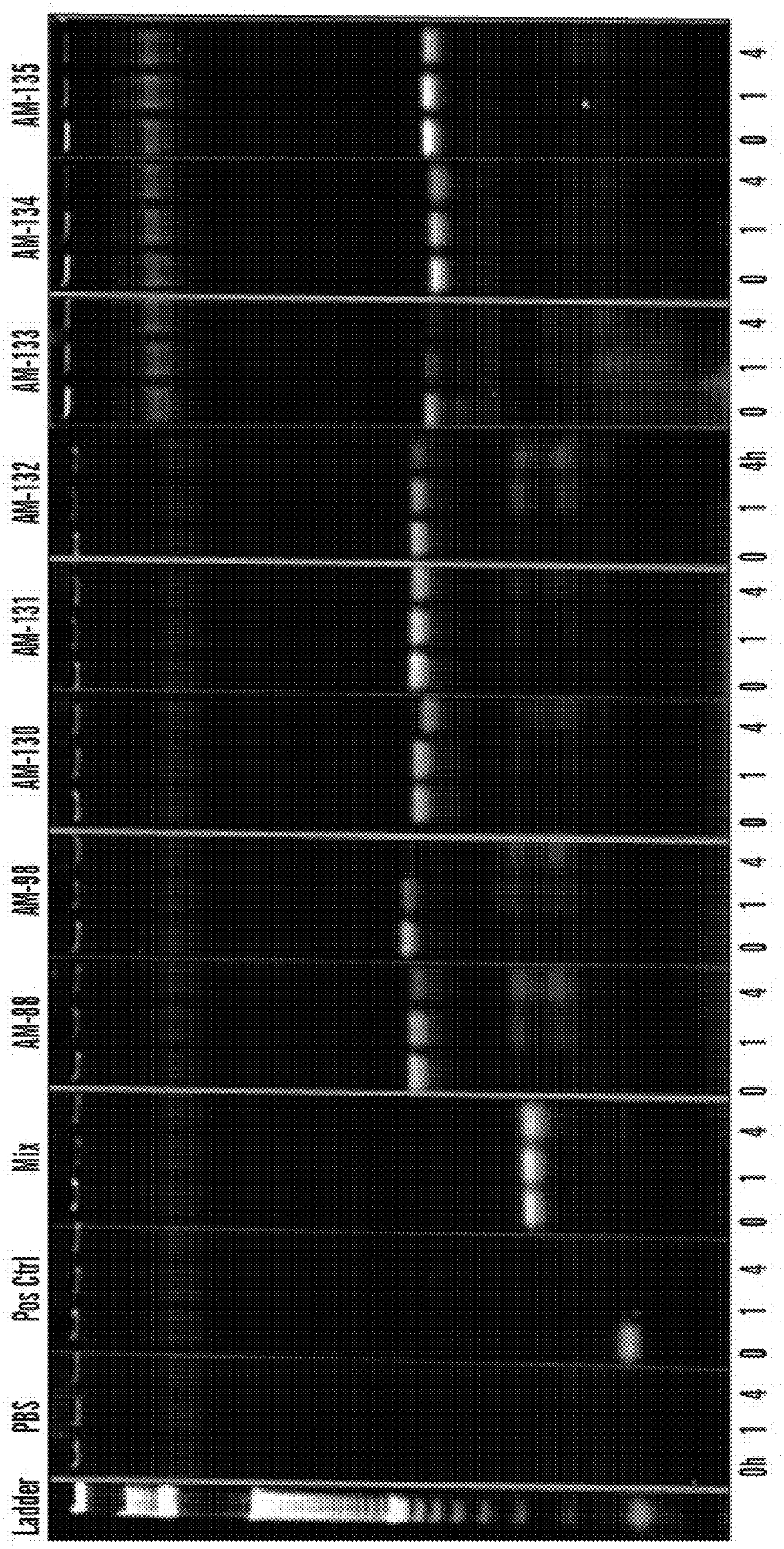
Figure 8B:
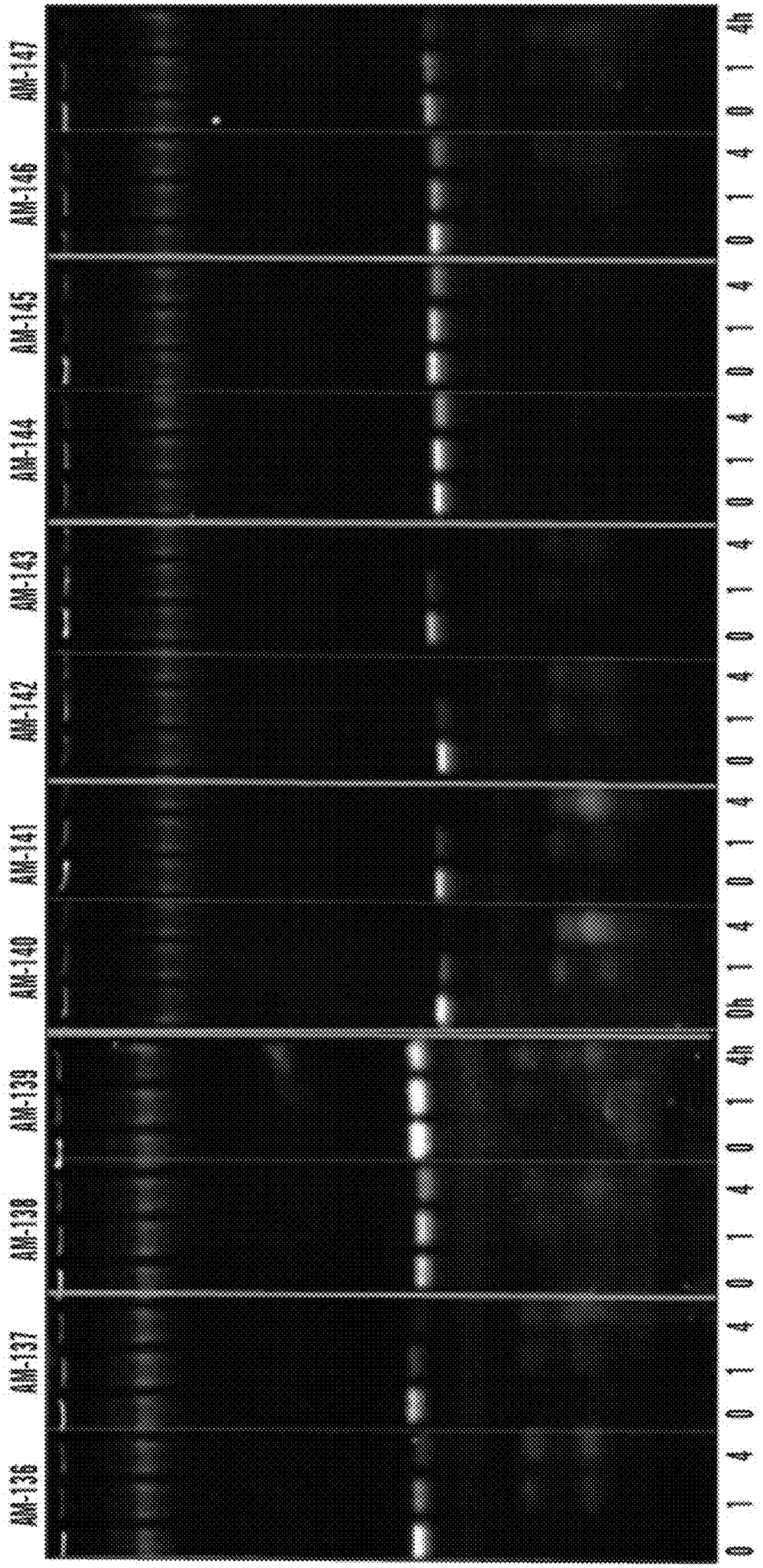

FIGS. 8A-8B shows degradation of bis(siRNA) designs AM-130-AM-147. Compounds were incubated with rat tritosomes and the products were analyzed by gel electrophoresis to determine cleavability of the likers as described above. C5 linker provides benefit for cleavage over C2 linker. GluNAc-C5 and GalNAc-C5 show fastest rate of cleavage (fully cleaved by 4 h) whereas mannose sugar linker was most stable in 4 h. Galactose and glucose derived linkers underwent cleavage, but intact linkers were present after 4 h incubation in rat tritosome. In 24 hours, all combination of sugar-based linkers underwent degradation. Less shown for AM-112 (2xQ303 flanked by Q48s) and AM-118 (Q198+2xQ303). DNA and 2'-fluoro constructs showed no degradation in 24 h.

Figure 9:
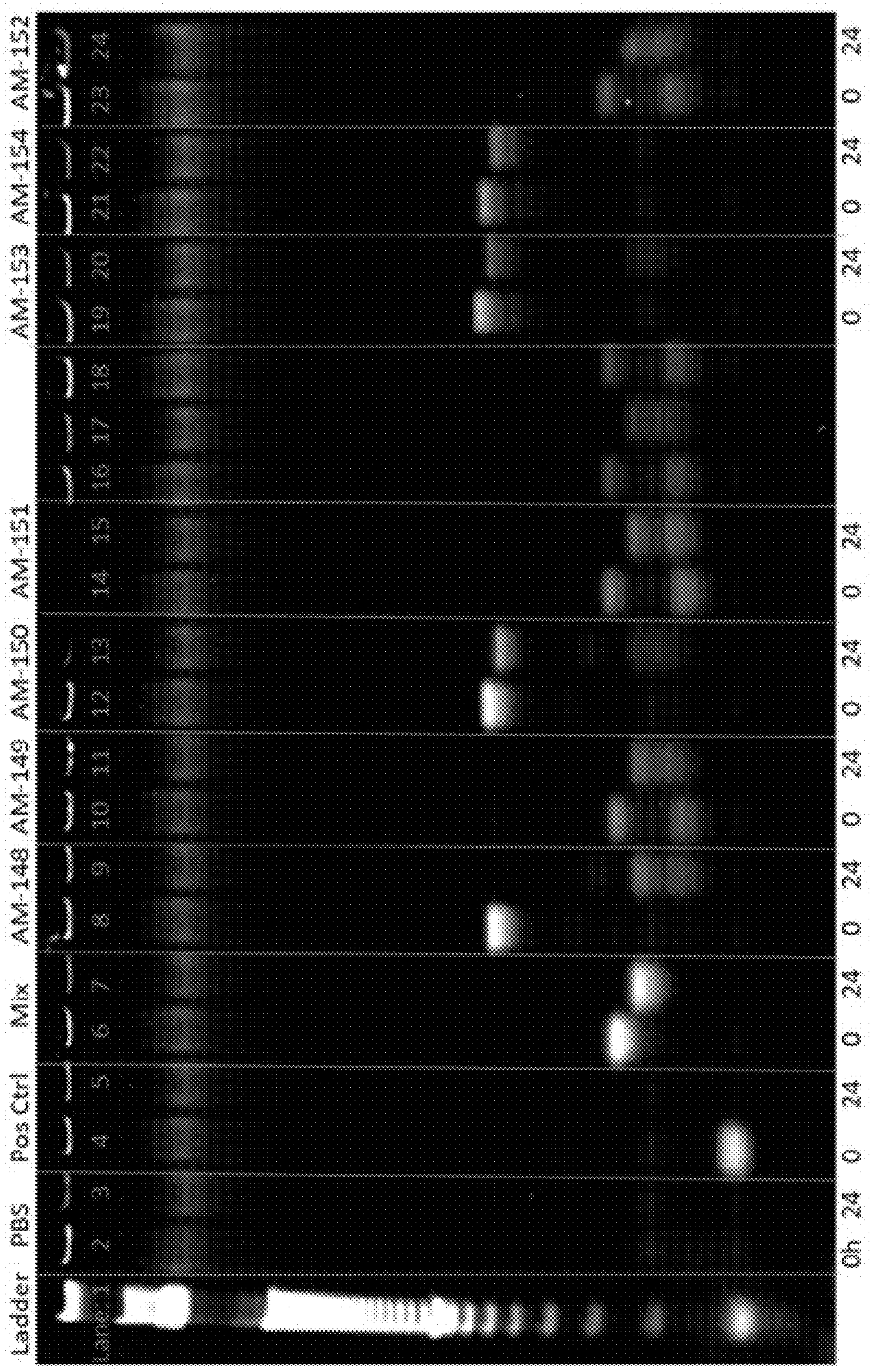

FIG. 9 shows degradation of bis(siRNA) designs AM-148-AM-154. Compounds were incubated with rat tritosomes and the products were analyzed by gel electrophoresis to determine cleavability of the likers as described above. RNA based linkers showed similar cleavage kinetics as that of sugar based linkers.

Figure 10:
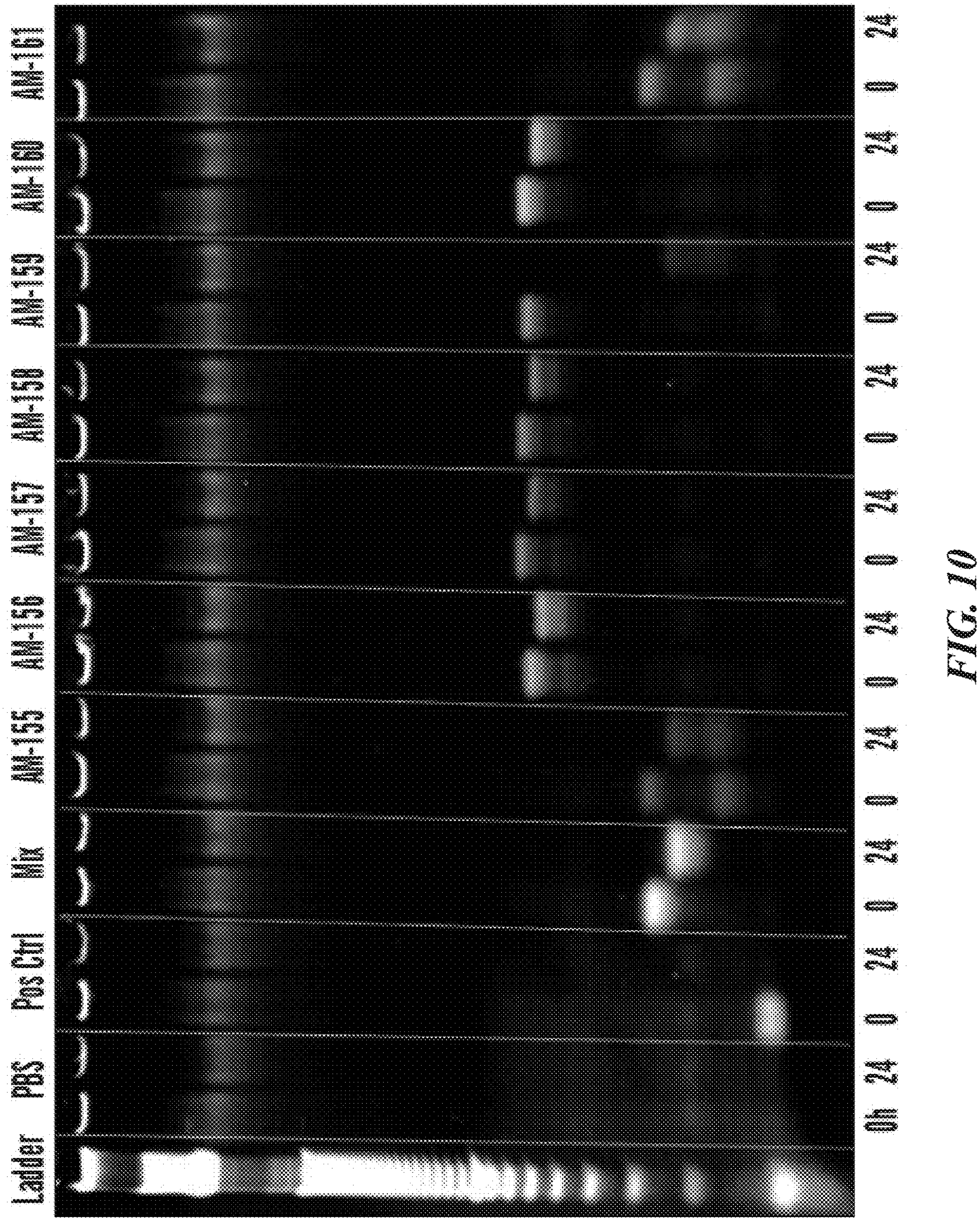

FIG. 10 shows degradation of bis(siRNA) designs AM-155-AM-161. Compounds were incubated with rat tritosomes and the products were analyzed by gel electrophoresis to determine cleavability of the likers as described above.

TABLE 1

Bis(siRNA) design for evaluating cleavable linkers#

| Multiplex Name | Strand | Sequence (5'-3') | SEQ ID NO: |
|---|---|---|---|
| AM-106 | sense | asascaguGfuUfCfUfugcucuauaaQ198Q48Q303Q303Q48csaggauCfaUfCfUfcaagucuuaaL96 | 40 & 41 |
| | antis | usUfsauaGfaGfCfaagaAfcAfcuguusus u/usUfsaagAfcuUfgagaUfgAfuccugsgsc | 42 & 43 |
| AM-107 | sense | asascaguGfuUfCfUfugcucuauaaQ198Q303Q48Q303csaggauCfaUfCfUfcaagucuuaaL96 | 40 & 41 |
| | antis | auaGfaGfCfaagaAfcAfcuguusus u/usUfsaagAfcuUfgagaUfgAfuccugsgsc | 44 & 43 |
| AM-108 | sense | asascaguGfuUfCfUfugcucuauaaQ198Q48Q303Q303Q48dAcsaggauCfaUfCfUfcaagucuuaaL96 | 40 & 45 |
| | antis | auaGfaGfCfaagaAfcAfcuguusus u/usUfsaagAfcuUfgagaUfgAfuccugsgsc | 44 & 43 |
| AM-109 | sense | asascaguGfuUfCfUfugcucuauaaQ198Q303Q48Q303dAcsaggauCfaUfCfUfcaagucuuaaL96 | 40 & 45 |
| | antis | auaGfaGfCfaagaAfcAfcuguusus u/usUfsaagAfcuUfgagaUfgAfuccugsgsc | 44 & 43 |
| AM-110 | sense | asascaguGfuUfCfUfugcucuauaaQ198Q303Q303Q303Q303csaggauCfaUfCfUfcaagucuuaaL96 | 40 & 41 |
| | antis | auaGfaGfCfaagaAfcAfcuguusus u/usUfsaagAfcuUfgagaUfgAfuccugsgsc | 44 & 43 |
| AM-111 | sense | asascaguGfuUfCfUfugcucuauaaQ198Q303Q303Q303csaggauCfaUfCfUfcaagucuuaaL96 | 40 & 41 |
| | antis | auaGfaGfCfaagaAfcAfcuguusus u/usUfsaagAfcuUfgagaUfgAfuccugsgsc | 44 & 43 |
| AM-112 | sense | asascaguGfuUfCfUfugcucuauaaQ198Q303Q303csaggauCfaUfCfUfcaagucuuaaL96 | 40 & 41 |
| | antis | auaGfaGfCfaagaAfcAfcuguusus u/usUfsaagAfcuUfgagaUfgAfuccugsgsc | 44 & 43 |
| AM-113 | sense | asascaguGfuUfCfUfugcucuauaaQ198Q304Q304Q304Q304csaggauCfaUfCfUfcaagucuuaaL96 | 40 & 41 |
| | antis | auaGfaGfCfaagaAfcAfcuguusus u/usUfsaagAfcuUfgagaUfgAfuccugsgsc | 44 & 43 |
| AM-114 | sense | asascaguGfuUfCfUfugcucuauaaQ198Q304Q304Q304csaggauCfaUfCfUfcaagucuuaaL96 | 40 & 41 |
| | antis | auaGfaGfCfaagaAfcAfcuguusus u/usUfsaagAfcuUfgagaUfgAfuccugsgsc | 44 & 43 |
| AM-115 | sense | asascaguGfuUfCfUfugcucuauaaQ198Q304Q304csaggauCfaUfCfUfcaagucuuaaL96 | 40 & 41 |
| | antis | auaGfaGfCfaagaAfcAfcuguusus u/usUfsaagAfcuUfgagaUfgAfuccugsgsc | 44 & 43 |
| AM-116 | sense | asascaguGfuUfCfUfugcucuauaaQ198Q48Q303Q303Q48csasggauCfaUfCfUfcaagucuuaaL96 | 40 & 46 |
| | antis | auaGfaGfCfaagaAfcAfcuguusus u/usUfsaagAfcuUfgagaUfgAfuccugsgsc | 44 & 43 |
| AM-117 | sense | asascaguGfuUfCfUfugcucuauaaQ198Q303Q48Q303csasggauCfaUfCfUfcaagucuuaaL96 | 40 & 46 |
| | antis | auaGfaGfCfaagaAfcAfcuguusus u/usUfsaagAfcuUfgagaUfgAfuccugsgsc | 44 & 43 |
| AM-118 | sense | asascaguGfuUfCfUfugcucuauaaQ198Q303Q303csasggauCfaUfCfUfcaagucuuaaL96 | 40 & 46 |
| | antis | auaGfaGfCfaagaAfcAfcuguusus u/usUfsaagAfcuUfgagaUfgAfuccugsgsc | 44 & 43 |
| AM-119 | sense | asascaguGfuUfCfUfugcucuausasaQ48Q303Q303Q48csasggauCfaUfCfUfcaagucuuaaL96 | 47 & 46 |
| | antis | auaGfaGfCfaagaAfcAfcuguusus u/usUfsaagAfcuUfgagaUfgAfuccugsgsc | 44 & 43 |
| AM-120 | sense | asascaguGfuUfCfUfugcucuausasaQ303Q48Q303csasggauCfaUfCfUfcaagucuuaaL96 | 47 & 46 |
| | antis | auaGfaGfCfaagaAfcAfcuguusus u/usUfsaagAfcuUfgagaUfgAfuccugsgsc | 44 & 43 |
| AM-121 | sense | asascaguGfuUfCfUfugcucuausasaQ303Q303csasggauCfaUfCfUfcaagucuuaaL96 | 47 & 46 |
| | antis | auaGfaGfCfaagaAfcAfcuguusus u/usUfsaagAfcuUfgagaUfgAfuccugsgsc | 44 & 43 |
| AM-122 | sense | asascaguGfuUfCfUfugcucuauaaQ198dGdAdTcsaggauCfaUfCfUfcaagucuuaaL96 | 40 & 48 |
| | antis | auaGfaGfCfaagaAfcAfcuguusus u/usUfsaagAfcuUfgagaUfgAfuccugsgsc | 44 & 43 |
| AM-123 | sense | asascaguGfuUfCfUfugcucuauaaQ198dGdAdTcsasggauCfaUfCfUfcaagucuuaaL96 | 40 & 49 |
| | antis | auaGfaGfCfaagaAfcAfcuguusus u/usUfsaagAfcuUfgagaUfgAfuccugsgsc | 44 & 43 |
| AM-124 | sense | asascaguGfuUfCfUfugcucuausasadGdAdTcsaggauCfaUfCfUfcaagucuuaaL96 | 50 |
| | antis | auaGfaGfCfaagaAfcAfcuguusus u/usUfsaagAfcuUfgagaUfgAfuccugsgsc | 44 & 43 |
| AM-125 | sense | asascaguGfuUfCfUfugcucuauasadGdAdTcsaggauCfaUfCfUfcaagucuuaaL96 | 51 |
| | antis | auaGfaGfCfaagaAfcAfcuguusus u/usUfsaagAfcuUfgagaUfgAfuccugsgsc | 44 & 43 |
| AM-126 | sense | asascaguGfuUfCfUfugcucuauaaQ198GfAfUfcsaggauCfaUfCfUfcaagucuuaaL96 | 40 & 52 |
| | antis | auaGfaGfCfaagaAfcAfcuguusus u/usUfsaagAfcuUfgagaUfgAfuccugsgsc | 44 & 43 |
| AM-127 | sense | asascaguGfuUfCfUfugcucuauaaQ198GfAfUfcsasggauCfaUfCfUfcaagucuuaaL96 | 40 & 53 |
| | antis | auaGfaGfCfaagaAfcAfcuguusus u/usUfsaagAfcuUfgagaUfgAfuccugsgsc | 44 & 43 |
| AM-128 | sense | asascaguGfuUfCfUfugcucuausasaGfAfUfcsaggauCfaUfCfUfcaagucuuaaL96 | 54 |
| | antis | auaGfaGfCfaagaAfcAfcuguusus u/usUfsaagAfcuUfgagaUfgAfuccugsgsc | 44 & 43 |
| AM-129 | sense | asascaguGfuUfCfUfugcucuauasaGfAfUfcsaggauCfaUfCfUfcaagucuuaaL96 | 55 |
| | antis | auaGfaGfCfaagaAfcAfcuguusus u/usUfsaagAfcuUfgagaUfgAfuccugsgsc | 44 & 43 |
| AM-130 | sense | asascaguGfuUfCfUfugcucuausasaQ312Q312csasggauCfaUfCfUfcaagucuuaaL96 | 47 & 46 |
| | antis | auaGfaGfCfaagaAfcAfcuguusus u/usUfsaagAfcuUfgagaUfgAfuccugsgsc | 44 & 43 |

TABLE 1-continued

Bis(siRNA) design for evaluating cleavable linkers#

| Multi-plex Name | Strand | Sequence (5'-3') | SEQ ID NO: |
|---|---|---|---|
| AM-131 | sense | asascaguGfuUfCfUfugcucuausasaQ312Q312Q312csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-132 | sense | asascaguGfuUfCfUfugcucuausasaQ313Q313csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-133 | sense | asascaguGfuUfCfUfugcucuausasaQ313Q313Q313csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-134 | sense | asascaguGfuUfCfUfugcucuausasaQ314Q314csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-135 | sense | asascaguGfuUfCfUfugcucuausasaQ314Q314Q314csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-136 | sense | asascaguGfuUfCfUfugcucuausasaQ315Q315csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-137 | sense | asascaguGfuUfCfUfugcucuausasaQ315Q315Q315csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-138 | sense | asascaguGfuUfCfUfugcucuausasaQ316Q316csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-139 | sense | asascaguGfuUfCfUfugcucuausasaQ316Q316Q316csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-140 | sense | asascaguGfuUfCfUfugcucuausasaQ317Q317csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-141 | sense | asascaguGfuUfCfUfugcucuausasaQ317Q317Q317csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-142 | sense | asascaguGfuUfCfUfugcucuausasaQ304Q304csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-143 | sense | asascaguGfuUfCfUfugcucuausasaQ304Q304Q304csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-144 | sense | asascaguGfuUfCfUfugcucuausasaQ305Q305csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-145 | sense | asascaguGfuUfCfUfugcucuausasaQ305Q305Q305csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-146 | sense | asascaguGfuUfCfUfugcucuausasaQ306Q306csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-147 | sense | asascaguGfuUfCfUfugcucuausasaQ306Q306Q306csasggauCfaUfCfUfcaagucuuaaL96 | 47 & 46 |
| | antis | auaGfaGfCfaagaAfcAfcuguusu$\text{s}$u/usUfsaagAfcuUfgagaUfgAfuccugsgsc | 44 & 43 |
| AM-148 | sense | asascaguGfuUfCfUfugcucuausasaGAfUfcsasggauCfaUfCfUfcaagucuuaaL96 | 56 |
| | antis | auaGfaGfCfaagaAfcAfcuguusu$\text{s}$u/usUfsaagAfcuUfgagaUfgAfuccugsgsc | 44 & 43 |
| AM-149 | sense | asascaguGfuUfCfUfugcucuausasaGfAUfcsasggauCfaUfCfUfcaagucuuaaL96 | 57 |
| | antis | auaGfaGfCfaagaAfcAfcuguusu$\text{s}$u/usUfsaagAfcuUfgagaUfgAfuccugsgsc | 44 & 43 |
| AM-150 | sense | asascaguGfuUfCfUfugcucuausasaGfAfUcsasggauCfaUfCfUfcaagucuuaaL96 | 58 |
| | antis | auaGfaGfCfaagaAfcAfcuguusu$\text{s}$u/usUfsaagAfcuUfgagaUfgAfuccugsgsc | 44 & 43 |
| AM-151 | sense | asascaguGfuUfCfUfugcucuausasaUdAdTcsasggauCfaUfCfUfcaagucuuaaL96 | 59 |
| | antis | auaGfaGfCfaagaAfcAfcuguusu$\text{s}$u/usUfsaagAfcuUfgagaUfgAfuccugsgsc | 44 & 43 |
| AM-152 | sense | asascaguGfuUfCfUfugcucuausasadGAdTcsasggauCfaUfCfUfcaagucuuaaL96 | 60 |
| | antis | auaGfaGfCfaagaAfcAfcuguusu$\text{s}$u/usUfsaagAfcuUfgagaUfgAfuccugsgsc | 44 & 43 |
| AM-153 | sense | asascaguGfuUfCfUfugcucuausasadGdAGcsasggauCfaUfCfUfcaagucuuaaL96 | 61 |
| | antis | auaGfaGfCfaagaAfcAfcuguusu$\text{s}$u/usUfsaagAfcuUfgagaUfgAfuccugsgsc | 44 & 43 |
| AM-154 | sense | asascaguGfuUfCfUfugcucuausasadGdAdTcsasggauCfaUfCfUfcaagucuuaaL96 | 62 |
| | antis | auaGfaGfCfaagaAfcAfcuguusu$\text{s}$u/usUfsaagAfcuUfgagaUfgAfuccugsgsc | 44 & 43 |

TABLE 1-continued

| Bis(siRNA) design for evaluating cleavable linkers[#] | | | |
|---|---|---|---|
| Multi-plex Name | Strand | Sequence (5'-3') | SEQ ID NO: |
| AM-155 | sense | asascaguGfuUfCfUfugcucuausasaUAGcsasggauCfaUfCfUfcaagucuuaaL96 | 63 |
| | antis | auaGfaGfCfaagaAfcAfcuguususu/usUfsaagAfcuUfgagaUfgAfuccugsgsc | 44 & 43 |
| AM-156 | sense | asascaguGfuUfCfUfugcucuausasaGfAfUfcsasggauCfaUfCfUfcaagucuuaaL96 | 64 |
| | antis | auaGfaGfCfaagaAfcAfcuguususu/usUfsaagAfcuUfgagaUfgAfuccugsgsc | 44 & 43 |
| AM-157 | sense | asascaguGfuUfCfUfugcucuausasadTdTdTcsasggauCfaUfCfUfcaagucuuaaL96 | 65 |
| | antis | auaGfaGfCfaagaAfcAfcuguususu/usUfsaagAfcuUfgagaUfgAfuccugsgsc | 44 & 43 |
| AM-158 | sense | asascaguGfuUfCfUfugcucuausasaUfUfUfcsasggauCfaUfCfUfcaagucuuaaL96 | 66 |
| | antis | auaGfaGfCfaagaAfcAfcuguususu/usUfsaagAfcuUfgagaUfgAfuccugsgsc | 44 & 43 |
| AM-159 | sense | asascaguGfuUfCfUfugcucuausasaGdAdTcsasggauCfaUfCfUfcaagucuuaaL96 | 67 |
| | antis | auaGfaGfCfaagaAfcAfcuguususu/usUfsaagAfcuUfgagaUfgAfuccugsgsc | 44 & 43 |
| AM-160 | sense | asascaguGfuUfCfUfugcucuausasadGdAUcsasggauCfaUfCfUfcaagucuuaaL96 | 68 |
| | antis | auaGfaGfCfaagaAfcAfcuguususu/usUfsaagAfcuUfgagaUfgAfuccugsgsc | 44 & 43 |
| AM-161 | sense | asascaguGfuUfCfUfugcucuausasaGAUcsasggauCfaUfCfUfcaagucuuaaL96 | 69 |
| | antis | auaGfaGfCfaagaAfcAfcuguususu/usUfsaagAfcuUfgagaUfgAfuccugsgsc | 44 & 43 |
| AM-162 | sense | asascaguGfuUfCfUfugcucuausasaUUUcsasggauCfaUfCfUfcaagucuuaaL96 | 70 |
| | antis | auaGfaGfCfaagaAfcAfcuguususu/usUfsaagAfcuUfgagaUfgAfuccugsgsc | 44 & 43 |

[#]N, Nf and dN indicates 2'-hydroxyl, 2'-deoxy-2'-fluoro (2'-F) and 2'-deoxy ribonucleotides respectively; lower case letters a, c, g and u indicates 2'-O-methylribonucleotides and the lowercase letter 's' indicates phosphophorothioate linkage. See FIGS. 1A-1B for the description on linkers used.

TABLE 2

| Degradation of linkers in rat tritosome | | | | | |
|---|---|---|---|---|---|
| Multiplex Name | Sugar, nucleotide and sugar-nucleotide combination linkers* | Number of sugar units | Number of nucleotides | Additional spacers | Tritosome cleavability (rank order)* |
| AM-106 | ~Q198Q48Q303Q303Q48~ | 2 | 0 | 3 | ++ |
| AM-107 | ~Q198Q303Q48Q303~ | 2 | 0 | 2 | ++ |
| AM-108 | ~Q198Q48Q303Q303Q48dA~ | 2 | 1 | 23 | ++ |
| AM-109 | ~Q198Q303Q48Q303dA~ | 2 | 1 | 2 | ++ |
| AM-110 | ~Q198Q303Q303Q303Q303~ | 4 | 0 | 1 | ++ |
| AM-111 | ~Q198Q303Q303Q303~ | 3 | 0 | 1 | ++ |
| AM-112 | ~Q198Q303Q303~ | 2 | 0 | 1 | + |
| AM-113 | ~Q198Q304Q304Q304Q304~ | 4 | 0 | 1 | +++ |
| AM-114 | ~Q198Q304Q304Q304~ | 3 | 0 | 1 | +++ |
| AM-115 | ~Q198Q304Q304~ | 2 | 0 | 1 | ++ |
| AM-116 | ~Q198Q48Q303Q303Q48~ | 2 | 0 | 3 | ++ |
| AM-117 | ~Q198Q303Q48Q303~ | 2 | 0 | 2 | ++ |
| AM-118 | ~Q198Q303Q303~ | 2 | 0 | 1 | + |
| AM-119 | ~Q48Q303Q303Q48~ | 2 | 0 | 2 | ++ |
| AM-120 | ~Q303Q48Q303~ | 2 | 0 | 1 | ++ |
| AM-121 | ~Q303Q303~ | 2 | 0 | 0 | ++ |
| AM-122 | ~Q198dGdAdT~ | 0 | 3 | 1 | − |
| AM-123 | ~Q198dGdAdT~ | 0 | 3 | 1 | − |
| AM-124 | ~dGdAdT~ | 0 | 3 | 0 | − |
| AM-125 | ~dGdAdT~ | 0 | 3 | 0 | − |
| AM-126 | ~Q198GfAfUf~ | 0 | 3 | 1 | − |
| AM-127 | ~Q198GfAfUf~ | 0 | 3 | 1 | − |
| AM-128 | ~GfAfUf~ | 0 | 3 | 0 | − |
| AM-129 | ~GfAfUf~ | 0 | 3 | 0 | − |
| AM-130 | ~Q312Q312~ | 2 | 0 | 0 | + |
| AM-131 | ~Q312Q312Q312~ | 3 | 0 | 0 | + |
| AM-132 | ~Q313Q313~ | 2 | 0 | 0 | ++ |
| AM-133 | ~Q313Q313Q313~ | 3 | 0 | 0 | ++ |
| AM-134 | ~Q314Q314~ | 2 | 0 | 0 | + |
| AM-135 | ~Q314Q314Q314~ | 3 | 0 | 0 | + |
| AM-136 | ~Q315Q315~ | 2 | 0 | 0 | ++ |
| AM-137 | ~Q315Q315Q315~ | 3 | 0 | 0 | ++ |
| AM-138 | ~Q316Q316~ | 2 | 0 | 0 | + |
| AM-139 | ~Q316Q316Q316~ | 3 | 0 | 0 | + |
| AM-140 | ~Q317Q317~ | 2 | 0 | 0 | +++ |
| AM-141 | ~Q317Q317Q317~ | 3 | 0 | 0 | +++ |

TABLE 2-continued

Degradation of linkers in rat tritosome

| Multiplex Name | Sugar, nucleotide and sugar-nucleotide combination linkers* | Number of sugar units | Number of nucleotides | Additional spacers | Tritosome cleavability (rank order)* |
|---|---|---|---|---|---|
| AM-142 | ~Q304Q304~ | 2 | 0 | 0 | +++ |
| AM-143 | ~Q304Q304Q304~ | 3 | 0 | 0 | +++ |
| AM-144 | ~Q305Q305~ | 2 | 0 | 0 | + |
| AM-145 | ~Q305Q305Q305~ | 3 | 0 | 0 | + |
| AM-146 | ~Q306Q306~ | 2 | 0 | 0 | + |
| AM-147 | ~Q306Q306Q306~ | 3 | 0 | 0 | + |
| AM-148 | ~GAfUf~ | 0 | 3 | 0 | ++ |
| AM-149 | ~GfAUf~ | 0 | 3 | 0 | +++ |
| AM-150 | ~GfAfU~ | 0 | 3 | 0 | + |
| AM-151 | ~UdAdT~ | 0 | 3 | 0 | +++ |
| AM-152 | ~dGAdT~ | 0 | 3 | 0 | +++ |
| AM-153 | ~dGdAG~ | 0 | 3 | 0 | + |
| AM-154 | ~dGdAdT~ | 0 | 3 | 0 | + |
| AM-155 | ~UAG~ | 0 | 3 | 0 | +++ |
| AM-156 | ~GfAfUf~ | 0 | 3 | 0 | + |
| AM-157 | ~dTdTdT~ | 0 | 3 | 0 | + |
| AM-158 | ~UfUfUf~ | 0 | 3 | 0 | + |
| AM-159 | ~GdAdT~ | 0 | 3 | 0 | ++ |
| AM-160 | ~dGdAU~ | 0 | 3 | 0 | + |
| AM-161 | ~GAU~ | 0 | 3 | 0 | + |
| AM-162 | ~UUU~ | 0 | 3 | 0 | nd |

Figure 1B:
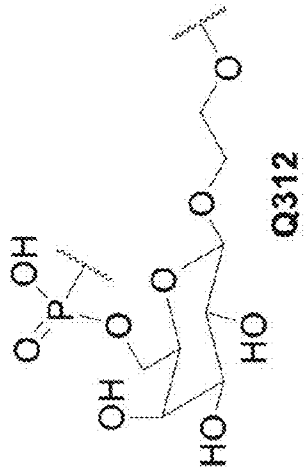
Figure 1B:
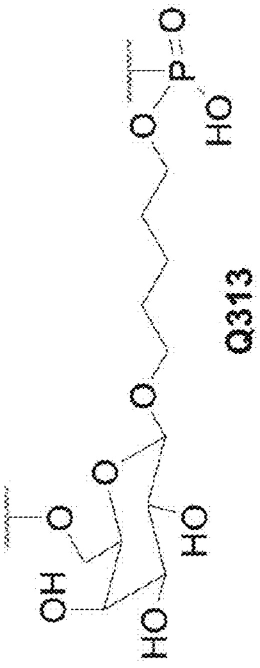
Figure 1B:
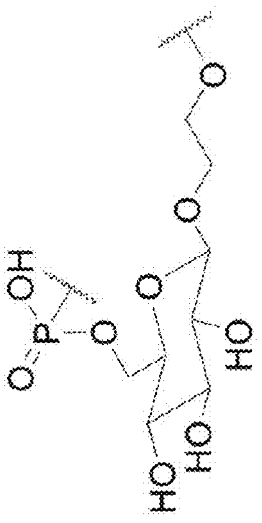
Figure 1B:
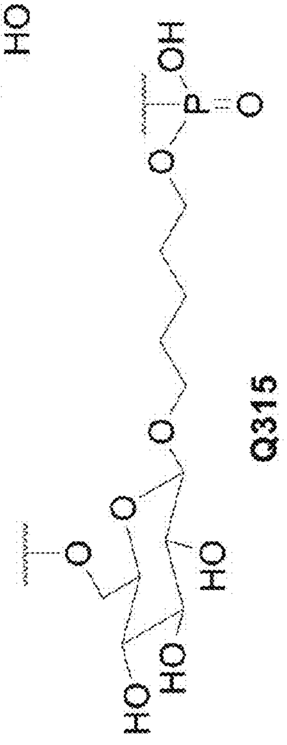
Figure 1B:
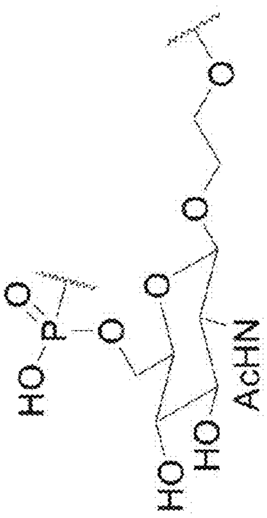
Figure 1B:
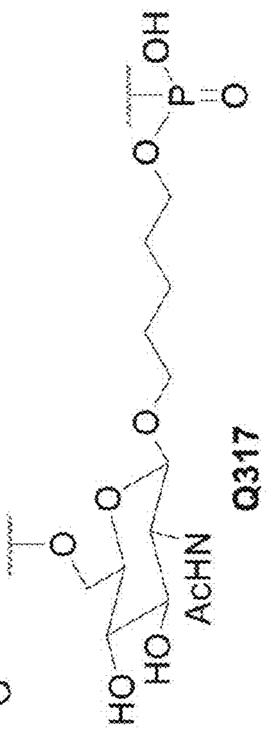
Figure 2A:
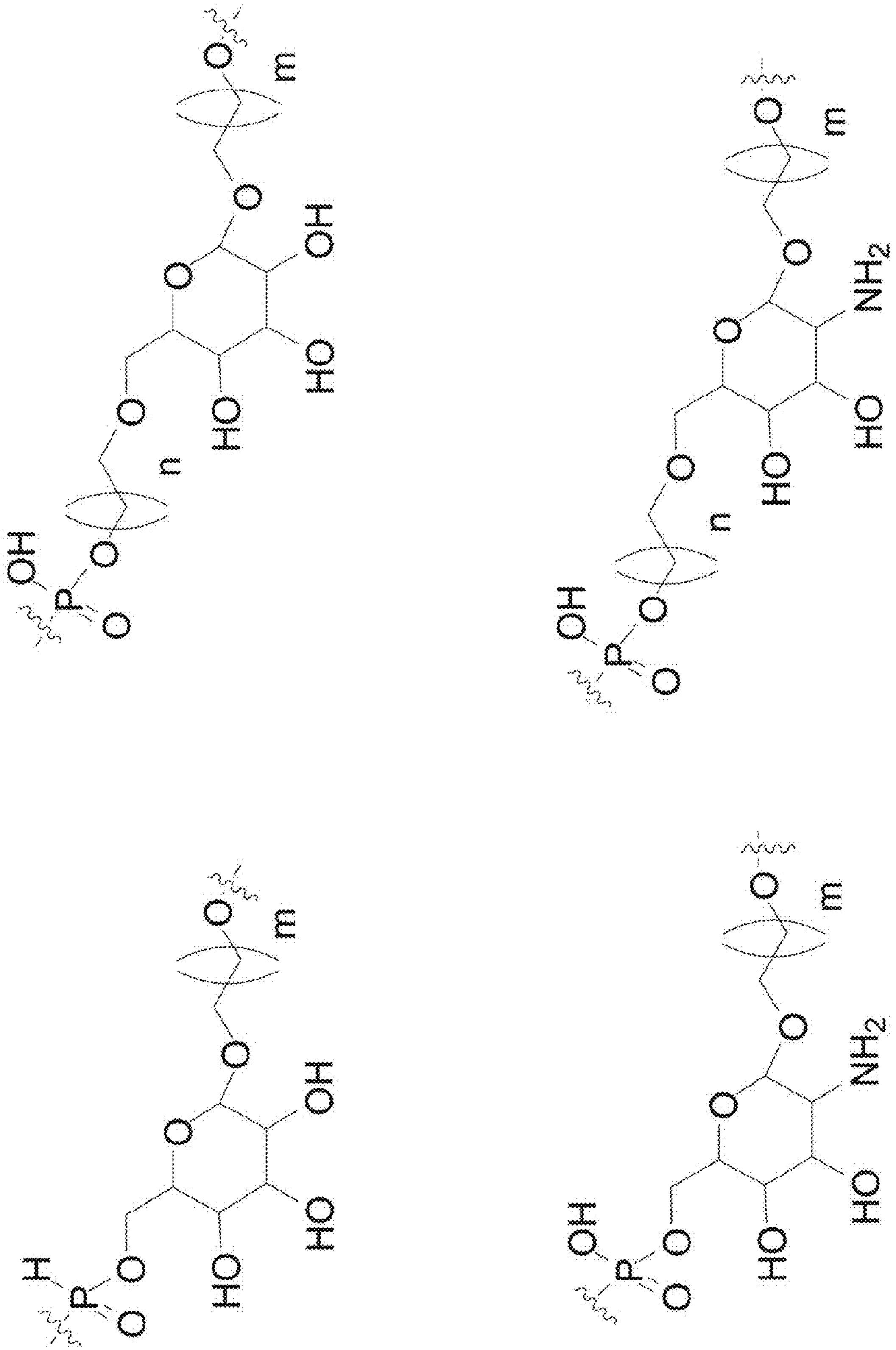
Figure 2B:
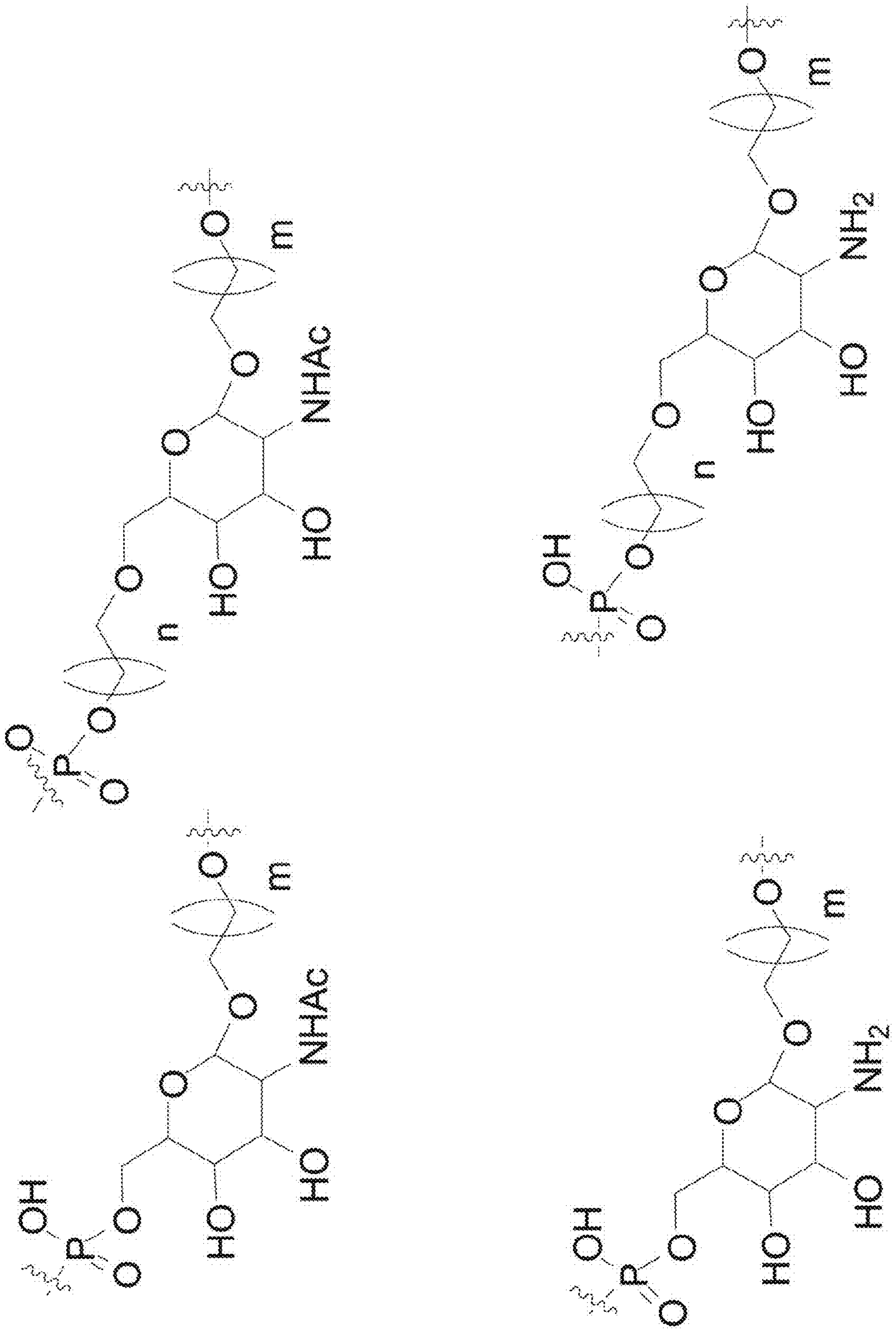
Figure 2D:
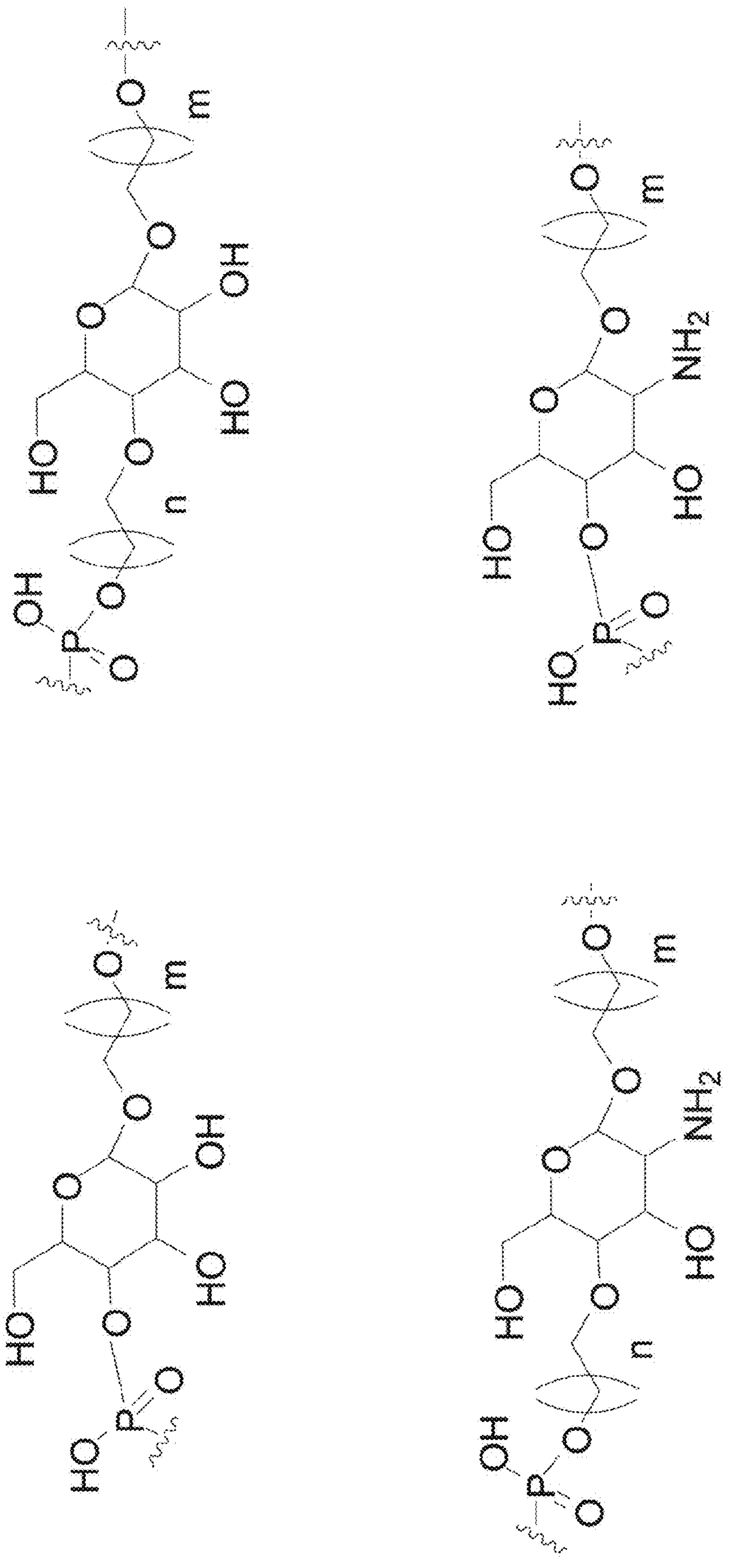
Figure 2E:
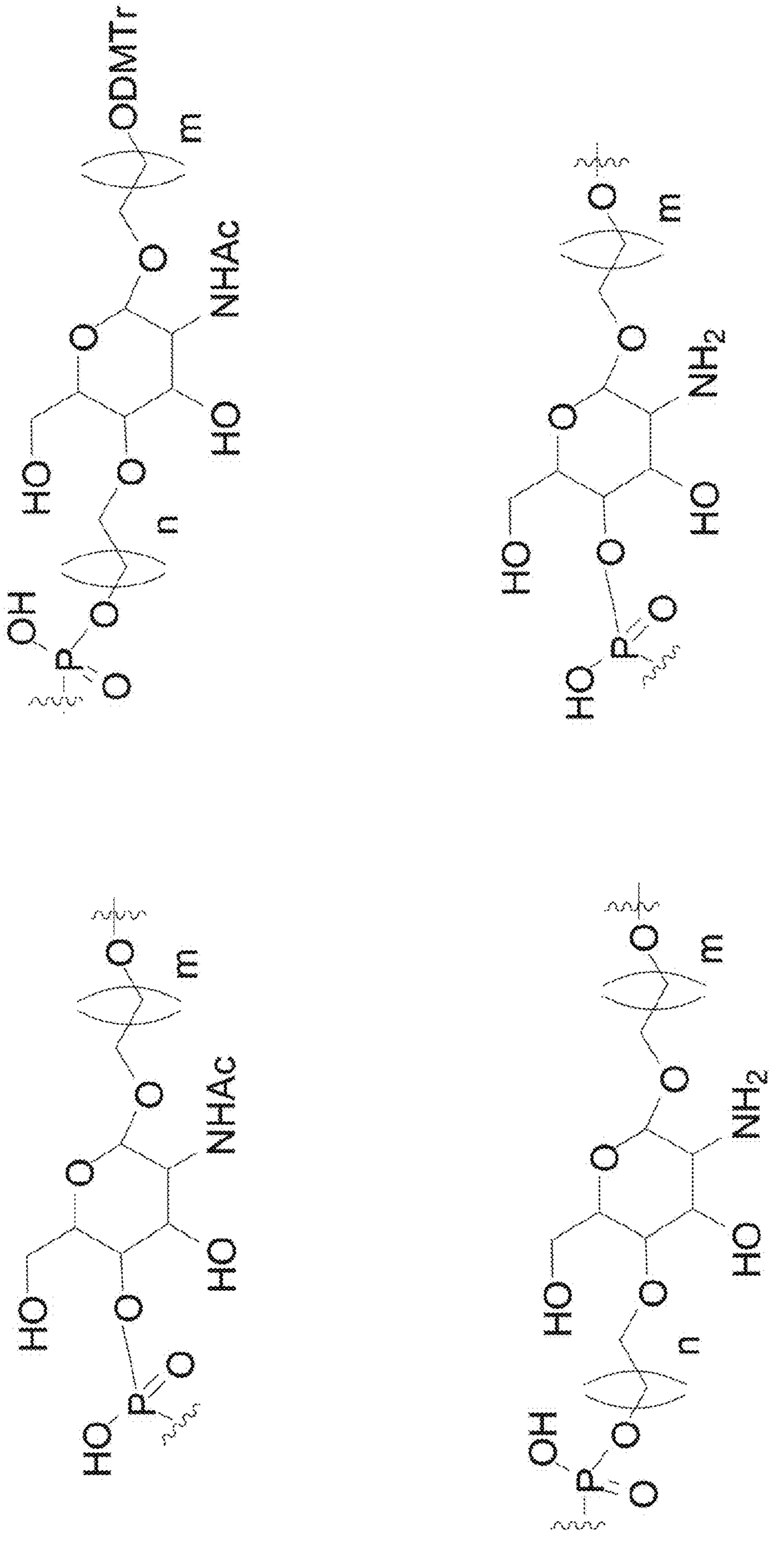
Figure 2F:
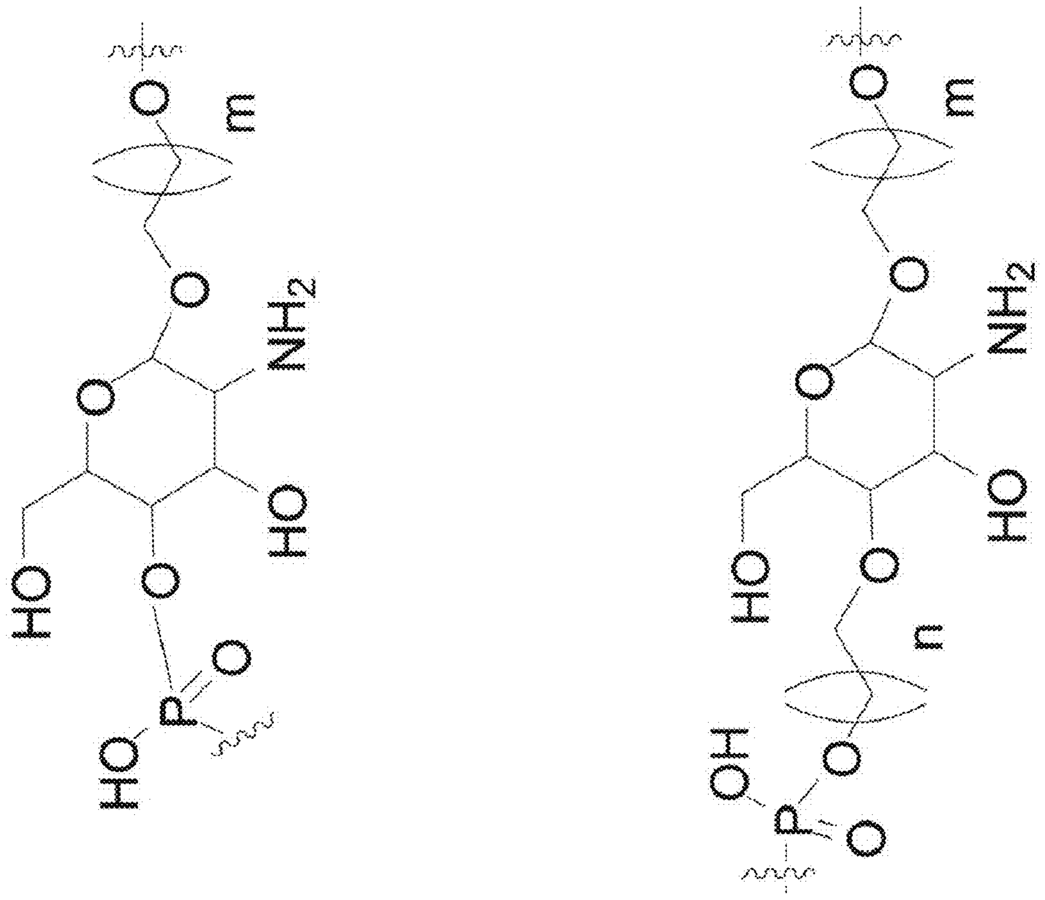
Figure 2G:
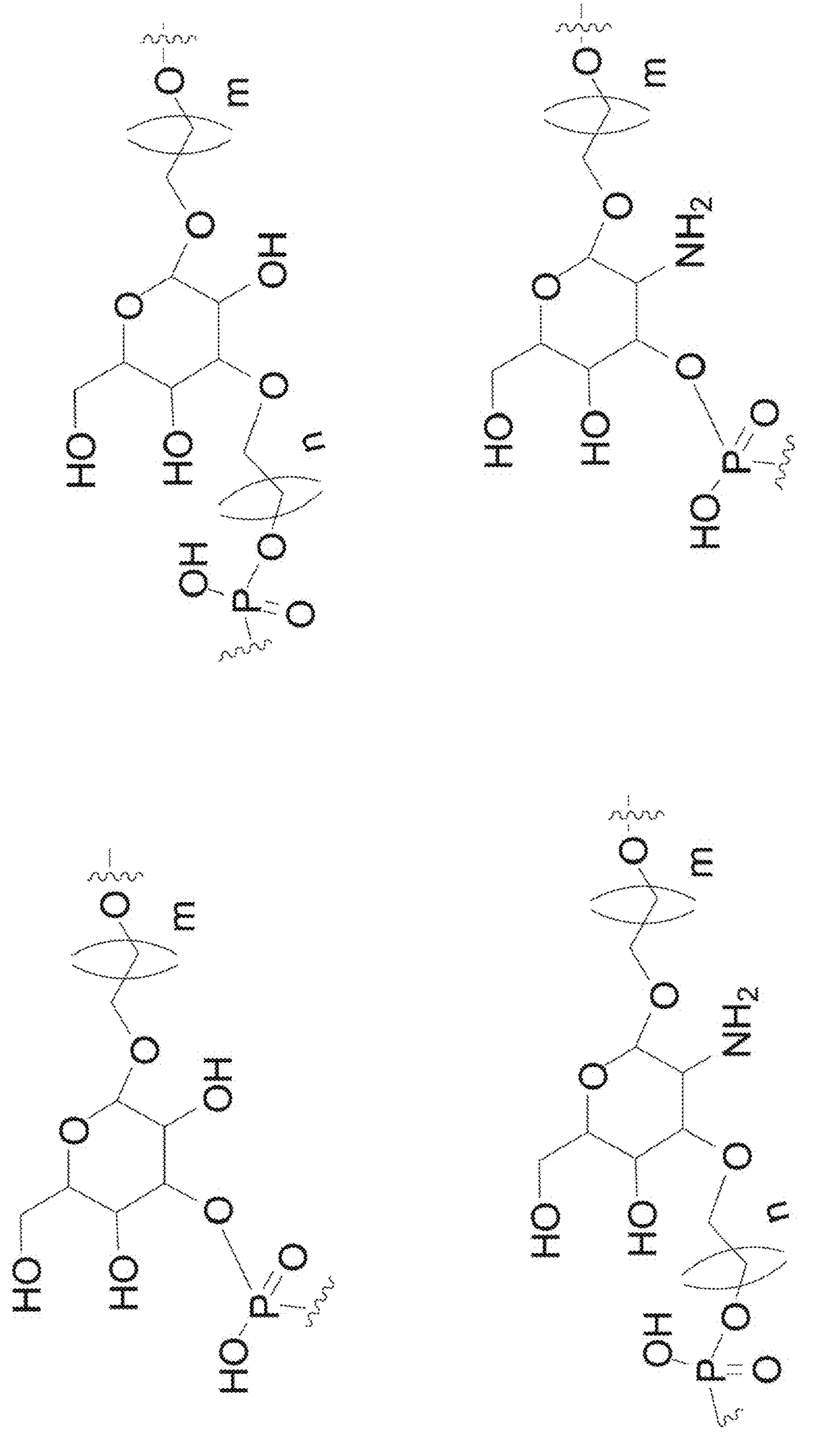
Figure 2H:
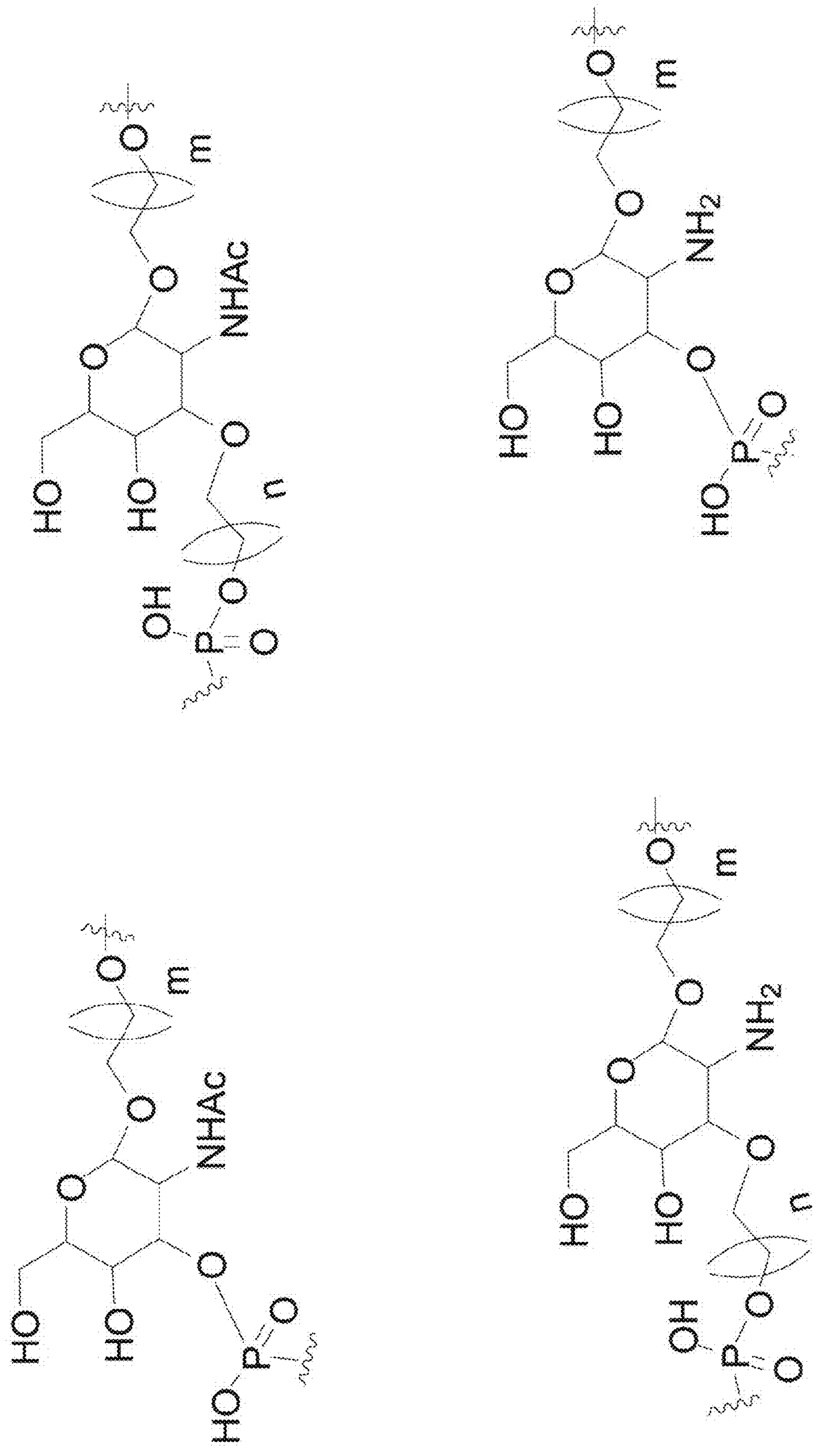
Figure 2I:
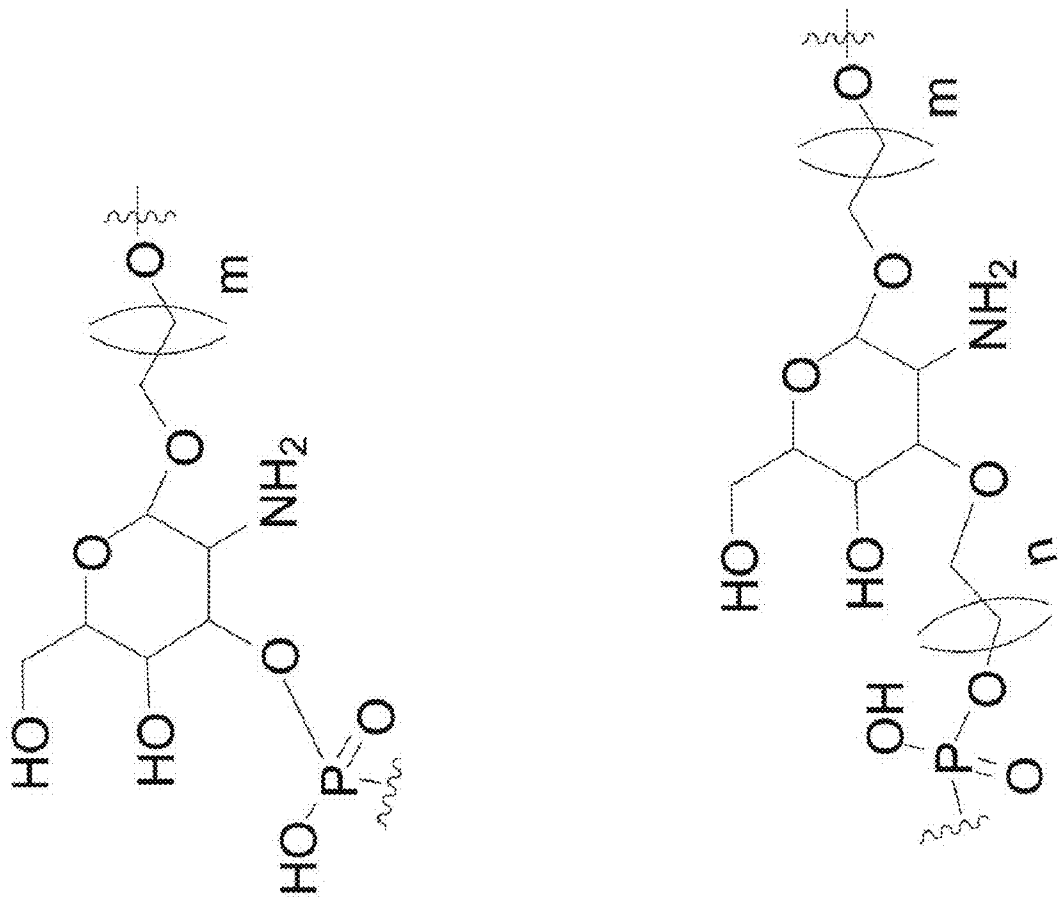
Figure 3A:
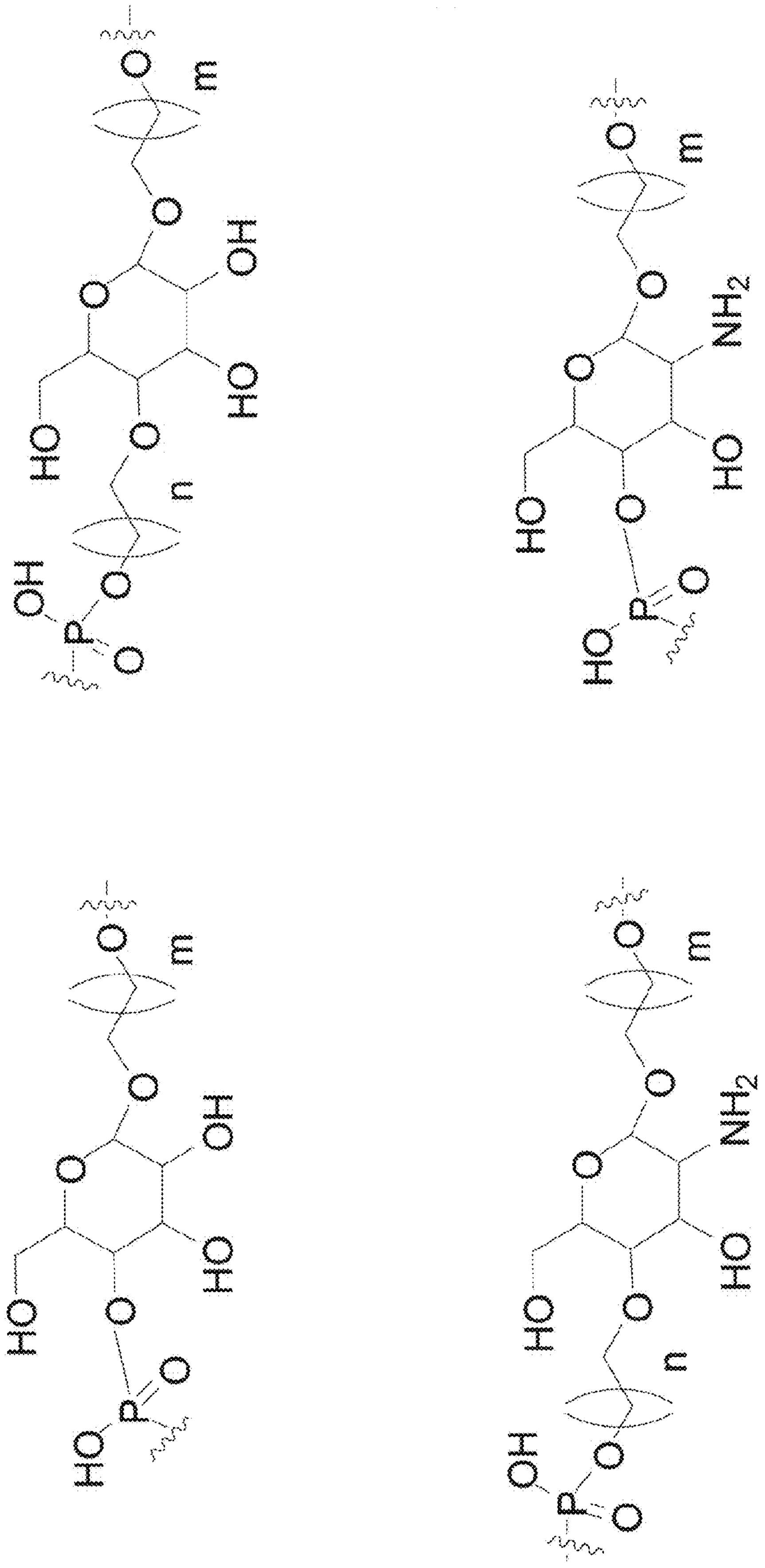
Figure 3B:
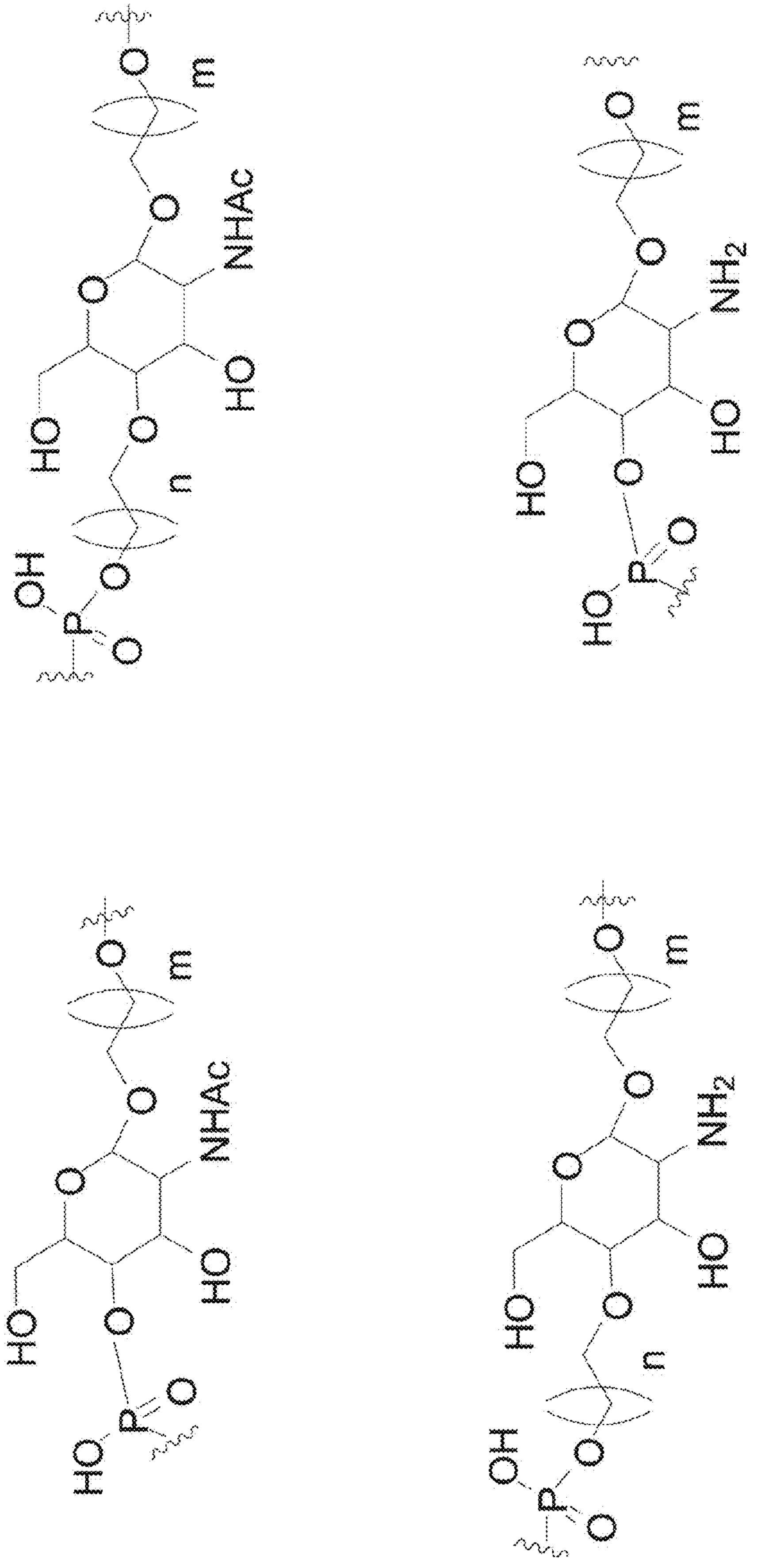
Figure 3C:
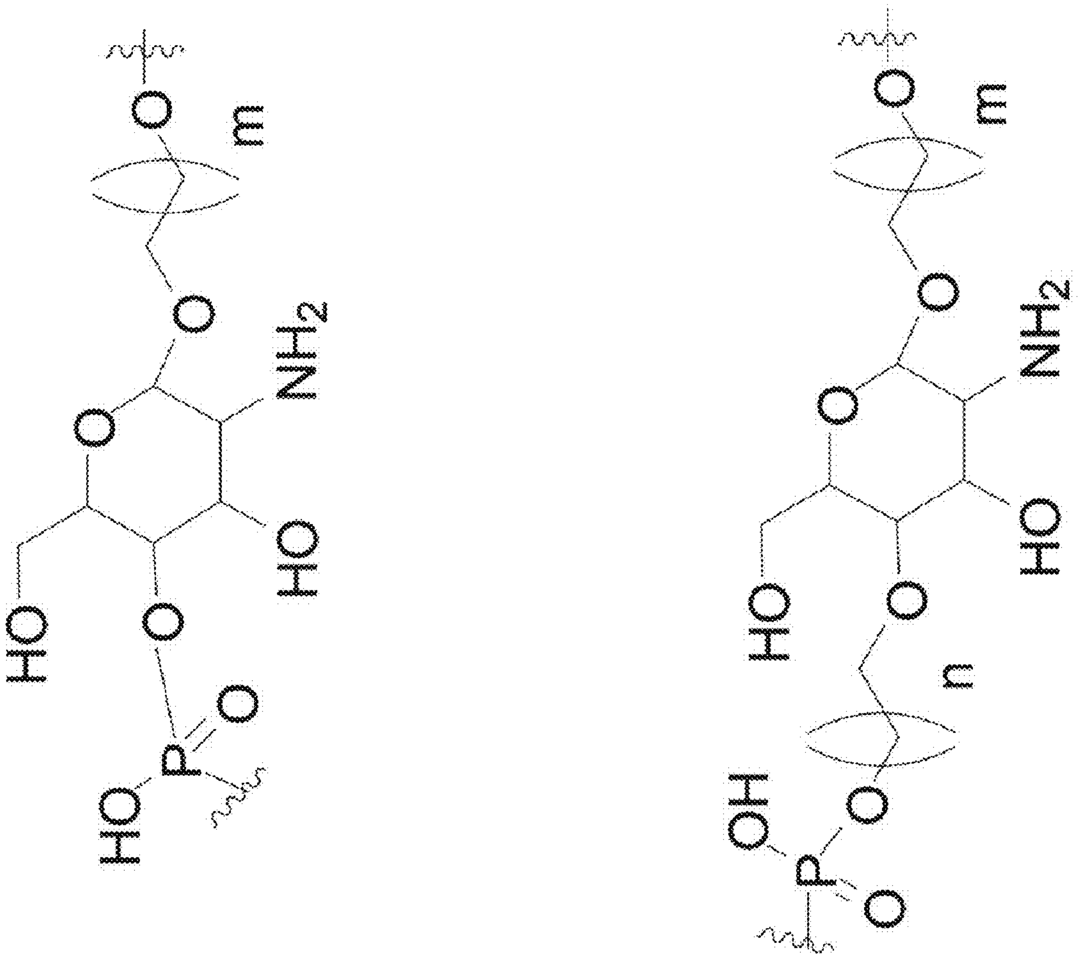
Figure 3D:
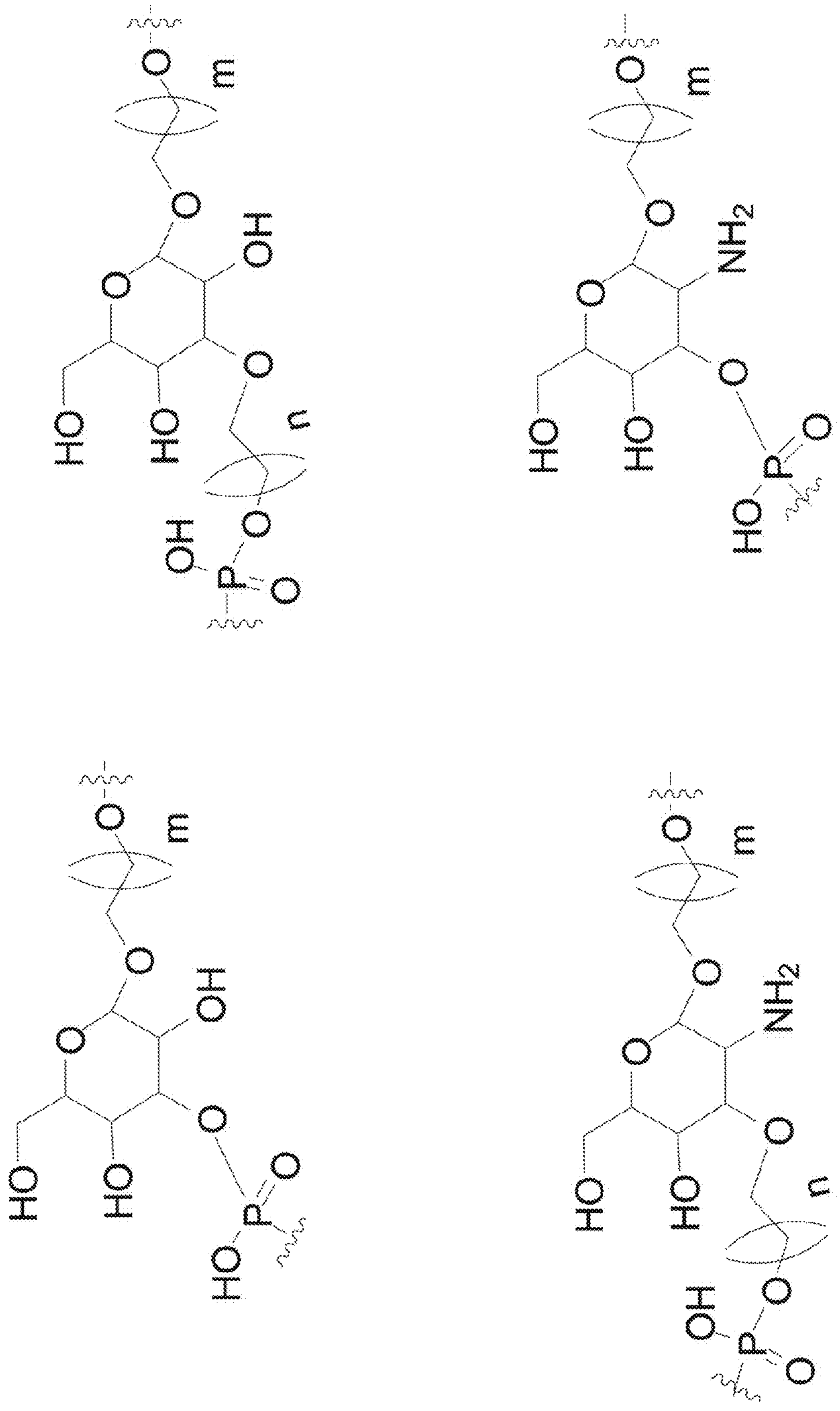
Figure 3E:
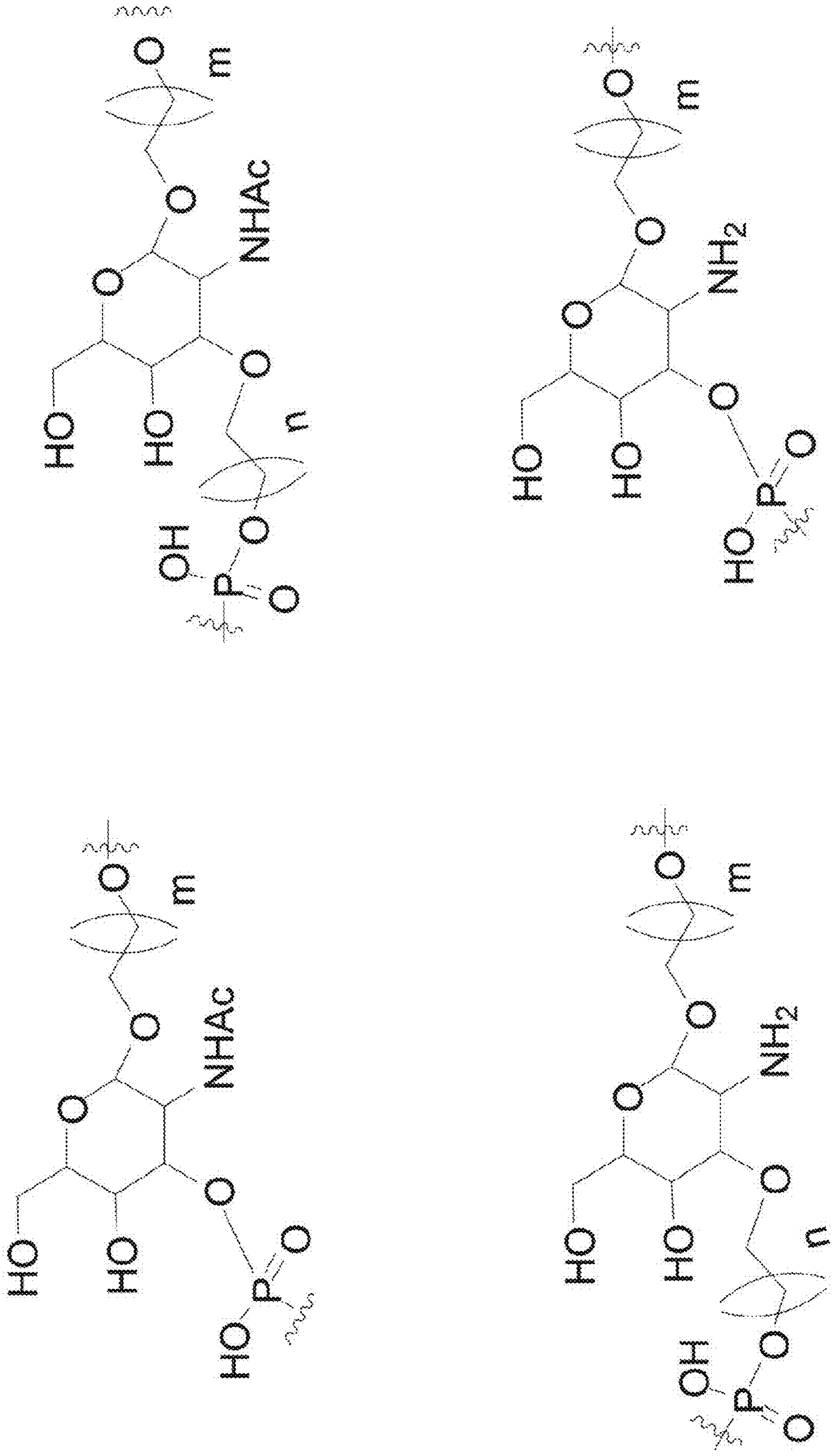
Figure 3F:
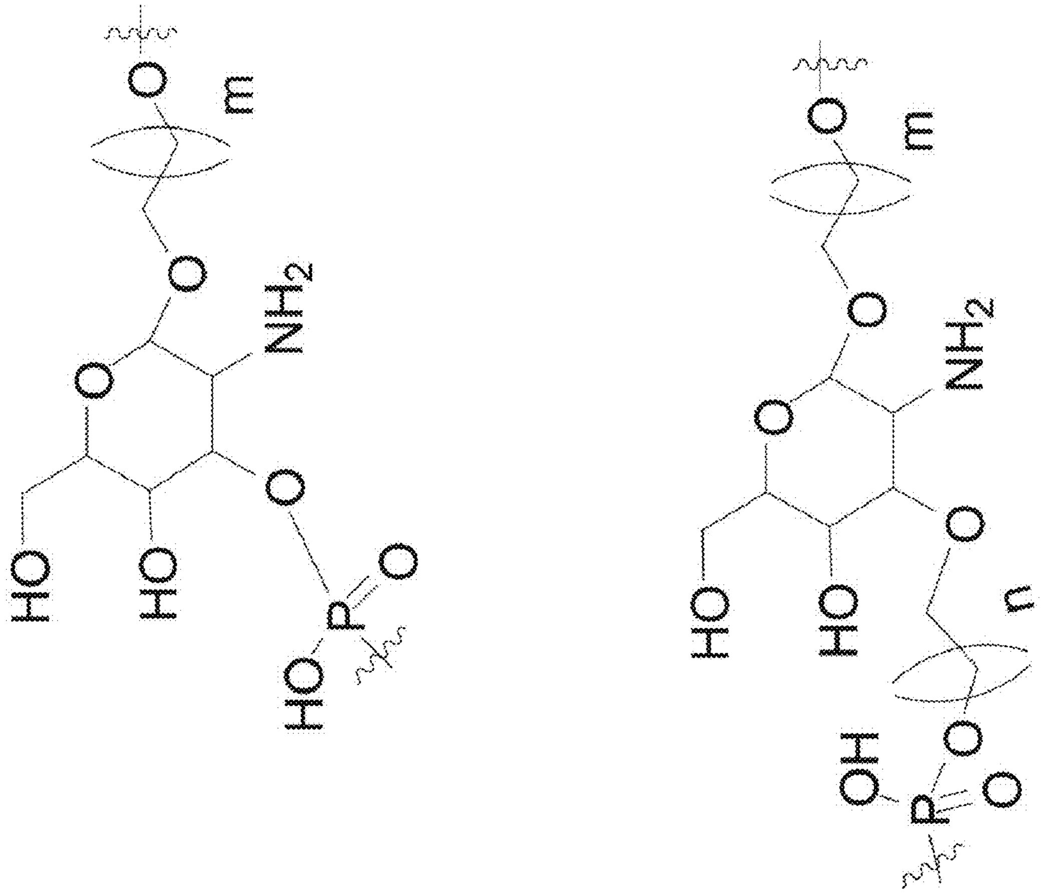
Figure 4A:
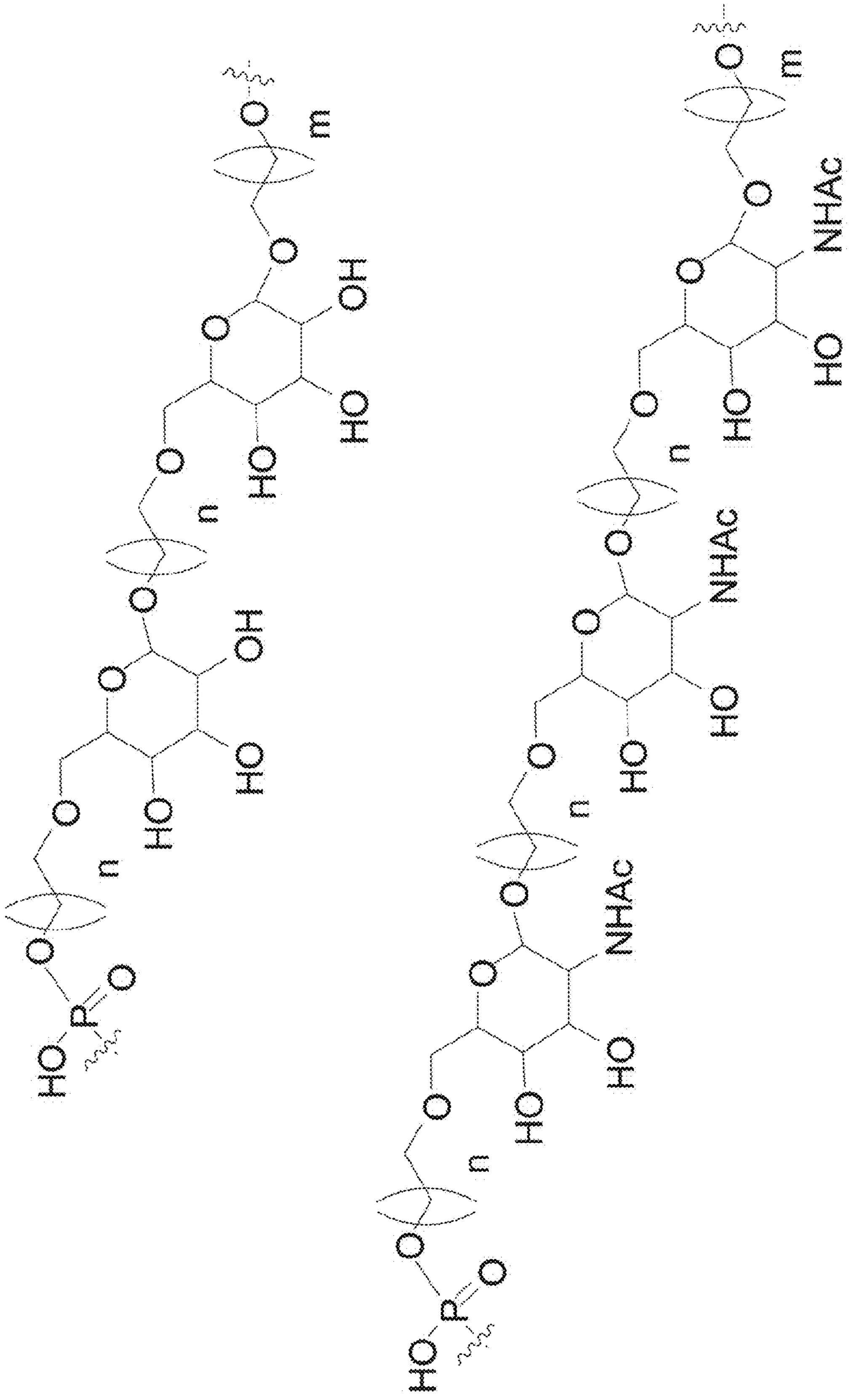
Figure 4B:
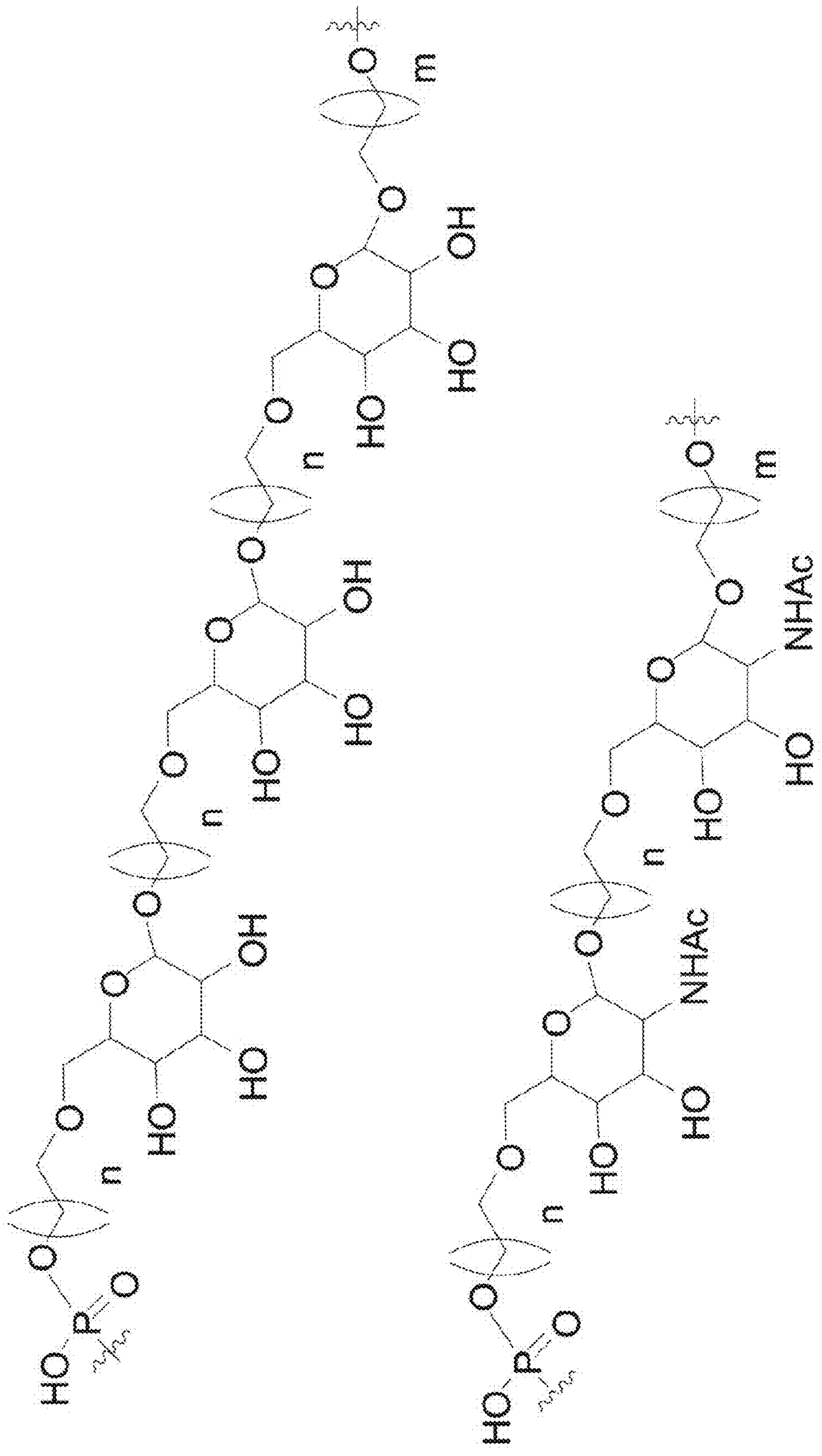
Figure 5A:
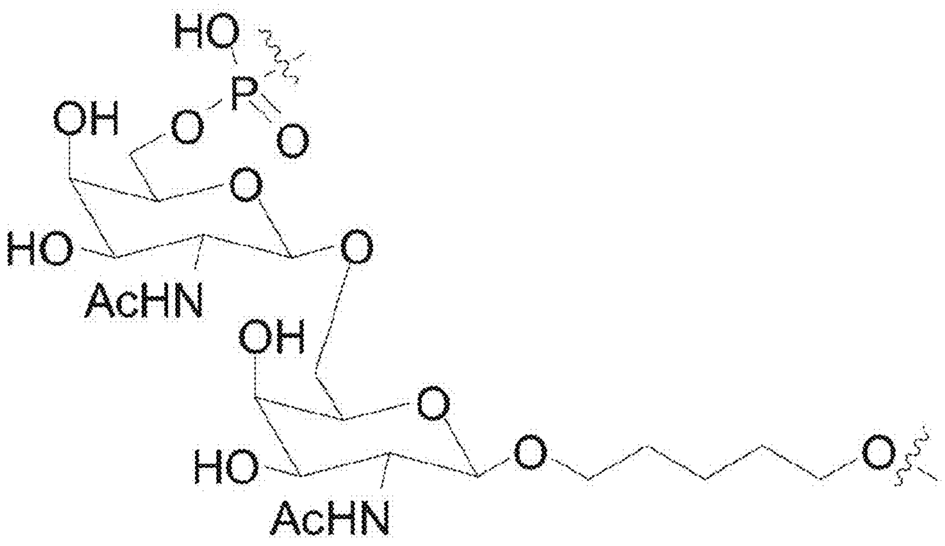
Figure 5A:
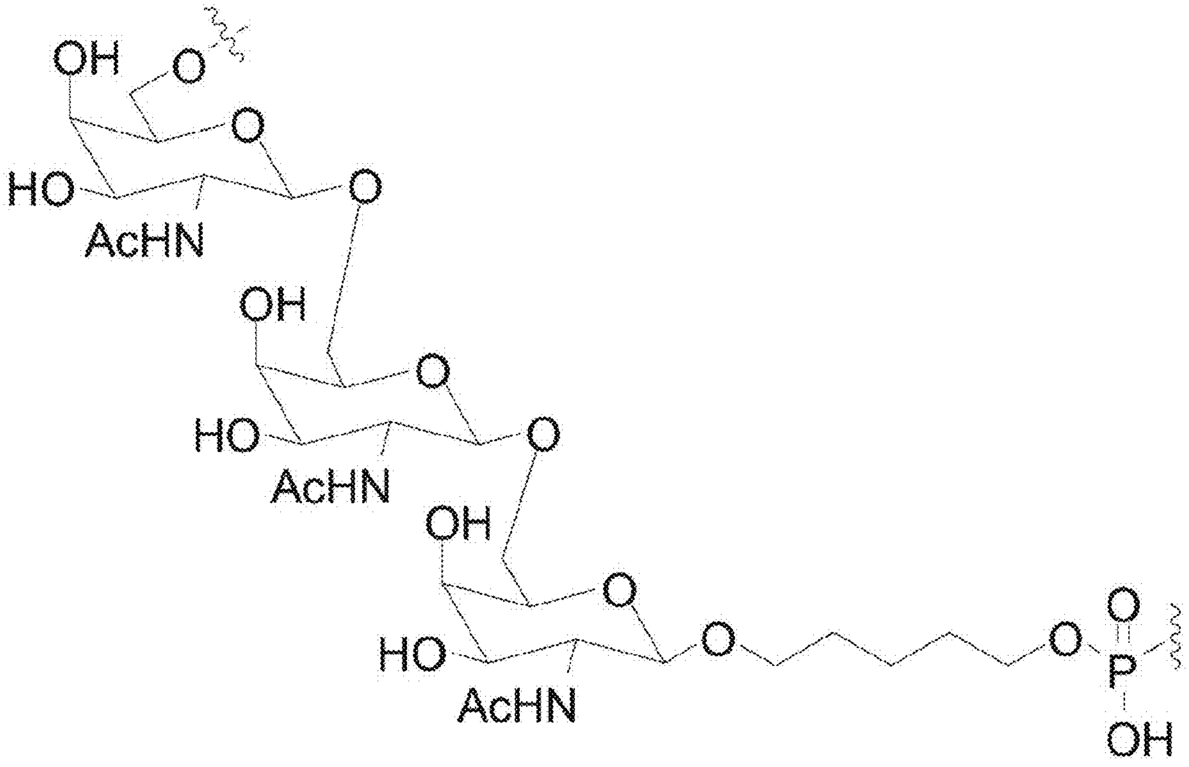
Figure 5B:
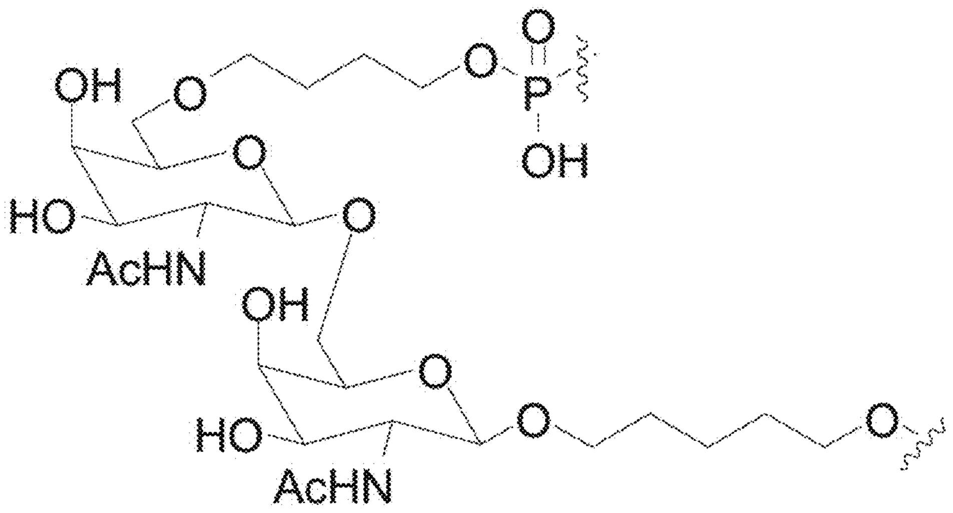
Figure 5B:
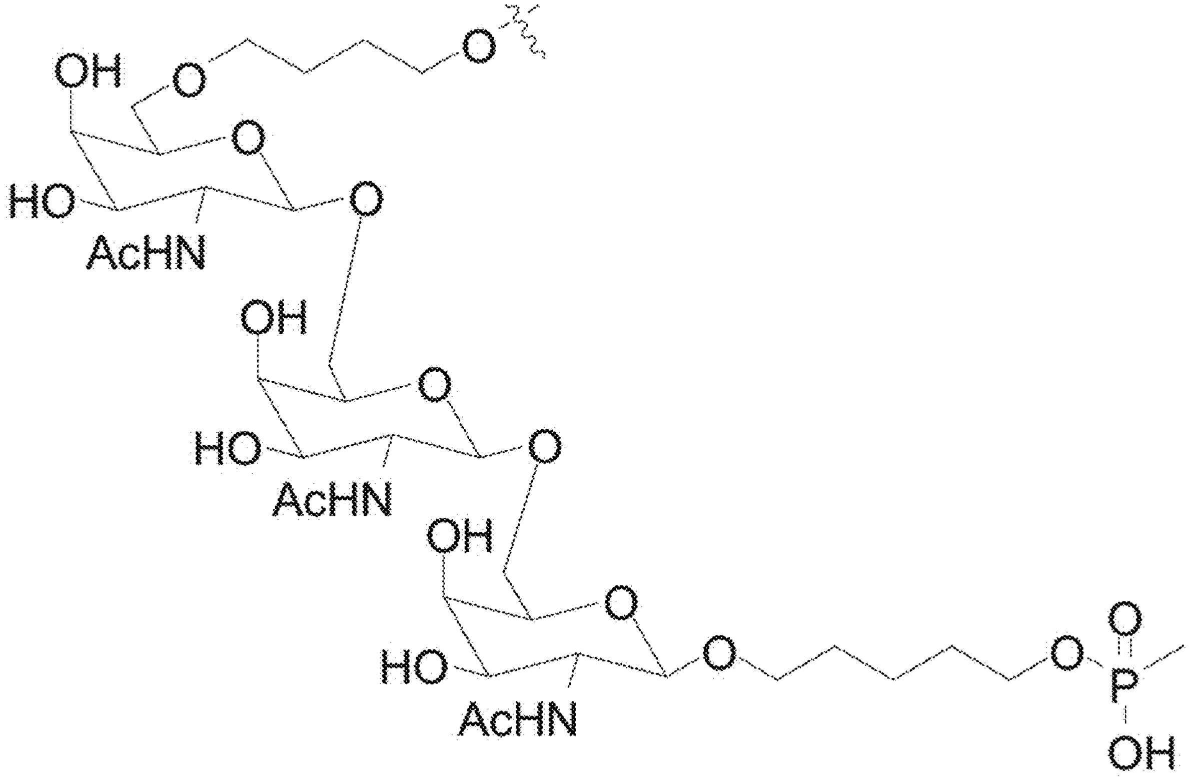
Figure 5C:
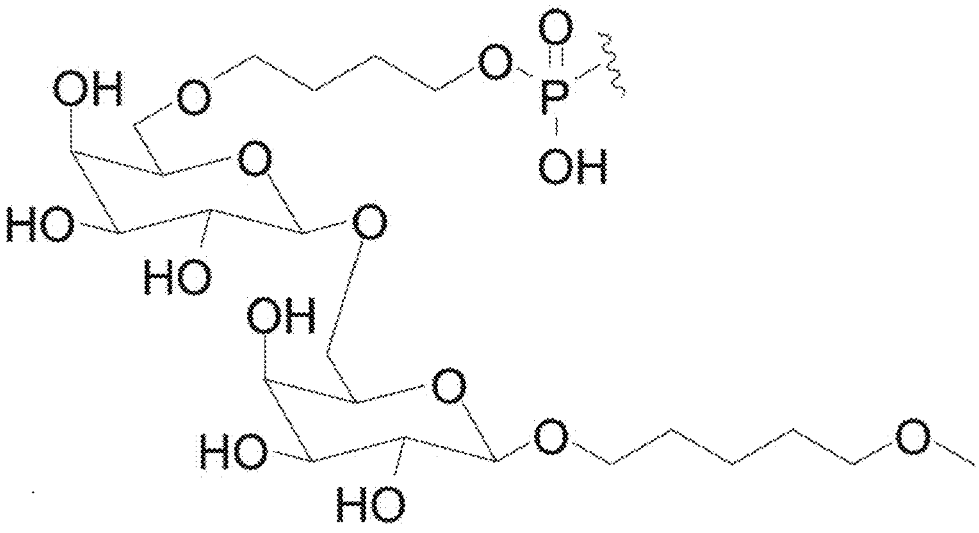
Figure 5C:
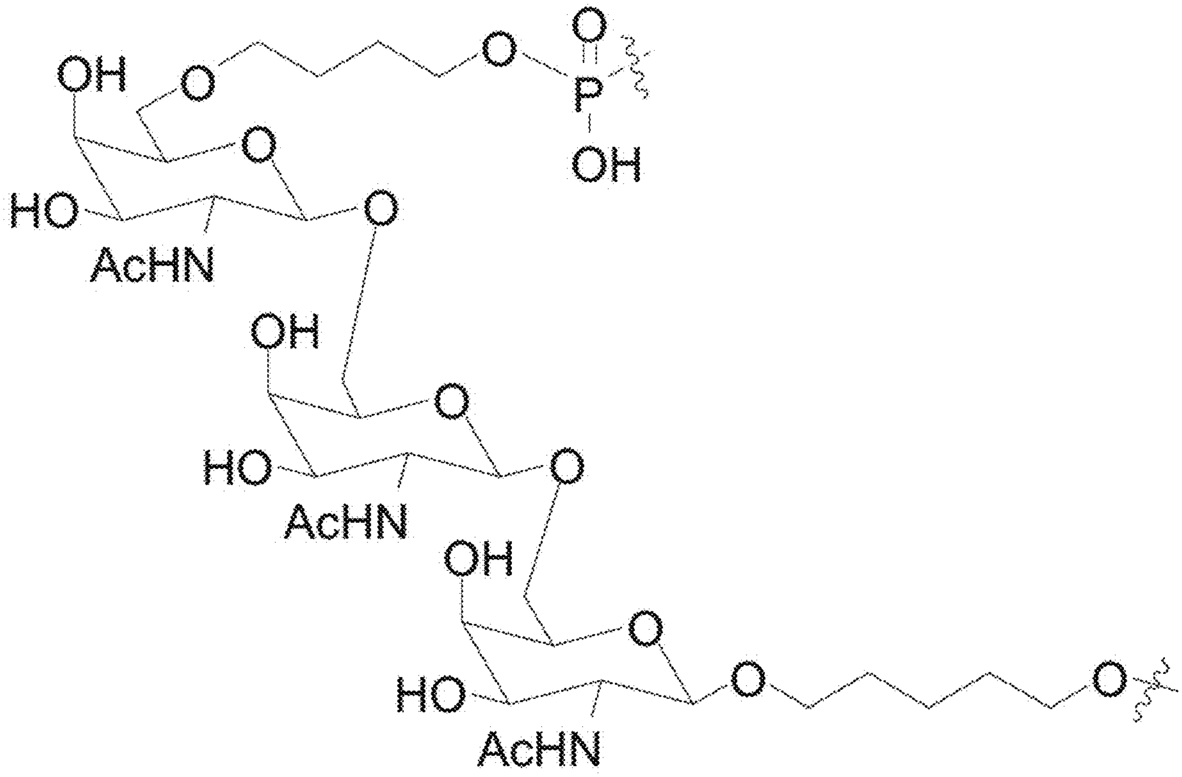
Figure 5D:
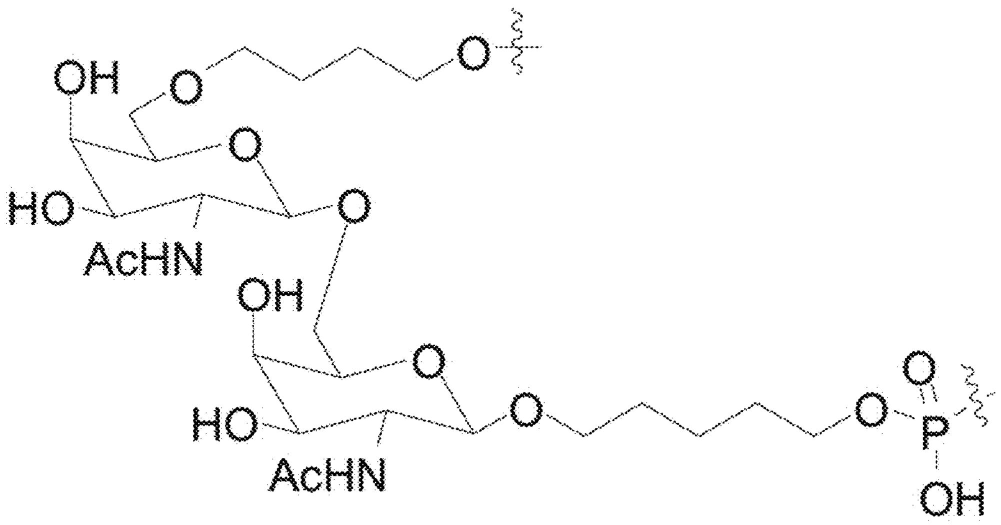
Figure 5D:
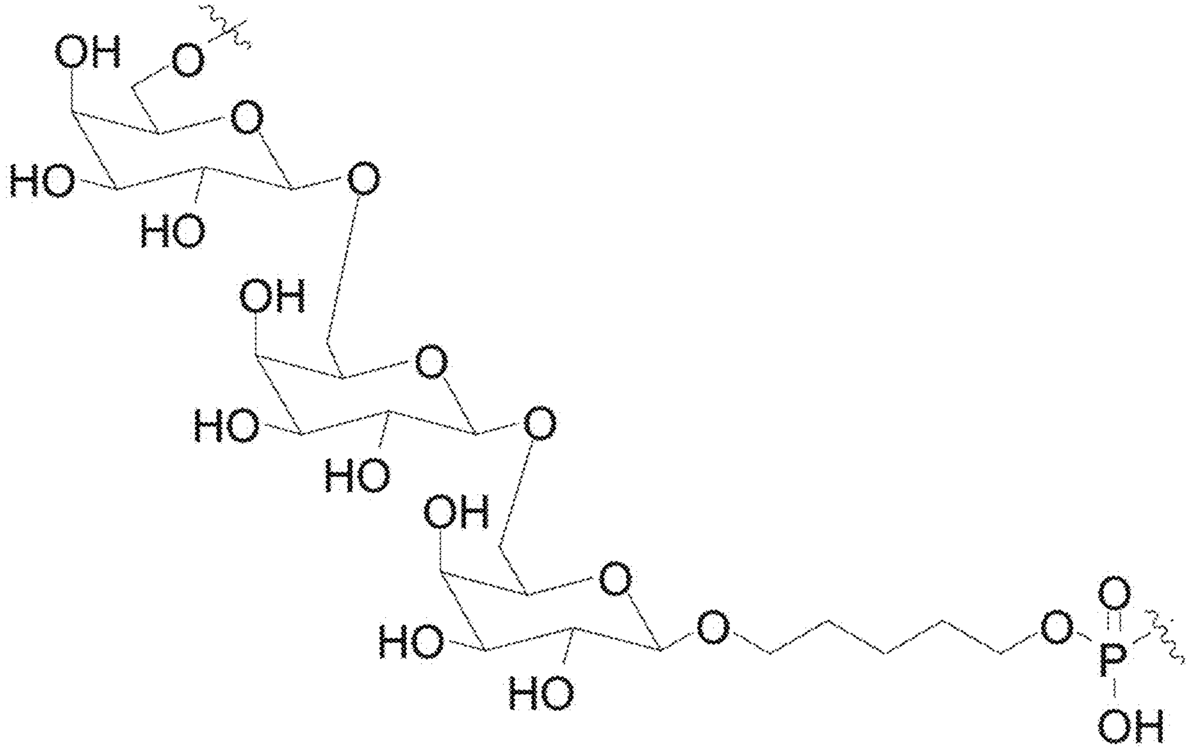
Figure 5E:
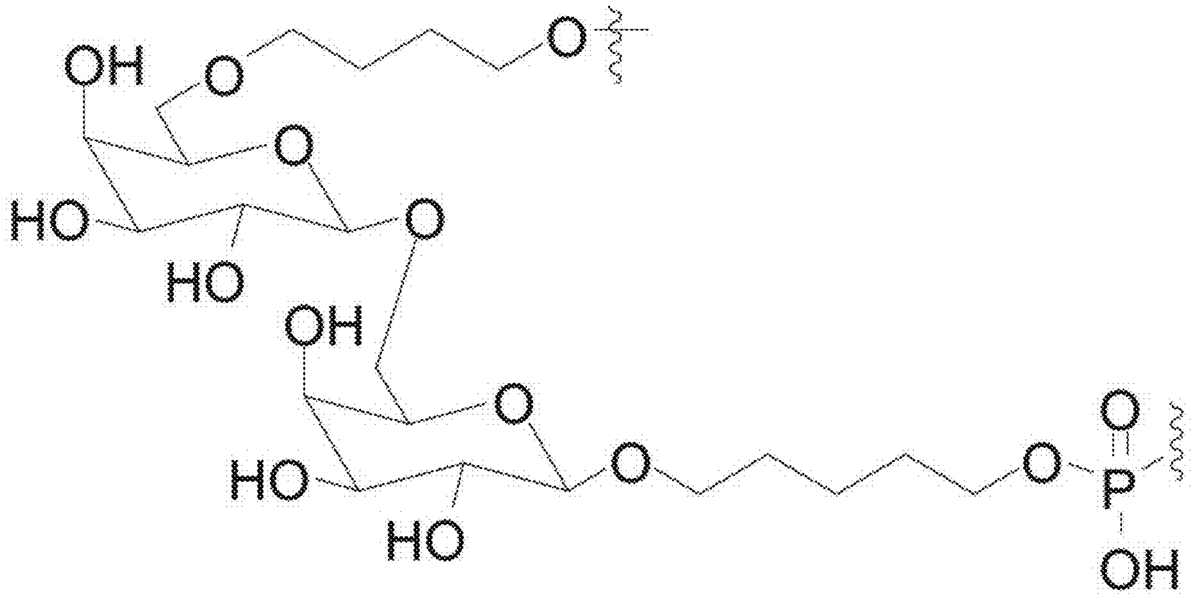
Figure 5F:
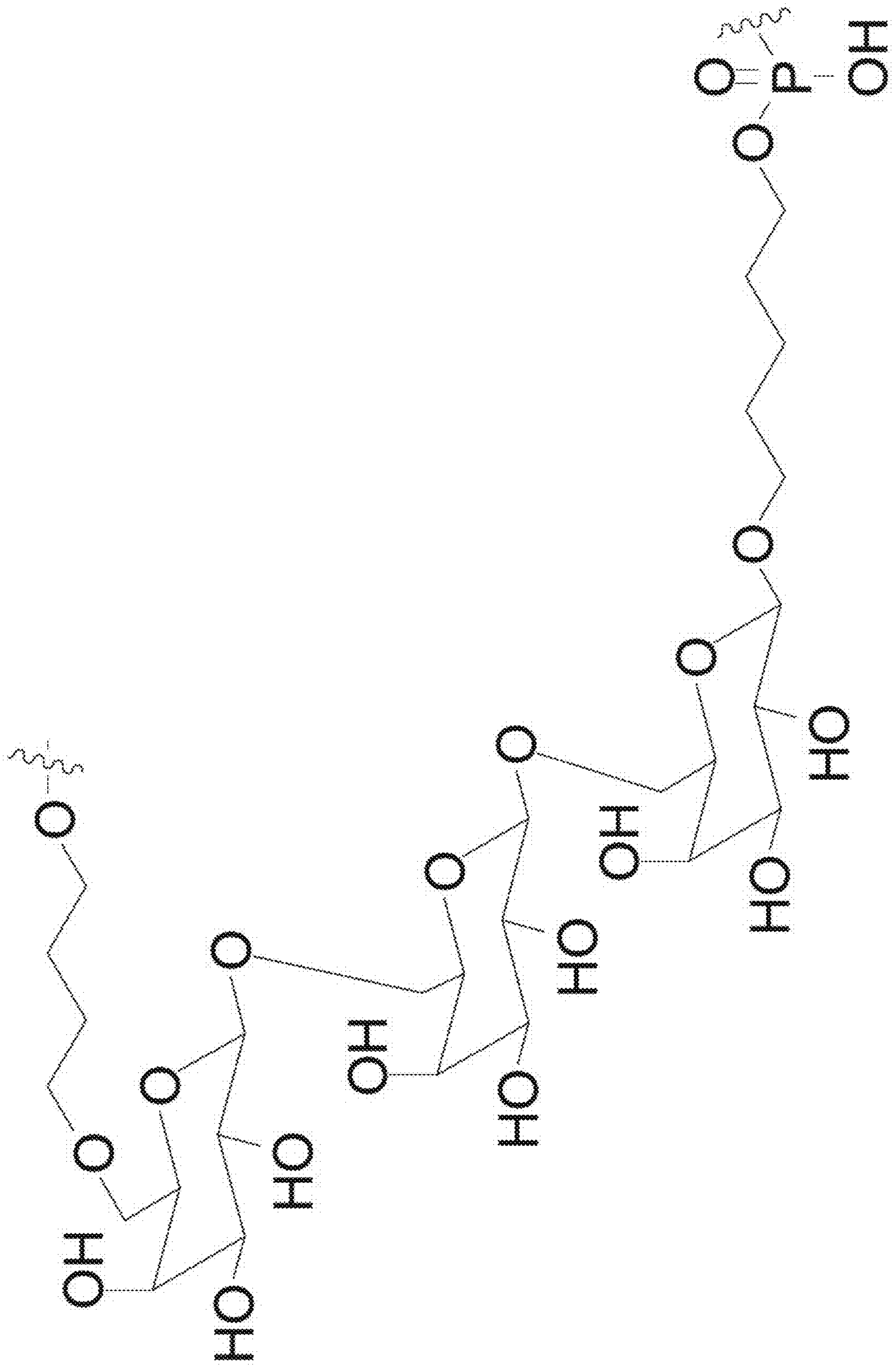
Figure 5G:
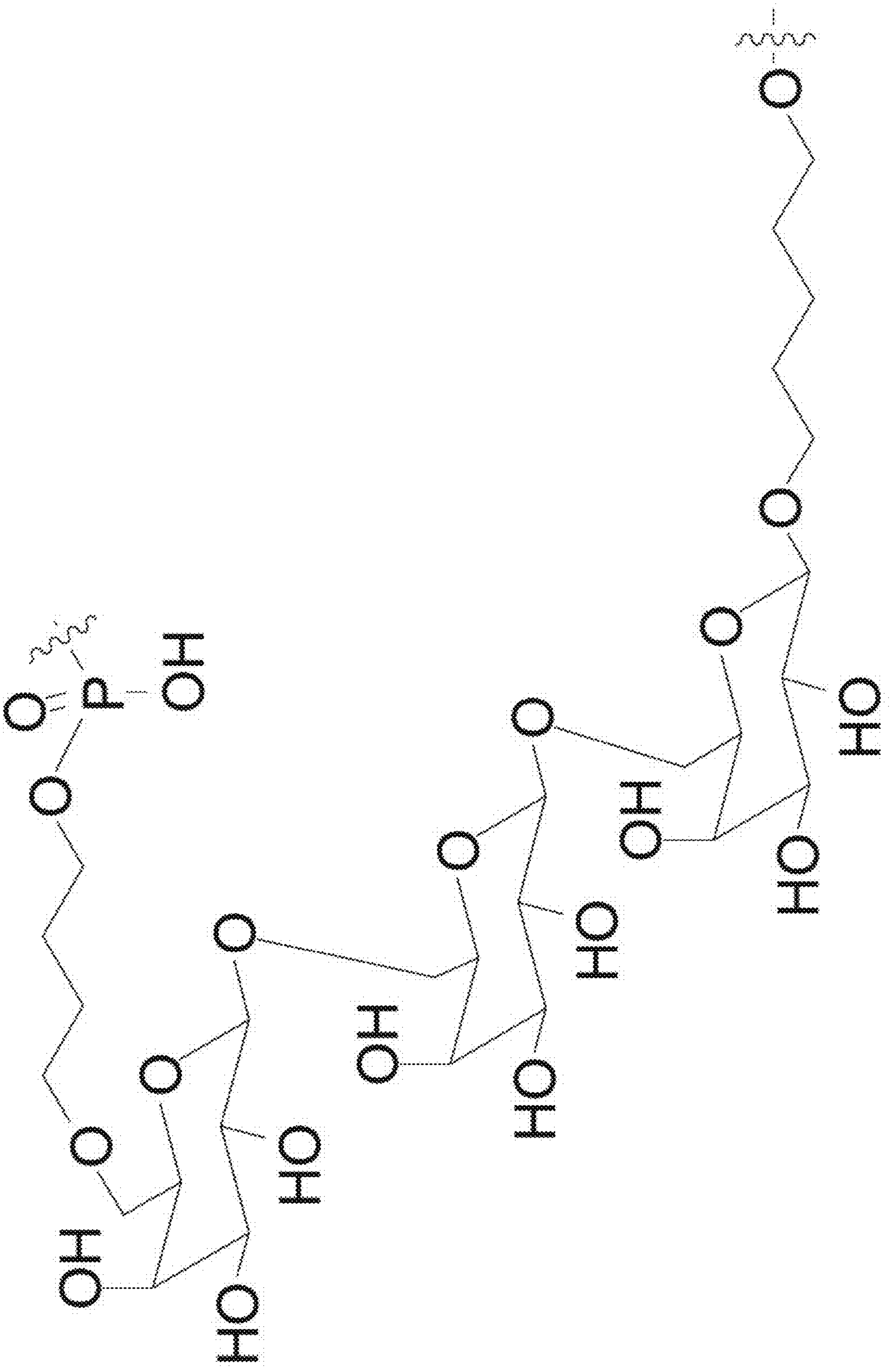
Figure 5H:
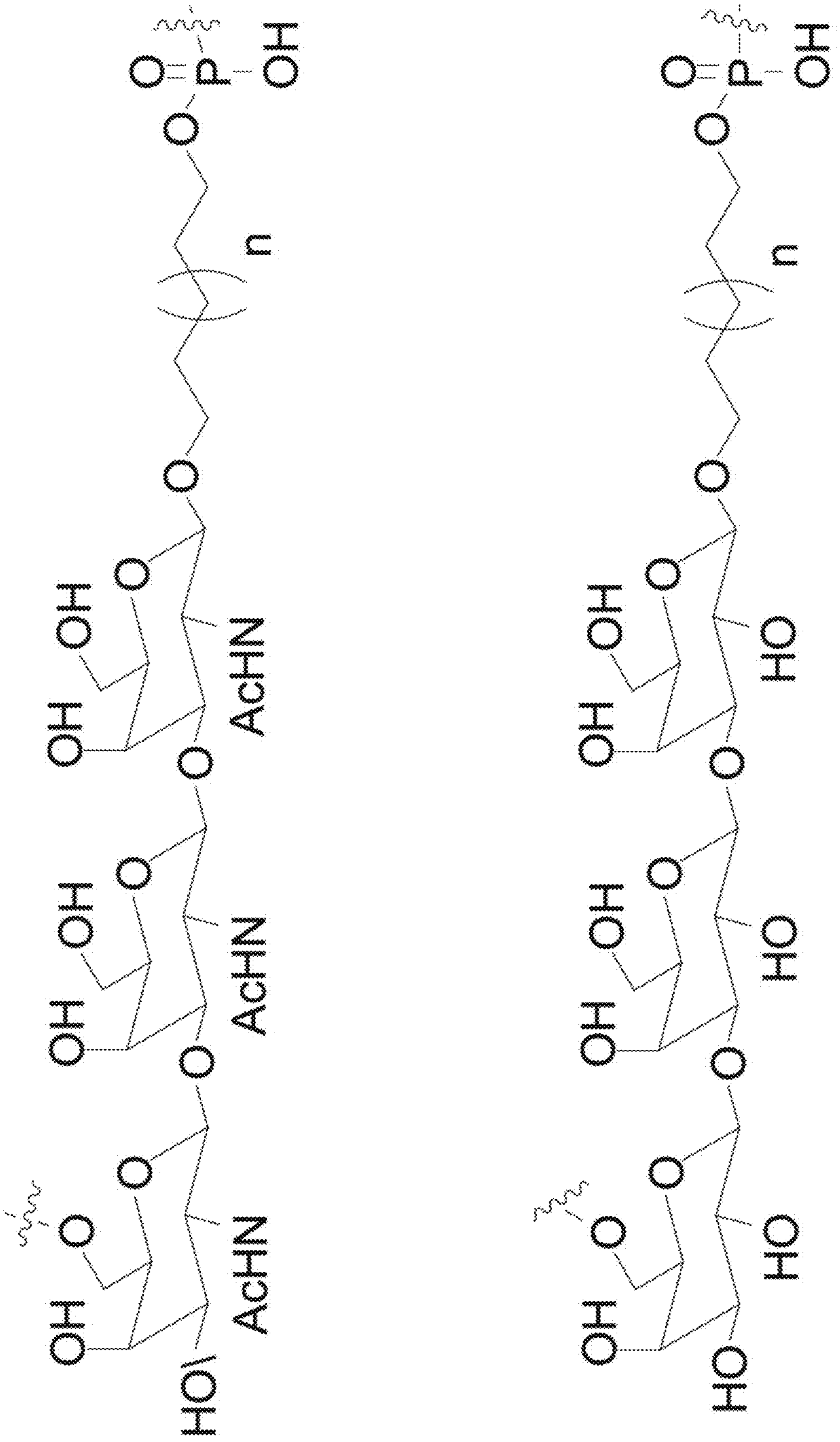
Figure 5I:
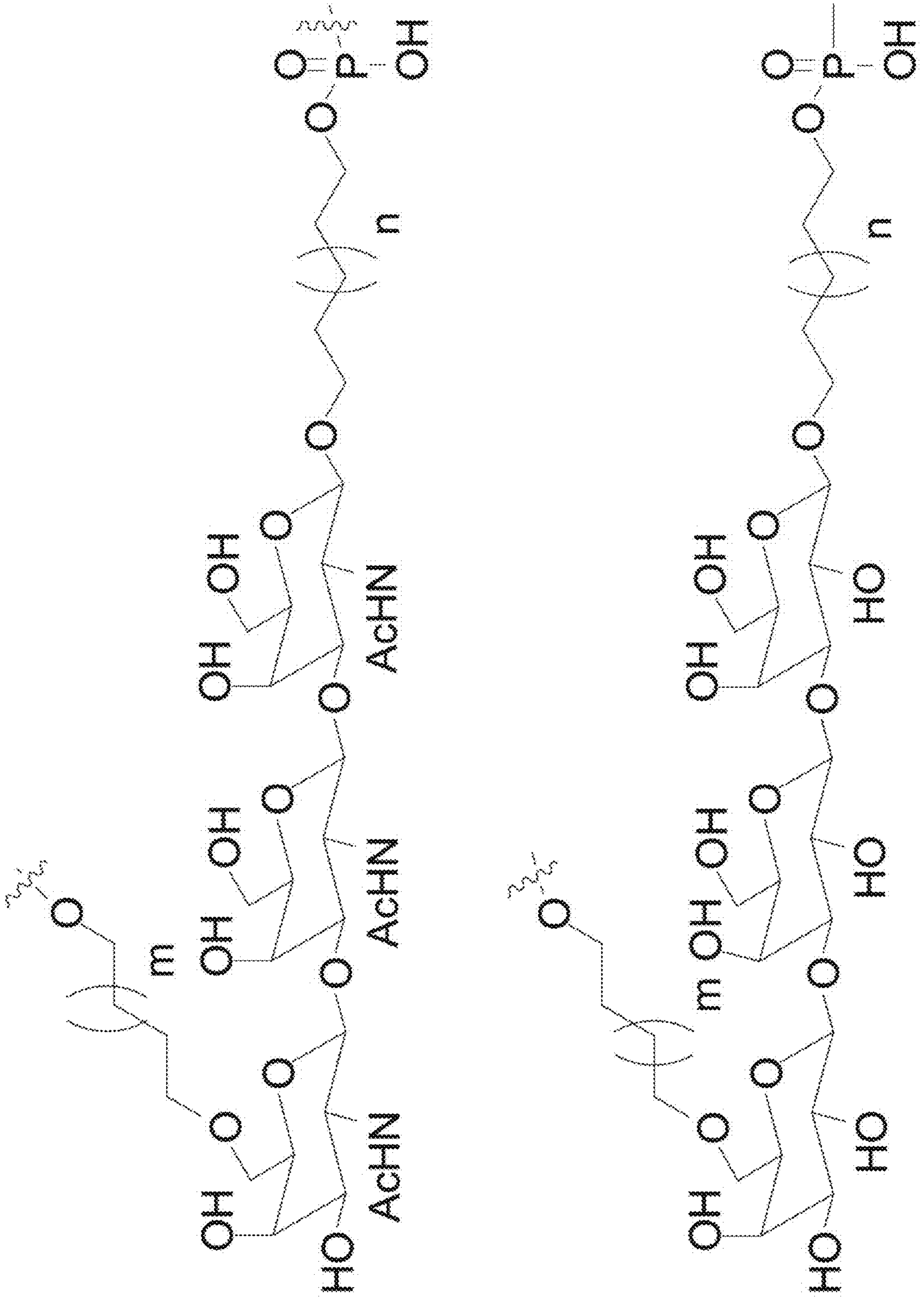
Figure 5J:
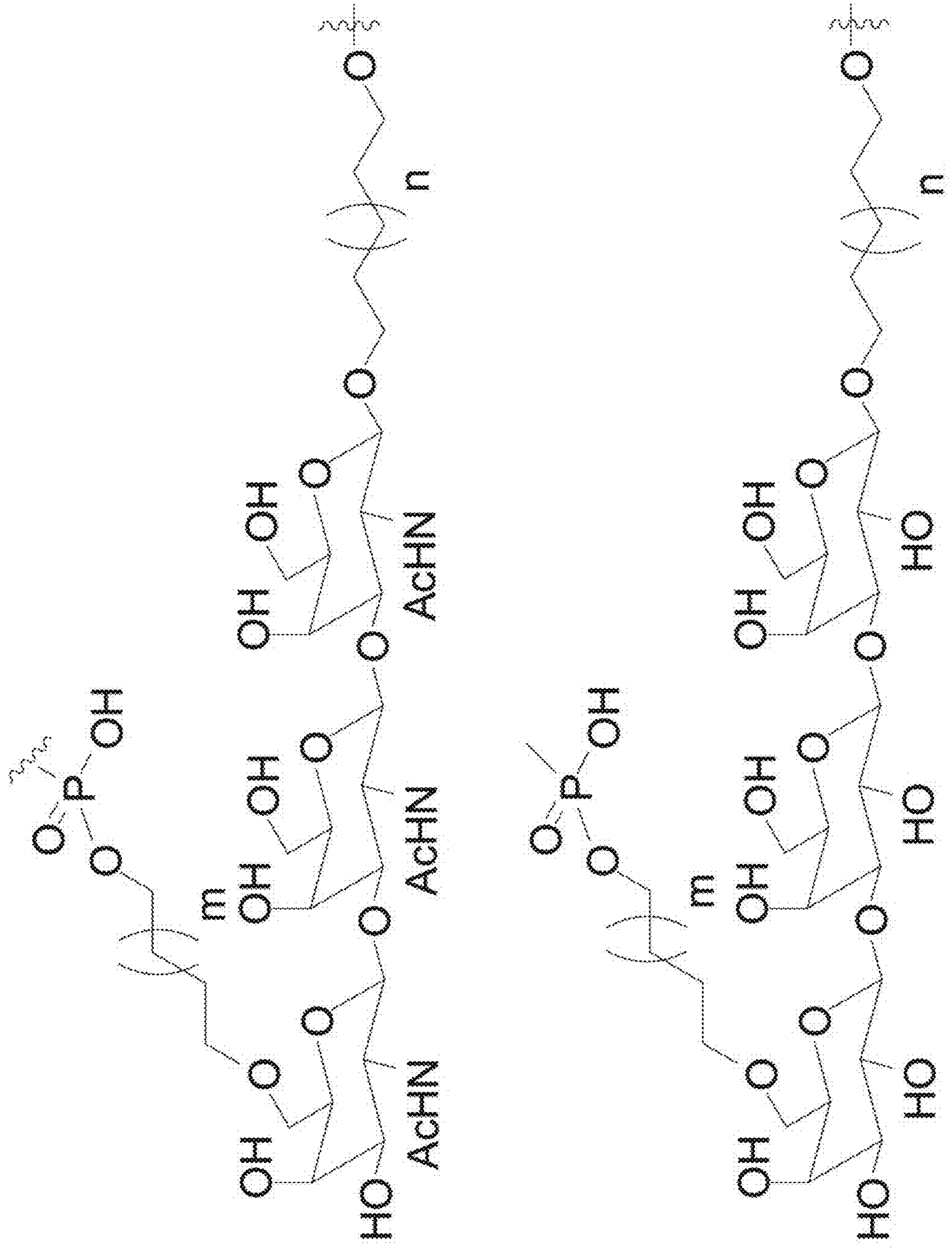
Figure 5K:
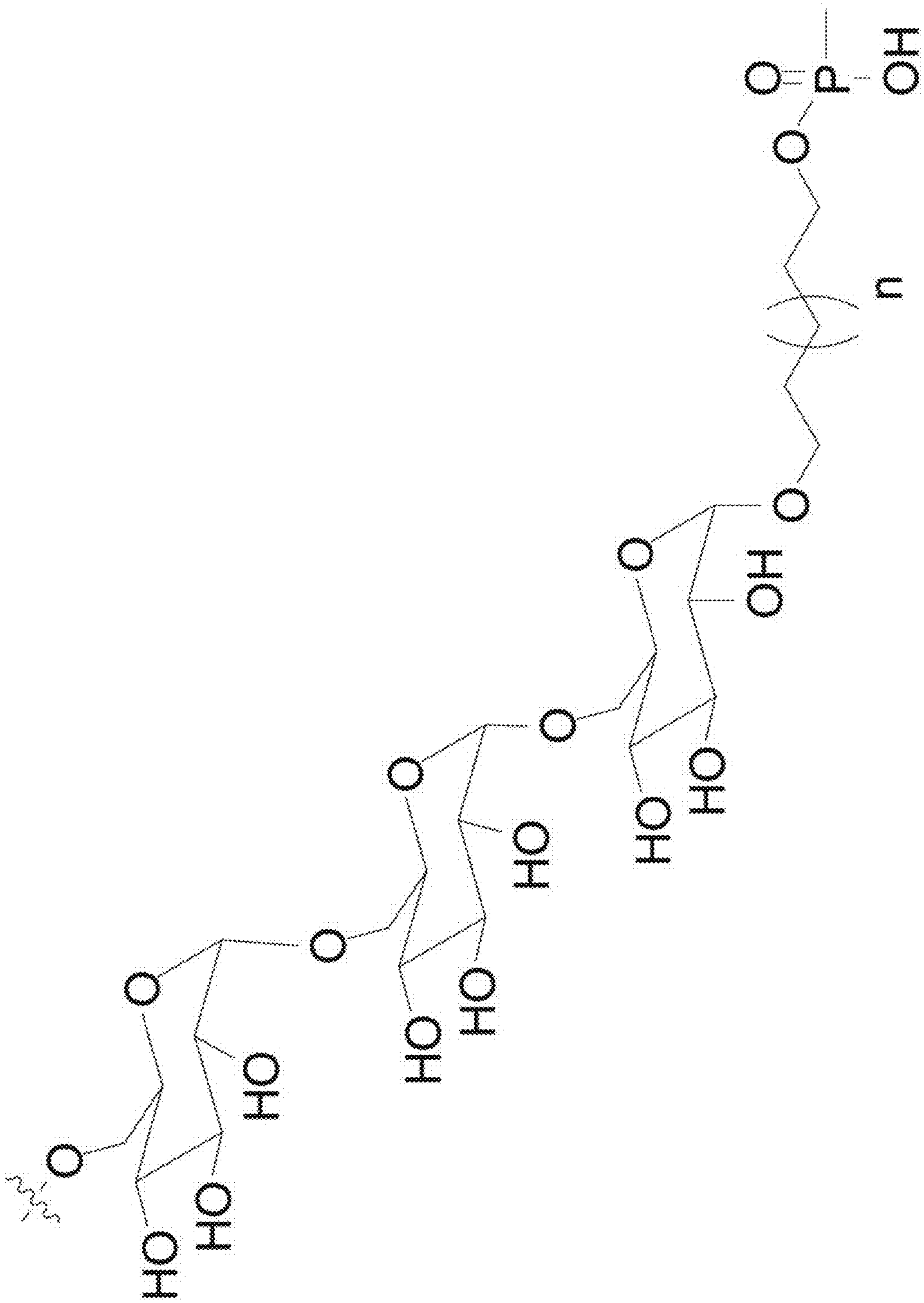
Figure 5L:
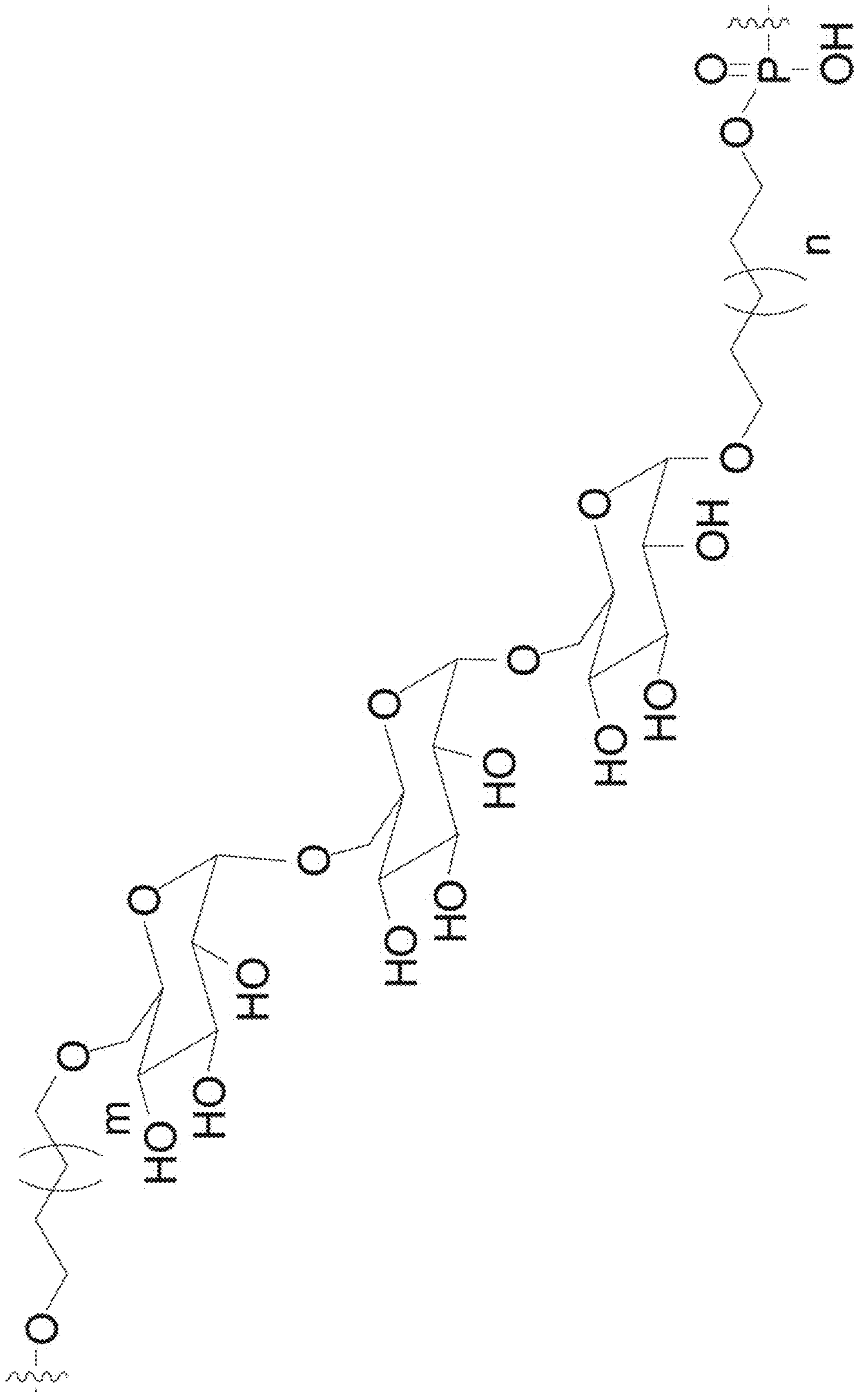
Figure 5M:
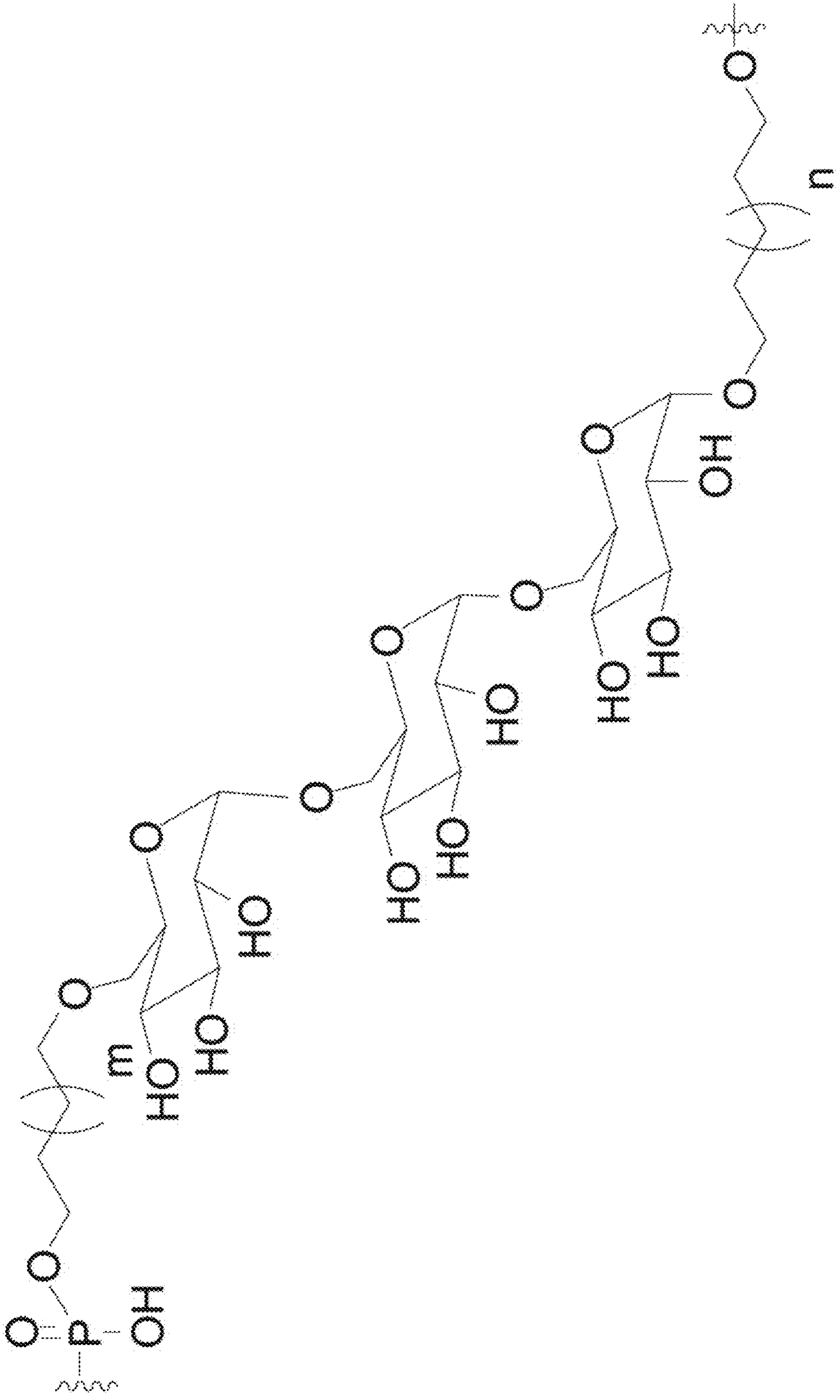
Figure 6:
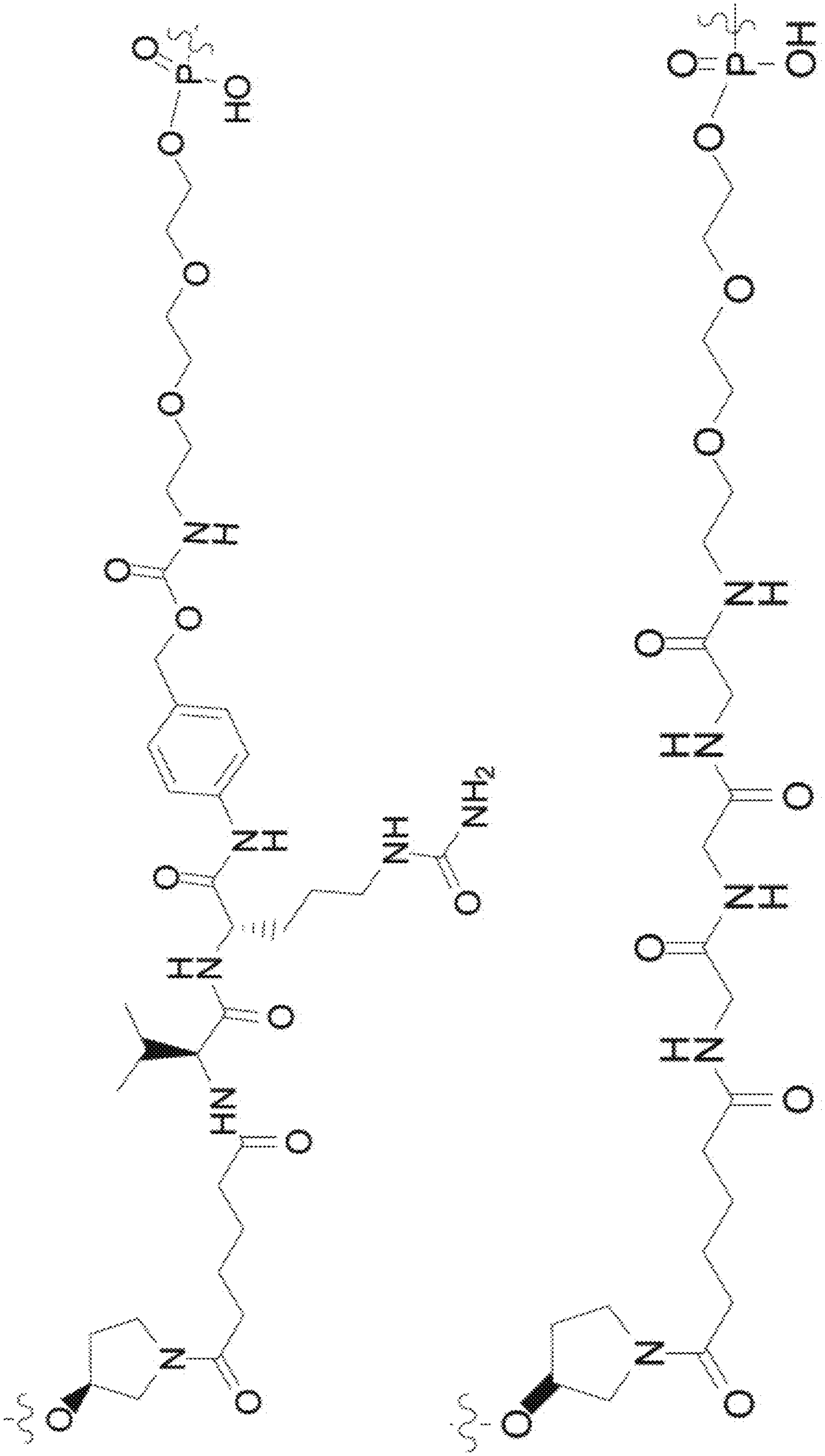

*Structures of linkers are shown in FIGS. 1A-1B;

+++ rapid cleavage; ++ moderate/medium cleavage; + slower cleavage;

– no degradation; Q198 - N-(acetyl)prolinol-4-phosphate; Q48 - hexaethyleneglycolphosphate; nd not determined.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A molecule comprising at least two effector molecules, wherein the effector molecules are connected together via an endosomal cleavable linker, wherein:

the effector molecules are selected independently from the group consisting of siRNA, shRNA, antisense oligonucleotide, microRNA, anti-microRNA or antimir, supermir, antagomir, ribozyme, triplex-forming oligonucleotide, decoy oligonucleotide, splice-switching oligonucleotide, immunostimulatory oligonucleotide, RNA activator, U1 adaptor, and any combinations thereof; and the endosomal cleavable linker comprises one or more saccharide units independently selected from:

Q303

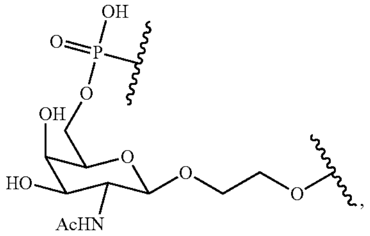

,

Q304

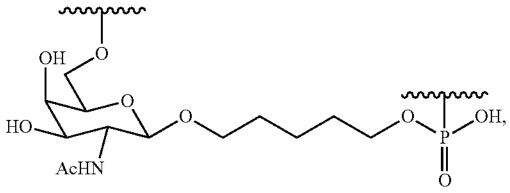

,

Q305

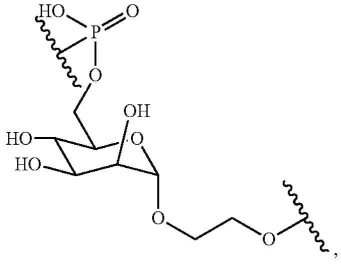

,

-continued

Q306

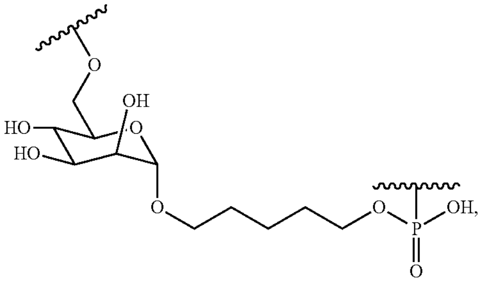

,

Q312

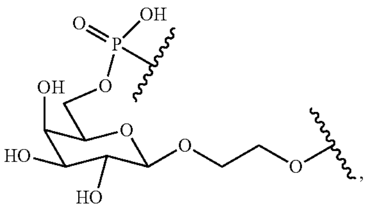

,

Q313

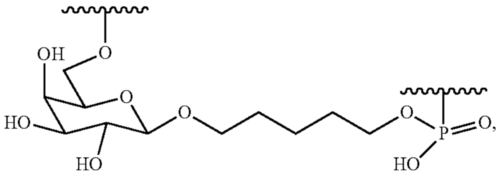

,

Q314

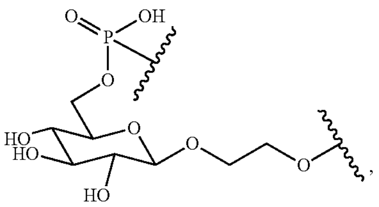

,

Q315

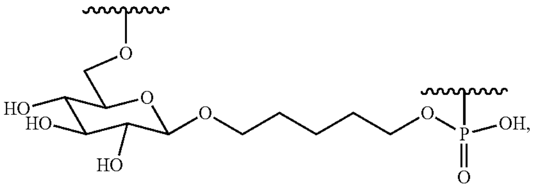

,

-continued
Q316
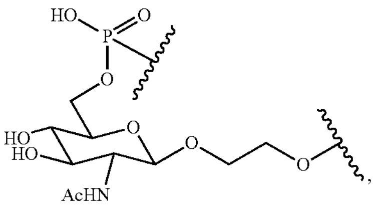
Q317
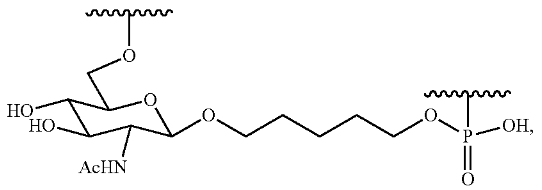
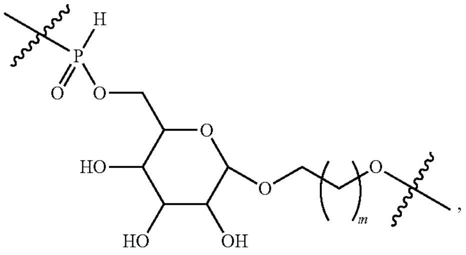
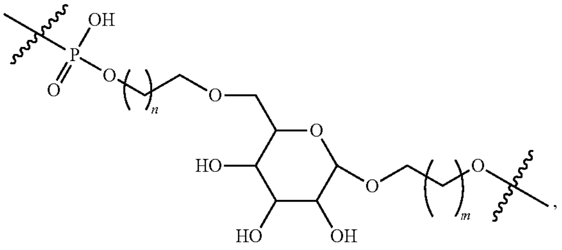
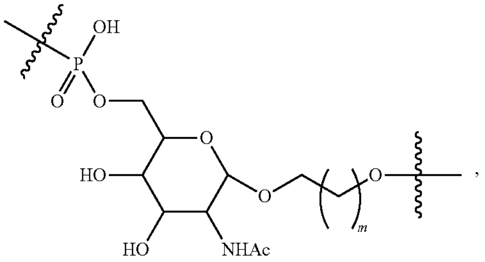
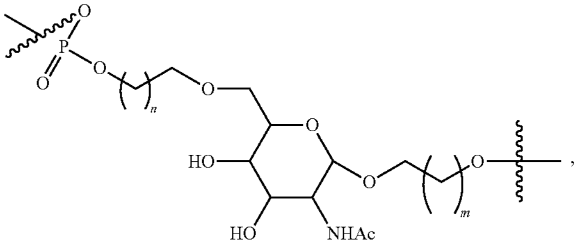
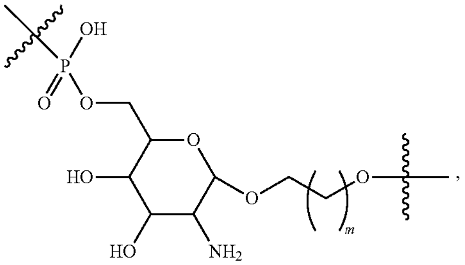
-continued
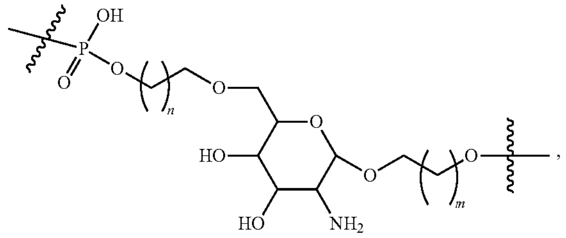
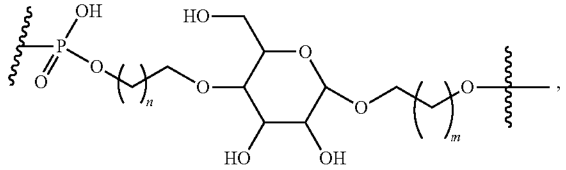
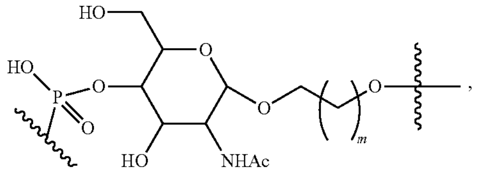
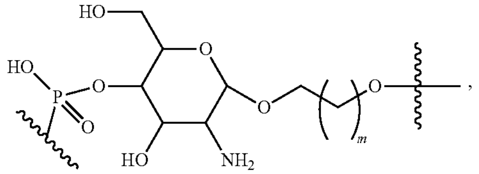
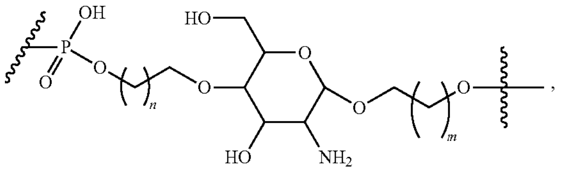
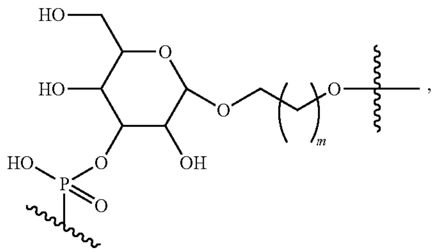
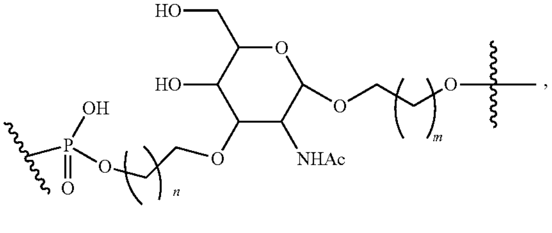

-continued

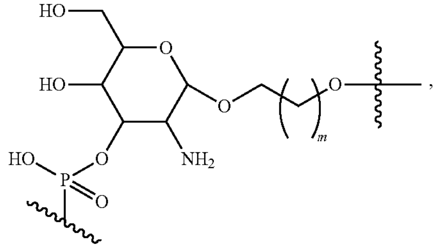

,

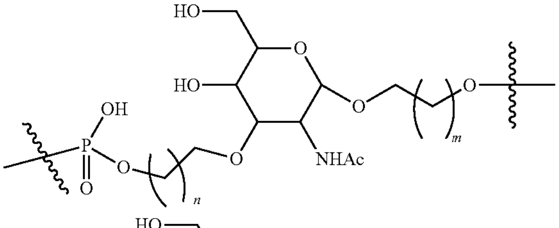

,

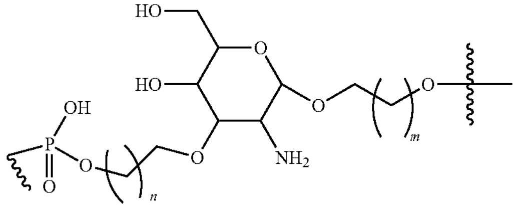

, or

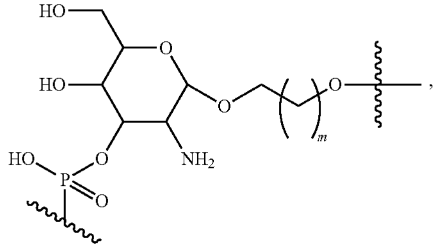

, wherein m and n are each independently an integer selected from 1 to 12.

2. The molecule of claim 1, wherein endosomal cleavable linker comprises two or more the saccharide units.

3. The molecule of claim 1, wherein endosomal cleavable linker comprises 1-10 of the saccharide units.

4. The molecule of claim 1, wherein endosomal cleavable linker comprises 2-10 of the saccharide units.

5. The molecule of claim 4, wherein the saccharide units are selected from the group consisting of Q303, Q304, Q305, Q306, Q312, Q313, Q314, Q315, Q316 and Q317.

6. The molecule of claim 1, wherein the endosomal cleavable linker comprises 2, 3, or 4 of the saccharide units.

7. The molecule of claim 6, wherein the saccharide units are selected from the group consisting of Q303, Q304, Q305, Q306, Q312, Q313, Q314, Q315, Q316 and Q317.

8. The molecule of claim 7, wherein the saccharide units are Q304.

9. The molecule of claim 7, the endosomal cleavable linker comprises -Q303Q303-, -Q303Q303Q303-, -Q303Q303Q303Q303-, -Q304Q304-, -Q304Q304Q304-, -Q304Q304Q304Q304-, -Q305Q305-, -Q305Q305Q305-, -Q306Q306-, -Q306Q306Q306-, -Q312Q312-, -Q312Q312Q312-, -Q313Q313-, -Q313Q313Q313-, -Q314Q314-, -Q314Q314Q314-, -Q315Q315-, -Q315Q315Q315-, -Q316Q316-, -Q316Q316Q316-, -Q317Q317-, or -Q317Q317Q317-.

10. The molecule of claim 6, wherein endosomal cleavable linker further comprises

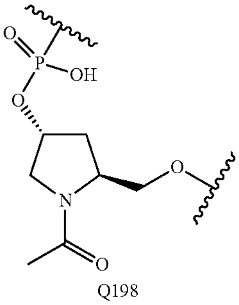

or

Q198

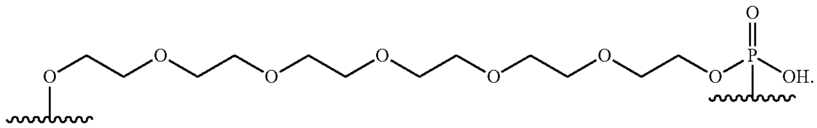

.

Q48

11. The molecule of claim 10, the endosomal cleavable linker comprises -Q198Q48Q303Q303Q48-, -Q198Q303Q48Q303-, -Q198Q48Q303Q303Q48-, -Q198Q303Q48Q303-, -Q198Q303Q303Q303Q303-, -Q198Q303Q303Q303-, -Q198Q303Q303-, -Q198Q304Q304Q304Q304-, -Q198Q304Q304Q304-, -Q198Q304Q304-, -Q198Q48Q303Q303Q48-, -Q198Q303Q48Q303-, -Q198Q303Q303-, -Q48Q303Q303Q48-, or -Q303Q48Q303-.

12. The molecule of claim 1, further comprising at least one ligand is conjugated with the molecule.

13. The molecule of claim 12, wherein the ligand is conjugated at a 3'-end of one of said at least two effector molecules.

14. The molecule of claim 12, wherein the ligand is conjugated at a 5'-end of one of said at least two effector molecules.

15. The molecule of claim 1, wherein the effector molecules are selected independently from the group consisting of siRNA, shRNA, antisense oligonucleotide, ribozyme, and any combinations thereof.

16. The molecule of claim 1, wherein one of said at least two effector molecules modulate gene expression of a first target nucleic acid and another one of said at least two effector molecules modulates gene expression of a second nucleic acid.

17. The molecule of claim 16, wherein the first target nucleic acid and the second target nucleic acid are the same.

18. The molecule of claim 17, wherein the first target nucleic acid comprises a nucleotide sequence identical to the nucleotide sequence of the second target nucleic acid target.

19. The molecule of claim 1, wherein one of said at least two effector molecules is a first double-stranded siRNA molecule comprising a sense strand and an antisense strand, and another one of said at least two effector molecules is a second double-stranded siRNA molecule comprising a sense strand an antisense strand.

20. The molecule of claim 19, wherein the sense strand of the first siRNA molecule is covalently linked to the sense strand of the second siRNA molecule.

21. The molecule of claim 19, wherein the sense strand of the first siRNA molecule is covalently linked to the antisense strand of the second siRNA molecule.

22. The molecule of claim 19, wherein the antisense strand of the first siRNA molecule is covalently linked to the antisense strand of the second siRNA molecule.

23. The molecule of claim 19, further comprising a ligand conjugated with one of the sense strands.

24. The molecule of claim 19, further comprising a ligand conjugated with one of the antisense strands.

25. The molecule of claim 19, wherein the molecule comprises at least one modification selected from the group consisting of modified internucleoside linkage, modified nucleobase, modified sugar, and any combinations thereof.

26. The molecule of claim 25, wherein said at least one modification is comprised in a sense strand or an antisense strand.

27. A conjugate comprising an effector molecule linked to a ligand via an endosomal cleavable linker or a protease cleavable linker, and wherein the endosomal cleavable linker or the protease cleavable linker comprises one or more saccharide units independently selected from:

Q303

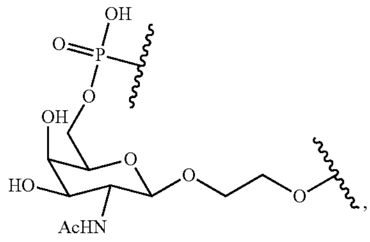

Q304

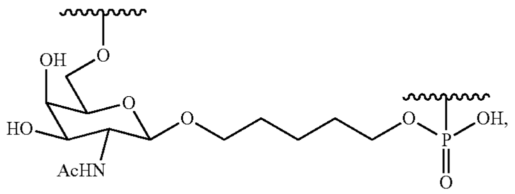

Q305

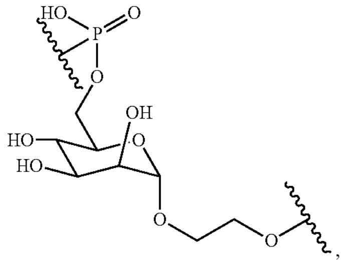

Q306

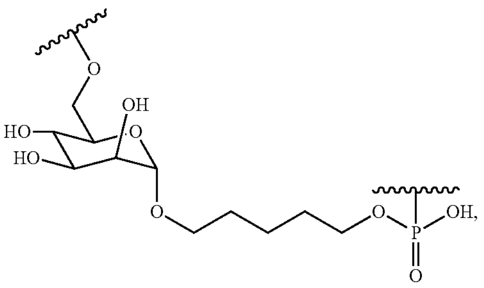

Q312

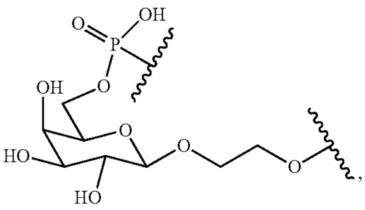

Q313

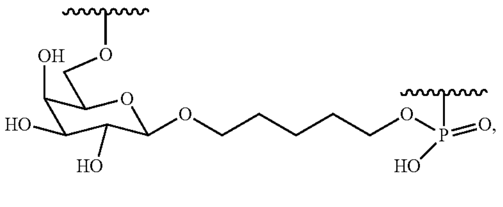

-continued
Q314
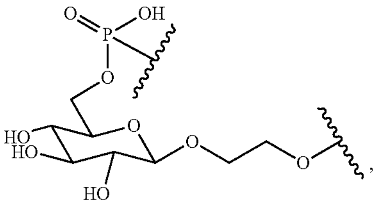
,
Q315
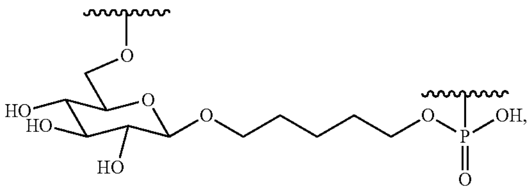
,
Q316
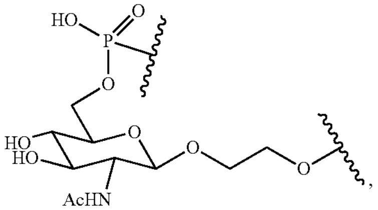
,
Q317
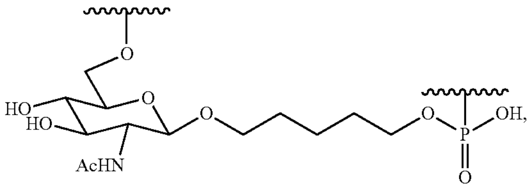
,
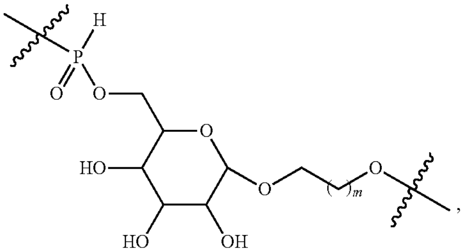
,
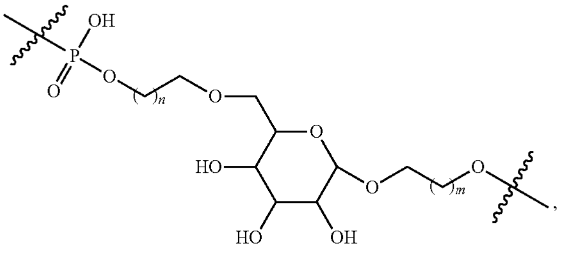
,
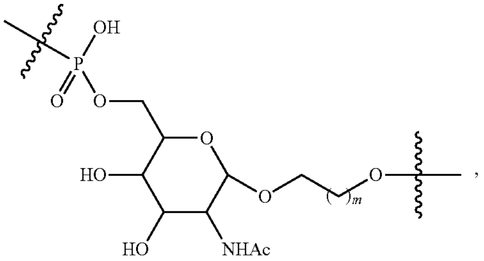
,
-continued
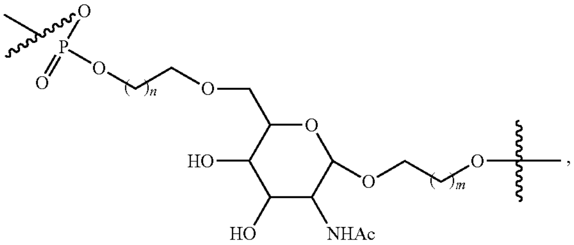
,
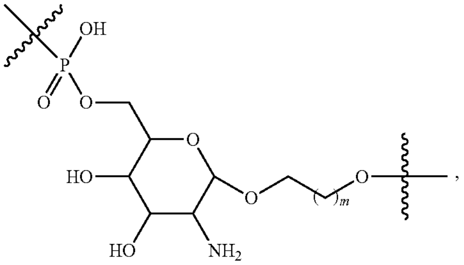
,
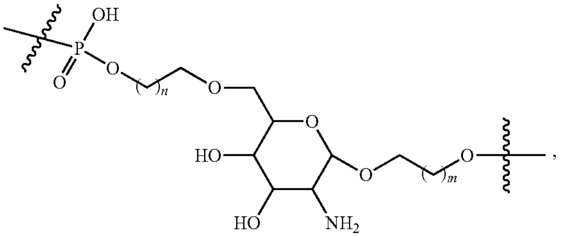
,
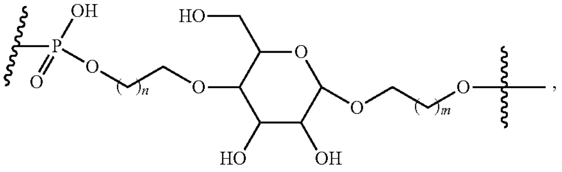
,
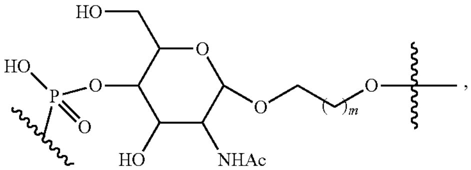
,
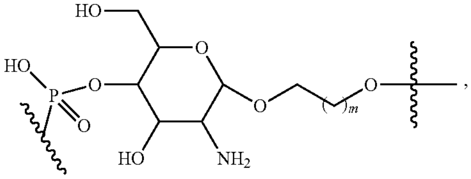
,
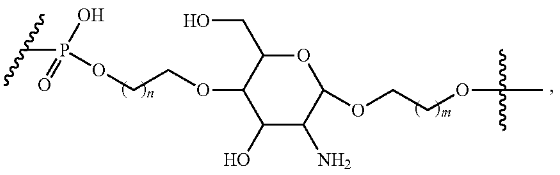
,
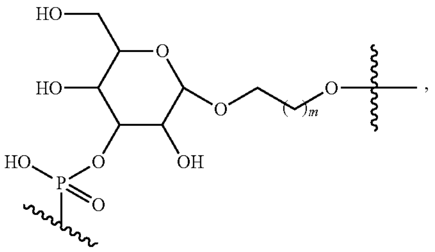
, -continued

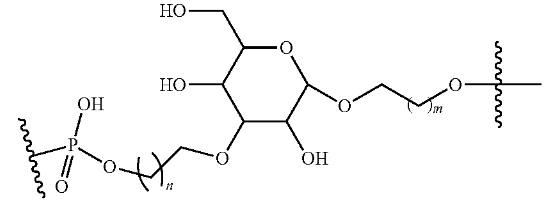,

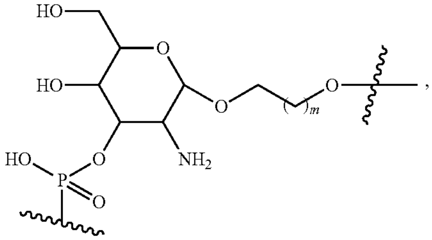,

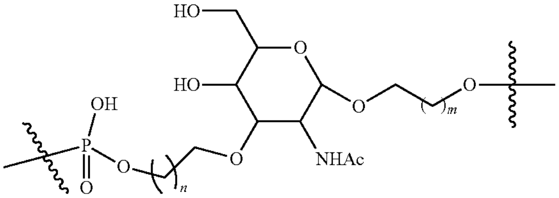,

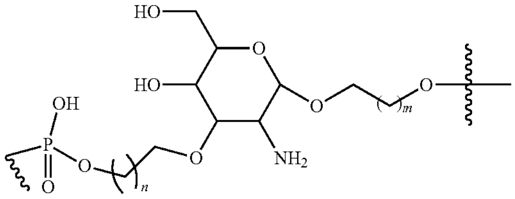, or

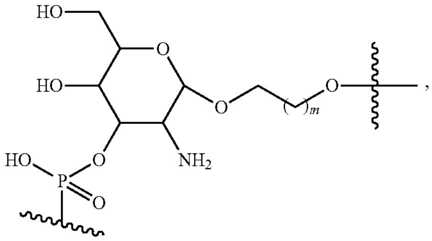, wherein m and n are each independently an integer selected from 1 to 12.

28. A conjugate comprising an endosomolytic agent linked with a ligand via an endosomal cleavable linker or a protease cleavable linker, wherein the endosomal cleavable linker or the protease cleavable linker comprises one or more saccharide units independently selected from:

Q303

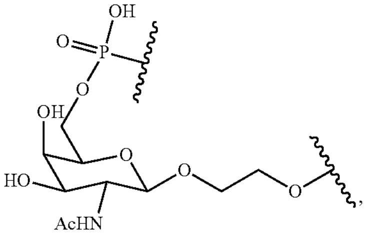,

-continued

Q304

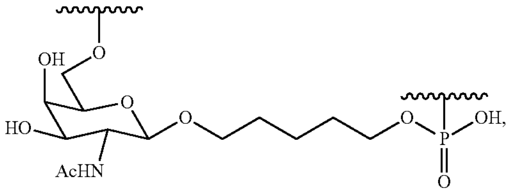,

Q305

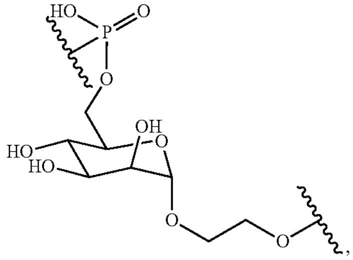,

Q306

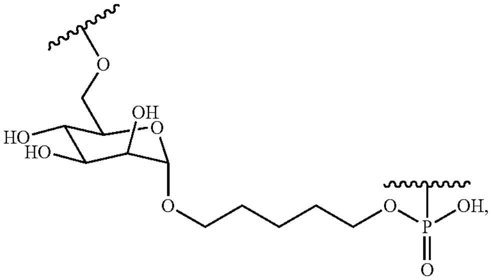,

Q312

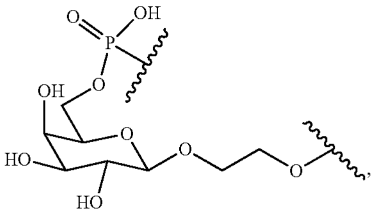,

Q313

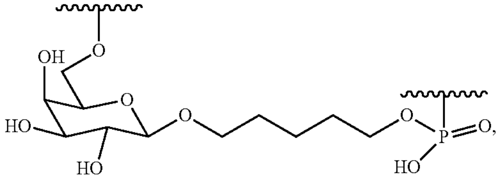,

Q314

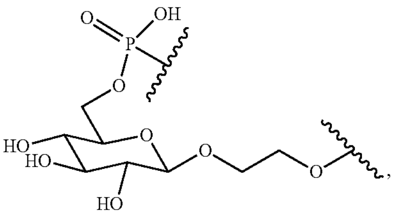,

Q315

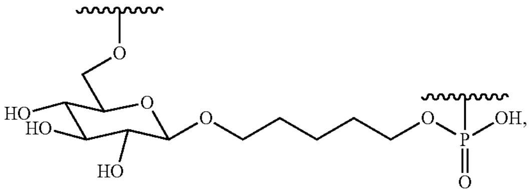,

-continued
Q316
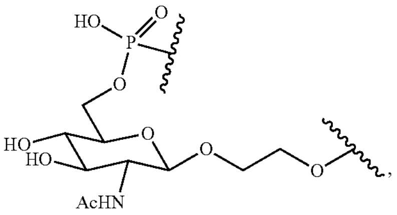
Q317
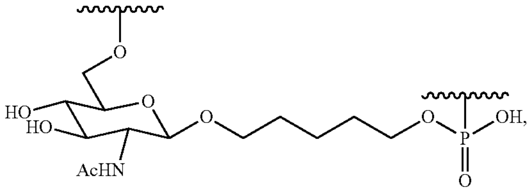
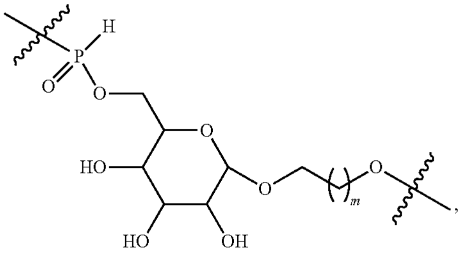
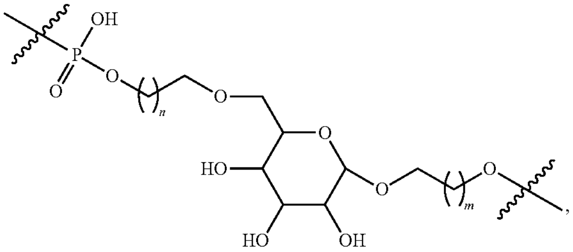
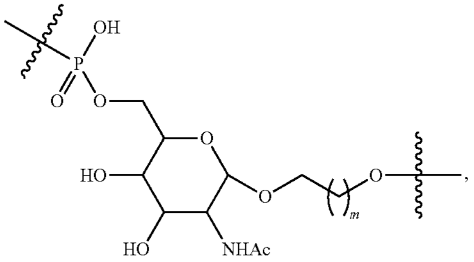
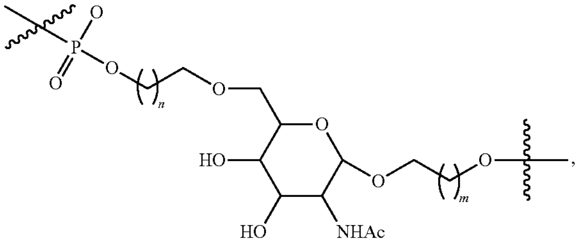
-continued
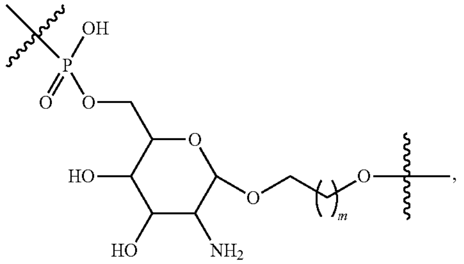
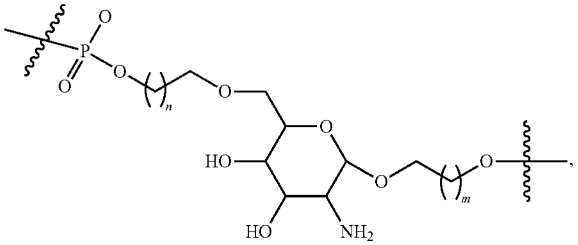
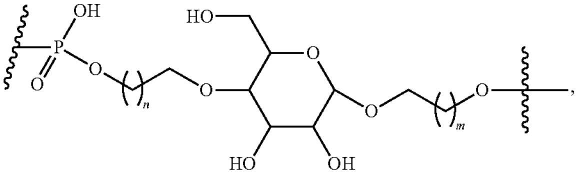
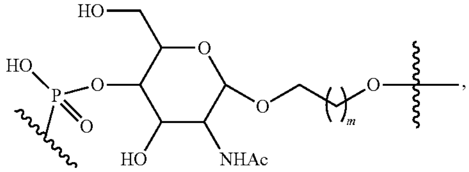
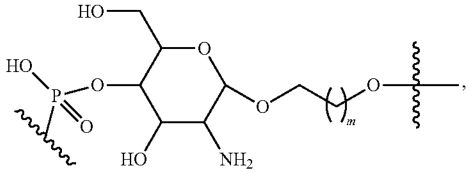
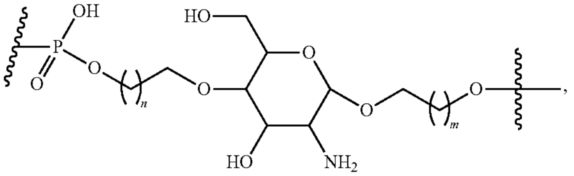
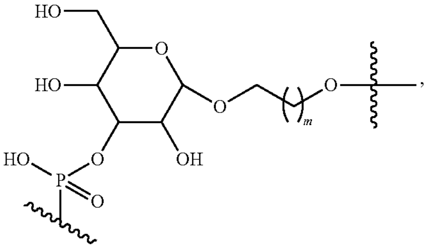
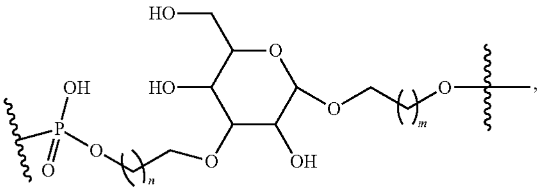

-continued
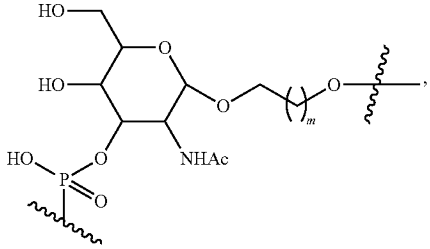
,
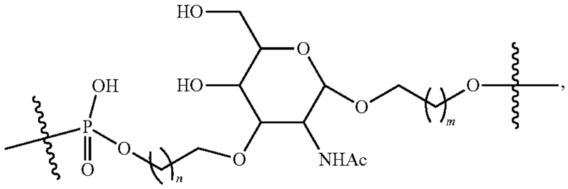
,
-continued
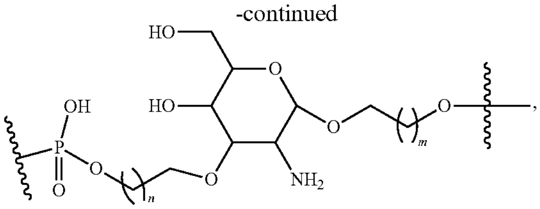
, or
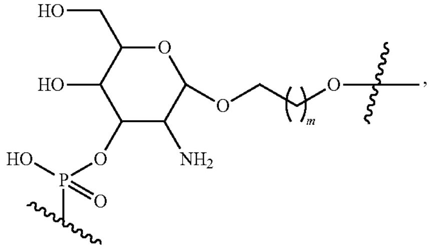
,
wherein m and n are each independently an integer selected from 1 to 12.
* * * * *